(12) United States Patent
Bammert et al.

(10) Patent No.: US 12,084,494 B2
(45) Date of Patent: Sep. 10, 2024

(54) INTERLEUKIN-31 MONOCLONAL ANTIBODIES FOR VETERINARY USE

(71) Applicant: Zoetis Services LLC, Parsippany, NJ (US)

(72) Inventors: Gary Francis Bammert, Portage, MI (US); Steven Alan Dunham, Kalamazoo, MI (US); Sebastian C. J. Steiniger, Kalamazoo, MI (US)

(73) Assignee: Zoetis Services LLC, Parsippany, NJ (US)

( * ) Notice: Subject to any disclaimer, the term of this patent is extended or adjusted under 35 U.S.C. 154(b) by 250 days.

(21) Appl. No.: 17/571,117

(22) Filed: Jan. 7, 2022

(65) Prior Publication Data
US 2022/0127351 A1    Apr. 28, 2022

Related U.S. Application Data

(63) Continuation of application No. 16/256,223, filed on Jan. 24, 2019, now Pat. No. 11,530,262.

(60) Provisional application No. 62/643,940, filed on Mar. 16, 2018.

(51) Int. Cl.
| | | |
|---|---|---|
| *A61K 39/00* | (2006.01) | |
| *A61P 17/00* | (2006.01) | |
| *A61P 35/00* | (2006.01) | |
| *A61P 37/00* | (2006.01) | |
| *C07K 16/24* | (2006.01) | |
| *G01N 33/68* | (2006.01) | |

(52) U.S. Cl.
CPC ............ *C07K 16/244* (2013.01); *A61P 17/00* (2018.01); *A61P 35/00* (2018.01); *A61P 37/00* (2018.01); *G01N 33/6869* (2013.01); *A61K 2039/505* (2013.01); *A61K 2039/552* (2013.01); *C07K 2317/24* (2013.01); *C07K 2317/33* (2013.01); *C07K 2317/34* (2013.01); *C07K 2317/76* (2013.01); *C07K 2317/92* (2013.01); *G01N 2333/54* (2013.01)

(58) Field of Classification Search
CPC .................................................. A61K 39/395
See application file for complete search history.

(56) References Cited

U.S. PATENT DOCUMENTS

| | | | |
|---|---|---|---|
| 6,989,145 | B2 | 1/2006 | Shitara et al. |
| 7,531,637 | B2 | 5/2009 | Siadak et al. |
| 7,615,213 | B2 | 11/2009 | Kasaian et al. |
| 7,939,068 | B2 | 5/2011 | Yao et al. |
| 8,133,899 | B2 | 3/2012 | Mitton-Fry et al. |
| 8,790,651 | B2 | 6/2014 | Bammert et al. |
| 9,206,253 | B2 | 12/2015 | Bammert et al. |
| 9,670,279 | B2 | 6/2017 | Ab et al. |
| 2002/0052030 | A1 | 5/2002 | Wonderling et al. |
| 2004/0208870 | A1 | 10/2004 | Allan |
| 2006/0063228 | A1 | 3/2006 | Kasaian et al. |
| 2006/0228329 | A1 | 10/2006 | Brady et al. |
| 2009/0208494 | A1 | 8/2009 | Bondensgaard et al. |
| 2009/0252732 | A1 | 10/2009 | Siadak et al. |
| 2010/0221244 | A1 | 9/2010 | Yao et al. |
| 2013/0022616 | A1 | 1/2013 | Bammert et al. |
| 2014/0286958 | A1 | 9/2014 | Bammert et al. |

FOREIGN PATENT DOCUMENTS

| | | |
|---|---|---|
| EP | 17200091.1 | 5/2019 |
| WO | WO 03/060080 A2 | 7/2003 |
| WO | WO 2006/088855 A1 | 8/2006 |
| WO | WO 2006/088955 A2 | 8/2006 |
| WO | WO 2006/104978 A2 | 10/2006 |
| WO | WO 2007/133816 A2 | 11/2007 |
| WO | WO 2007/143231 A2 | 12/2007 |
| WO | WO 2008/021976 A2 | 2/2008 |
| WO | WO 2008/028192 A2 | 3/2008 |
| WO | WO 2010/117448 A2 | 10/2010 |
| WO | WO 2011/047262 A2 | 4/2011 |
| WO | WO 2011/065935 A1 | 6/2011 |
| WO | WO 2013/011407 A1 | 1/2013 |
| WO | WO 2013/184871 A1 | 12/2013 |
| WO | WO 2017/042212 A1 | 3/2017 |
| WO | WO 2017/186813 A1 | 11/2017 |
| WO | WO 2018/162577 A1 | 9/2018 |
| WO | WO 2019/086694 A1 | 5/2019 |

OTHER PUBLICATIONS

Roitt, I. et al., Immunology, 2001, pp. 105-118.
Singer, M. et al., "Genes and Genomes": a changing perspective, 1991, Part 1, Chapter 1, 1.3, pp. 59-71.
Almagro et al., "Antibody modeling assessment," Proteins: Structure, Function, Bioinformatics 79 (2011) pp. 3050-3066.
Aaronson, D.S. et al., "A Road Map for Those Who Don't know JAK-STAT," Science, vol. 296, May 31, 2002, pp. 1653-1655.
Bachmann, M.F. et al., "Vaccination against IL-31 for the treatment of atopic dermatitis in dogs," Letters to the Editor, J Allergy Clin. Immunol. Jul. 2018, vol. 142, No. 1, pp. 279-281.
Bieber, T., "Mechanisms of Disease, Atopic Dermatitis," The New England Journal of Medicine, 2008, 358, pp. 1483-1494.

(Continued)

*Primary Examiner* — Prema M Mertz
(74) *Attorney, Agent, or Firm* — Gloria K. Szakiel

(57) ABSTRACT

A monoclonal antibody, or antigen-binding portion thereof is provided that specifically binds to a region on a mammalian IL-31 protein involved with interaction of the IL-31 protein with its co-receptor, wherein the binding of said antibody to said region is impacted by mutations in a 15H05 epitope binding region selected from: a region between about amino acid residues 124 and 135 of a feline IL-31 sequence represented by SEQ ID NO: 157 (Feline_IL31_wildtype); a region between about amino acid residues 124 and 135 of a canine IL-31 sequence represented by SEQ ID NO: 155 (Canine_IL31); and a region between about amino acid residues 118 and 129 of an equine IL-31 sequence represented by SEQ ID NO: 165 (Equine_IL31). Such antibodies can be in the form of veterinary compositions useful for treating IL-31-mediated disorders in cats, dogs, or horses.

6 Claims, 28 Drawing Sheets

Specification includes a Sequence Listing.

(56) References Cited

OTHER PUBLICATIONS

Bilsborough, J. et al. "IL-31 is Associated with Cutaneous Lymphocyte Antigen-Positive Skin Homing T Cells in Patients with Atopic Dermatitis" J Allergy Clin. Immunol. 2006 117(2): pp. 418-425.
Buckley, L., "Treatment of presumed allergic skin disease in cats," In Practice, Jun. 2017, vol. 39, pp. 242-254.
Buddenkotte, J. et al. "Pathophysiology and therapy of pruritus in allergic and atopic diseases," Allergy 65, 2010; 65: pp. 805-821.
Carr, M.N. et al., "Investigation of the pruritogenic effects of histamine, serotonin, tryptase, substance P and interleukin-2 in healthy dogs," 2009 The Authors, Journal compilation, pp. 105-110.
Casset, F. et al., "A peptide mimetic of an anti-CD4 monoclonal antibody by rational design," Biochemical and Biophysical Research Communications, 307 (2003), pp. 198-205.
Cevikbas, F. et al., Interleukin-31 directly regulates neuronal function in inflammation and itch, Journal of Investigative Dermatology (2010), Abstract, vol. 130, p. S117.
Chattopadhyay, S. et al. "Interleukin-31 and Oncostatin-M Mediate Distince Signaling Reactions and Response Patterns in Lung Epithelial Cells" Journal of Biological Chemistry 2007; 282, pp. 3014-3026.
Chen, Y. et al., "Selection and Analysis of an Optimized Anti-VEGF Antibody: Crystal Structure of an Affinity-matured Fab in Complex with Antigen," J. Mol. Biol. 1999; 293, pp. 865-881.
Chin, R. et al., Transcript of Q1 2017 Earnings, Conference Call of May 3, 2017 of Dr. Richard Chin.
Dambucher, J. et al., "Interleukin 31 mediates MAP kinase and STAT1/3 activation in intestinal epithelial cells and its expression is upregulated in inflammatory bowel disease," Gut 2007; 56: pp. 1257-1265.
De Bellis, F., "Latest Thinking on Atopic Dermatitis in Cats and Dogs," Vet Times, https://www.vettimes.co.uk, pp. 1-23, 2014.
Dillon, S. R. et al., "Interleukin31, a Cytokine Produced by Activated T Cells, Induces Dermatitis in Mice," Nature Immunology 2004; 5, pp. 752-760.
Diveu, C. et al., "Predominant expression of the long isoform of GP130-like (GPL) receptor is required for interleukin-31 signaling," Eur. Cytokine Netw., vol. 15, No. 4, Dec. 2004, pp. 291-302.
European Medicines Agency, EPAR summary for the public of Cytopoint, 2017.
Excerpt from the UniProt database, Interleukin 31, Oct. 13, 2009.
Fadok, V.A., "Update on Equine Allergies," Vet. Clin. Equine, 29, 2013, pp. 541-550.
Favrot, C., "Feline allergic dermatitis: clinical aspects and diagnosis" Update on feline hypersensitivity dermatoses Dermatology Service, Vetsuisse Faculty, University of Zurich, Zurich, Switzerland, 2013.
Furue, M. et al., "Emerging role of interleukin-31 and interleukin-31 receptor in pruritus in atopic dermatitis," Allergy, 2018, vol. 73, pp. 29-36.
Felsburg, P.J., "Overview of immune system development in the dog: comparison with humans," Human & Experimental Toxicology (2002) 21, pp. 487-492.
Gonzales, A.J., et al., "Abstracts of the 26th Annual Congress of the ECVD-ESVD, Sep. 19-21, 2013, Valencia, Spain," Veterinary Dermatology, 2013; 24: pp. 377-397.
Gonzales, A.J. et al., "Oclacitinib (Apoquel®) is a novel Janus kinase inhibitor with activity against cytokines involved in allergy," Journal of Veterinary Pharmacology and Therapeutics, 2014, pp. 1-8.
Gonzales, A.J. et al., "Interleukin-31: its role in canine pruritus and naturally occurring canine atopic dermatitis," Veterinary Dermatology, 2013; 24: pp. 48-53.
Gonzales, A.J. et al., "Plenary Session Abstracts from the Seventh World Congress of Veterinary Dermatology Meeting held Jul. 24-28, 2012, Vancouver, Canada," Veterinary Dermatology, 23 (Suppl. 1), pp. 2-104.
Grimstad, O. et al., "The Effect of Anti-interleukin-31-Antibodies on Scratching Behaviour and Development of Dermatitis on NC/Nga Mice" Inflammation Research Supplement 3 Jun. 2007, pp. S 396-397.
Grimstad, O. et al., "Anti-interleukin-31 Antibodies Ameliorate Scratching Behaviour in NC/Nga Mice: a Model of Atopic Dermatitis" Experimental Dermatology 2009;18: pp. 35-43.
Halliwell, R.E.W., "The immunopathogenesis of allergic skin diseases in dogs and cats," Dermatology, EJCAP—vol. 19—Issue 3 Dec. 2009, pp. 213-218.
Hobi, S. et al., "Clinical characteristics and causes of pruritus in cats: a multicentre study on feline hypersensitivity-associated dermatoses," Veterinary Dermatology, 22, pp. 406-413, 2011.
Hill, P.B., et al., "Pilot study of the effect of individualized homeopathy on the pruritus associated with atopic dermatitis in dogs," Veterinary Record, 2009 vol. 164, Issue 12, pp. 364-370.
Hillier, A. et al. "The ACVD Task Force on Canine Atopic Dermatitis (I): Incidence and Prevalence" Veterinary Immunology and Immunopathology 2001; 81: pp. 147-151.
Holm, P. et al., "Functional mapping and single chain construction of the anti-cytokeratin 8 monoclonal antibody TS1," Molecular Immunology 2007, 44(6), pp. 1075-1084.
Hvid, M. et al., "IL-25 in Atopic Dermatitis: A Possible Link between Inflammation and Skin Barrier Dysfunction?" Journal of Investigative Dermatology (2011) 131, pp. 150-157.
Janeway, et al., Immunology, $3^{rd}$ ed., 1997, Garland Publications, Inc., pp. 3:1-3:11.
Javens, C. et al., Abstract, "Oclacitinib inhibits canine IL-4 and IL-13-activated JAK-STAT pathways in canine DH82 cells," Veterinary Dermatology, Annual Conference of the North American Veterinary Dermatology Forum, 2018, pp. 1-2.
Kamayev, A.V. et al., Pruritus in atopic dermatitis in children: known mechanisms and possibilities for its long-term control, RMJ, No. 3, 2015, pp. 142-146, Non-English.
Le Saux, S. et al. "Molecular Dissection of Human Interleukin-31-mediated Signal Transduction Through Site-directed Mutagenesis" The Journal of Biological Chemistry Jan. 29, 2010;285(5), pp. 3470-3477.
Maeda, S. et al. "Expression of CC Chemokine Receptor 4 (CCR4) mRNA in Canine Atopic Skin Lesion" Veterinary Immunology Immunopathology 2002b; 90, pp. 145-154.
Maeda, S. et al., "Lesional expression of thymus and activation-regulated chemokine in canine atopic dermatitis," Veterinary Immunology and Immunopathology 88 (2002), pp. 79-87.
Maeda, S. et al. "Production of a Monoclonal Antibody to Canine Thymus and Activation-regulated Chemokine (TARC) and Detection of TARC in Lesional Skin from Dogs with Atopic Dermatitis" Veterinary Immunology Immunopathology 2005; 103, pp. 83-92.
Maeda, S. et al. "Expression Analysis of CCL27 and CCL28 mRNA in Lesional and Non-Lesional Skin of Dogs with Atopic Dermatitis" Journal Veterinary Medical Science 2008; 70, pp. 51-55.
Mariuzza, R.A., "The structural basis of antigen-antibody recognition", Ann. Rev. Biophys. Biophys Chem., 1987, vol. 16, pp. 139-159.
Marsella, R. et al., "Canine Models of Atopic Dermatitis: A Useful Tool with Untapped Potential," Journal of Investigative Dermatology (2009) 129, pp. 2351-2357.
Marsella, R. et al., "Current understanding of the pathophysiologic mechanisms of canine atopic dermatitis," Vet Med Today: Reference Point, JAVMA, vol. 241, No. 2, Jul. 15, 2012, pp. 194-207.
Marsella, R., "Equine Allergy Therapy, Update on the Treatment of Environmental, Insect Bite Hypersensitivity, and Food Allergies," Vet Clin. Equine, 29 (2013), pp. 551-557.
Mac Callum, R. M. et al., "Antibody-antigen Interactions: Contact Analysis and Binding Site Topography," J. Mol. Biol. 1996; 262, pp. 732-745.
Michels, G.M. et al., "A blinded, randomized, placebo-controlled, dose determination trial of lokivetmab (ZTS-00103289), a caninized, anti-canine IL-31 monoclonal antibody in client owned dogs with atopic dermatitis," Vet. Dermatol. 2016; 27, pp. 478-e129.
Mizuno, T. et al., "Molecular Cloning of Canine Interleukin-31 and its Expression in Various Tissues" Veterinary Immunology and Immunopathology 2009; 131, pp. 140-143.

(56) References Cited

OTHER PUBLICATIONS

Neis, M. M. et al., "Enhanced Expression Levels of IL-31 Correlate with IL-4 and IL-13 in Atopic and Allergic Contact Dermatitis" Journal Allergy Clinical Immunology 2006; 118, pp. 930-937.
Nuttall, T.J. et al., "T-helper 1, T-helper 2 and Immunosuppressive Cytokines in Canine Atopic Dermatitis" Veterinary Immunology Immunopathology 2002; 87, pp. 379-384.
O'Kennedy, R. et al., "A Review of Enzyme-Immunoassay and a Description of a Competitive Enzyme-Linked Immunosorbent Assay for the Detection of Immunoglobulin Concentrations," Biochemical Education 18(3) 1990, pp. 136-140.
Olivry, T. et al., "The ACVD Task Force on Canine Atopic Dermatitis: Forewords and Lexicon" Veterinary Immunology and Immunopathology 2001; 81: pp. 143-146.
Olivry, T. et al., "Animal Models of Atopic Dermatitis" 2001 supra; Marsella & Olivry Clinics in Dermatology 2003; 21: pp. 122-133.
Olivry, T. et al., "Treatment of canine atopic dermatitis: 2010 clinical practice guidelines from the International Task Force on Canine Atopic Dermatitis," Veterinary Dermatology, 21, pp. 233-248.
Pakula, A. et al., "Genetic Analysis of Protein Stability and Function," Annu. Rev. Genet, 1989; 23, pp. 289-310.
Paul, W., Fundamental Immunology, 3rd edition, 1993, Raven Press, New York, pp. 292-295.
Paul, William E., "Diversity and Constraints on the Sequence and Structure of CDR-H3," Fundamental Immunology, Sixth Edition Philadelphia: Lippincott Williams & Wilkins, 2008, pp. 135-136.
PCT International Search Report PCT/IP2012/053450 Mailed Jan. 30, 2014.
"Predicted: Felis catus interleukin 31 (IL31), mRNA", GenBank, Feb. 10, 2015 (Feb. 10, 2015), XP002770325, Retrieved from the Internet: URL:https://www.ncbi.nlm.nih.gov/nuccor.
Picco, F. et al., "A Prospective Study on Canine Atopic Dermatitis and Food-Induced Allergic Dermatitis in Switzerland," Veterinary Dermatology 2008; 19: pp. 150-155.
Product Information from ImmunoGlobe Antikorpertechnik GmbH, last modified Jan. 29, 2018.
Prost, C., "Feline atopic dermatitis: Clinical signs and diagnosis" Dermatology, EJCAP—vol. 19—Issue 3 Dec. 2009, pp. 223-229.
Raap, U. et al., "Correlation of IL-31 Serum Levels with Severity of Atopic Dermatitis" Journal Allergy Clinical Immunology 2008;122(2), pp. 421-423.
Raap, U. et al., "Increased Levels of Serum IL-31 in Chronic Spontaneous Urticaria" Experimental Dermatology 2010;19(5), pp. 464-466.
Ravens, P. A. et al., "Feline atopic dermatitis: a retrospective study of 45 cases (2001-2012)," Veterinary Dermatology, 2014; 25, 95-e28.
Riechmann, L. et al., "Reshaping human antibodies for therapy," 1988, Nature, vol. 332, pp. 323-327.
Roitt, I. et al., Immunology, Seventh Edition, Mosby, 2006, p. 67.
Rudikoff, et al., Proc. Natl. Acad. Sci. USA, Mar. 1982, vol. 79, pp. 1979-1983.
Scott, D.W. et al., "Treatment of Canine Atopic Dermatitis with a Commercial Homeopathic Remedy: A Single-Blinded, Placebo-Controlled Study," Canadian Veterinary Journal 2002; 43, pp. 601-603.
Jean-Pierre Y. Scheerlinck, "Functional and structural comparison of cytokines in different species," Veterinary Immunology and Immunopathology 72 (1999) pp. 39-44.
Schwartzman, et al. "Canine Reaginic Antibody" "Characterization of the Spontaneous Anti-Ragweed and Induced Anti-Dinitrophenyl Reaginic Antibodies of the Atopic Dog" Clin. Exp. Immunol. 1971; 9, pp. 549-569.
Singer, M. et al., Genes & Genomes, a Changing Perspective, University of Science Books, Mill Valley, California, 1991, pp. 31, 67 and 70.
Sonkoly, E. et al., "IL-31: A New Link Between T Cells and Pruritus in Atopic Skin Inflammation," Journal Allergy Clinical Immunology 2006; 117, pp. 411-417.
Soumelis, V. et al., "Human epithelial cells trigger dendritic cell-mediated allergic inflammation by producing TSLP," Nature Immunology, vol. 3, No. 7, Jul. 2002, pp. 673-680.
Sousa & Marsella "The ACVD Task Force on Canine Atopic Dermatitis (II): Genetic Factors" Veterinary Immunology and Immunopathology 2001; 81, pp. 153-157.
Spencer, G. "Analysis Sheds Light on Human Disease; Differences Among Canine Breeds," Researchers Publish Dog Genome Sequence—National Human Genome Research Institute, Dec. 7, 2005, pp. 1-2.
Strachan, D. P., "Family size, infection and atopy: the first decade of the "hygiene hypothesis"," Thorax 2000; 55 (Suppl 1): pp. S2-S10.
Tang, Liang "Molecular cloning of canine IL-13 receptor α chain (α1 and α2) cDNAs and detection of corresponding mRNAs in canine tissues", Veterinary Immunology and Immunopathology, 79 (2001), pp. 181-195.
Takaoka, A. et al., "Expression of IL-31 Gene Transcripts in NC/Nga Mice with Atopic Dermatitis" European Journal of Pharmacology 2005; 516, pp. 180-181.
Takaoka, A. et al., "Involvement of IL-31 on Scratching Behavior in NC/Nga Mice with Atopic-Like Dermatitis" Experimental Dermatology 2006; 15, pp. 161-167.
Terada, Y. et al., "Clinical comparison of human and canine atopic dermatitis using human diagnostic criteria (Japanese Dermatological Association, 2009): Proposal of provisional diagnostic criteria for canine atopic dermatitis," Journal of Dermatology 2011; 38: pp. 784-790.
TGR BioSciences, "AlphaScreen® SureFire® STAT3 (p-Tyr705) Assay Kits," Manual, pp. 1-8, Mar. 27, 2018.
Torres, S.M.F., editor, Advances in Veterinary Dermatology, vol. 7, Proceedings of the Seventh World Congress of Veterinary Dermatology Vancouver, Canada, Jul. 24-28, 2012.
Vajdos, F. F. et al., "Comprehensive Functional Maps of the Antigen-binding Site of an Anti-Erb82 Antibody Obtained with Shotgun Scanning Mutagenesis," J. Mol. Biol. 2002, 320(2), pp. 415-428.
Wai K. IP et al., "Interleukin-31 Induces Cytokine and Chemokine Production from Human Bronchial Epithelial Cells Through Activation of Mitogen-activated Protein Kinase Signalling Pathways: Implications for the Allergic Response" Immunology, 2007; 122, pp. 532-541.
White, S.D., "Advances in Equine Atopic Dermatitis, Serologic and Intradermal Allergy Testing," Clin. Tech. Equine Practice, 4, 2005, pp. 311-313.
Yagi, Y. et al., "Interleukin-31 Stimulates Production of Inflammatory Mediators from Human Colonic Subepithelial Myofibroblasts" International Journal of Molecular Medicine 2007; 19(6), pp. 941-946.
Zhang, Q. et al., "Structures and biological functions of IL-31 and IL-31 receptors," Cytokine Growth Factor Rev. 2008; 19(5-6): pp. 347-356.
Zoetis Press Release, Dec. 21, 2016—Zoetis Receives USDA License for Cytopoint™.
Zoetis Press Release, Apr. 26, 2017—Zoetis Received European Commission Marketing Authorization for Cytopoint® (lokivetmab).
Zucker, K. et al., "Cloning of the cDNA for Canine Interferon-γ," Journal of Interferon Research, 12, pp. 191-194 (1992).
Russian Office Action, Application No. 2020129449/10(052907), dated Jun. 22, 2021, Non-English.
Russian Office Action, Application No. 2020129449/10(052907), dated Jun. 22, 2021, English Translation.
ROSPATENT Search Report, Application No. 2020129449/10(052907), Date of actual completion of the search: Jun. 22, 2021, Non-English.
ROSPATENT Search Report, Application No. 2020129449/10(052907), Date of actual completion of the search: Jun. 22, 2021, English Translation.

| | | |
|---|---|---|
| SEQ_ID_NO_165_Canine_iL31 | 1 MLSHTQPSRFALFLLCSMETLLSSHMAPTHQLPP.SDVRKITLELQPLSRQLLEDTQ | 56 |
| SEQ_ID_NO_167_Feline_iL31_wildtype | 1 MLSHAPPARFALFLLCCMETLLSSHMAPDAHRLQP.SDIRKITLELRPMSKQLLQDYL | 56 |
| SEQ_ID_NO_165_Equine_iL31 | 1 .......MDHHSCILFLVATATSVHSQFIYQLQP.KEIQAIIVELQHLSKKLLEDIL | 49 |
| SEQ_ID_NO_161_Human_iL31 | 1 MASHSQPSTSVLFLFCCLQMSLASHTLPVRLLRPSDDVQKIVEELQSLSRMLLKDVE | 57 |
| SEQ_ID_NO_165_Canine_iL31 | 57 RKETSVPESNRTLLLLTLSDSQPP.RLNSSAILPYFRA.RPLSDKNIIDKIIEQLQK | 112 |
| SEQ_ID_NO_167_Feline_iL31_wildtype | 57 KKEIDLPESNHSSLPCLSSDSQLF.HINGSAILPYFRA.RPLSDKRTIDKIIEQLQK | 112 |
| SEQ_ID_NO_165_Equine_iL31 | 50 NKEKEVQKFDSDLPSCFTSDSQAPSHINSSAILPYFKA.SPSLNNDKSLYIEQLQK | 106 |
| SEQ_ID_NO_161_Human_iL31 | 58 .EEKSVLVSQNTTLPCLSPDAQPPNIHSPAIRAYLKTIRQLDKKSVIDEIIEHLDK | 113 |
| SEQ_ID_NO_165_Canine_iL31 | 113 LKFQHEPETEISVPADTFECKSFILTLQQFSACLESVFKSLNSQPQ...... | 159 |
| SEQ_ID_NO_167_Feline_iL31_wildtype | 113 LKFQREFEAKVSMPADNFERKNFILAVLQQFSACLEHVLQSLNSSPQHHHHHH | 165 |
| SEQ_ID_NO_165_Equine_iL31 | 107 LNFQNAPETEVSMFTDRFERKPFILTLRMFSNCLEHRAQHHHHHH...... | 152 |
| SEQ_ID_NO_161_Human_iL31 | 114 LIFQDAFETNISVPTDTHECKRFILTISQQFSECMDLALKSLTSGAQQAIT.. | 164 |

FIG. 1A

| | Percent Identity | | |
|---|---|---|---|
| | Feline_IL31 | Horse_IL31 | Human_IL31 |
| Canine_IL31 | 74 | 57 | 56 |
| Feline_IL31 | | 56 | 49 |
| Horse_IL31 | | | 48 |

FIG. 1B

Antibodies with CDRs of Mouse Origin

| | Antibody | VH | VL | Affinity to Feline IL-31 ka (M⁻¹s⁻¹) | kd (s⁻¹) | KD (M) | Affinity to Canine IL-31 ka (M⁻¹s⁻¹) | kd (s⁻¹) | KD (M) |
|---|---|---|---|---|---|---|---|---|---|
| A | HBS-EP | | | no binding | | | no binding | | |
| | MU-15H05 | MU-15H05-VH | MU-15H05-VL | 4.84E+04 | 1.69E-05 | 3.48E-10 | 1.35E+05 | 6.56E-07 | 4.87E-12 |
| | MU-11E12 | MU-11E12-VH | MU-11E12-VL | 1.67E+05 | 1.23E-04 | 7.38E-10 | 6.29E+05 | 4.80E-07 | 7.63E-13 |
| | Mouse:Canine 15H05 Chimera | MU-15E05-VH | MU-15H05-VL | | | | | | |
| | Mouse:Feline 15H05 Chimera | MU-15E05-VH | MU-15H05-VL | 1.65E+05 | 7.29E-05 | 6.99E-09 | 1.26E+04 | 1.62E-07 | 1.29E-11 |
| | Mouse:Canine 11E12 Chimera | MU-11E12-VH | MU-11E12-VL | 4.37E+05 | 1.08E-04 | 2.48E-10 | 7.93E+05 | 6.55E-07 | 8.26E-13 |
| | Mouse:Feline 11E12 Chimera | MU-11E12-VH | MU-11E12-VL | 3.88E+05 | 5.06E-05 | 1.30E-10 | 6.84E+05 | 8.70E-08 | 1.27E-13 |
| B | Feline 11E12 1.1 | FEL-11E12-VH1 | FEL-11E12-VL1 | 2.00E+04 | 4.44E-04 | 2.22E-08 | 1.85E+05 | 1.41E-04 | 7.64E-10 |
| | Feline 11E12 1.2 | FEL-11E12-VH1 | FEL-11E12-VL2 | no binding | | | no binding | | |
| | Feline_11E12 1.1_FW2 | FEL-11E12-VH1 | FEL-11E12-VL1_FW2 | 8.52E+05 | 6.39E-04 | 7.50E-10 | 4.52E+04 | 3.18E-04 | 7.02E-09 |
| | Feline 11E12 1.1 K46Q | FEL-11E12-VH1 | FEL-11E12-VL1_K46Q | 1.15E+04 | 1.45E-04 | 1.26E-08 | 4.64E+04 | 8.85E-05 | 1.91E-09 |
| C | Feline 15H05 1.1 | FEL-15H05-VH1 | FEL-15H05-VL1 | 9.71E+04 | 1.31E-03 | 1.35E-08 | 2.70E+04 | 1.36E-07 | 5.04E-12 |
| | Feline 15H05 1.2 | FEL-15H05-VH1 | FEL-15H05-VL2 | 1.41E+04 | 1.47E-03 | 1.04E-07 | 3.30E+04 | 1.15E-04 | 3.48E-09 |
| | Feline 15H05 1.3 | FEL-15H05-VH1 | FEL-15H05-VL3 | 3.80E+04 | 3.28E-03 | 8.64E-08 | 2.97E+04 | 1.90E-04 | 6.38E-09 |
| | Feline 15H05 2.1 | FEL-15H05-VH2 | FEL-15H05-VL1 | 2.08E+05 | 4.65E-03 | 2.23E-08 | 5.25E+05 | 8.66E-04 | 1.65E-09 |
| | Feline 15H05 2.2 | FEL-15H05-VH2 | FEL-15H05-VL2 | 9.05E+05 | 1.95E-03 | 2.15E-09 | 2.77E+04 | 1.09E-05 | 3.93E-10 |
| | Feline 15H05 2.3 | FEL-15H05-VH2 | FEL-15H05-VL3 | 3.41E+05 | 5.35E-04 | 1.57E-09 | no binding | | |
| | Feline 15H05 3.1 | FEL-15H05-VH3 | FEL-15H05-VL1 | 4.47E+05 | 1.66E-03 | 3.71E-08 | 2.65E+04 | 2.11E-05 | 7.95E-10 |
| | Feline 15H05 3.2 | FEL-15H05-VH3 | FEL-15H05-VL2 | 1.32E+05 | 1.66E-03 | 1.26E-08 | 2.97E+04 | 6.04E-06 | 2.04E-10 |
| | Feline 15H05 3.3 | FEL-15H05-VH3 | FEL-15H05-VL3 | 7.63E+04 | 8.86E-04 | 1.16E-08 | no binding | | |
| | Feline 15H05 VH1 mouse VL | FEL-15H05-VH1 | MU-15H05-VL | 1.31E+05 | 2.20E-05 | 1.68E-10 | 1.08E+05 | 2.66E-07 | 2.46E-12 |
| | Feline 15H05 VH2 mouse VL | FEL-15H05-VH2 | MU-15H05-VL | 3.40E+04 | 5.47E-05 | 1.61E-09 | 1.71E+05 | 3.79E-04 | 2.22E-09 |
| | Feline 15H05 VH3 mouse VL | FEL-15H05-VH3 | MU-15H05-VL | 8.89E+04 | 1.57E-05 | 1.77E-10 | 1.00E+05 | 2.64E-07 | 2.64E-12 |
| | Feline 15H05 1.1 FW1 | FEL-15H05-VH1 | FEL-15H05-VL1_FW1 | 5.06E+03 | 2.86E-03 | 5.64E-07 | 1.92E+04 | 1.56E-02 | 8.13E-07 |
| | Feline 15H05 1.1 FW2 | FEL-15H05-VH1 | FEL-15H05-VL1_FW2 | 3.83E+05 | 2.49E-05 | 6.50E-11 | 3.84E+05 | 1.66E-07 | 4.31E-13 |
| | Feline 15H05 1.1 FW3 | FEL-15H05-VH1 | FEL-15H05-VL1_FW3 | 2.14E+05 | 1.21E-05 | 5.64E-11 | 3.00E+05 | 3.91E-07 | 1.30E-10 |
| | Feline 15H05 1.1 FW1_2 | FEL-15H05-VH1 | FEL-15H05-VL1_FW1_FW2 | 7.56E+03 | 6.70E-06 | 8.87E-10 | 6.91E+03 | 3.82E-06 | 2.63E-10 |
| | Feline 15H05 1.1 FW2_3 | FEL-15H05-VH1 | FEL-15H05-VL1_FW2_FW3 | 9.49E+05 | 1.16E-07 | 1.23E-07 | 9.05E+03 | 1.93E-03 | 2.14E-07 |
| | Feline 15H05 1.1 FW1_3 | FEL-15H05-VH1 | FEL-15H05-VL1_FW1_FW3 | 4.48E+05 | 3.02E-05 | 6.74E-11 | | | |
| | Feline 15H05 1.1 V43I | FEL-15H05-VH1 | FEL-15H05-VL1_FW2_V43I | 1.63E-03 | 1.10E-02 | 6.77E-06 | | | |
| | Feline 15H05 1.1 L46V | FEL-15H05-VH1 | FEL-15H05-VL1_FW2_L46V | 2.94E+04 | 4.01E-04 | 1.36E-08 | | | |
| | Feline 15H05 1.1 Y49N | FEL-15H05-VH1 | FEL-15H05-VL1_FW2_Y49N | 3.55E+04 | 8.11E-04 | 2.28E-08 | | | |
| | Feline 15H05 1.1 K42N | FEL-15H05-VH1 | FEL-15H05-VL1_FW2_K42N | 2.40E+04 | 9.50E-04 | 3.95E-08 | | | |
| | Feline 15H05 1.1 K42N V43I | FEL-15H05-VH1 | FEL-15H05-VL1_FW2_K42N_V43I | 2.34E+05 | 2.20E-03 | 9.42E-09 | 6.59E+03 | 2.88E-08 | 4.36E-12 |
| D | ZTS-927 | FEL-15H05-VH1 | FEL-15H05-VL1_FW2 | 3.74E+04 | 2.30E-05 | 6.14E-10 | | | |
| | ZTS-361 | FEL-15H05-VH1 | FEL-15H05-VL1_FW2 | 4.60E+04 | 2.18E-05 | 4.74E-10 | | | |

FIG. 2

Potency of Antibodies with CDRs of Mouse Origin

| | IC$_{50}$ (μg/ml) | | | |
|---|---|---|---|---|
| | Canine DH82 cells | | Feline FCWF4 cells | |
| Antibody | Canine IL-31 | Feline IL-31 | Canine IL-31 | Feline IL-31 |
| Mouse | | | | |
| 11E12 | Not Tested | 2.47 | Not Tested | 2.01 |
| 15H05 | 11.17 | 2.7 | 25.68 | 4.26 |
| Chimera | | | | |
| Mouse:Feline 11E12 | Not Tested | 4.4 | Not Tested | 3.45 |
| Mouse:Canine 11E12 | Not Tested | Not Tested | Not Tested | 1.15 |
| Mouse:Feline 15H05 | 28.61 | 5.59 | Not Tested | 3.25 |
| Mouse:Canine 15H05 | 12.69 | 0.71 | Not Tested | 3.11 |
| Felinized | | | | |
| 11E12 1.1 | Not Tested | 28.98 | Not Tested | 4.47 |
| 11E12 1.2 | Not Tested | > 100 | Not Tested | > 100 |
| 11E12 1.1 FW2 | Not Tested | 5.66 | Not Tested | 4.38 |
| ZTS-927 | 23.18 | 1.57 | 39.57 | 5.26 |
| ZTS-361 | 22.99 | 2.01 | 38.80 | 4.89 |

Not Tested

Binding of Antibodies with CDRs of Dog Origin

| | SEQ ID NO: | | Binding (ELISA OD) | | Binding (Biacore) | | | | |
|---|---|---|---|---|---|---|---|---|---|
| | | | 157 | 163 | 155 | 157 | 165 | 181 | 163 | 161 |
| | | | Feline IL-31 | Feline IL-31 15H05 Mutant | Canine | Feline IL-31 wildtype | Equine | Human | Feline IL-31 15H05 Mutant | Feline IL-31 11E12 Mutant |
| Antibody | VH | VL | Feline IL-31 wildtype | Feline IL-31 15H05 Mutant | | | | | | |
| ZIL1 | 75 | 77 | 1.89 | 0.92 | - | + | + | - | - | +/- |
| ZIL8 | 79 | 81 | 0.57 | 0.08 | - | + | - | - | - | - |
| ZIL9 | 83 | 85 | 1.80 | 0.73 | - | + | + | - | - | + |
| ZIL11 | 87 | 89 | 1.32 | 0.33 | +/- | + | - | - | - | + |
| ZIL69 | 91 | 93 | 1.48 | 0.92 | + | + | - | - | - | + |
| ZIL94 | 95 | 97 | 1.67 | 1.30 | - | + | - | - | + | + |
| ZIL154 | 99 | 101 | 1.62 | 1.38 | + | + | - | - | + | - |
| ZIL159 | 103 | 105 | 1.60 | 1.31 | + | + | - | - | +/- | + |
| ZIL171 | 107 | 109 | 1.42 | 0.93 | - | + | + | - | - | - |
| Controls | | | | | | | | | | |
| Mouse 11E12 | 71 | 73 | 1.15 | 1.33 | + | + | - | - | + | - |
| Mouse 15H05 | 67 | 69 | 1.94 | 0.05 | + | + | + | - | - | + |

| SEQ_ID_NO_157_Feline_IL31_wildtype | 1 | MLSHAGPARFALFLLCCMETLLPSHMAPAHRLQPSDIRKIILELR | 45 |
| SEQ_ID_NO_161_Feline_IL31_11E12_mutant | 1 | MLSHAGPARFALFLLCCMETLLPSHMAPAHRLQPSDIRKIILELR | 45 |
| SEQ_ID_NO_163_Feline_IL31_15H05_mutant | 1 | MLSHAGPARFALFLLCCMETLLPSHMAPAHRLQPSDIRKIILELR | 45 |

| SEQ_ID_NO_157_Feline_IL31_wildtype | 46 | PMSKGLLQDYLKKEIGLPESNHSSLPCLSSDSQLPHINQSAILPY | 90 |
| SEQ_ID_NO_161_Feline_IL31_11E12_mutant | 46 | PMSKGLLQDYLKKEIGLPESNHSSLPCLSSDSQLPHINQSAILPY | 90 |
| SEQ_ID_NO_163_Feline_IL31_15H05_mutant | 46 | PMSKGLLQDYLKKEIQLPESNHSSLPCLSSDSQLPHINSSAILPY | 90 |

| SEQ_ID_NO_157_Feline_IL31_wildtype | 91 | FRAIRPLSDKNTIDKIIEQLDKLKFQREPEARVSMPADNFERKNF | 135 |
| SEQ_ID_NO_161_Feline_IL31_11E12_mutant | 91 | FRAIRPLSDKNTIAVIAEQLDKLKFQREPEARVSMPADNFERKNF | 135 |
| SEQ_ID_NO_163_Feline_IL31_15H05_mutant | 91 | FRAIRPLSDKNTIDKIIEQLDKLKFQREPEARVSMAAANFERKNF | 135 |

| SEQ_ID_NO_157_Feline_IL31_wildtype | 136 | ILAVLQQFSACLEHVLQSLNSGPQHHHHHH | 165 |
| SEQ_ID_NO_161_Feline_IL31_11E12_mutant | 136 | ILAVLQQFSACLEHVLQSLNSGPQHHHHHH | 165 |
| SEQ_ID_NO_163_Feline_IL31_15H05_mutant | 136 | ILAVLQQFSACLEHVLQSLNSGPQHHHHHH | 165 |

FIG. 6A

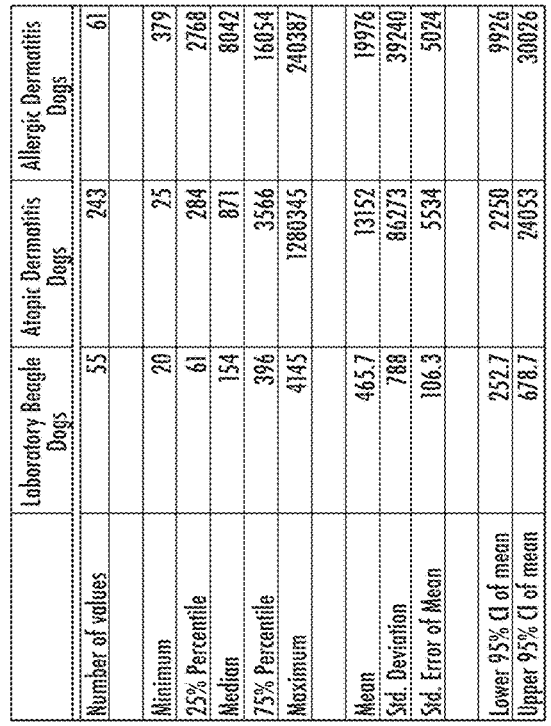
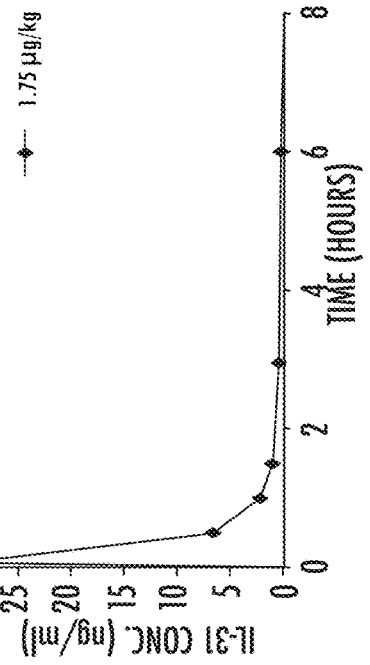
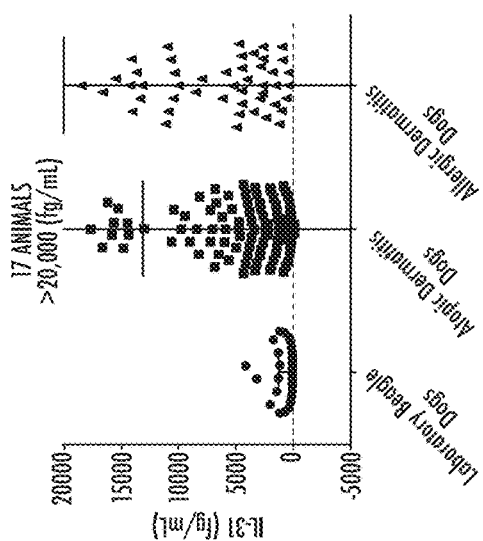
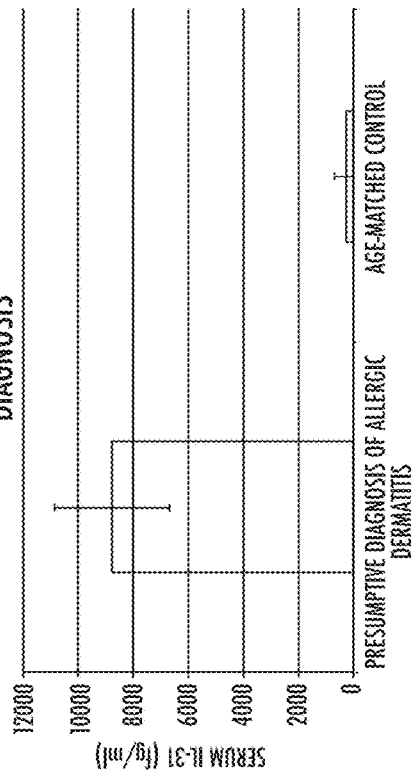
FIG. 11A
FIG. 11B
FIG. 11C

Non-Reducing SDS PAGE of Felinized anti IL-31 ZTS-361 CHO Derived IgG from Individual Stable Clones

| Lane # | ZTS-361 Clone ID | %Monomer | %Monomer |
|---|---|---|---|
| 1 | Ref. Std. | 95.6 | 4.4 |
| 2 | 10 | 82.0 | 17.1 |
| 3 | 12 | 81.3 | 18.7 |
| 4 | 20 | 81.4 | 18.6 |
| 5 | 22 | 85.9 | 14.1 |
| 6 | 34 | 86.0 | 14.0 |
| 7 | 58 | 80.2 | 19.8 |
| 8 | Ref. Std. | 97.9 | 2.1 |
| 9 | 63 | 81.8 | 18.2 |
| 10 | 66 | 80.5 | 19.5 |

Non-Reducing CGE of Felinized anti IL-31 ZTS-361 CHO Derived IgG from Individual Stable Clones

| ZTS-361 Clone ID | % Monomer | % Fragments |
|---|---|---|
| 10 | 85.3 | 14.7 |
| 12 | 87.4 | 12.6 |
| 20 | 86.6 | 13.4 |
| 22 | 85.8 | 14.2 |
| 34 | 86.4 | 13.6 |
| 58 | 85.2 | 14.8 |
| 63 | 87.5 | 12.5 |
| 66 | 86.5 | 13.5 |
| Ref. Std. | 96.4 | 3.6 |
| Average | 86.3 | 13.7 |

C-Terminal Amino Acids Residues of Several Ig Kappa Light Chain Constant Domains

| | | | | | | | | Percent Kappa Light Chain Usage | |
|---|---|---|---|---|---|---|---|---|---|
| Canine LC Kappa wt<br>SEQ ID NO:194 | S<br>AGC | E<br>GAG | C<br>TGT | Q<br>CAG | R<br>AGA | V<br>GTG | D<br>GAC | *<br>TAA | 9% | Restricted |
| Feline LC Kappa G-<br>SEQ ID NO:175 | S<br>AGC | E<br>GAG | C<br>TGT | Q<br>CAG | R<br>AGA | E<br>GAG | *<br>TAG | | 8% | |
| Pig LC Kappa G-<br>SEQ ID NO:196 | N<br>AAC | E<br>GAG | C<br>TGT | E<br>GAG | A<br>GCT | *<br>TAG | | | ~50% | Allowed |
| Mink LC Kappa<br>SEQ ID NO:198 | S<br>AGC | E<br>GAG | C<br>TGC | Q<br>CAA | *<br>TGA | | | | 46% | |
| Human LC Kappa<br>SEQ ID NO:192 | N<br>AAC | R<br>AGG | G<br>GGA | E<br>GAG | C<br>TGT | *<br>TAG | | | ~50% | |
| Mouse LC Kappa<br>SEQ ID NO:190 | N<br>AAC | R<br>AGG | N<br>AAT | E<br>GAG | C<br>TGT | *<br>TAG | | | 95% | Preferred |

Cysteine involved with inter-chain disulphide bond with IgG heavy chain

Note - Underlined nucleotides denote positions where codon is one nucleotide different from a stop codon

FIG. 15

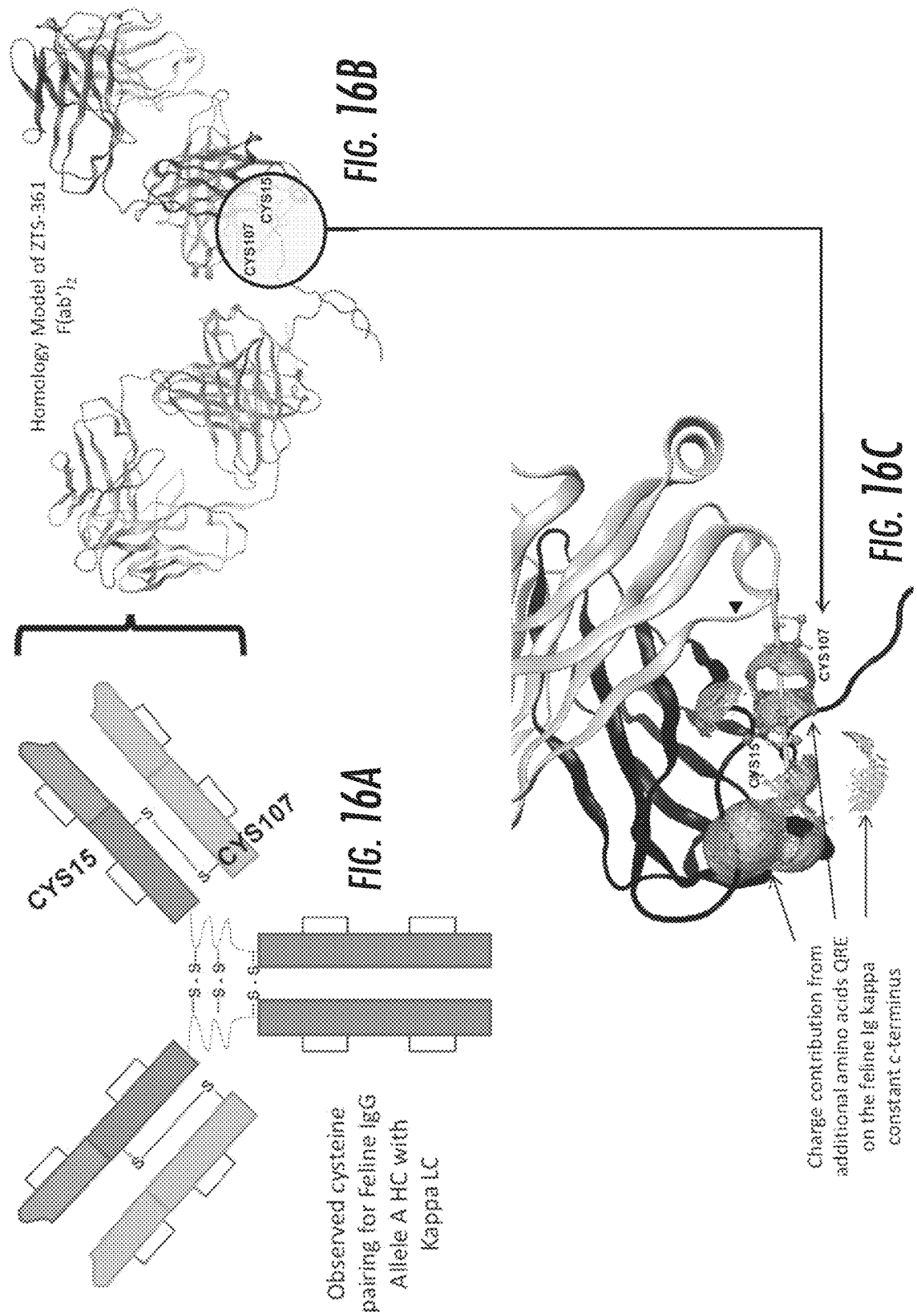

FIG. 17A

| Antibody | Description | VH | VL | HC | LC |
|---|---|---|---|---|---|
| ZTS-361 | Stable CHO cell line | 121 | 135 | 173 | 175 |
| ZTS-1505 | Stable CHO cell line | 121 | 135 | 173 | 186 |

SEQ ID NO

FIG. 17B

Non-Reducing CGE of Felinized anti IL-31 ZTS-1505 CHO Derived IgG from Individual Stable Clones

| ZTS-1505 Clone ID | % Monomer | % Fragments |
|---|---|---|
| 11 | 90 | 10 |
| 17 | 91 | 9 |
| 18 | 91.5 | 8.5 |
| 24 | 89.7 | 10.3 |
| 26 | 90.5 | 9.5 |
| 31 | 90.3 | 9.7 |
| 37 | 87.4 | 12.6 |
| 75 | 91.2 | 8.8 |
| 77 | 87.2 | 12.8 |
| 80 | 90.6 | 9.4 |
| 83 | 90.3 | 9.7 |
| 94 | 91.6 | 8.4 |
| 96 | 91.4 | 8.6 |
| 99 | 91.6 | 8.4 |
| 113 | 90.6 | 9.4 |
| 132 | 90.3 | 9.7 |
| 133 | 90.9 | 9.1 |
| 137 | 89 | 11 |
| 143 | 88.6 | 11.4 |
| 152 | 89.2 | 10.8 |
| 179 | 90.1 | 9.9 |
| 182 | 89.8 | 10.2 |
| 190 | 89.2 | 10.8 |
| Ref. Std. | 95.6 | 4.4 |
| Average | 90.3 | 9.7 |

FIG. 17C

Antibody Yield and % Monomer by NR-CGE Comparing an Individual Stable CHO Clones of ZTS-361 and ZTS-1505 in Different Culture Conditions

| Antibody | Culture Condition | Percent Viability (Day 14) | Titer (g/L) | % Monomer NR-CGE |
|---|---|---|---|---|
| ZTS-361 | A | 78.30 | 0.6 | 84.00 |
| ZTS-1505 | A | 74.30 | 1.4 | 89.90 |
| ZTS-361 | B | 85.20 | 1 | 81.70 |
| ZTS-1505 | B | 75.70 | 3 | 89.00 |
| ZTS-361 | C | 69.90 | 0.6 | 78.90 |
| ZTS-1505 | C | 75.50 | 2.5 | 82.90 |
| ZTS-361 | D | 78.50 | 0.8 | 89.90 |
| ZTS-1505 | D | 74.70 | 2.9 | 93.40 |
| ZTS-361 | E | 82.30 | 0.9 | 87.70 |
| ZTS-1505 | E | 77.90 | 3.3 | 95.50 |
| ZTS-361 | F | 70.80 | 0.6 | 89.70 |
| ZTS-1505 | F | 76.30 | 2.5 | 91.90 |
| ZTS-361 | G | 71.10 | 0.6 | 85.60 |
| ZTS-1505 | G | 76.70 | 2.5 | 91.60 |

| Antibody | | | | |
|---|---|---|---|---|
| ZTS-361 | | 76.59 | 0.73 | 85.36 |
| ZTS-1505 | | 75.87 | 2.59 | 90.60 |

ClustalW Alignment of the Shared Variable Heavy Chains from anti IL-31 Antibodies ZTS-361 and ZTS-1505 to the Shared Variable Heavy Chains of anti NGF ZTS-768 and ZTS-943

ClustalW Alignment of the Shared Variable Light Chains from anti IL-31 Antibodies ZTS-361 and ZTS-1505 to the Shared Variable Light Chains of anti NGF ZTS-768 and ZTS-943

NR CGE Results from Anti IL-31 and Anti NGF Antibodies Purified from Stable CHO Pools Comparing the Wildtype Feline Kappa Light Chain Constant to the Modified Kappa Constant C-terminus

| mAb ID | Target | Description | SEQ ID NO VH | VL | HC | LC | % Monomer | % HHL | % HL | % H | % L |
|---|---|---|---|---|---|---|---|---|---|---|---|
| ZTS-361 | Feline IL-31 | wildtype light chain | 121 | 135 | 173 | 175 | 80.74 | 8.71 | 0.37 | 0.16 | 1.21 |
| ZTS-1505 | Feline IL-31 | truncated light chain | 121 | 135 | 173 | 186 | 89.17 | 5.90 | 0.28 | 0.16 | 0.86 |
| ZTS-768 | Feline NGF | wildtype light chain | 220 | 222 | 171 | 175 | 80.81 | 12.33 | 0.16 | 0.13 | 1.96 |
| ZTS-943 | Feline NGF | truncated light chain | 224 | 226 | 171 | 186 | 88.59 | 5.98 | 0.24 | 0.00 | 0.92 |

HHL = Heavy Heavy Light
HL = Heavy Light
H = Heavy
L = Light

Alanine Substitution Mutagenesis of ZTS-1505 Heavy Chain CDRs Comparing Binding and IL-31 Mediated pSAT Signaling Inhibition to the Wildtype Antibody

| Sample ID | Heavy Chain | Light Chain | Binding Similarity score | % Inhibition Relative to Parent | CDR Residue |
|---|---|---|---|---|---|
| A04 | SEQ ID NO 121 | SEQ ID NO 135 | 96.96 | 100.0 | |
| A30 | SEQ ID NO 121 T30A | SEQ ID NO 135 | 78.96 | 28.4 | |
| A32 | SEQ ID NO 121 S31A | SEQ ID NO 135 | 39.25 | 40.3 | |
| A33 | SEQ ID NO 121 Y32A | SEQ ID NO 135 | 31.83 | 42.2 | CDRH1 |
| A34 | SEQ ID NO 121 T33A | SEQ ID NO 135 | 3.37 | 0.0 | |
| A35 | SEQ ID NO 121 I34A | SEQ ID NO 135 | 97.52 | 92.5 | |
| A36 | SEQ ID NO 121 H35A | SEQ ID NO 135 | 10.42 | 25.2 | |
| A37 | SEQ ID NO 121 N50A | SEQ ID NO 135 | 46.13 | 52.1 | |
| A38 | SEQ ID NO 121 I51A | SEQ ID NO 135 | 55.15 | 42.2 | |
| A39 | SEQ ID NO 121 N52A | SEQ ID NO 135 | 100 | 25.1 | |
| A40 | SEQ ID NO 121 P53A | SEQ ID NO 135 | 2.7 | 5.7 | |
| A42 | SEQ ID NO 121 T54A | SEQ ID NO 135 | 44.91 | 83.6 | |
| A43 | SEQ ID NO 121 S55A | SEQ ID NO 135 | 100 | 47.4 | |
| A44 | SEQ ID NO 121 G56A | SEQ ID NO 135 | 55.77 | 36.9 | CDRH2 |
| A45 | SEQ ID NO 121 Y57A | SEQ ID NO 135 | 31.85 | 22.8 | |
| A46 | SEQ ID NO 121 Y58A | SEQ ID NO 135 | 66.14 | 30.0 | |
| A47 | SEQ ID NO 121 E59A | SEQ ID NO 135 | 100 | 18.0 | |
| A48 | SEQ ID NO 121 N60A | SEQ ID NO 135 | 70.22 | 47.3 | |
| A49 | SEQ ID NO 121 N61A | SEQ ID NO 135 | 37.03 | 46.6 | |
| A50 | SEQ ID NO 121 Q62A | SEQ ID NO 135 | 58.62 | 55.5 | |
| A52 | SEQ ID NO 121 W99A | SEQ ID NO 135 | 2.4 | -2.1 | |
| A53 | SEQ ID NO 121 G100A | SEQ ID NO 135 | 11.02 | 1.1 | |
| A54 | SEQ ID NO 121 F101A | SEQ ID NO 135 | 17.64 | -1.0 | |
| A55 | SEQ ID NO 121 K102A | SEQ ID NO 135 | 12.64 | 66.8 | |
| A56 | SEQ ID NO 121 Y103A | SEQ ID NO 135 | 10.24 | 22.2 | |
| A57 | SEQ ID NO 121 D104A | SEQ ID NO 135 | 38.9 | 85.4 | |
| A58 | SEQ ID NO 121 G105A | SEQ ID NO 135 | 16.73 | 15.3 | CDRH3 |
| A59 | SEQ ID NO 121 E106A | SEQ ID NO 135 | 35.5 | 3.5 | |
| A60 | SEQ ID NO 121 W107A | SEQ ID NO 135 | 2.4 | -8.7 | |
| A62 | SEQ ID NO 121 S108A | SEQ ID NO 135 | 46.15 | 22.6 | |
| A63 | SEQ ID NO 121 F109A | SEQ ID NO 135 | 2.9 | -6.0 | |
| A64 | SEQ ID NO 121 D110A | SEQ ID NO 135 | 2.7 | 6.9 | |
| A65 | SEQ ID NO 121 V111A | SEQ ID NO 135 | 50.45 | 26.8 | |

*FIG. 23*

Alanine Substitution Mutagenesis of ZTS-1505 Light Chain CDRs Comparing Binding and IL-31 Mediated pSAT Signaling Inhibition to the Wildtype Antibody

| Sample ID | Heavy Chain | Light Chain | Binding Similarity score | % Inhibition Relative to Parent | CDR Residue |
|---|---|---|---|---|---|
| A04 | SEQ ID NO 121 | SEQ ID NO 135 | 96.96 | 100.0 | |
| A05 | SEQ ID NO 121 | SEQ ID NO 135 R24A | 25.64 | 0.0 | |
| A06 | SEQ ID NO 121 | SEQ ID NO 135 S26A | 89.7 | 40.0 | |
| A07 | SEQ ID NO 121 | SEQ ID NO 135 Q27A | 74.43 | 93.6 | |
| A03 | SEQ ID NO 121 | SEQ ID NO 135 G28A | 58.03 | 52.9 | CDRL1 |
| A09 | SEQ ID NO 121 | SEQ ID NO 135 I29A | 100 | 28.0 | |
| A10 | SEQ ID NO 121 | SEQ ID NO 135 S30A | 63.35 | 26.0 | |
| A12 | SEQ ID NO 121 | SEQ ID NO 135 I31A | 25.73 | 19.3 | |
| A13 | SEQ ID NO 121 | SEQ ID NO 135 W32A | 2.4 | 4.4 | |
| A14 | SEQ ID NO 121 | SEQ ID NO 135 N49A | 8.4 | -5.4 | |
| A15 | SEQ ID NO 121 | SEQ ID NO 135 K50A | 11.6 | 34.1 | |
| A16 | SEQ ID NO 121 | SEQ ID NO 135 S52A | 57.95 | 69.3 | |
| A17 | SEQ ID NO 121 | SEQ ID NO 135 N53A | 11.22 | -19.1 | CDRL2 |
| A18 | SEQ ID NO 121 | SEQ ID NO 135 L54A | 100 | 49.4 | |
| A19 | SEQ ID NO 121 | SEQ ID NO 135 H55A | 14.92 | -15.0 | |
| A20 | SEQ ID NO 121 | SEQ ID NO 135 I56A | 31.33 | 29.0 | |
| A22 | SEQ ID NO 121 | SEQ ID NO 135 S91A | 8.34 | -4.3 | |
| A23 | SEQ ID NO 121 | SEQ ID NO 135 Q92A | 64.84 | 29.2 | |
| A24 | SEQ ID NO 121 | SEQ ID NO 135 T93A | 100 | 56.7 | |
| A25 | SEQ ID NO 121 | SEQ ID NO 135 Y94A | 4.4 | 1.3 | CDRL3 |
| A26 | SEQ ID NO 121 | SEQ ID NO 135 P95A | 20.86 | 43.7 | |
| A27 | SEQ ID NO 121 | SEQ ID NO 135 L96A | 11.74 | 7.2 | |
| A28 | SEQ ID NO 121 | SEQ ID NO 135 T97A | 42.16 | 59.7 | |
| A29 | SEQ ID NO 121 | SEQ ID NO 135 F98A | 66.68 | 59.3 | |

FIG. 24

Binding of two Felinized forms of the ZIL8 antibody to Feline IL-31 using Biacore

| Sample Name | SEQ ID NO | | | | Biacore Binding to Feline IL-31 (SEQ ID NO 157) | | |
|---|---|---|---|---|---|---|---|
| | VH | VL | HC | LC | ka (M-1 s-1) | kd (s-1) | KD (M) |
| ZTS-5864 | 228 | 230 | 173 | 236 | 1.08E+05 | 6.16E+05 | 5.71E-10 |
| ZTS-5865 | 232 | 234 | 173 | 236 | 7.62E+04 | 1.61E+04 | 2.12E-09 |

Cellular Potency Data with Felinized Antibodies Speciated from ZIL8

SEQUENCE LISTING

<160> NUMBER OF SEQ ID NOS: 237

<210> SEQ ID NO 1
<211> LENGTH: 5

-continued

```
<212> TYPE: PRT
<213> ORGANISM: Mus musculus

<400> SEQUENCE: 1

Ser Tyr Thr Ile His
1               5

<210> SEQ ID NO 2
<211> LENGTH: 17
<212> TYPE: PRT
<213> ORGANISM: Mus musculus

<400> SEQUENCE: 2

Asn Ile Asn Pro Thr Ser Gly Tyr Thr Glu Asn Asn Gln Arg Phe Lys
1               5                   10                  15
Asp

<210> SEQ ID NO 3
<211> LENGTH: 13
<212> TYPE: PRT
<213> ORGANISM: Mus musculus

<400> SEQUENCE: 3

Trp Gly Phe Lys Tyr Asp Gly Glu Trp Ser Phe Asp Val
1               5                   10

<210> SEQ ID NO 4
<211> LENGTH: 11
<212> TYPE: PRT
<213> ORGANISM: Mus musculus

<400> SEQUENCE: 4

Arg Ala Ser Gln Gly Ile Ser Ile Trp Leu Ser
1               5                   10

<210> SEQ ID NO 5
<211> LENGTH: 7
<212> TYPE: PRT
<213> ORGANISM: Mus musculus

<400> SEQUENCE: 5

Lys Ala Ser Asn Leu His Ile
1               5

<210> SEQ ID NO 6
<211> LENGTH: 9
<212> TYPE: PRT
<213> ORGANISM: Mus musculus

<400> SEQUENCE: 6

Leu Gln Ser Gln Thr Tyr Pro Leu Thr
1               5

<210> SEQ ID NO 7
<211> LENGTH: 5
<212> TYPE: PRT
<213> ORGANISM: Mus musculus

<400> SEQUENCE: 7

Tyr Tyr Asp Ile Asn
1               5

<210> SEQ ID NO 8
<211> LENGTH: 17
```

```
<212> TYPE: PRT
<213> ORGANISM: Mus musculus

<400> SEQUENCE: 8

Trp Ile Phe Pro Gly Asp Gly Gly Thr Lys Tyr Asn Glu Thr Phe Lys
1               5                   10                  15
Gly

<210> SEQ ID NO 9
<211> LENGTH: 14
<212> TYPE: PRT
<213> ORGANISM: Mus musculus

<400> SEQUENCE: 9

Ala Arg Gly Gly Thr Ser Val Ile Arg Asp Ala Met Asp Tyr
1               5                   10

<210> SEQ ID NO 10
<211> LENGTH: 15
<212> TYPE: PRT
<213> ORGANISM: Mus musculus

<400> SEQUENCE: 10

Arg Ala Ser Glu Ser Val Asp Asn Tyr Gly Ile Ser Phe Met His
1               5                   10                  15

<210> SEQ ID NO 11
<211> LENGTH: 7
<212> TYPE: PRT
<213> ORGANISM: Mus musculus

<400> SEQUENCE: 11

Arg Ala Ser Asn Leu Glu Ser
1               5

<210> SEQ ID NO 12
<211> LENGTH: 9
<212> TYPE: PRT
<213> ORGANISM: Mus musculus

<400> SEQUENCE: 12

Gln Gln Ser Asn Lys Asp Pro Leu Thr
1               5

<210> SEQ ID NO 13
<211> LENGTH: 5
<212> TYPE: PRT
<213> ORGANISM: Canis familiaris

<400> SEQUENCE: 13

Ser Tyr Gly Met Ser
1               5

<210> SEQ ID NO 14
<211> LENGTH: 17
<212> TYPE: PRT
<213> ORGANISM: Canis familiaris

<400> SEQUENCE: 14

His Ile Asn Ser Gly Gly Ser Ser Thr Tyr Tyr Ala Asp Ala Val Lys
1               5                   10                  15
Gly
```

```
<210> SEQ ID NO 15
<211> LENGTH: 15
<212> TYPE: PRT
<213> ORGANISM: Canis familiaris

<400> SEQUENCE: 15

Val Tyr Thr Thr Leu Ala Ala Phe Trp Thr Asp Asn Phe Asp Tyr
1               5                   10                  15

<210> SEQ ID NO 16
<211> LENGTH: 13
<212> TYPE: PRT
<213> ORGANISM: Canis familiaris

<400> SEQUENCE: 16

Ser Gly Ser Thr Asn Asn Ile Gly Ile Leu Ala Ala Thr
1               5                   10

<210> SEQ ID NO 17
<211> LENGTH: 7
<212> TYPE: PRT
<213> ORGANISM: Canis familiaris

<400> SEQUENCE: 17

Ser Asp Gly Asn Arg Pro Ser
1               5

<210> SEQ ID NO 18
<211> LENGTH: 11
<212> TYPE: PRT
<213> ORGANISM: Canis familiaris

<400> SEQUENCE: 18

Gln Ser Phe Asp Thr Thr Leu Asp Ala Tyr Val
1               5                   10

<210> SEQ ID NO 19
<211> LENGTH: 5
<212> TYPE: PRT
<213> ORGANISM: Canis familiaris

<400> SEQUENCE: 19

Asp Tyr Ala Met Ser
1               5

<210> SEQ ID NO 20
<211> LENGTH: 17
<212> TYPE: PRT
<213> ORGANISM: Canis familiaris

<400> SEQUENCE: 20

Gly Ile Asp Ser Val Gly Ser Gly Thr Ser Tyr Ala Asp Ala Val Lys
1               5                   10                  15
Gly

<210> SEQ ID NO 21
<211> LENGTH: 8
<212> TYPE: PRT
<213> ORGANISM: Canis familiaris

<400> SEQUENCE: 21

Gly Phe Pro Gly Ser Phe Glu His
1               5
```

```
<210> SEQ ID NO 22
<211> LENGTH: 13
<212> TYPE: PRT
<213> ORGANISM: Canis familiaris

<400> SEQUENCE: 22

Thr Gly Ser Ser Ser Asn Ile Gly Ser Gly Tyr Val Gly
1               5                   10

<210> SEQ ID NO 23
<211> LENGTH: 7
<212> TYPE: PRT
<213> ORGANISM: Canis familiaris

<400> SEQUENCE: 23

Tyr Asn Ser Asp Arg Pro Ser
1               5

<210> SEQ ID NO 24
<211> LENGTH: 10
<212> TYPE: PRT
<213> ORGANISM: Canis familiaris

<400> SEQUENCE: 24

Ser Val Tyr Asp Arg Thr Phe Asn Ala Val
1               5                   10

<210> SEQ ID NO 25
<211> LENGTH: 5
<212> TYPE: PRT
<213> ORGANISM: Canis familiaris

<400> SEQUENCE: 25

Ser Tyr Asp Met Thr
1               5

<210> SEQ ID NO 26
<211> LENGTH: 17
<212> TYPE: PRT
<213> ORGANISM: Canis familiaris

<400> SEQUENCE: 26

Asp Val Asn Ser Gly Gly Thr Gly Thr Ala Tyr Ala Val Ala Val Lys
1               5                   10                  15

Gly

<210> SEQ ID NO 27
<211> LENGTH: 9
<212> TYPE: PRT
<213> ORGANISM: Canis familiaris

<400> SEQUENCE: 27

Leu Gly Val Arg Asp Gly Leu Ser Val
1               5

<210> SEQ ID NO 28
<211> LENGTH: 11
<212> TYPE: PRT
<213> ORGANISM: Canis familiaris

<400> SEQUENCE: 28

Ser Gly Glu Ser Leu Asn Glu Tyr Tyr Thr Gln
1               5                   10
```

```
<210> SEQ ID NO 29
<211> LENGTH: 7
<212> TYPE: PRT
<213> ORGANISM: Canis familiaris

<400> SEQUENCE: 29

Arg Asp Thr Glu Arg Pro Ser
1               5

<210> SEQ ID NO 30
<211> LENGTH: 10
<212> TYPE: PRT
<213> ORGANISM: Canis familiaris

<400> SEQUENCE: 30

Glu Ser Ala Val Asp Thr Gly Thr Leu Val
1               5                   10

<210> SEQ ID NO 31
<211> LENGTH: 5
<212> TYPE: PRT
<213> ORGANISM: Canis familiaris

<400> SEQUENCE: 31

Thr Tyr Val Met Asn
1               5

<210> SEQ ID NO 32
<211> LENGTH: 17
<212> TYPE: PRT
<213> ORGANISM: Canis familiaris

<400> SEQUENCE: 32

Ser Ile Asn Gly Gly Gly Ser Ser Pro Thr Tyr Ala Asp Ala Val Arg
1               5                   10                  15

Gly

<210> SEQ ID NO 33
<211> LENGTH: 8
<212> TYPE: PRT
<213> ORGANISM: Canis familiaris

<400> SEQUENCE: 33

Ser Met Val Gly Pro Phe Asp Tyr
1               5

<210> SEQ ID NO 34
<211> LENGTH: 11
<212> TYPE: PRT
<213> ORGANISM: Canis familiaris

<400> SEQUENCE: 34

Ser Gly Glu Ser Leu Ser Asn Tyr Tyr Ala Gln
1               5                   10

<210> SEQ ID NO 35
<211> LENGTH: 7
<212> TYPE: PRT
<213> ORGANISM: Canis familiaris

<400> SEQUENCE: 35

Lys Asp Thr Glu Arg Pro Ser
1               5
```

```
<210> SEQ ID NO 36
<211> LENGTH: 10
<212> TYPE: PRT
<213> ORGANISM: Canis familiaris

<400> SEQUENCE: 36

Glu Ser Ala Val Ser Ser Asp Thr Ile Val
1               5                   10

<210> SEQ ID NO 37
<211> LENGTH: 5
<212> TYPE: PRT
<213> ORGANISM: Canis familiaris

<400> SEQUENCE: 37

Ser Tyr Ala Met Lys
1               5

<210> SEQ ID NO 38
<211> LENGTH: 17
<212> TYPE: PRT
<213> ORGANISM: Canis familiaris

<400> SEQUENCE: 38

Thr Ile Asn Asn Asp Gly Thr Arg Thr Gly Tyr Ala Asp Ala Val Arg
1               5                   10                  15

Gly

<210> SEQ ID NO 39
<211> LENGTH: 15
<212> TYPE: PRT
<213> ORGANISM: Canis familiaris

<400> SEQUENCE: 39

Gly Asn Ala Glu Ser Gly Cys Thr Gly Asp His Cys Pro Pro Tyr
1               5                   10                  15

<210> SEQ ID NO 40
<211> LENGTH: 11
<212> TYPE: PRT
<213> ORGANISM: Canis familiaris

<400> SEQUENCE: 40

Ser Gly Glu Ser Leu Asn Lys Tyr Tyr Ala Gln
1               5                   10

<210> SEQ ID NO 41
<211> LENGTH: 7
<212> TYPE: PRT
<213> ORGANISM: Canis familiaris

<400> SEQUENCE: 41

Lys Asp Thr Glu Arg Pro Ser
1               5

<210> SEQ ID NO 42
<211> LENGTH: 10
<212> TYPE: PRT
<213> ORGANISM: Canis familiaris

<400> SEQUENCE: 42

Glu Ser Ala Val Ser Ser Glu Thr Asn Val
1               5                   10
```

```
<210> SEQ ID NO 43
<211> LENGTH: 5
<212> TYPE: PRT
<213> ORGANISM: Canis familiaris

<400> SEQUENCE: 43

Thr Tyr Phe Met Ser
1               5

<210> SEQ ID NO 44
<211> LENGTH: 17
<212> TYPE: PRT
<213> ORGANISM: Canis familiaris

<400> SEQUENCE: 44

Leu Ile Ser Ser Asp Gly Ser Gly Thr Tyr Tyr Ala Asp Ala Val Lys
1               5                   10                  15

Gly

<210> SEQ ID NO 45
<211> LENGTH: 7
<212> TYPE: PRT
<213> ORGANISM: Canis familiaris

<400> SEQUENCE: 45

Phe Trp Arg Ala Phe Asn Asp
1               5

<210> SEQ ID NO 46
<211> LENGTH: 14
<212> TYPE: PRT
<213> ORGANISM: Canis familiaris

<400> SEQUENCE: 46

Gly Leu Asn Ser Gly Ser Val Ser Thr Ser Asn Tyr Pro Gly
1               5                   10

<210> SEQ ID NO 47
<211> LENGTH: 7
<212> TYPE: PRT
<213> ORGANISM: Canis familiaris

<400> SEQUENCE: 47

Asp Thr Gly Ser Arg Pro Ser
1               5

<210> SEQ ID NO 48
<211> LENGTH: 10
<212> TYPE: PRT
<213> ORGANISM: Canis familiaris

<400> SEQUENCE: 48

Ser Leu Tyr Thr Asp Ser Asp Ile Leu Val
1               5                   10

<210> SEQ ID NO 49
<211> LENGTH: 5
<212> TYPE: PRT
<213> ORGANISM: Canis familiaris

<400> SEQUENCE: 49

Asp Arg Gly Met Ser
1               5
```

<210> SEQ ID NO 50
<211> LENGTH: 17
<212> TYPE: PRT
<213> ORGANISM: Canis familiaris

<400> SEQUENCE: 50

Tyr Ile Arg Tyr Asp Gly Ser Arg Thr Asp Tyr Ala Asp Ala Val Glu
1               5                   10                  15

Gly

<210> SEQ ID NO 51
<211> LENGTH: 8
<212> TYPE: PRT
<213> ORGANISM: Canis familiaris

<400> SEQUENCE: 51

Trp Asp Gly Ser Ser Phe Asp Tyr
1               5

<210> SEQ ID NO 52
<211> LENGTH: 16
<212> TYPE: PRT
<213> ORGANISM: Canis familiaris

<400> SEQUENCE: 52

Lys Ala Ser Gln Ser Leu Leu His Ser Asp Gly Asn Thr Tyr Leu Asp
1               5                   10                  15

<210> SEQ ID NO 53
<211> LENGTH: 7
<212> TYPE: PRT
<213> ORGANISM: Canis familiaris

<400> SEQUENCE: 53

Lys Val Ser Asn Arg Asp Pro
1               5

<210> SEQ ID NO 54
<211> LENGTH: 9
<212> TYPE: PRT
<213> ORGANISM: Canis familiaris

<400> SEQUENCE: 54

Met Gln Ala Ile His Phe Pro Leu Thr
1               5

<210> SEQ ID NO 55
<211> LENGTH: 5
<212> TYPE: PRT
<213> ORGANISM: Canis familiaris

<400> SEQUENCE: 55

Ser Tyr Val Met Thr
1               5

<210> SEQ ID NO 56
<211> LENGTH: 17
<212> TYPE: PRT
<213> ORGANISM: Canis familiaris

<400> SEQUENCE: 56

Gly Ile Asn Ser Glu Gly Ser Arg Thr Ala Tyr Ala Asp Ala Val Lys
1               5                   10                  15

Gly

```
<210> SEQ ID NO 57
<211> LENGTH: 10
<212> TYPE: PRT
<213> ORGANISM: Canis familiaris

<400> SEQUENCE: 57

Gly Asp Ile Val Ala Thr Gly Thr Ser Tyr
1               5                   10

<210> SEQ ID NO 58
<211> LENGTH: 11
<212> TYPE: PRT
<213> ORGANISM: Canis familiaris

<400> SEQUENCE: 58

Ser Gly Glu Thr Leu Asn Arg Phe Tyr Thr Gln
1               5                   10

<210> SEQ ID NO 59
<211> LENGTH: 7
<212> TYPE: PRT
<213> ORGANISM: Canis familiaris

<400> SEQUENCE: 59

Lys Asp Thr Glu Arg Pro Ser
1               5

<210> SEQ ID NO 60
<211> LENGTH: 10
<212> TYPE: PRT
<213> ORGANISM: Canis familiaris

<400> SEQUENCE: 60

Lys Ser Ala Val Ser Ile Asp Val Gly Val
1               5                   10

<210> SEQ ID NO 61
<211> LENGTH: 5
<212> TYPE: PRT
<213> ORGANISM: Canis familiaris

<400> SEQUENCE: 61

Thr Tyr Val Met Asn
1               5

<210> SEQ ID NO 62
<211> LENGTH: 17
<212> TYPE: PRT
<213> ORGANISM: Canis familiaris

<400> SEQUENCE: 62

Ser Ile Asn Gly Gly Gly Ser Ser Pro Thr Tyr Ala Asp Ala Val Arg
1               5                   10                  15

Gly

<210> SEQ ID NO 63
<211> LENGTH: 8
<212> TYPE: PRT
<213> ORGANISM: Canis familiaris

<400> SEQUENCE: 63

Ser Met Val Gly Pro Phe Asp Tyr
1               5
```

-continued

<210> SEQ ID NO 64
<211> LENGTH: 11
<212> TYPE: PRT
<213> ORGANISM: Canis familiaris

<400> SEQUENCE: 64

Ser Gly Lys Ser Leu Ser Tyr Tyr Tyr Ala Gln
1               5                   10

<210> SEQ ID NO 65
<211> LENGTH: 7
<212> TYPE: PRT
<213> ORGANISM: Canis familiaris

<400> SEQUENCE: 65

Lys Asp Thr Glu Arg Pro Ser
1               5

<210> SEQ ID NO 66
<211> LENGTH: 10
<212> TYPE: PRT
<213> ORGANISM: Canis familiaris

<400> SEQUENCE: 66

Glu Ser Ala Val Ser Ser Asp Thr Ile Val
1               5                   10

<210> SEQ ID NO 67
<211> LENGTH: 122
<212> TYPE: PRT
<213> ORGANISM: Mus musculus

<400> SEQUENCE: 67

Gln Val Gln Leu Gln Gln Ser Ala Ala Glu Leu Ala Arg Pro Gly Ala
1               5                   10                  15

Ser Val Lys Met Ser Cys Lys Thr Ser Gly Tyr Thr Phe Thr Ser Tyr
            20                  25                  30

Thr Ile His Trp Ile Lys Gln Arg Pro Gly Gln Gly Leu Glu Trp Ile
        35                  40                  45

Gly Asn Ile Asn Pro Thr Ser Gly Tyr Thr Glu Asn Asn Gln Arg Phe
    50                  55                  60

Lys Asp Lys Thr Thr Leu Thr Val Asp Arg Ser Ser Asn Thr Ala Tyr
65                  70                  75                  80

Leu Gln Leu His Ser Leu Thr Ser Glu Asp Ser Ala Val Tyr Phe Cys
                85                  90                  95

Ala Arg Trp Gly Phe Lys Tyr Asp Gly Glu Trp Ser Phe Asp Val Trp
            100                 105                 110

Gly Ala Gly Thr Thr Val Thr Val Ser Ser
        115                 120

<210> SEQ ID NO 68
<211> LENGTH: 366
<212> TYPE: DNA
<213> ORGANISM: Mus musculus

<400> SEQUENCE: 68
caggtccagc tgcagcagtc tgcagctgaa ctggcaagac ctggggcctc agtgaagatg      60
tcctgcaaga cttctggcta cacattact tcctacacga tacactggat aaaacagagg     120
cctggacagg gtctggaatg gattggaaac attaatccca ccagtggata cactgagaac     180

```
aatcagaggt tcaaggacaa gaccacattg actgtagaca gatcctccaa cacagcctat    240
ttgcaactgc acagcctgac atctgaggac tctgcggtct atttctgtgc aagatggggc    300
tttaaatatg acggagaatg gtccttcgat gtctggggcg cagggaccac ggtcaccgtc    360
tcctca                                                               366

<210> SEQ ID NO 69
<211> LENGTH: 107
<212> TYPE: PRT
<213> ORGANISM: Mus musculus

<400> SEQUENCE: 69

Asp Ile Gln Met Asn Gln Ser Pro Ser Ser Leu Ser Ala Ser Leu Gly
1               5                   10                  15

Asp Thr Ile Thr Val Thr Cys Arg Ala Ser Gln Gly Ile Ser Ile Trp
            20                  25                  30

Leu Ser Trp Tyr Gln Gln Lys Pro Gly Asn Ile Pro Lys Val Leu Ile
        35                  40                  45

Asn Lys Ala Ser Asn Leu His Ile Gly Val Pro Pro Arg Phe Ser Gly
    50                  55                  60

Ser Gly Ser Gly Thr His Phe Thr Leu Thr Ile Thr Ser Leu Gln Pro
65                  70                  75                  80

Glu Asp Ile Ala Thr Tyr Tyr Cys Leu Gln Ser Gln Thr Tyr Pro Leu
                85                  90                  95

Thr Phe Gly Gly Gly Thr Lys Leu Glu Ile Asn
            100                 105

<210> SEQ ID NO 70
<211> LENGTH: 321
<212> TYPE: DNA
<213> ORGANISM: Mus musculus

<400> SEQUENCE: 70
gacatccaaa tgaaccagtc tccatccagt ctgtctgcat ccctcggaga cacaatcacc     60
gtcacttgcc gtgccagtca gggcatcagt atttggttaa gctggtacca gcagaaacca    120
ggaaatattc ctaaagtatt gatcaataag gcttccaact tgcacatagg agtcccacca    180
aggtttagtg gcagtggatc tggaacacat ttcacattaa ctatcaccag cctacagcct    240
gaagacattg ccacttacta ctgtctacag agtcaaactt atcctctcac gttcggaggg    300
gggaccaagc tggaaataaa c                                              321

<210> SEQ ID NO 71
<211> LENGTH: 121
<212> TYPE: PRT
<213> ORGANISM: Mus musculus

<400> SEQUENCE: 71

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Lys Tyr Tyr
            20                  25                  30

Asp Ile Asn Trp Val Arg Gln Arg Pro Glu Gln Gly Leu Glu Trp Ile
        35                  40                  45

Gly Trp Ile Phe Pro Gly Asp Gly Gly Thr Lys Tyr Asn Glu Thr Phe
    50                  55                  60
```

Lys Gly Lys Ala Thr Leu Thr Thr Asp Lys Ser Ser Thr Ala Tyr
65                  70                  75                  80

Met Gln Leu Ser Arg Leu Thr Ser Glu Asp Ser Ala Val Tyr Phe Cys
                85                  90                  95

Ala Arg Gly Gly Thr Ser Val Ile Arg Asp Ala Met Asp Tyr Trp Gly
            100                 105                 110

Gln Gly Thr Ser Val Thr Val Ser Ser
        115                 120

<210> SEQ ID NO 72
<211> LENGTH: 363
<212> TYPE: DNA
<213> ORGANISM: Mus musculus

<400> SEQUENCE: 72
caggttcagc tgcagcagtc tggagctgaa ctggtaaagc ctggggcttc agtgaagttg      60
tcctgcaagg cttctggcta caccttcaaa tactatgata taaactgggt gaggcagagg     120
cctgaacagg gacttgagtg gattggatgg attttcctg agatggtgg tactaagtac       180 aatgagacgt tcaagggcaa ggccacactg actacagaca atcctccag cacagcctac      240 atgcagctca gcaggctgac atctgaggac tctgctgtct atttctgtgc aagagggggg     300
acttcggtga taggatgcta tatggactac tggggtcaag gaacctcagt caccgtctcc     360
tca                                                                   363

<210> SEQ ID NO 73
<211> LENGTH: 111
<212> TYPE: PRT
<213> ORGANISM: Mus musculus

<400> SEQUENCE: 73

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Thr Asp Asp Val Ala Thr Tyr Tyr Cys Gln Gln Ser Asn
                85                  90                  95

Lys Asp Pro Leu Thr Phe Gly Ala Gly Thr Lys Leu Glu Leu Lys
            100                 105                 110

<210> SEQ ID NO 74
<211> LENGTH: 333
<212> TYPE: DNA
<213> ORGANISM: Mus musculus

<400> SEQUENCE: 74
gacattgtgc tgacccaatc tccagcttct ttggctgtgt ctctagggca gagggccacc      60
atctcctgca gagccagcga aagtgttgat aattatggca ttagttttat gcactggtac     120
cagcagaaac aggacagcc acccaaactc ctcatctatc gtgcatccaa cctagaatct      180
gggatccctg ccaggttcag tggcagtggg tctaggacag acttcaccct caccattaat     240

```
cctgtggaga ctgatgatgt tgcaacctat tactgtcagc aaagtaataa ggatccgctc    300
acgttcggtg ctgggaccaa gctggagctg aaa                                 333

<210> SEQ ID NO 75
<211> LENGTH: 124
<212> TYPE: PRT
<213> ORGANISM: Canis familiaris

<400> SEQUENCE: 75

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met Ser Trp Val Arg Gln Ala Pro Gly Lys Gly Leu Gln Trp Val
        35                  40                  45

Ala His Ile Asn Ser Gly Gly Ser Ser Thr Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Val Glu Val Tyr Thr Thr Leu Ala Ala Phe Trp Thr Asp Asn Phe Asp
            100                 105                 110

Tyr Trp Gly Gln Gly Thr Leu Val Thr Val Ser Ser
        115                 120

<210> SEQ ID NO 76
<211> LENGTH: 372
<212> TYPE: DNA
<213> ORGANISM: Canis familiaris

<400> SEQUENCE: 76
gaggtgcagc tggtggagtc tgggggagac ctggtgaagc ctggggggtc cctgagactc     60
tcctgtgtgg cttctggatt caccttcagt agttatggca tgagctgggt ccgccaggct    120
ccagggaagg ggctgcagtg ggtcgcacac attaacagtg gtggaagtag cacatactac    180
gcagacgctg tgaagggacg attcaccatc tccagagaca acgccaagaa cacgctctat    240
ctgcagatga acagcctgag agctgaggac acggccgtct attactgtgt ggaggtttac    300
actacgttag ctgcattctg gacagacaat tttgactact ggggccaggg aaccctggtc    360
accgtctcct ca                                                        372

<210> SEQ ID NO 77
<211> LENGTH: 110
<212> TYPE: PRT
<213> ORGANISM: Canis familiaris

<400> SEQUENCE: 77

Gln Ser Val Leu Thr Gln Pro Thr Ser Val Ser Gly Ser Leu Gly Gln
1               5                   10                  15

Arg Val Thr Ile Ser Cys Ser Gly Ser Thr Asn Asn Ile Gly Ile Leu
            20                  25                  30

Ala Ala Thr Trp Tyr Gln Gln Leu Pro Gly Lys Ala Pro Lys Val Leu
        35                  40                  45

Val Tyr Ser Asp Gly Asn Arg Pro Ser Gly Val Pro Asp Arg Phe Ser
    50                  55                  60
```

Gly Ser Lys Ser Gly Asn Ser Ala Thr Leu Thr Ile Thr Gly Leu Gln
65                  70                  75                  80

Ala Glu Asp Glu Ala Asp Tyr Tyr Cys Gln Ser Phe Asp Thr Thr Leu
                85                  90                  95

Asp Ala Tyr Val Phe Gly Ser Gly Thr Gln Leu Thr Val Leu
            100                 105                 110

<210> SEQ ID NO 78
<211> LENGTH: 330
<212> TYPE: DNA
<213> ORGANISM: Canis familiaris

<400> SEQUENCE: 78
cagtctgtgc tgactcagcc gacctcagtg tcggggtccc ttggccagag ggtcaccatc    60
tcctgctctg gaagcacgaa caacatcggt attcttgctg cgacctggta ccaacaactc   120
ccaggaaagg cccctaaagt cctcgtgtac agtgatggga atcgaccgtc aggggtccct   180
gaccggtttt ccggctccaa gtctggcaac tcagccaccc tgaccatcac tgggcttcag   240
gctgaggacg aggctgatta ttactgccag tcctttgata ccacgcttga tgcttacgtg   300
ttcggctcag gaacccaact gaccgtcctt                                    330

<210> SEQ ID NO 79
<211> LENGTH: 117
<212> TYPE: PRT
<213> ORGANISM: Canis familiaris

<400> SEQUENCE: 79

Glu Val Gln Leu Val Glu Ser Gly Gly Asp Leu Val Lys Pro Ala Gly
1               5                   10                  15

Ser Leu Arg Leu Ser Cys Val Ala Ser Gly Phe Thr Phe Ser Asp Tyr
            20                  25                  30

Ala Met Ser Trp Val Arg Gln Ala Pro Gly Arg Gly Leu Gln Trp Val
        35                  40                  45

Ala Gly Ile Asp Ser Val Gly Ser Gly Thr Ser Tyr Ala Asp Ala Val
    50                  55                  60

Lys Gly Arg Phe Thr Ile Ser Arg Asp Asp Ala Lys Asn Thr Leu Tyr
65                  70                  75                  80

Leu Gln Met Phe Asn Leu Arg Ala Glu Asp Thr Ala Ile Tyr Tyr Cys
                85                  90                  95

Ala Ser Gly Phe Pro Gly Ser Phe Glu His Trp Gly Gln Gly Thr Leu
            100                 105                 110

Val Thr Val Ser Ser
        115

<210> SEQ ID NO 80
<211> LENGTH: 351
<212> TYPE: DNA
<213> ORGANISM: Canis familiaris

<400> SEQUENCE: 80
gaggtgcagc tggtggagtc tgggggagac ctggtgaagc ctgcagggtc cctgagactg    60
tcctgtgtgg cctctggatt caccttcagt gactatgcca tgagctgggt ccgccaggct   120
cctgggaggg gactgcagtg ggtcgcaggt attgacagtg ttggaagtgg cacaagctac   180
gcagacgctg tgaagggccg attcacaatc tccagagacg acgccaagaa cacactgtat   240

```
ctgcagatgt tcaacctgag agccgaggac acggccatat attactgtgc gagcgggttc    300
cctgggtcct ttgagcactg gggccagggc accctggtca ccgtctcctc a             351
```

<210> SEQ ID NO 81
<211> LENGTH: 104
<212> TYPE: PRT
<213> ORGANISM: Canis familiaris

<400> SEQUENCE: 81

```
Gln Ser Val Leu Thr Gln Pro Ala Ser Val Ser Gly Ser Leu Gly Gln
1               5                   10                  15

Lys Val Thr Ile Ser Cys Thr Gly Ser Ser Asn Ile Gly Ser Gly
            20                  25                  30

Tyr Val Gly Trp Tyr Gln Gln Leu Pro Gly Thr Gly Pro Arg Thr Leu
        35                  40                  45

Ile Tyr Tyr Asn Ser Asp Arg Pro Ser Gly Val Pro Asp Arg Phe Ser
    50                  55                  60

Gly Ser Arg Ser Gly Thr Thr Ala Thr Leu Thr Ile Ser Gly Leu Gln
65                  70                  75                  80

Ala Glu Asp Glu Ala Asp Tyr Tyr Cys Ser Val Tyr Asp Arg Thr Phe
                85                  90                  95

Asn Ala Val Phe Gly Gly Gly Thr
            100
```

<210> SEQ ID NO 82
<211> LENGTH: 327
<212> TYPE: DNA
<213> ORGANISM: Canis familiaris

<400> SEQUENCE: 82

```
cagtctgtac tgactcagcc ggcctcagtg tctgggtccc tgggcagaa ggtcaccatc    60 tcctgcactg gaagtagttc aacattggt agtggttatg tgggctggta ccagcagctc    120
ccaggaacag gccccagaac cctcatctat tataacagtg accgaccttc gggggtcccc    180
gatcgattct ctggctccag gtcaggcacc acagcaaccc tgaccatctc tggactccag    240
gctgaggacg aggctgatta ttactgctca gtatatgaca ggactttcaa tgctgtgttc    300
ggcggaggca cccacctgac cgtcctc                                        327
```

<210> SEQ ID NO 83
<211> LENGTH: 118
<212> TYPE: PRT
<213> ORGANISM: Canis familiaris

<400> SEQUENCE: 83

```
Glu Val Gln Leu Val Glu Ser Gly Gly Asp Leu Val Lys Pro Pro Gly
1               5                   10                  15

Ser Leu Arg Leu Ser Cys Val Ala Ser Gly Phe Thr Phe Ser Ser Tyr
            20                  25                  30

Asp Met Thr Trp Val Arg Gln Ala Pro Gly Lys Gly Leu Gln Trp Val
        35                  40                  45

Ala Asp Val Asn Ser Gly Gly Thr Gly Thr Ala Tyr Ala Val Ala Val
    50                  55                  60

Lys Gly Arg Phe Thr Ile Ser Arg Asp Asn Ala Lys Lys Thr Leu Tyr
65                  70                  75                  80

Leu Gln Met Asn Ser Leu Arg Ala Glu Asp Thr Ala Val Tyr Tyr Cys
                85                  90                  95
```

Ala Lys Leu Gly Val Arg Asp Gly Leu Ser Val Trp Gly Gln Gly Thr
            100                 105                 110

Leu Val Thr Val Ser Ser
        115

<210> SEQ ID NO 84
<211> LENGTH: 354
<212> TYPE: DNA
<213> ORGANISM: Canis familiaris

<400> SEQUENCE: 84
gaggtgcagc tggtggagtc tgggggagac ctggtgaagc ctccagggtc cctgagactg     60
tcctgtgtgg cctctggatt caccttcagc agttatgaca tgacctgggt ccgccaggct    120
cctgggaagg gactgcagtg ggtcgcagat gttaacagtg gtggaactgg cacggcctac    180
gcagtcgctg tgaagggccg attcaccatc tccagagaca cgccaagaa acactctat     240 ttacagatga acagcctgag agccgaagac acggccgttt attattgtgc gaaactaggt    300
gtgagagatg gtctttctgt ctggggccag ggcaccctgg tcaccgtctc ctcg          354

<210> SEQ ID NO 85
<211> LENGTH: 107
<212> TYPE: PRT
<213> ORGANISM: Canis familiaris

<400> SEQUENCE: 85

Ser Ser Val Leu Thr Gln Pro Pro Ser Val Ser Val Ser Leu Gly Gln
1               5                   10                  15

Thr Ala Thr Ile Ser Cys Ser Gly Glu Ser Leu Asn Glu Tyr Tyr Thr
            20                  25                  30

Gln Trp Phe Gln Gln Lys Ala Gly Gln Ala Pro Val Leu Val Ile Tyr
        35                  40                  45

Arg Asp Thr Glu Arg Pro Ser Gly Ile Pro Arg Phe Ser Gly Ser
    50                  55                  60

Ser Ser Gly Asn Thr His Thr Leu Thr Ile Ser Gly Ala Arg Ala Glu
65                  70                  75                  80

Asp Glu Ala Asp Tyr Tyr Cys Glu Ser Ala Val Asp Thr Gly Thr Leu
                85                  90                  95

Val Phe Gly Gly Gly Thr His Leu Ala Val Leu
            100                 105

<210> SEQ ID NO 86
<211> LENGTH: 321
<212> TYPE: DNA
<213> ORGANISM: Canis familiaris

<400> SEQUENCE: 86
tccagtgtgc tgactcagcc tccctcggta tcagtgtctc tgggacagac agcaaccatc     60
tcctgctctg gagagagtct gaatgaatat tatacacaat ggttccagca gaaggcaggc    120
caagcccctg tcttggtcat atatagggac actgagcggc cctctgggat ccctgaccga    180
ttctctggct ccagttcagg gaacacacac accctaacca tcagcggggc tcgggccgag    240
gacgaggctg actattactg cgagtcagcg gtcgacactg gaacccttgt ctttggcgga    300
ggcacccacc tggccgtcct c                                              321

<210> SEQ ID NO 87
<211> LENGTH: 117

<212> TYPE: PRT
<213> ORGANISM: Canis familiaris

<400> SEQUENCE: 87

Glu Val Gln Leu Val Glu Ser Gly Gly Asp Leu Val Lys Pro Ala Gly
1               5                   10                  15

Ser Leu Arg Leu Ser Cys Val Ala Ser Gly Phe Thr Phe Arg Thr Tyr
            20                  25                  30

Val Met Asn Trp Val Arg Gln Ala Pro Gly Lys Gly Leu Gln Trp Val
        35                  40                  45

Ala Ser Ile Asn Gly Gly Ser Ser Pro Thr Tyr Ala Asp Ala Val
    50                  55                  60

Arg Gly Arg Phe Thr Val Ser Arg Asp Asn Ala Gln Asn Ser Leu Phe
65                  70                  75                  80

Leu Gln Met Asn Ser Leu Arg Ala Glu Asp Thr Ala Val Tyr Phe Cys
                85                  90                  95

Val Val Ser Met Val Gly Pro Phe Asp Tyr Trp Gly Gln Gly Thr Leu
            100                 105                 110

Val Thr Val Ser Ser
        115

<210> SEQ ID NO 88
<211> LENGTH: 351
<212> TYPE: DNA
<213> ORGANISM: Canis familiaris

<400> SEQUENCE: 88
gaggtgcagc tggtggagtc tgggggagac ctggtgaagc ctgcagggtc cctgagactg      60
tcctgtgtgg cctctggatt caccttcagg acctatgtca tgaactgggt ccgccaggct     120
cctgggaagg ggctgcaatg ggtcgcaagt attaacggtg gtggaagtag cccaacctac     180
gcagacgctg tgaggggccg attcaccgtc tccaggaca acgccagaa ctcactgttt       240 ctgcagatga acagcctgag agccgaggac acagccgtgt attttttgtgt cgtgtcgatg   300 gttgggccct cgactactg gggccaaggg accctggtca ccgtgtcctc a               351

<210> SEQ ID NO 89
<211> LENGTH: 102
<212> TYPE: PRT
<213> ORGANISM: Canis familiaris

<400> SEQUENCE: 89

Ser Ser Val Leu Thr Gln Pro Pro Ser Val Ser Val Ser Leu Gly Gln
1               5                   10                  15

Thr Ala Thr Ile Ser Cys Ser Gly Glu Ser Leu Ser Asn Tyr Tyr Ala
            20                  25                  30

Gln Trp Phe Gln Gln Lys Ala Gly Gln Ala Pro Val Leu Val Ile Tyr
        35                  40                  45

Lys Asp Thr Glu Arg Pro Ser Gly Ile Pro Asp Arg Phe Ser Gly Ser
    50                  55                  60

Ser Ser Gly Asn Thr His Thr Leu Thr Ile Ser Gly Ala Arg Ala Glu
65                  70                  75                  80

Asp Glu Ala Asp Tyr Tyr Cys Glu Ser Ala Val Ser Ser Asp Thr Ile
                85                  90                  95

Val Phe Gly Gly Gly Thr
            100

<210> SEQ ID NO 90
<211> LENGTH: 321
<212> TYPE: DNA
<213> ORGANISM: Canis familiaris

<400> SEQUENCE: 90

```
tccagtgtgc tgactcagcc tccctcggta tcagtgtctc tggggcagac agcaaccatc    60
tcctgctctg gagagagtct gagtaactat tatgcacaat ggttccagca gaaggcaggc   120
caagcccctg tgttggtcat atataaggac actgagcggc cctctgggat ccctgaccga   180
ttctctggct ccagttcagg gaacacacac accctgacca tcagcggggc tcgggccgag   240
gacgaggctg actattactg tgagtcagca gtcagttctg atactattgt gttcggcgga   300
ggcacccacc tgaccgtcct c                                             321
```

<210> SEQ ID NO 91
<211> LENGTH: 124
<212> TYPE: PRT
<213> ORGANISM: Canis familiaris

<400> SEQUENCE: 91

```
Glu Val Gln Leu Val Glu Ser Gly Gly Asp Leu Val Lys Pro Ala Gly
1               5                   10                  15

Ser Leu Arg Leu Ser Cys Val Ala Ser Gly Phe Thr Phe Ser Ser Tyr
            20                  25                  30

Ala Met Lys Trp Val Arg Gln Ala Pro Gly Lys Gly Leu Gln Trp Val
        35                  40                  45

Ala Thr Ile Asn Asn Asp Gly Thr Arg Thr Gly Tyr Ala Asp Ala Val
    50                  55                  60

Arg Gly Arg Phe Thr Ile Ser Lys Asp Asn Ala Lys Asn Thr Leu Tyr
65                  70                  75                  80

Leu Gln Met Asp Ser Leu Arg Ala Asp Asp Thr Ala Val Tyr Tyr Cys
                85                  90                  95

Thr Lys Gly Asn Ala Glu Ser Gly Cys Thr Gly Asp His Cys Pro Pro
            100                 105                 110

Tyr Trp Gly Gln Gly Thr Leu Val Thr Val Ser Ser
        115                 120
```

<210> SEQ ID NO 92
<211> LENGTH: 372
<212> TYPE: DNA
<213> ORGANISM: Canis familiaris

<400> SEQUENCE: 92

```
gaggtgcagc tggtggagtc tgggggagac ctggtgaagc ctgcggggtc cctgagactg    60
tcctgtgtgg cctctggatt caccttcagt agttatgcca tgaaatgggt ccgccaggct   120
cctgggaagg gctgcagtg ggtcgcgact attaacaatg atggaaccag aacaggctac   180
gcagacgctg tgaggggccg attcaccatc tccaaagaca cgccaaaaa cacactgtat   240
ctgcagatgg acagcctgag agccgacgac acggccgtct attactgtac aaagggcaat   300
gccgaatccg gctgtactgg tgatcactgt cctcccctact ggggccaggg aaccctggtc   360
accgtctcct ca                                                      372
```

<210> SEQ ID NO 93
<211> LENGTH: 107
<212> TYPE: PRT
<213> ORGANISM: Canis familiaris

<400> SEQUENCE: 93

Ser Ser Val Leu Thr Gln Pro Pro Ser Val Ser Val Ser Leu Gly Gln
1               5                   10                  15

Thr Ala Thr Ile Ser Cys Ser Gly Glu Ser Leu Asn Lys Tyr Tyr Ala
            20                  25                  30

Gln Trp Phe Gln Gln Lys Ala Gly Gln Ala Pro Val Leu Val Ile Tyr
        35                  40                  45

Lys Asp Thr Glu Arg Pro Ser Gly Ile Pro Asp Arg Phe Ser Gly Ser
50                  55                  60

Ser Ala Gly Asn Thr His Thr Leu Thr Ile Ser Gly Ala Arg Ala Glu
65                  70                  75                  80

Asp Glu Ala Asp Tyr Tyr Cys Glu Ser Ala Val Ser Ser Glu Thr Asn
                85                  90                  95

Val Phe Gly Ser Gly Thr Gln Leu Thr Val Leu
            100                 105

<210> SEQ ID NO 94
<211> LENGTH: 321
<212> TYPE: DNA
<213> ORGANISM: Canis familiaris

<400> SEQUENCE: 94
tccagtgtgc tgactcagcc tccctcggta tcagtgtctc tgggacagac agcaaccatc    60
tcctgctctg gagagagtct gaataaatat tatgcacaat ggttccaaca gaaggcaggc   120
caagcccctg tgttggtcat atataaggac actgagcggc cctctgggat ccctgaccga   180
ttctccggct ccagtgcagg caacacacac accctgacca tcagcggggc tcgggccgag   240
gacgaggctg actattactg cgagtcagca gtcagttctg aaactaacgt gttcggctca   300
ggaacccaac tgaccgtcct t                                              321

<210> SEQ ID NO 95
<211> LENGTH: 116
<212> TYPE: PRT
<213> ORGANISM: Canis familiaris

<400> SEQUENCE: 95

Glu Val Gln Leu Val Asp Ser Gly Gly Asp Leu Val Lys Pro Gly Gly
1               5                   10                  15

Ser Leu Arg Leu Ser Cys Val Ala Ser Gly Phe Thr Phe Ser Thr Tyr
            20                  25                  30

Phe Met Ser Trp Val Arg Gln Ala Pro Gly Arg Gly Leu Gln Trp Val
        35                  40                  45

Ala Leu Ile Ser Ser Asp Gly Ser Gly Thr Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Ile Phe Trp Arg Ala Phe Asn Asp Trp Gly Gln Gly Thr Leu Val
            100                 105                 110

Thr Val Ser Ser
        115

<210> SEQ ID NO 96
<211> LENGTH: 348
<212> TYPE: DNA

<213> ORGANISM: Canis familiaris

<400> SEQUENCE: 96

```
gaggtacaac tggtggactc tgggggagac ctggtgaagc ctggggggtc cctgagactc    60
tcctgtgtgg cctctggatt caccttcagt acctacttca tgtcctgggt ccgccaggct   120
ccagggaggg ggcttcagtg ggtcgcactt attagcagtg atggaagtgg cacatactac   180
gcagacgctg tgaagggccg attcaccatc tccagagaca atgccaagaa cacgctgtat   240
ctgcagatga acagcctgag agccgaggac acggctatgt attactgtgc gatattctgg   300
cgggcctttta cgactgggg ccagggcacc ctggtcaccg tctcctca                348
```

<210> SEQ ID NO 97
<211> LENGTH: 110
<212> TYPE: PRT
<213> ORGANISM: Canis familiaris

<400> SEQUENCE: 97

Gln Thr Val Val Ile Gln Glu Pro Ser Leu Ser Val Ser Pro Gly Gly
1               5                   10                  15

Thr Val Thr Leu Thr Cys Gly Leu Asn Ser Gly Ser Val Ser Thr Ser
            20                  25                  30

Asn Tyr Pro Gly Trp Tyr Gln Gln Thr Arg Gly Arg Thr Pro Arg Thr
        35                  40                  45

Ile Ile Tyr Asp Thr Gly Ser Arg Pro Ser Gly Val Pro Asn Arg Phe
    50                  55                  60

Ser Gly Ser Ile Ser Gly Asn Lys Ala Ala Leu Thr Ile Thr Gly Ala
65                  70                  75                  80

Gln Pro Glu Asp Glu Ala Asp Tyr Tyr Cys Ser Leu Tyr Thr Asp Ser
                85                  90                  95

Asp Ile Leu Val Phe Gly Gly Gly Thr His Leu Thr Val Leu
            100                 105                 110

<210> SEQ ID NO 98
<211> LENGTH: 330
<212> TYPE: DNA
<213> ORGANISM: Canis familiaris

<400> SEQUENCE: 98

```
cagactgtgg taatccagga gccatcactc tcagtgtctc caggagggac agtcacactc    60
acatgtggcc tcaactctgg gtcagtctcc acaagtaatt accctggctg gtaccagcag   120
acccgaggcc ggactcctcg cacgattatc tacgacacag cagtcgccc ctctggggtc   180
cctaatcgct tctccggatc catctctgga aacaaagccg ccctcaccat cacaggagcc   240
cagcccgagg atgaggctga ctattactgt tccttatata cggatagtga cattcttgtt   300
ttcggcggag gcacccacct gaccgtcctc                                    330
```

<210> SEQ ID NO 99
<211> LENGTH: 117
<212> TYPE: PRT
<213> ORGANISM: Canis familiaris

<400> SEQUENCE: 99

Glu Val His Leu Val Glu Ser Gly Gly Asp Leu Val Lys Pro Trp Gly
1               5                   10                  15

Ser Leu Arg Leu Ser Cys Val Ala Ser Gly Phe Thr Phe Ser Asp Arg
            20                  25                  30

Gly Met Ser Trp Val Arg Gln Ser Pro Gly Lys Gly Leu Gln Trp Val
        35                  40                  45

Ala Tyr Ile Arg Tyr Asp Gly Ser Arg Thr Tyr Ala Asp Ala Val
 50                  55                  60

Glu Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Trp Asp Gly Ser Ser Phe Asp Tyr Trp Gly Gln Gly Thr Leu
             100                 105                 110

Val Thr Val Ser Ser
        115

<210> SEQ ID NO 100
<211> LENGTH: 351
<212> TYPE: DNA
<213> ORGANISM: Canis familiaris

<400> SEQUENCE: 100
gaggtgcatt tggtggagtc tgggggagac ctggtgaagc cttggggtc cttgagactg      60 tcctgtgtgg cctctggatt caccttagt gatcgtggca tgagctgggt ccgtcagtct     120
ccagggaagg ggctgcagtg ggtcgcatat attaggtatg atgggagtag gacagactac    180
gcagacgctg tggagggccg attcaccatc tccagagaca cgccaagaa cacgctctac    240 ctgcagatga acagcctgag agccgaggac acggccgtgt attactgtgc gagatgggac    300
ggtagttctt ttgactattg gggccagggc accctggtca ccgtctcctc a             351

<210> SEQ ID NO 101
<211> LENGTH: 112
<212> TYPE: PRT
<213> ORGANISM: Canis familiaris

<400> SEQUENCE: 101

Asp Ile Val Val Thr Gln Thr Pro Leu Ser Leu Ser Val Ser Pro Gly
 1               5                  10                  15

Glu Thr Ala Ser Phe Ser Cys Lys Ala Ser Gln Ser Leu Leu His Ser
                 20                  25                  30

Asp Gly Asn Thr Tyr Leu Asp Trp Phe Arg Gln Lys Pro Gly Gln Ser
             35                  40                  45

Pro Gln Arg Leu Ile Tyr Lys Val Ser Asn Arg Asp Pro Gly Val Pro
 50                  55                  60

Asp Arg Phe Ser Gly Ser Gly Ser Gly Thr Asp Phe Thr Leu Arg Ile
 65                  70                  75                  80

Ser Gly Val Glu Ala Asp Asp Ala Gly Leu Tyr Tyr Cys Met Gln Ala
                 85                  90                  95

Ile His Phe Pro Leu Thr Phe Gly Ala Gly Thr Lys Val Glu Leu Lys
             100                 105                 110

<210> SEQ ID NO 102
<211> LENGTH: 336
<212> TYPE: DNA
<213> ORGANISM: Canis familiaris

<400> SEQUENCE: 102
gatattgtcg tgacacagac cccgctgtcc ctgtccgtca gcctggaga gactgcctcc      60 ttctcctgca aggccagtca gagcctcctg cacagtgatg gaaacacgta tttggattgg    120

```
ttccgacaga agccaggcca gtctccacag cgtttgatct acaaggtctc caacagagac      180
cctggggtcc cagacaggtt cagtggcagc gggtcaggga cagatttcac cctgagaatc      240
agcggagtgg aggctgacga tgctggactt tattactgca tgcaagcaat acactttcct      300
ctgacgttcg gagcaggaac caaggtggag ctcaaa                                336
```

<210> SEQ ID NO 103
<211> LENGTH: 119
<212> TYPE: PRT
<213> ORGANISM: Canis familiaris

<400> SEQUENCE: 103

```
Glu Val Gln Leu Val Glu Ser Gly Gly Asp Leu Val Lys Pro Ala Gly
1               5                   10                  15

Ser Leu Arg Leu Ser Cys Val Ala Ser Gly Phe Thr Phe Ser Ser Tyr
            20                  25                  30

Val Met Thr Trp Val Arg Gln Ala Pro Gly Lys Gly Leu Gln Trp Val
        35                  40                  45

Ala Gly Ile Asn Ser Glu Gly Ser Arg Thr Ala Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Ile Asp Ser Leu Arg Ala Glu Asp Thr Ala Ile Tyr Tyr Cys
                85                  90                  95

Ala Thr Gly Asp Ile Val Ala Thr Gly Thr Ser Tyr Trp Gly Gln Gly
            100                 105                 110

Thr Leu Val Thr Val Ser Ser
        115
```

<210> SEQ ID NO 104
<211> LENGTH: 357
<212> TYPE: DNA
<213> ORGANISM: Canis familiaris

<400> SEQUENCE: 104

```
gaggtgcagc tggtggagtc tgggggagac ctggtgaagc tgcagggtc cctgagactg        60 tcctgtgtgg cctctggatt caccttcagt agttatgtca tgacctgggt ccgccaggct      120
cctgggaagg gactgcagtg gtcgcaggc attaatagtg agggagtag acagcctac         180 gcagacgctg tgaagggccg attcaccatc tccagagaca cgccaagaa tacactttat       240 ctacaaatag acagcctgag agccgaggac acggccatat attactgtgc gacaggcgat      300
atagtagcga ctggtacttc gtattggggc cagggcaccc tggtcaccgt ctcctca         357
```

<210> SEQ ID NO 105
<211> LENGTH: 107
<212> TYPE: PRT
<213> ORGANISM: Canis familiaris

<400> SEQUENCE: 105

```
Ser Asn Val Leu Thr Gln Pro Pro Ser Val Ser Val Ser Leu Gly Gln
1               5                   10                  15

Thr Ala Thr Ile Ser Cys Ser Gly Glu Thr Leu Asn Arg Phe Tyr Thr
            20                  25                  30

Gln Trp Phe Gln Gln Lys Ala Gly Gln Ala Pro Val Leu Val Ile Tyr
        35                  40                  45

Lys Asp Thr Glu Arg Pro Ser Gly Ile Pro Asp Arg Phe Ser Gly Ser
    50                  55                  60
```

-continued

```
Ser Ser Gly Asn Ile His Thr Leu Thr Ile Ser Gly Ala Arg Ala Glu
 65                  70                  75                  80

Asp Glu Ala Ala Tyr Tyr Cys Lys Ser Ala Val Ser Ile Asp Val Gly
                 85                  90                  95

Val Phe Gly Gly Gly Thr His Leu Thr Val Phe
            100                 105
```

<210> SEQ ID NO 106
<211> LENGTH: 321
<212> TYPE: DNA
<213> ORGANISM: Canis familiaris

<400> SEQUENCE: 106

```
tccaatgtac tgactcagcc tccctcggta tcagtgtctc tgggacagac agcaaccatc      60
tcctgctctg agagactct gaatagattt tatacacaat ggttccagca gaaggcaggc     120
caagcccctg tgttggtcat atataaggac actgagcggc cctctgggat ccctgaccga    180
ttctccggct ccagttcagg gaacatacac accctgacca tcagcggggc tcgggccgag    240
gacgaggctg cctattactg caagtcagca gtcagtattg atgttggtgt gttcggcgga    300
ggcacccacc tgaccgtctt c                                              321
```

<210> SEQ ID NO 107
<211> LENGTH: 117
<212> TYPE: PRT
<213> ORGANISM: Canis familiaris

<400> SEQUENCE: 107

```
Glu Val Gln Leu Val Glu Ser Gly Gly Asp Leu Val Lys Pro Ala Gly
  1               5                  10                  15

Ser Leu Arg Leu Ser Cys Val Ala Ser Gly Phe Thr Phe Arg Thr Tyr
                 20                  25                  30

Val Met Asn Trp Val Arg Gln Ala Pro Gly Lys Gly Leu Gln Trp Val
             35                  40                  45

Ala Ser Ile Asn Gly Gly Gly Ser Ser Pro Thr Tyr Ala Asp Ala Val
         50                  55                  60

Arg Gly Arg Phe Thr Val Ser Arg Asp Asn Ala Gln Asn Ser Leu Phe
 65                  70                  75                  80

Leu Gln Met Asn Ser Leu Arg Ala Glu Asp Thr Ala Ile Tyr Phe Cys
                 85                  90                  95

Val Val Ser Met Val Gly Pro Phe Asp Tyr Trp Gly His Gly Thr Leu
            100                 105                 110

Val Thr Val Ser Ser
            115
```

<210> SEQ ID NO 108
<211> LENGTH: 351
<212> TYPE: DNA
<213> ORGANISM: Canis familiaris

<400> SEQUENCE: 108

```
gaggtgcagc tggtggagtc tgggggagac ctggtgaagc ctgcagggtc cctgagactg      60
tcctgtgtgg cctctggatt caccttcagg acctatgtca tgaactgggt ccgccaggct    120
cctgggaagg gactgcaatg ggtcgcaagt attaacggtg gtggaagtag cccaacctac    180
gcagacgctg tgaggggccg attcaccgtc tccagggaca acgcccagaa ctcactgttt    240
```

-continued

```
ctgcagatga acagcctgag agccgaggac acagccatat attttgtgt cgtgtcgatg    300 gttgggccct tcgactactg gggccatggg accctggtca ccgtgtcctc a            351
```

<210> SEQ ID NO 109
<211> LENGTH: 107
<212> TYPE: PRT
<213> ORGANISM: Canis familiaris

<400> SEQUENCE: 109

Ser Ser Val Leu Thr Gln Pro Pro Ser Val Ser Val Ser Leu Gly Gln
1               5                   10                  15

Thr Ala Thr Ile Ser Cys Ser Gly Lys Ser Leu Ser Tyr Tyr Tyr Ala
            20                  25                  30

Gln Trp Phe Gln Gln Lys Ala Gly Gln Ala Pro Val Leu Val Ile Tyr
        35                  40                  45

Lys Asp Thr Glu Arg Pro Ser Gly Ile Pro Asp Arg Phe Ser Gly Ser
    50                  55                  60

Ser Ser Gly Asn Thr His Thr Leu Thr Ile Ser Gly Ala Arg Ala Glu
65                  70                  75                  80

Asp Glu Ala Asp Tyr Tyr Cys Glu Ser Ala Val Ser Ser Asp Thr Ile
                85                  90                  95

Val Phe Gly Gly Gly Thr His Leu Thr Val Leu
            100                 105

<210> SEQ ID NO 110
<211> LENGTH: 321
<212> TYPE: DNA
<213> ORGANISM: Canis familiaris

<400> SEQUENCE: 110

```
tccagtgtgc tgactcagcc tccctcggta tcagtgtctc tggggcagac agcaaccatc    60
tcctgctctg gaaagagtct gagttactat tatgcacaat ggttccagca gaaggcaggc    120
caagcccctg tgttggtcat atataaggac actgagcggc cctctgggat ccctgaccga    180
ttctctggct ccagttcagg gaacacacac accctgacca tcagcggggc tcgggccgag    240
gacgaggctg actattactg tgagtcagca gtcagttctg atactattgt gttcggcgga    300
ggcacccacc tgaccgtcct c                                              321
```

<210> SEQ ID NO 111
<211> LENGTH: 121
<212> TYPE: PRT
<213> ORGANISM: Artificial Sequence
<220> FEATURE:
<223> OTHER INFORMATION: Felinized variable heavy mAb sequence, from Mus
      musculus and Felis catus

<400> SEQUENCE: 111

Gln Val Leu Leu Val Gln Ser Gly Ala Glu Val Lys Lys Pro Gly Ala
1               5                   10                  15

Ser Val Lys Ile Phe Cys Lys Ala Ser Gly Tyr Ser Phe Thr Tyr Tyr
            20                  25                  30

Asp Ile Asn Trp Leu Arg Gln Ala Pro Glu Gln Gly Leu Glu Trp Met
        35                  40                  45

Gly Trp Ile Phe Pro Gly Asp Gly Gly Thr Lys Tyr Asn Glu Thr Phe
    50                  55                  60

Lys Gly Arg Leu Thr Leu Thr Ala Asp Thr Ser Thr Asn Thr Val Tyr
65                  70                  75                  80

```
Met Glu Leu Ser Ser Leu Arg Ser Ala Asp Thr Ala Met Tyr Tyr Cys
                85                  90                  95

Ala Arg Gly Gly Thr Ser Val Ile Arg Asp Ala Met Asp Tyr Trp Gly
            100                 105                 110

Gln Gly Ala Leu Val Thr Val Ser Ser
        115                 120
```

<210> SEQ ID NO 112
<211> LENGTH: 363
<212> TYPE: DNA
<213> ORGANISM: Artificial Sequence
<220> FEATURE:
<223> OTHER INFORMATION: Nucleotide sequence encoding felinized variable
      heavy mAb sequence, from Mus musculus and Felis catus

<400> SEQUENCE: 112

```
caggtgctgc tggtccagtc aggagcagag gtaaaaaagc ccggggcgag tgtcaagatt    60
ttctgtaagg cctccggata ctcttttacg tattacgata ttaactggct tcgccaggcc   120
cctgagcagg ggctcgaatg gatgggttgg atattccccg agatgggggg aaccaagtac   180
aacgaaacct tcaaggggag gctgaccctg actgcagata ccagcacgaa cacagtgtat   240
atggagttgt cctcactgcg atctgctgat actgccatgt actactgcgc tcgcggcggc   300
acttcagtta tcagggatgc catggactat tgggggcagg gcgcactcgt cactgtctcg   360
agc                                                                 363
```

<210> SEQ ID NO 113
<211> LENGTH: 106
<212> TYPE: PRT
<213> ORGANISM: Artificial Sequence
<220> FEATURE:
<223> OTHER INFORMATION: Felinized variable light mAb sequence, from Mus
      musculus and Felis catus

<400> SEQUENCE: 113

```
Glu Ile Gln Met Thr Gln Ser Pro Ser Ser Leu Ser Ala Ser Pro Gly
1               5                   10                  15

Asp Arg Val Thr Ile Thr Cys Arg Ala Ser Glu Ser Val Asp Asn Tyr
            20                  25                  30

Gly Ile Ser Phe Met His Trp Tyr Gln Gln Lys Pro Gly Lys Val Pro
        35                  40                  45

Lys Leu Leu Ile Tyr Arg Ala Ser Asn Leu Glu Ser Gly Val Pro Ser
50                  55                  60

Arg Phe Ser Gly Ser Gly Ser Gly Thr Asp Phe Thr Leu Thr Ile Ser
65                  70                  75                  80

Ser Leu Glu Pro Glu Asp Ala Ala Thr Tyr Tyr Cys Gln Gln Ser Asn
                85                  90                  95

Lys Asp Pro Leu Thr Phe Gly Gln Gly Thr
                100                 105
```

<210> SEQ ID NO 114
<211> LENGTH: 333
<212> TYPE: DNA
<213> ORGANISM: Artificial Sequence
<220> FEATURE:
<223> OTHER INFORMATION: Nucleotide sequence encoding felinized variable
      light mAb sequence, from Mus musculus and Felis catus

<400> SEQUENCE: 114

```
gaaatccaga tgacacaatc tcccagctcc ctcagcgcat ctcctggcga cagggtaacc      60
atcacctgcc gcgccagcga gtcagtagac aactatggca tatccttcat gcactggtat    120
caacaaaagc ccgggaaagt ccccaaactg ttgatttaca gagcaagcaa tctcgagtca    180
ggagtcccat ctcgcttctc tggttccggt tccggaaccg acttcactct gacaatttct    240
tctctggagc ccgaggatgc cgctacatat tactgtcagc aaagcaataa agatccactg    300
accttcggac agggtaccaa gctggagatc aaa                                  333
```

<210> SEQ ID NO 115
<211> LENGTH: 106
<212> TYPE: PRT
<213> ORGANISM: Artificial Sequence
<220> FEATURE:
<223> OTHER INFORMATION: Felinized variable light mAb sequence, from Mus musculus and Felis catus

<400> SEQUENCE: 115

```
Glu Val Val Leu Thr Gln Ser Ser Ala Phe Leu Ser Arg Thr Leu Lys
1               5                   10                  15

Glu Lys Ala Thr Ile Thr Cys Arg Ala Ser Glu Ser Val Asp Asn Tyr
            20                  25                  30

Gly Ile Ser Phe Met His Trp Tyr Gln Gln Lys Pro Asn Gln Ala Pro
        35                  40                  45

Lys Leu Leu Val Lys Arg Ala Ser Asn Leu Glu Ser Gly Ala Pro Ser
    50                  55                  60

Arg Phe Ser Gly Ser Gly Ser Gly Thr Asp Phe Thr Leu Thr Ile Ser
65                  70                  75                  80

Ser Pro Glu Pro Glu Asp Ala Ala Thr Tyr Tyr Cys Gln Gln Ser Asn
                85                  90                  95

Lys Asp Pro Leu Thr Phe Gly Gln Gly Thr
            100                 105
```

<210> SEQ ID NO 116
<211> LENGTH: 318
<212> TYPE: DNA
<213> ORGANISM: Artificial Sequence
<220> FEATURE:
<223> OTHER INFORMATION: Nucleotide sequence encoding felinized variable light mAb sequence, from Mus musculus and Felis catus

<400> SEQUENCE: 116

```
gaggtggtgc tgactcagag tagcgcgttt ctgtctcgga ccctgaaaga aaagctacc      60
atcacgtgca gggcaagcga gagcgtggac aactatggta tcagcttcat gcattggtat    120
cagcagaaac ctaatcaggc gcctaagctg ctcgtgaaaa gagcctccaa ccttgagagc    180
ggcgcaccat caaggttttc aggaagtggc agcgggacag acttcaccct tacaatctct    240
agtccagagc cggaggacgc agctacctac tattgccagc aatccaataa agacccgttg    300
acattcggcc aaggtacc                                                   318
```

<210> SEQ ID NO 117
<211> LENGTH: 106
<212> TYPE: PRT
<213> ORGANISM: Artificial Sequence
<220> FEATURE:
<223> OTHER INFORMATION: Felinized variable light mAb sequence, from Mus musculus and Felis catus

<400> SEQUENCE: 117

Glu Ile Gln Met Thr Gln Ser Pro Ser Ser Leu Ser Ala Ser Pro Gly
1               5                   10                  15

Asp Arg Val Thr Ile Thr Cys Arg Ala Ser Glu Ser Val Asp Asn Tyr
            20                  25                  30

Gly Ile Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Ser
50                  55                  60

Arg Phe Ser Gly Ser Gly Ser Gly Thr Asp Phe Thr Leu Thr Ile Ser
65                  70                  75                  80

Ser Leu Glu Pro Glu Asp Ala Ala Thr Tyr Tyr Cys Gln Gln Ser Asn
                85                  90                  95

Lys Asp Pro Leu Thr Phe Gly Gln Gly Thr
            100                 105

<210> SEQ ID NO 118
<211> LENGTH: 318
<212> TYPE: DNA
<213> ORGANISM: Artificial Sequence
<220> FEATURE:
<223> OTHER INFORMATION: Nucleotide sequence encoding felinized variable
      light mAb sequence, from Mus musculus and Felis catus

<400> SEQUENCE: 118
gagatccaga tgacccagtc tccatcctca ctgagtgcta gcccggggga tcgagtgact      60
ataacatgtc gggccagtga atcagtggac aactatggaa tcagtttat gcactggtat     120 cagcagaagc ccggccagcc accgaagctg ttgatttatc gcgcaagcaa tctggagtca     180
ggagtgccct ctagattttc tgggagcggt tctggcacag atttcacact cacaatatca     240
tccttggaac cggaagacgc agccacatac tattgccagc agagtaacaa ggacccttg      300 acttttggcc agggtacc                                                   318

<210> SEQ ID NO 119
<211> LENGTH: 106
<212> TYPE: PRT
<213> ORGANISM: Artificial Sequence
<220> FEATURE:
<223> OTHER INFORMATION: Felinized variable light mAb sequence, from Mus
      musculus and Felis catus

<400> SEQUENCE: 119

Glu Ile Gln Met Thr Gln Ser Pro Ser Ser Leu Ser Ala Ser Pro Gly
1               5                   10                  15

Asp Arg Val Thr Ile Thr Cys Arg Ala Ser Glu Ser Val Asp Asn Tyr
            20                  25                  30

Gly Ile Ser Phe Met His Trp Tyr Gln Gln Lys Pro Gly Gln Val Pro
        35                  40                  45

Lys Leu Leu Ile Tyr Arg Ala Ser Asn Leu Glu Ser Gly Val Pro Ser
50                  55                  60

Arg Phe Ser Gly Ser Gly Ser Gly Thr Asp Phe Thr Leu Thr Ile Ser
65                  70                  75                  80

Ser Leu Glu Pro Glu Asp Ala Ala Thr Tyr Tyr Cys Gln Gln Ser Asn
                85                  90                  95

Lys Asp Pro Leu Thr Phe Gly Gln Gly Thr
            100                 105

```
<210> SEQ ID NO 120
<211> LENGTH: 318
<212> TYPE: DNA
<213> ORGANISM: Artificial Sequence
<220> FEATURE:
<223> OTHER INFORMATION: Nucleotide sequence encoding felinized variable
      light mAb sequence, from Mus musculus and Felis catus

<400> SEQUENCE: 120
gagatccaga tgacccagtc tccatcctca ctgagtgcta gcccggggga tcgagtgact      60
ataacatgtc gggccagtga atcagtggac aactatggaa tcagttttat gcactggtat    120
cagcagaagc ccggccaggt cccgaagctg ttgatttatc gcgcaagcaa tctggagtca    180
ggagtgccct ctagattttc tgggagcggt tctggcacag atttcacact cacaatatca    240
tccttggaac cggaagacgc agccacatac tattgccagc agagtaacaa ggaccctttg    300
acttttggcc agggtacc                                                  318

<210> SEQ ID NO 121
<211> LENGTH: 122
<212> TYPE: PRT
<213> ORGANISM: Artificial Sequence
<220> FEATURE:
<223> OTHER INFORMATION: Felinized variable heavy mAb sequence, from Mus
      musculus and Felis catus

<400> SEQUENCE: 121

Gln Val Leu Leu Val Gln Ser Gly Ala Glu Val Arg Thr Pro Gly Ala
1               5                   10                  15

Ser Val Lys Ile Phe Cys Lys Ala Ser Gly Tyr Ser Phe Thr Ser Tyr
                20                  25                  30

Thr Ile His Trp Leu Arg Gln Ala Pro Ala Gln Gly Leu Glu Trp Met
            35                  40                  45

Gly Asn Ile Asn Pro Thr Ser Gly Tyr Thr Glu Asn Asn Gln Arg Phe
        50                  55                  60

Lys Asp Arg Leu Thr Leu Thr Ala Asp Thr Ser Thr Asn Thr Ala Tyr
65                  70                  75                  80

Met Glu Leu Ser Ser Leu Arg Ser Ala Asp Thr Ala Met Tyr Tyr Cys
                85                  90                  95

Ala Arg Trp Gly Phe Lys Tyr Asp Gly Glu Trp Ser Phe Asp Val Trp
                100                 105                 110

Gly Ala Gly Thr Thr Val Thr Val Ser Ser
            115                 120

<210> SEQ ID NO 122
<211> LENGTH: 366
<212> TYPE: DNA
<213> ORGANISM: Artificial Sequence
<220> FEATURE:
<223> OTHER INFORMATION: Nucleotide sequence encoding felinized variable
      heavy mAb sequence, from Mus musculus and Felis catus

<400> SEQUENCE: 122
caagtgcttc tggtgcaaag cggggcggaa gttaggaccc caggagcctc agtaaaaatt      60
ttttgtaagg catccggcta cagtttcacc agctacacta ttcactggct gaggcaggcc    120
ccggcccaag gctggagtg gatgggaaat atcaatccca cgtctggcta cacagagaat    180
aaccaaaggt ttaaggatag gctgactctg acagctgaca catcaaccaa tacggcatac    240
atggagctct cctctctccg gagtgccgac accgccatgt actactgtgc tcggtggggg    300
```

```
tttaaatacg atggcgagtg gagcttcgac gtgtggggcg cgggcacaac cgtgaccgtc    360
tcgagc                                                               366

<210> SEQ ID NO 123
<211> LENGTH: 122
<212> TYPE: PRT
<213> ORGANISM: Artificial Sequence
<220> FEATURE:
<223> OTHER INFORMATION: Felinized variable heavy mAb sequence, from Mus
      musculus and Felis catus

<400> SEQUENCE: 123

Gln Val Leu Leu Val Gln Ser Gly Ala Glu Val Arg Thr Pro Gly Ala
1               5                   10                  15

Ser Val Lys Ile Phe Cys Lys Ala Ser Gly Tyr Gly Phe Thr Ser Tyr
                20                  25                  30

Thr Ile His Trp Val Arg Gln Ser Pro Ala Gln Gly Leu Glu Trp Met
            35                  40                  45

Gly Asn Ile Asn Pro Thr Ser Gly Tyr Thr Glu Asn Asn Gln Arg Phe
        50                  55                  60

Lys Asp Arg Leu Thr Leu Thr Ala Asp Thr Ser Thr Asn Thr Ala Tyr
65                  70                  75                  80

Met Glu Leu Ser Ser Leu Arg Ser Ala Asp Thr Ala Met Tyr Tyr Cys
                85                  90                  95

Ala Arg Trp Gly Phe Lys Tyr Asp Gly Glu Trp Ser Phe Asp Val Trp
                100                 105                 110

Gly Ala Gly Thr Thr Val Thr Val Ser Ser
            115                 120

<210> SEQ ID NO 124
<211> LENGTH: 366
<212> TYPE: DNA
<213> ORGANISM: Artificial Sequence
<220> FEATURE:
<223> OTHER INFORMATION: Nucleotide sequence encoding felinized variable
      heavy mAb sequence, from Mus musculus and Felis catus

<400> SEQUENCE: 124
caggtgctgc tcgtgcagag cggagccgaa gtgaggacac ccggtgcgag tgtaaaaatt    60
ttttgcaagg caagcggcta cgggtttaca tcctatacca tccactgggt gaggcagtcc    120
ccagcgcagg gacttgaatg gatgggaaat attaatccaa caagcgggta tactgaaaac    180
aaccaaagat ttaaggacag actgacactc accgcagata catctacaaa tacagcctac    240
atggagttgt cttccctgcg gagtgccgac acggctatgt actactgtgc tcggtggggg    300
tttaagtatg atggcgaatg gtccttcgac gtctggggag ctggaaccac cgtgaccgtc    360
tcgagc                                                               366

<210> SEQ ID NO 125
<211> LENGTH: 122
<212> TYPE: PRT
<213> ORGANISM: Artificial Sequence
<220> FEATURE:
<223> OTHER INFORMATION: Felinized variable heavy mAb sequence, from Mus
      musculus and Felis catus

<400> SEQUENCE: 125

Gln Val Leu Leu Val Gln Ser Gly Ala Glu Val Arg Lys Pro Gly Ala
1               5                   10                  15
```

```
Ser Val Lys Ile Phe Cys Lys Ala Ser Gly Tyr Ser Phe Thr Ser Tyr
            20                  25                  30

Thr Ile His Trp Leu Arg Gln Ala Pro Glu Gln Gly Leu Glu Trp Met
            35                  40                  45

Gly Asn Ile Asn Pro Thr Ser Gly Tyr Thr Glu Asn Asn Gln Arg Phe
            50                  55                  60

Lys Asp Arg Leu Thr Leu Thr Ala Asp Thr Ser Thr Asn Thr Ala Tyr
 65              70                  75                  80

Met Glu Leu Ser Ser Leu Arg Ser Ala Asp Thr Ala Met Tyr Tyr Cys
                85                  90                  95

Ala Arg Trp Gly Phe Lys Tyr Asp Gly Glu Trp Ser Phe Asp Val Trp
            100                 105                 110

Gly Ala Gly Thr Thr Val Thr Val Ser Ser
            115                 120
```

<210> SEQ ID NO 126
<211> LENGTH: 366
<212> TYPE: DNA
<213> ORGANISM: Artificial Sequence
<220> FEATURE:
<223> OTHER INFORMATION: Nucleotide sequence encoding felinized variable heavy mAb sequence, from Mus musculus and Felis catus

<400> SEQUENCE: 126

```
caggtcctct tggttcaaag cggagccgaa gtccgaaaac cgggtgcctc agtgaaaatc      60
ttctgtaagg cctccggcta tagtttcacg agttacacaa tccactggct gcgacaggca     120
ccagagcagg gactggagtg gatgggaaat ataaatccga cgtctgggta cacagaaaac     180
aaccagagat tcaaggatag attgacactg accgcggata ctagtacaaa tacggcttac     240
atggaactgt cctcactccg gtcagccgac accgccatgt attactgtgc tcgctggggg     300
ttcaagtatg atggagagtg gagcttcgac gtatgggag ccggaaccac tgtgaccgtc     360
tcgagc                                                               366
```

<210> SEQ ID NO 127
<211> LENGTH: 107
<212> TYPE: PRT
<213> ORGANISM: Artificial Sequence
<220> FEATURE:
<223> OTHER INFORMATION: Felinized variable light mAb sequence, from Mus musculus and Felis catus

<400> SEQUENCE: 127

```
Glu Ile Gln Met Thr Gln Ser Pro Ser Ser Leu Ser Ala Ser Pro Gly
 1               5                  10                  15

Asp Arg Val Thr Ile Thr Cys Arg Ala Ser Gln Gly Ile Ser Ile Trp
            20                  25                  30

Leu Ser Trp Tyr Gln Gln Lys Pro Gly Lys Val Pro Lys Leu Leu Ile
            35                  40                  45

Tyr Lys Ala Ser Asn Leu His Ile Gly Val Pro Ser Arg Phe Ser Gly
            50                  55                  60

Ser Gly Ser Gly Thr Asp Phe Thr Leu Thr Ile Ser Ser Leu Glu Pro
 65              70                  75                  80

Glu Asp Ala Ala Thr Tyr Tyr Cys Leu Gln Ser Gln Thr Tyr Pro Leu
                85                  90                  95

Thr Phe Gly Gly Gly Thr Lys Leu Glu Ile Lys
            100                 105
```

```
<210> SEQ ID NO 128
<211> LENGTH: 321
<212> TYPE: DNA
<213> ORGANISM: Artificial Sequence
<220> FEATURE:
<223> OTHER INFORMATION: Nucleotide sequence encoding felinized variable
      light mAb sequence, from Mus musculus and Felis catus

<400> SEQUENCE: 128
gaaattcaga tgactcaatc accttcatct ttgagtgcat cacccggaga tagagttaca      60
atcacctgca gggcgagtca agggatctcc atatggttgt catggtatca gcagaaaccc     120
ggaaaggtcc cgaaactctt gatctacaag gcctctaacc tgcacattgg cgtgccaagc     180
cgattcagcg ggagcggaag tggcaccgac tttactctga cgatcagttc actggagccc     240
gaggacgctg caacatacta ttgtctgcaa tctcagacct accctctcac ctttggagga     300
ggtaccaagc tggagatcaa a                                                321

<210> SEQ ID NO 129
<211> LENGTH: 107
<212> TYPE: PRT
<213> ORGANISM: Artificial Sequence
<220> FEATURE:
<223> OTHER INFORMATION: Felinized variable light mAb sequence, from Mus
      musculus and Felis catus

<400> SEQUENCE: 129

Glu Ile Thr Met Thr Gln Ser Pro Gly Ser Leu Ala Gly Ser Pro Gly
1               5                   10                  15

Gln Gln Val Thr Met Asn Cys Arg Ala Ser Gln Gly Ile Ser Ile Trp
            20                  25                  30

Leu Ser Trp Tyr Gln Gln Lys Pro Gly Gln His Pro Lys Leu Leu Ile
        35                  40                  45

Tyr Lys Ala Ser Asn Leu His Ile Gly Val Pro Asp Arg Phe Ser Gly
    50                  55                  60

Ser Gly Ser Gly Thr Asp Phe Thr Leu Thr Ile Ser Asn Leu Gln Ala
65                  70                  75                  80

Glu Asp Val Ala Ser Tyr Tyr Cys Leu Gln Ser Gln Thr Tyr Pro Leu
                85                  90                  95

Thr Phe Gly Gly Gly Thr Lys Leu Glu Ile Lys
            100                 105

<210> SEQ ID NO 130
<211> LENGTH: 321
<212> TYPE: DNA
<213> ORGANISM: Artificial Sequence
<220> FEATURE:
<223> OTHER INFORMATION: Nucleotide sequence encoding felinized variable
      light mAb
      sequence, from Mus musculus and Felis catus

<400> SEQUENCE: 130
gaaattacca tgacacaaag ccccggctcc ctggccggct cccccggaca gcaagtgacc      60
atgaattgtc gggccagcca gggaatttct atatggctct cttggtatca gcaaaaaccc     120
ggacagcacc ctaaacttct gatctacaaa gcaagtaact tgcacatcgg cgtccctgat     180
cgattcagtg gctcaggttc cggtacagat tttactctta ccatcagcaa tctgcaggct     240
gaggatgtgg caagctatta ctgtctccaa agtcagactt accctctgac atttggggc      300 ggtaccaagc tggagatcaa a                                                321
```

<210> SEQ ID NO 131
<211> LENGTH: 107
<212> TYPE: PRT
<213> ORGANISM: Artificial Sequence
<220> FEATURE:
<223> OTHER INFORMATION: Felinized variable light mAb sequence, from Mus
      musculus and Felis catus

<400> SEQUENCE: 131

Glu Val Val Leu Thr Gln Ser Ser Ala Phe Leu Ser Arg Thr Leu Lys
1               5                   10                  15

Glu Lys Ala Thr Ile Thr Cys Arg Ala Ser Gln Gly Ile Ser Ile Trp
            20                  25                  30

Leu Ser Trp Tyr Gln Gln Lys Pro Asn Gln Ala Pro Lys Leu Leu Val
        35                  40                  45

Lys Lys Ala Ser Asn Leu His Ile Gly Ala Pro Ser Arg Phe Ser Gly
    50                  55                  60

Ser Gly Ser Gly Thr Asp Phe Thr Leu Thr Ile Ser Ser Pro Glu Pro
65                  70                  75                  80

Glu Asp Ala Ala Thr Tyr Tyr Cys Leu Gln Ser Gln Thr Tyr Pro Leu
                85                  90                  95

Thr Phe Gly Gly Gly Thr Lys Leu Gly Asp Gln
            100                 105

<210> SEQ ID NO 132
<211> LENGTH: 322
<212> TYPE: DNA
<213> ORGANISM: Artificial Sequence
<220> FEATURE:
<223> OTHER INFORMATION: Nucleotide sequence encoding felinized variable
      light mAb sequence, from Mus musculus and Felis catus

<400> SEQUENCE: 132
gaggtagtgc tgactcagtc ctccgccttc ttgtcaagaa ctctcaaaga gaaagcaaca      60
atcacttgtc gggcgtctca agggatatca atttggctga gctggtatca gcagaaacca     120
aatcaagcgc cgaaactgct ggtgaagaag gcctccaatc tccacattgg cgcacccagc     180
aggttttccg gcagtggctc tggcacagat tcactctga ccatcagctc acccgagccc      240
gaagacgccg ctacatacta ttgcttgcaa tcccagacat accccctgac ttttggggga     300
ggtaccaagc tgggagatca aa                                              322

<210> SEQ ID NO 133
<211> LENGTH: 107
<212> TYPE: PRT
<213> ORGANISM: Artificial Sequence
<220> FEATURE:
<223> OTHER INFORMATION: Felinized variable light mAb sequence, from Mus
      musculus and Felis catus

<400> SEQUENCE: 133

Asp Ile Gln Met Asn Gln Ser Pro Ser Ser Leu Ser Ala Ser Leu Gly
1               5                   10                  15

Asp Thr Ile Thr Val Thr Cys Arg Ala Ser Gln Gly Ile Ser Ile Trp
            20                  25                  30

Leu Ser Trp Tyr Gln Gln Lys Pro Gly Lys Val Pro Lys Leu Leu Ile
        35                  40                  45

Tyr Lys Ala Ser Asn Leu His Ile Gly Val Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Ala Ala Thr Tyr Tyr Cys Leu Gln Ser Gln Thr Tyr Pro Leu
                85                  90                  95

Thr Phe Gly Gly Gly Thr Lys Leu Glu Ile Lys
            100                 105

<210> SEQ ID NO 134
<211> LENGTH: 321
<212> TYPE: DNA
<213> ORGANISM: Artificial Sequence
<220> FEATURE:
<223> OTHER INFORMATION: Nucleotide sequence encoding felinized variable
      light mAb sequence, from Mus musculus and Felis catus

<400> SEQUENCE: 134
gacattcaga tgaatcagtc tcctagctca ctgtcagcca gccttggaga caccattaca      60
gtcacttgca gggcgagtca agggatctcc atatggttgt catggtatca gcagaaaccc     120
ggaaaggtcc cgaaactctt gatctacaag gcctctaacc tgcacattgg cgtgccaagc     180
cgattcagcg ggagcggaag tggcaccgac tttactctga cgatcagttc actggagccc     240
gaggacgctg caacatacta ttgtctgcaa tctcagacct accctctcac ctttggagga     300
ggtaccaagc tggagatcaa a                                                321

<210> SEQ ID NO 135
<211> LENGTH: 107
<212> TYPE: PRT
<213> ORGANISM: Artificial Sequence
<220> FEATURE:
<223> OTHER INFORMATION: Felinized variable light mAb sequence, from Mus
      musculus and Felis catus

<400> SEQUENCE: 135

Glu Ile Gln Met Thr Gln Ser Pro Ser Ser Leu Ser Ala Ser Pro Gly
1               5                   10                  15

Asp Arg Val Thr Ile Thr Cys Arg Ala Ser Gln Gly Ile Ser Ile Trp
            20                  25                  30

Leu Ser Trp Tyr Gln Gln Lys Pro Gly Asn Ile Pro Lys Val Leu Ile
        35                  40                  45

Asn Lys Ala Ser Asn Leu His Ile Gly Val Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Ala Ala Thr Tyr Tyr Cys Leu Gln Ser Gln Thr Tyr Pro Leu
                85                  90                  95

Thr Phe Gly Gly Gly Thr Lys Leu Glu Ile Lys
            100                 105

<210> SEQ ID NO 136
<211> LENGTH: 321
<212> TYPE: DNA
<213> ORGANISM: Artificial Sequence
<220> FEATURE:
<223> OTHER INFORMATION: Nucleotide sequence encoding felinized variable
      light mAb sequence, from Mus musculus and Felis catus

<400> SEQUENCE: 136
gaaattcaga tgactcaatc accttcatct ttgagtgcat caccggaga tagagttaca       60 atcacctgca gggcgagtca agggatctcc atatggttgt catggtatca gcagaaaccg     120
ggcaatatcc caaaggtgct gattaacaag gcctctaacc tgcacattgg cgtgccaagc     180

```
cgattcagcg ggagcggaag tggcaccgac tttactctga cgatcagttc actggagccc      240
gaggacgctg caacatacta ttgtctgcaa tctcagacct accctctcac ctttggagga      300
ggtaccaagc tggagatcaa a                                                 321
```

<210> SEQ ID NO 137
<211> LENGTH: 107
<212> TYPE: PRT
<213> ORGANISM: Artificial Sequence
<220> FEATURE:
<223> OTHER INFORMATION: Felinized variable light mAb sequence, from Mus
      musculus and Felis catus

<400> SEQUENCE: 137

```
Glu Ile Gln Met Thr Gln Ser Pro Ser Ser Leu Ser Ala Ser Pro Gly
1               5                   10                  15

Asp Arg Val Thr Ile Thr Cys Arg Ala Ser Gln Gly Ile Ser Ile Trp
            20                  25                  30

Leu Ser Trp Tyr Gln Gln Lys Pro Gly Lys Val Pro Lys Leu Leu Ile
        35                  40                  45

Tyr Lys Ala Ser Asn Leu His Ile Gly Val Pro Pro Arg Phe Ser Gly
    50                  55                  60

Ser Gly Ser Gly Thr His Phe Thr Leu Thr Ile Thr Ser Leu Gln Pro
65                  70                  75                  80

Glu Asp Ile Ala Thr Tyr Tyr Cys Leu Gln Ser Gln Thr Tyr Pro Leu
                85                  90                  95

Thr Phe Gly Gly Gly Thr Lys Leu Glu Ile Lys
            100                 105
```

<210> SEQ ID NO 138
<211> LENGTH: 321
<212> TYPE: DNA
<213> ORGANISM: Artificial Sequence
<220> FEATURE:
<223> OTHER INFORMATION: Nucleotide sequence encoding felinized variable
      light mAb sequence, from Mus musculus and Felis catus

<400> SEQUENCE: 138

```
gaaattcaga tgactcaatc accttcatct ttgagtgcat cacccggaga tagagttaca      60
atcacctgca gggcgagtca agggatctcc atatggttgt catggtatca gcagaaaccc     120
ggaaaggtcc cgaaactctt gatctacaag gcctctaacc tgcacattgg gtcccccca      180 aggttcagcg gatctggatc cgggacccac tttactctga ccataacaag cctgcagcct     240
gaagacattg ctacctatta ctgcctgcaa tctcagacct accctctcac ctttggagga     300
ggtaccaagc tggagatcaa a                                                321
```

<210> SEQ ID NO 139
<211> LENGTH: 107
<212> TYPE: PRT
<213> ORGANISM: Artificial Sequence
<220> FEATURE:
<223> OTHER INFORMATION: Felinized variable light mAb sequence, from Mus
      musculus and Felis catus

<400> SEQUENCE: 139

```
Asp Ile Gln Met Asn Gln Ser Pro Ser Ser Leu Ser Ala Ser Leu Gly
1               5                   10                  15

Asp Thr Ile Thr Val Thr Cys Arg Ala Ser Gln Gly Ile Ser Ile Trp
            20                  25                  30
```

```
Leu Ser Trp Tyr Gln Gln Lys Pro Gly Asn Ile Pro Lys Val Leu Ile
        35                  40                  45

Asn Lys Ala Ser Asn Leu His Ile Gly Val Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Ala Ala Thr Tyr Tyr Cys Leu Gln Ser Gln Thr Tyr Pro Leu
                85                  90                  95

Thr Phe Gly Gly Gly Thr Lys Leu Glu Ile Lys
            100                 105
```

<210> SEQ ID NO 140
<211> LENGTH: 321
<212> TYPE: DNA
<213> ORGANISM: Artificial Sequence
<220> FEATURE:
<223> OTHER INFORMATION: Nucleotide sequence encoding felinized variable
    light mAb sequence, from Mus musculus and Felis catus

<400> SEQUENCE: 140

```
gacattcaga tgaatcagtc tcctagctca ctgtcagcca gccttggaga caccattaca      60
gtcacttgca gggcgagtca agggatctcc atatggttgt catggtatca gcagaaaccg     120
ggcaatatcc caaggtgctg attaacaag gcctctaacc tgcacattgg cgtgccaagc     180
cgattcagcg ggagcggaag tggcaccgac tttactctga cgatcagttc actggagccc     240
gaggacgctg caacatacta ttgtctgcaa tctcagacct accctctcac ctttggagga     300
ggtaccaagc tggagatcaa a                                               321
```

<210> SEQ ID NO 141
<211> LENGTH: 107
<212> TYPE: PRT
<213> ORGANISM: Artificial Sequence
<220> FEATURE:
<223> OTHER INFORMATION: Felinized variable light mAb sequence, from Mus
    musculus and Felis catus

<400> SEQUENCE: 141

```
Asp Ile Gln Met Asn Gln Ser Pro Ser Ser Leu Ser Ala Ser Leu Gly
1               5                   10                  15

Asp Thr Ile Thr Val Thr Cys Arg Ala Ser Gln Gly Ile Ser Ile Trp
            20                  25                  30

Leu Ser Trp Tyr Gln Gln Lys Pro Gly Lys Val Pro Lys Leu Leu Ile
        35                  40                  45

Tyr Lys Ala Ser Asn Leu His Ile Gly Val Pro Pro Arg Phe Ser Gly
    50                  55                  60

Ser Gly Ser Gly Thr His Phe Thr Leu Thr Ile Thr Ser Leu Gln Pro
65                  70                  75                  80

Glu Asp Ile Ala Thr Tyr Tyr Cys Leu Gln Ser Gln Thr Tyr Pro Leu
                85                  90                  95

Thr Phe Gly Gly Gly Thr Lys Leu Glu Ile Lys
            100                 105
```

<210> SEQ ID NO 142
<211> LENGTH: 321
<212> TYPE: DNA
<213> ORGANISM: Artificial Sequence
<220> FEATURE:
<223> OTHER INFORMATION: Nucleotide sequence encoding felinized variable
    light mAb sequence, from Mus musculus and Felis catus

<400> SEQUENCE: 142

```
gacattcaga tgaatcagtc tcctagctca ctgtcagcca gccttggaga caccattaca    60
gtcacttgca gggcgagtca agggatctcc atatggttgt catggtatca gcagaaaccc   120
ggaaaggtcc cgaaactctt gatctacaag gcctctaacc tgcacattgg ggtcccccca   180
aggttcagcg gatctggatc cgggacccac tttactctga ccataacaag cctgcagcct   240
gaagacattg ctacctatta ctgcctgcaa tctcagacct accctctcac ctttggagga   300
ggtaccaagc tggagatcaa a                                              321
```

<210> SEQ ID NO 143
<211> LENGTH: 107
<212> TYPE: PRT
<213> ORGANISM: Artificial Sequence
<220> FEATURE:
<223> OTHER INFORMATION: Felinized variable light mAb sequence, from Mus
      musculus and Felis catus

<400> SEQUENCE: 143

```
Glu Ile Gln Met Thr Gln Ser Pro Ser Ser Leu Ser Ala Ser Pro Gly
1               5                   10                  15

Asp Arg Val Thr Ile Thr Cys Arg Ala Ser Gln Gly Ile Ser Ile Trp
            20                  25                  30

Leu Ser Trp Tyr Gln Gln Lys Pro Gly Asn Ile Pro Lys Val Leu Ile
        35                  40                  45

Asn Lys Ala Ser Asn Leu His Ile Gly Val Pro Pro Arg Phe Ser Gly
    50                  55                  60

Ser Gly Ser Gly Thr His Phe Thr Leu Thr Ile Thr Ser Leu Gln Pro
65                  70                  75                  80

Glu Asp Ile Ala Thr Tyr Tyr Cys Leu Gln Ser Gln Thr Tyr Pro Leu
                85                  90                  95

Thr Phe Gly Gly Gly Thr Lys Leu Glu Ile Lys
            100                 105
```

<210> SEQ ID NO 144
<211> LENGTH: 321
<212> TYPE: DNA
<213> ORGANISM: Artificial Sequence
<220> FEATURE:
<223> OTHER INFORMATION: Nucleotide sequence encoding felinized variable
      light mAb sequence, from Mus musculus and Felis catus

<400> SEQUENCE: 144

```
gaaattcaga tgactcaatc accttcatct ttgagtgcat cacccggaga tagagttaca    60
atcacctgca gggcgagtca agggatctcc atatggttgt catggtatca gcagaaaccg   120
ggcaatatcc caaaggtgct gattaacaag gcctctaacc tgcacattgg ggtcccccca   180
aggttcagcg gatctggatc cgggacccac tttactctga ccataacaag cctgcagcct   240
gaagacattg ctacctatta ctgcctgcaa tctcagacct accctctcac ctttggagga   300
ggtaccaagc tggagatcaa a                                              321
```

<210> SEQ ID NO 145
<211> LENGTH: 107
<212> TYPE: PRT
<213> ORGANISM: Artificial Sequence
<220> FEATURE:
<223> OTHER INFORMATION: Felinized variable light mAb sequence, from Mus
      musculus and Felis catus

<400> SEQUENCE: 145

Glu Ile Gln Met Thr Gln Ser Pro Ser Ser Leu Ser Ala Ser Pro Gly
1               5                   10                  15

Asp Arg Val Thr Ile Thr Cys Arg Ala Ser Gln Gly Ile Ser Ile Trp
            20                  25                  30

Leu Ser Trp Tyr Gln Gln Lys Pro Gly Asn Val Pro Lys Leu Leu Ile
        35                  40                  45

Tyr Lys Ala Ser Asn Leu His Ile Gly Val Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Ala Ala Thr Tyr Tyr Cys Leu Gln Ser Gln Thr Tyr Pro Leu
                85                  90                  95

Thr Phe Gly Gly Gly Thr Lys Leu Glu Ile Lys
            100                 105

<210> SEQ ID NO 146
<211> LENGTH: 321
<212> TYPE: DNA
<213> ORGANISM: Artificial Sequence
<220> FEATURE:
<223> OTHER INFORMATION: Nucleotide sequence encoding felinized variable
      light mAb sequence, from Mus musculus and Felis catus

<400> SEQUENCE: 146
gaaatccaga tgacacagtc ccccagtagc ctttccgctt caccgggcga tagagtcact      60
attacgtgca gggcctccca gggtatttct atctggctga gctggtatca gcagaagccc    120
ggtaatgtgc caaagctctt gatctacaag gcatctaacc ttcatatcgg agtgccctca    180
agatttagtg gtcaggcag cggaaccgat ttcacattga ccattagttc tctggaacca    240
gaggacgctg ccacttacta ctgcctgcag tcccaaacat acccttttgac ttttgggggg    300 ggtaccaagc tggagatcaa a                                             321

<210> SEQ ID NO 147
<211> LENGTH: 107
<212> TYPE: PRT
<213> ORGANISM: Artificial Sequence
<220> FEATURE:
<223> OTHER INFORMATION: Felinized variable light mAb sequence, from Mus
      musculus and Felis catus

<400> SEQUENCE: 147

Glu Ile Gln Met Thr Gln Ser Pro Ser Ser Leu Ser Ala Ser Pro Gly
1               5                   10                  15

Asp Arg Val Thr Ile Thr Cys Arg Ala Ser Gln Gly Ile Ser Ile Trp
            20                  25                  30

Leu Ser Trp Tyr Gln Gln Lys Pro Gly Lys Ile Pro Lys Leu Leu Ile
        35                  40                  45

Tyr Lys Ala Ser Asn Leu His Ile Gly Val Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Ala Ala Thr Tyr Tyr Cys Leu Gln Ser Gln Thr Tyr Pro Leu
                85                  90                  95

Thr Phe Gly Gly Gly Thr Lys Leu Glu Ile Lys
            100                 105

```
<210> SEQ ID NO 148
<211> LENGTH: 321
<212> TYPE: DNA
<213> ORGANISM: Artificial Sequence
<220> FEATURE:
<223> OTHER INFORMATION: Nucleotide sequence encoding felinized variable
      light mAb sequence, from Mus musculus and Felis catus

<400> SEQUENCE: 148
gagattcaga tgacccagag cccatcaagc ctctccgctt cccccggaga ccgggtgacc      60
atcacatgca gagcttcaca gggaatctca atctggctca gctggtatca gcagaagcca     120
ggcaagattc cgaagttgct tatctataag gccagtaacc tgcatatcgg agttccatca     180
agattcagtg gtagcggaag tgggacagat ttcactctca ccatcagctc cctcgaacca     240
gaggacgctg caacttacta ctgcctgcag tcccagacat atccacttac tttcggcggg     300
ggtaccaagc tggagatcaa a                                                321

<210> SEQ ID NO 149
<211> LENGTH: 107
<212> TYPE: PRT
<213> ORGANISM: Artificial Sequence
<220> FEATURE:
<223> OTHER INFORMATION: Felinized variable light mAb sequence, from Mus
      musculus and Felis catus

<400> SEQUENCE: 149

Glu Ile Gln Met Thr Gln Ser Pro Ser Ser Leu Ser Ala Ser Pro Gly
1               5                   10                  15

Asp Arg Val Thr Ile Thr Cys Arg Ala Ser Gln Gly Ile Ser Ile Trp
            20                  25                  30

Leu Ser Trp Tyr Gln Gln Lys Pro Gly Lys Val Pro Lys Val Leu Ile
        35                  40                  45

Tyr Lys Ala Ser Asn Leu His Ile Gly Val Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Ala Ala Thr Tyr Tyr Cys Leu Gln Ser Gln Thr Tyr Pro Leu
                85                  90                  95

Thr Phe Gly Gly Gly Thr Lys Leu Glu Ile Lys
            100                 105

<210> SEQ ID NO 150
<211> LENGTH: 322
<212> TYPE: DNA
<213> ORGANISM: Artificial Sequence
<220> FEATURE:
<223> OTHER INFORMATION: Nucleotide sequence encoding felinized variable
      light mAb sequence, from Mus musculus and Felis catus

<400> SEQUENCE: 150
gagattcaga tgactcagag cccatctagt ctctctgcat ctcccggaga cagagttacg      60
atcacctgca gggctagcca aggatatca atttggctgt cctggtatca gcaaaaacct      120
ggcaaagtgc caaaggtctt gatttacaaa gcatccaatt tgcacatcgg cgtccctagt     180
cgcttttccg gtctggtag cggcaccgac ttcaccctca cataagctc actcgagccg      240 gaagatgccg ctacttacta ttgcctgcag tctcagactt accccctgac tttcggcgga     300
ggtaccaagc tggagatcaa ac                                              322

<210> SEQ ID NO 151
```

<211> LENGTH: 107
<212> TYPE: PRT
<213> ORGANISM: Artificial Sequence
<220> FEATURE:
<223> OTHER INFORMATION: Felinized variable light mAb sequence, from Mus
      musculus and Felis catus

<400> SEQUENCE: 151

Glu Ile Gln Met Thr Gln Ser Pro Ser Ser Leu Ser Ala Ser Pro Gly
1               5                   10                  15

Asp Arg Val Thr Ile Thr Cys Arg Ala Ser Gln Gly Ile Ser Ile Trp
            20                  25                  30

Leu Ser Trp Tyr Gln Gln Lys Pro Gly Lys Val Pro Lys Leu Leu Ile
        35                  40                  45

Asn Lys Ala Ser Asn Leu His Ile Gly Val Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Ala Ala Thr Tyr Tyr Cys Leu Gln Ser Gln Tyr Pro Leu
                85                  90                  95

Thr Phe Gly Gly Gly Thr Lys Leu Glu Ile Lys
            100                 105

<210> SEQ ID NO 152
<211> LENGTH: 321
<212> TYPE: DNA
<213> ORGANISM: Artificial Sequence
<220> FEATURE:
<223> OTHER INFORMATION: Nucleotide sequence encoding felinized variable
      light mAb sequence, from Mus musculus and Felis catus

<400> SEQUENCE: 152
gagatccaga tgacgcagag ccctagcagc ctctctgcat ccccaggaga cagagtaaca      60
attacctgtc gcgccagcca gggaatatct atatggctgt catggtatca acagaaaccg     120
ggaaaggttc caaagctctt gatcaataag gctagcaatc tgcatattgg agtgccctcc     180
cgcttctctg gtagcggaag tggcacagat ttcaccctga ccattagtag tctggagcct     240
gaggatgcgg ccacctacta ctgcctccag tcccaaacct atcccctgac cttcggagga     300
ggtaccaagc tggagatcaa a                                               321

<210> SEQ ID NO 153
<211> LENGTH: 107
<212> TYPE: PRT
<213> ORGANISM: Artificial Sequence
<220> FEATURE:
<223> OTHER INFORMATION: Felinized variable light mAb sequence, from Mus
      musculus and Felis catus

<400> SEQUENCE: 153

Glu Ile Gln Met Thr Gln Ser Pro Ser Ser Leu Ser Ala Ser Pro Gly
1               5                   10                  15

Asp Arg Val Thr Ile Thr Cys Arg Ala Ser Gln Gly Ile Ser Ile Trp
            20                  25                  30

Leu Ser Trp Tyr Gln Gln Lys Pro Gly Asn Ile Pro Lys Leu Leu Ile
        35                  40                  45

Tyr Lys Ala Ser Asn Leu His Ile Gly Val Pro Ser Arg Phe Ser Gly
    50                  55                  60

Ser Gly Ser Gly Thr Asp Phe Thr Leu Thr Ile Ser Ser Leu Glu Pro
65                  70                  75                  80

```
Glu Asp Ala Ala Thr Tyr Tyr Cys Leu Gln Ser Gln Thr Tyr Pro Leu
            85                  90                  95

Thr Phe Gly Gly Gly Thr Lys Leu Glu Ile Lys
            100                 105

<210> SEQ ID NO 154
<211> LENGTH: 321
<212> TYPE: DNA
<213> ORGANISM: Artificial Sequence
<220> FEATURE:
<223> OTHER INFORMATION: Nucleotide sequence encoding felinized variable
      light mAb sequence, from Mus musculus and Felis catus

<400> SEQUENCE: 154
gaaattcaga tgactcagag tcctagcagc ctgtccgcaa gcccaggtga ccgagtcacc     60
ataacctgca gggccagtca ggggatctcc atatggctct cttggtatca acagaaaccc    120
ggcaatatcc ctaagctcct gatttataaa gcgtcaaatc tgcatatcgg ggtgccatca    180
agattctctg gtccggctc aggaaccgac tttaccctga ccatttcttc tctcgaaccc     240
gaggatgccg ccacctatta ttgccttcaa agccagacat acccattgac cttcggcggc    300
ggtaccaagc tggagatcaa a                                              321

<210> SEQ ID NO 155
<211> LENGTH: 159
<212> TYPE: PRT
<213> ORGANISM: Canis familiaris

<400> SEQUENCE: 155

Met Leu Ser His Thr Gly Pro Ser Arg Phe Ala Leu Phe Leu Leu Cys
1               5                   10                  15

Ser Met Glu Thr Leu Leu Ser Ser His Met Ala Pro Thr His Gln Leu
            20                  25                  30

Pro Pro Ser Asp Val Arg Lys Ile Ile Leu Glu Leu Gln Pro Leu Ser
        35                  40                  45

Arg Gly Leu Leu Glu Asp Tyr Gln Lys Lys Glu Thr Gly Val Pro Glu
    50                  55                  60

Ser Asn Arg Thr Leu Leu Leu Cys Leu Thr Ser Asp Ser Gln Pro Pro
65                  70                  75                  80

Arg Leu Asn Ser Ser Ala Ile Leu Pro Tyr Phe Arg Ala Ile Arg Pro
                85                  90                  95

Leu Ser Asp Lys Asn Ile Ile Asp Lys Ile Ile Glu Gln Leu Asp Lys
            100                 105                 110

Leu Lys Phe Gln His Glu Pro Glu Thr Glu Ile Ser Val Pro Ala Asp
        115                 120                 125

Thr Phe Glu Cys Lys Ser Phe Ile Leu Thr Ile Leu Gln Gln Phe Ser
    130                 135                 140

Ala Cys Leu Glu Ser Val Phe Lys Ser Leu Asn Ser Gly Pro Gln
145                 150                 155

<210> SEQ ID NO 156
<211> LENGTH: 477
<212> TYPE: DNA
<213> ORGANISM: Canis familiaris

<400> SEQUENCE: 156
atgctctccc acacaggacc atccaggttt gccctgttcc tgctctgctc tatggaaacc     60
ttgctgtcct cccatatggc acccacccat cagctaccac caagtgatgt acgaaaaatc    120
```

```
atcttggaat tacagcccct gtcgaggga cttttggaag actatcagaa gaaagagaca        180
ggggtgccag aatccaaccg taccttgctg ctgtgtctca cctctgattc ccaaccacca        240
cgcctcaaca gctcagccat cttgccttat ttcagggcaa tcagaccatt atcagataag        300
aacattattg ataaaatcat agaacagctt gacaaactca aatttcaaca tgaaccagaa        360
acagaaattt ctgtgcctgc agatactttt gaatgtaaaa gcttcatctt gacgatttta        420
cagcagttct cggcgtgcct ggaaagtgtg tttaagtcac taaactctgg acctcag          477
```

<210> SEQ ID NO 157
<211> LENGTH: 165
<212> TYPE: PRT
<213> ORGANISM: Artificial Sequence
<220> FEATURE:
<223> OTHER INFORMATION: Amino acid sequence representing wild-type feline IL-31 with C-terminal His tag

<400> SEQUENCE: 157

```
Met Leu Ser His Ala Gly Pro Ala Arg Phe Ala Leu Phe Leu Leu Cys
1               5                  10                  15

Cys Met Glu Thr Leu Leu Pro Ser His Met Ala Pro Ala His Arg Leu
            20                  25                  30

Gln Pro Ser Asp Ile Arg Lys Ile Ile Leu Glu Leu Arg Pro Met Ser
        35                  40                  45

Lys Gly Leu Leu Gln Asp Tyr Leu Lys Lys Glu Ile Gly Leu Pro Glu
    50                  55                  60

Ser Asn His Ser Ser Leu Pro Cys Leu Ser Ser Asp Ser Gln Leu Pro
65                  70                  75                  80

His Ile Asn Gly Ser Ala Ile Leu Pro Tyr Phe Arg Ala Ile Arg Pro
                85                  90                  95

Leu Ser Asp Lys Asn Thr Ile Asp Lys Ile Ile Glu Gln Leu Asp Lys
            100                 105                 110

Leu Lys Phe Gln Arg Glu Pro Glu Ala Lys Val Ser Met Pro Ala Asp
        115                 120                 125

Asn Phe Glu Arg Lys Asn Phe Ile Leu Ala Val Leu Gln Gln Phe Ser
    130                 135                 140

Ala Cys Leu Glu His Val Leu Gln Ser Leu Asn Ser Gly Pro Gln His
145                 150                 155                 160

His His His His His
                165
```

<210> SEQ ID NO 158
<211> LENGTH: 495
<212> TYPE: DNA
<213> ORGANISM: Artificial Sequence
<220> FEATURE:
<223> OTHER INFORMATION: Nucleotide sequence representing wild-type feline IL-31 gene with encoded C-terminal His tag

<400> SEQUENCE: 158

```
atgctttcac acgctggacc agcccgattc gccctcttcc tcctctgctg tatggagact        60
ctgttgccgt cccacatggc cccggcacat aggctgcagc cgtctgacat ccggaagatc       120
attctcgaac tccgcccat gtcgaagggg ttgctgcaag actacctgaa gaaggagatc        180
ggcctgcccg aaagcaacca ctcctcgctg ccttgcctgt caagcgattc ccagctgccc       240
cacattaacg gttccgccat cctcccgtac ttcggggcca tcagaccact gtcggacaag       300
aacaccatcg acaagatcat tgaacagctg gacaagctga agtttcagcg cgagcctgaa       360
```

```
gccaaagtgt ccatgcccgc cgataacttc gagcggaaga atttcattct cgcggtgctg    420
cagcagttct ccgcgtgcct ggagcacgtc ctgcaatccc tgaacagcgg acctcagcac    480
caccatcacc accat                                                    495
```

<210> SEQ ID NO 159
<211> LENGTH: 148
<212> TYPE: PRT
<213> ORGANISM: Artificial Sequence
<220> FEATURE:
<223> OTHER INFORMATION: Amino acid sequence representing feline IL-31 protein with N-terminal His tag

<400> SEQUENCE: 159

```
Met Arg Gly Ser His His His His His His Gly Ser Ser His Met Ala
1               5                   10                  15

Pro Ala His Arg Leu Gln Pro Ser Asp Ile Arg Lys Ile Ile Leu Glu
            20                  25                  30

Leu Arg Pro Met Ser Lys Gly Leu Leu Gln Asp Tyr Leu Lys Lys Glu
        35                  40                  45

Ile Gly Leu Pro Glu Ser Asn His Ser Ser Leu Pro Cys Leu Ser Ser
    50                  55                  60

Asp Ser Gln Leu Pro His Ile Asn Gly Ser Ala Ile Leu Pro Tyr Phe
65                  70                  75                  80

Arg Ala Ile Arg Pro Leu Ser Asp Lys Asn Thr Ile Asp Lys Ile Ile
                85                  90                  95

Glu Gln Leu Asp Lys Leu Lys Phe Gln Arg Glu Pro Glu Ala Lys Val
            100                 105                 110

Ser Met Pro Ala Asp Asn Phe Glu Arg Lys Asn Phe Ile Leu Ala Val
        115                 120                 125

Leu Gln Gln Phe Ser Ala Cys Leu Glu His Val Leu Gln Ser Leu Asn
    130                 135                 140

Ser Gly Pro Gln
145
```

<210> SEQ ID NO 160
<211> LENGTH: 444
<212> TYPE: DNA
<213> ORGANISM: Artificial Sequence
<220> FEATURE:
<223> OTHER INFORMATION: Nucleotide sequence representing feline IL-31 gene with encoded N-terminal His tag

<400> SEQUENCE: 160

```
atgagaggat cccatcacca tcaccaccac ggctcatctc atatggcccc cgcacatcgc    60
ctgcagccga gtgacattcg taaaattatc ttggagctgc gcccgatgtc caagggctta    120
ctgcaggatt atctgaagaa agagatcggg ctgcctgaaa gcaaccatag tagcctgccg    180
tgtttatcgt ctgatagcca gttaccacac atcaatggct ctgcgatttt gccctacttt    240
cgcgccatcc gtccgctgtc cgataaaaat accatcgaca aaattatcga acaactggat    300
aaattgaagt ttcagcgcga gcctgaagcg aaagtttcga tgccagcmga taacttcgaa    360
cgcaaaaact ttattttagc ggtgttgcag cagttttctg cctgtctgga acacgtgctc    420
cagtcactca atagtgggcc acaa                                          444
```

<210> SEQ ID NO 161
<211> LENGTH: 165
<212> TYPE: PRT
<213> ORGANISM: Artificial Sequence

```
<220> FEATURE:
<223> OTHER INFORMATION: Amino acid sequence representing mutant Feline
      IL-31 11E12 protein with C-terminal His tag

<400> SEQUENCE: 161

Met Leu Ser His Ala Gly Pro Ala Arg Phe Ala Leu Phe Leu Leu Cys
1               5                   10                  15

Cys Met Glu Thr Leu Leu Pro Ser His Met Ala Pro Ala His Arg Leu
                20                  25                  30

Gln Pro Ser Asp Ile Arg Lys Ile Leu Glu Leu Arg Pro Met Ser
            35                  40                  45

Lys Gly Leu Leu Gln Asp Tyr Leu Lys Glu Ile Gly Leu Pro Glu
    50                  55                  60

Ser Asn His Ser Ser Leu Pro Cys Leu Ser Ser Asp Ser Gln Leu Pro
65                  70                  75                  80

His Ile Asn Gly Ser Ala Ile Leu Pro Tyr Phe Arg Ala Ile Arg Pro
                85                  90                  95

Leu Ser Asp Lys Asn Thr Ile Ala Lys Ile Ala Glu Gln Leu Asp Lys
                100                 105                 110

Leu Lys Phe Gln Arg Glu Pro Glu Ala Lys Val Ser Met Pro Ala Asp
            115                 120                 125

Asn Phe Glu Arg Lys Asn Phe Ile Leu Ala Val Leu Gln Gln Phe Ser
130                 135                 140

Ala Cys Leu Glu His Val Leu Gln Ser Leu Asn Ser Gly Pro Gln His
145                 150                 155                 160

His His His His His
                165

<210> SEQ ID NO 162
<211> LENGTH: 495
<212> TYPE: DNA
<213> ORGANISM: Artificial Sequence
<220> FEATURE:
<223> OTHER INFORMATION: Nucleotide sequence representing mutant feline
      IL-31 11E12 gene with encoded C-terminal His tag

<400> SEQUENCE: 162
atgctctctc acgccggtcc tgcccggttc gcactgttcc tcctctgttg catggagact    60
ctgcttccct cccacatggc accggcccat agactgcagc cgtccgacat cagaaagatc   120
atccttgaat tgcgccctat gagcaagggg ctgctgcagg attacctgaa aaaggagatc   180
ggcctgccgg aatcgaacca cagctcactg ccatgcctgt cctccgactc gcaactgccc   240
cacatcaatg gatccgccat tctgccgtac ttccgcgcta ttcggcctct ctccgacaag   300
aacaccatcg ccaagattgc cgagcagctg ataagctga agttccagag ggagccagaa   360
gccaaggtgt ccatgcccgc tgacaacttc gagcggaaga actttatcct cgcggtgctg   420
cagcagttct cagcgtgcct cgaacacgtc ttgcaaagcc tgaactcggg accccagcac   480
caccaccatc atcac                                                   495

<210> SEQ ID NO 163
<211> LENGTH: 165
<212> TYPE: PRT
<213> ORGANISM: Artificial Sequence
<220> FEATURE:
<223> OTHER INFORMATION: Amino acid sequence representing mutant feline
      IL-31 15H05 protein with C-terminal His tag
```

<400> SEQUENCE: 163

Met Leu Ser His Ala Gly Pro Ala Arg Phe Ala Leu Phe Leu Leu Cys
1               5                   10                  15

Cys Met Glu Thr Leu Leu Pro Ser His Met Ala Pro Ala His Arg Leu
            20                  25                  30

Gln Pro Ser Asp Ile Arg Lys Ile Ile Leu Glu Leu Arg Pro Met Ser
        35                  40                  45

Lys Gly Leu Leu Gln Asp Tyr Leu Lys Lys Glu Ile Gly Leu Pro Glu
50                  55                  60

Ser Asn His Ser Ser Leu Pro Cys Leu Ser Ser Asp Ser Gln Leu Pro
65                  70                  75                  80

His Ile Asn Gly Ser Ala Ile Leu Pro Tyr Phe Arg Ala Ile Arg Pro
                85                  90                  95

Leu Ser Asp Lys Asn Thr Ile Asp Lys Ile Ile Glu Gln Leu Asp Lys
            100                 105                 110

Leu Lys Phe Gln Arg Glu Pro Glu Ala Lys Val Ser Met Ala Ala Ala
        115                 120                 125

Asn Phe Glu Arg Lys Asn Phe Ile Leu Ala Val Leu Gln Gln Phe Ser
130                 135                 140

Ala Cys Leu Glu His Val Leu Gln Ser Leu Asn Ser Gly Pro Gln His
145                 150                 155                 160

His His His His His
                165

<210> SEQ ID NO 164
<211> LENGTH: 495
<212> TYPE: DNA
<213> ORGANISM: Artificial Sequence
<220> FEATURE:
<223> OTHER INFORMATION: Nucleotide sequence representing mutant feline
      IL-31 15H05 gene with encoded C-terminal His tag

<400> SEQUENCE: 164
atgctctctc acgccggtcc tgcccggttc gcactgttcc tcctctgttg catggagact    60
ctgcttccct cccacatggc accggcccat agactgcagc cgtccgacat cagaaagatc   120
atccttgaat gcgccctat gagcaagggg ctgctgcagg attacctgaa aaaggagatc   180
ggcctgccgg aatcgaacca cagctcactg ccatgcctgt cctccgactc gcaactgccc   240
cacatcaatg gatccgccat tctgccgtac ttccgcgcta ttcggcctct ctccgacaag   300
aacaccatcg acaagattat tgagcagctg gataagctga agttccagag ggagccagaa   360
gccaaggtgt ccatggccgc tgccaacttc gagcggaaga actttatcct cgcggtgctg   420
cagcagttct cagcgtgcct cgaacacgtc ttgcaaagcc tgaactcggg accccagcac   480
caccaccatc atcac                                                    495

<210> SEQ ID NO 165
<211> LENGTH: 152
<212> TYPE: PRT
<213> ORGANISM: Artificial Sequence
<220> FEATURE:
<223> OTHER INFORMATION: Amino acid sequence of Equine IL-31 protein
      with C-terminal His tag

<400> SEQUENCE: 165

Met Gly Trp Ser Cys Ile Ile Leu Phe Leu Val Ala Thr Ala Thr Gly
1               5                   10                  15

Val His Ser Gly Pro Ile Tyr Gln Leu Gln Pro Lys Glu Ile Gln Ala
            20                  25                  30

Ile Ile Val Glu Leu Gln Asn Leu Ser Lys Lys Leu Leu Asp Asp Tyr
        35                  40                  45

Leu Asn Lys Glu Lys Gly Val Gln Lys Phe Asp Ser Asp Leu Pro Ser
    50                  55                  60

Cys Phe Thr Ser Asp Ser Gln Ala Pro Gly Asn Ile Asn Ser Ser Ala
65                  70                  75                  80

Ile Leu Pro Tyr Phe Lys Ala Ile Ser Pro Ser Leu Asn Asn Asp Lys
                85                  90                  95

Ser Leu Tyr Ile Ile Glu Gln Leu Asp Lys Leu Asn Phe Gln Asn Ala
            100                 105                 110

Pro Glu Thr Glu Val Ser Met Pro Thr Asp Asn Phe Glu Arg Lys Arg
        115                 120                 125

Phe Ile Leu Thr Ile Leu Arg Trp Phe Ser Asn Cys Leu Glu His Arg
    130                 135                 140

Ala Gln His His His His His His
145                 150

<210> SEQ ID NO 166
<211> LENGTH: 456
<212> TYPE: DNA
<213> ORGANISM: Artificial Sequence
<220> FEATURE:
<223> OTHER INFORMATION: Nucleotide sequence of Equine IL-31 gene with
      encoded C-terminal His tag

<400> SEQUENCE: 166
atgggctggt cctgcatcat tctgtttctg gtggccacag ccaccggcgt gcactctgga      60
cctatctatc agctgcagcc caaagagatc caggccatca tcgtggaact gcagaacctg    120
agcaagaagc tgctggacga ctacctgaac aaagaaaagg gcgtgcagaa gttcgacagc    180
gacctgccta gctgcttcac cagcgattct caggcccctg gcaacatcaa cagcagcgcc    240
atcctgcctt acttcaaggc catctctccc agcctgaaca acgacaagag cctgtacatc    300
atcgagcagc tggacaagct gaacttccag aacgcccctg aaaccgaggt gtccatgcct    360
accgacaact tcgagcggaa gcggttcatc ctgaccatcc tgcggtggtt cagcaactgc    420
ctggaacaca gagcccagca ccaccaccat caccat                              456

<210> SEQ ID NO 167
<211> LENGTH: 652
<212> TYPE: PRT
<213> ORGANISM: Artificial Sequence
<220> FEATURE:
<223> OTHER INFORMATION: Amino acid sequence of extracellular domain of
      feline OSMR fused to human IgG1 Fc

<400> SEQUENCE: 167

Met Ala Leu Phe Ser Ala Phe Gln Thr Thr Phe Leu Leu Ala Leu Leu
1               5                   10                  15

Ser Leu Lys Thr Tyr Gln Ser Glu Val Leu Ser Glu Pro Leu Ser Leu
            20                  25                  30

Ala Pro Glu Ser Leu Glu Val Ser Ile Asp Ser Ala Arg Gln Cys Leu
        35                  40                  45

His Leu Lys Trp Ser Val His Asn Leu Ala Tyr His Gln Glu Leu Lys
    50                  55                  60

Met Val Phe Gln Ile Glu Ile Ser Arg Ile Lys Thr Ser Asn Val Ile
65                  70                  75                  80

```
Trp Val Glu Asn Tyr Ser Thr Thr Val Lys Arg Asn Gln Val Leu Arg
                85                  90                  95

Trp Ser Trp Glu Ser Lys Leu Pro Leu Glu Cys Ala Lys His Ser Val
            100                 105                 110

Arg Met Arg Gly Ala Val Asp Asp Ala Gln Val Pro Glu Leu Arg Phe
            115                 120                 125

Trp Ser Asn Trp Thr Ser Trp Glu Glu Val Asp Val Gln Ser Ser Leu
        130                 135                 140

Gly His Asp Pro Leu Phe Val Phe Pro Lys Asp Lys Leu Val Glu Glu
145                 150                 155                 160

Gly Ser Asn Val Thr Ile Cys Tyr Val Ser Arg Ser His Gln Asn Asn
                165                 170                 175

Ile Ser Cys Tyr Leu Glu Gly Val Arg Met His Gly Glu Gln Leu Asp
            180                 185                 190

Pro Asn Val Cys Val Phe His Leu Lys Asn Val Pro Phe Ile Arg Glu
        195                 200                 205

Thr Gly Thr Asn Ile Tyr Cys Lys Ala Asp Gln Gly Asp Val Ile Lys
        210                 215                 220

Gly Ile Val Leu Phe Val Ser Lys Val Phe Glu Glu Pro Lys Asp Phe
225                 230                 235                 240

Ser Cys Glu Thr Arg Asp Leu Lys Thr Leu Asn Cys Thr Trp Ala Pro
                245                 250                 255

Gly Ser Asp Ala Gly Leu Leu Thr Gln Leu Ser Gln Ser Tyr Thr Leu
            260                 265                 270

Phe Glu Ser Phe Ser Gly Lys Lys Thr Leu Cys Lys His Lys Ser Trp
        275                 280                 285

Cys Asn Trp Gln Val Ser Pro Asp Ser Gln Glu Met Tyr Asn Phe Thr
        290                 295                 300

Leu Thr Ala Glu Asn Tyr Leu Arg Lys Arg Ser Val His Leu Leu Phe
305                 310                 315                 320

Asn Leu Thr His Arg Val His Pro Met Ala Pro Phe Asn Val Phe Val
                325                 330                 335

Lys Asn Val Ser Ala Thr Asn Ala Thr Met Thr Trp Lys Val His Ser
            340                 345                 350

Ile Gly Asn Tyr Ser Thr Leu Leu Cys Gln Ile Glu Leu Asp Gly Glu
        355                 360                 365

Gly Lys Val Ile Gln Lys Gln Asn Val Ser Val Lys Val Asn Gly Lys
        370                 375                 380

His Leu Met Lys Lys Leu Glu Pro Ser Thr Glu Tyr Ala Ala Gln Val
385                 390                 395                 400

Arg Cys Ala Asn Ala Asn His Phe Trp Lys Trp Ser Glu Trp Thr Arg
                405                 410                 415

Arg Asn Phe Thr Thr Ala Glu Ala Ala Asp Lys Thr His Thr Cys Pro
            420                 425                 430

Pro Cys Pro Ala Pro Glu Leu Leu Gly Gly Pro Ser Val Phe Leu Phe
        435                 440                 445

Pro Pro Lys Pro Lys Asp Thr Leu Met Ile Ser Arg Thr Pro Glu Val
        450                 455                 460

Thr Cys Val Val Val Asp Val Ser His Glu Asp Pro Glu Val Lys Phe
465                 470                 475                 480

Asn Trp Tyr Val Asp Gly Val Glu Val His Asn Ala Lys Thr Lys Pro
                485                 490                 495
```

```
Arg Glu Glu Gln Tyr Asn Ser Thr Tyr Arg Val Val Ser Val Leu Thr
                500                 505                 510
Val Leu His Gln Asp Trp Leu Asn Gly Lys Glu Tyr Lys Cys Lys Val
        515                 520                 525
Ser Asn Lys Ala Leu Pro Ala Pro Ile Glu Lys Thr Ile Ser Lys Ala
        530                 535                 540
Lys Gly Gln Pro Arg Glu Pro Gln Val Tyr Thr Leu Pro Pro Ser Arg
545                 550                 555                 560
Glu Glu Met Thr Lys Asn Gln Val Ser Leu Thr Cys Leu Val Lys Gly
                565                 570                 575
Phe Tyr Pro Ser Asp Ile Ala Val Glu Trp Glu Ser Asn Gly Gln Pro
            580                 585                 590
Glu Asn Asn Tyr Lys Thr Thr Pro Pro Val Leu Asp Ser Asp Gly Ser
        595                 600                 605
Phe Phe Leu Tyr Ser Lys Leu Thr Val Asp Lys Ser Arg Trp Gln Gln
    610                 615                 620
Gly Asn Val Phe Ser Cys Ser Val Met His Glu Ala Leu His Asn His
625                 630                 635                 640
Tyr Thr Gln Lys Ser Leu Ser Leu Ser Pro Gly Lys
                645                 650
```

<210> SEQ ID NO 168
<211> LENGTH: 2076
<212> TYPE: DNA
<213> ORGANISM: Artificial Sequence
<220> FEATURE:
<223> OTHER INFORMATION: Nucleotide sequence encoding extracellular
      domain of feline OSMR fused to human IgG1 Fc

<400> SEQUENCE: 168

```
atggccctgt tcagcgcctt ccagaccacc ttcctgctgg ccctgctgag cctgaaaacc      60
taccagagcg aggtgctgag cgagcccctg tctctggccc ctgagagcct ggaagtgtcc     120
atcgacagcg ccagacagtg cctgcacctg aagtggagcg tgcacaacct ggcctaccac     180
caggaactga gatggtgtt  ccagatcgag atcagccgga tcaagaccag caacgtgatc     240
tgggtggaaa actacagcac caccgtgaag cggaaccagg tgctgcggtg gtcctgggag     300
tctaagctgc ctctggaatg cgccaagcac agcgtgcgga tgagaggcgc cgtggatgat     360
gcccaggtgc ccgagctgag attctggtcc aactggacct cctgggaaga ggtggacgtg     420
cagtctagcc tgggccacga ccccctgttc gtgttcccca aggacaagct ggtggaagag     480
ggctccaacg tgaccatctg ctacgtgtcc agaagccacc agaacaacat cagctgctac     540
ctggaaggcg tgcgcatgca cggcgagcag ctggacccta cgtgtgcgt  gttccacctg     600
aagaacgtgc ccttcatcag agagacaggc accaacatct actgcaaggc cgaccagggc     660
gacgtgatca agggcatcgt gctgtttgtg tccaaggtgt cgaggaacc  caaggacttc     720
agctgcgaga cacgggatct gaaaaccctg aactgtacct gggcccctgg ctccgatgcc     780
ggactgctga ctcagctgtc ccagagctac accctgttcg agagcttcag cggcaaaaag     840
accctgtgca gcacaagag  ctggtgcaac tggcaagtgt ccccgatag  ccaggaaatg     900
tacaacttca ccctgaccgc cgagaactac ctgcggaaga gatccgtgca tctgctgttc     960
aacctgaccc acagagtgca cccatggcc  cccttcaacg tgttcgtgaa gaatgtgtcc    1020
gccaccaacg ccaccatgac atggaaggtg cacagcatcg caactactc  cacccctgctg   1080
tgtcagatcg agctggacgg cgagggcaaa gtgatccaga acagaacgt  gtcagtgaaa    1140
```

```
gtgaacggca agcacctgat gaagaagctg aacccagca ccgagtacgc cgcccaggtg   1200
cgctgtgcca acgccaacca cttctggaag tggagtgaat ggacccggcg aacttcacc    1260 acagccgaag ccgccgctga aacgaggtg tccacaccta tgcaggccct gaccaccaac    1320
aaggacgacg acaacatcct gttccgggac tccgccaatg ccaccagcct gcctgtgcag   1380
gatagcagct ctgtgctgcc cgccaagccc gagaacatct cctgcgtgtt ctactacgag   1440
gaaaacttca cttgcacctg gtcccccgag aagaggcca gctacacctg gtacaaagtg    1500
aagagaacct acagctacgg ctacaagagc gacatctgcc ccagcgacaa cagcaccaga   1560
ggcaaccaca ccttctgcag ctttctgccc ccaccatca ccaaccccga caactacacc    1620
atccaggtgg aagcccagaa cgccgacggc atcatcaagt ccgacatcac ccactggtcc   1680
ctggacgcca tcacaaagat cgagcccccc gagatcttct ccgtgaagcc tgtgctgggc   1740
gtgaagagga tggtgcagat caagtggatc cggcccgtgc tggccccagt gtctagcacc   1800
ctgaagtaca ccctgcgggt caagaccgtg aacagcgcct actggatgga agtgaatttc    1860
accaaagagg acatcgaccg ggacgagaca tacaatctga ccggactgca ggccttcaca   1920
gagtacgtgc tggctctgag atgcgccacc aaagaatcca tgttttggag cggctggtcc   1980
caggaaaaga tgggcaccac cgaagagggt aagcctatcc ctaaccctct cctcggtctc    2040
gattctacgc gtaccggtca tcatcaccat caccat                              2076
```

<210> SEQ ID NO 169
<211> LENGTH: 474
<212> TYPE: PRT
<213> ORGANISM: Artificial Sequence
<220> FEATURE:
<223> OTHER INFORMATION: Amino acid sequence of feline IL-31-Ra fused to human IgG1 Fc

<400> SEQUENCE: 169

```
Met Met Trp Pro Gln Val Trp Gly Leu Glu Ile Gln Phe Ser Pro Gln
1               5                   10                  15

Pro Ala Cys Ile Asp Leu Gly Met Met Trp Ala His Ala Leu Trp Thr
                20                  25                  30

Leu Leu Leu Leu Cys Lys Phe Ser Leu Ala Val Leu Pro Ala Lys Pro
            35                  40                  45

Glu Asn Ile Ser Cys Val Phe Tyr Tyr Glu Glu Asn Phe Thr Cys Thr
        50                  55                  60

Trp Ser Pro Glu Lys Glu Ala Ser Tyr Thr Trp Tyr Lys Val Lys Arg
65                  70                  75                  80

Thr Tyr Ser Tyr Gly Tyr Lys Ser Asp Ile Cys Pro Ser Asp Asn Ser
                85                  90                  95

Thr Arg Gly Asn His Thr Phe Cys Ser Phe Leu Pro Pro Thr Ile Thr
            100                 105                 110

Asn Pro Asp Asn Tyr Thr Ile Gln Val Glu Ala Gln Asn Ala Asp Gly
        115                 120                 125

Ile Ile Lys Ser Asp Ile Thr His Trp Ser Leu Asp Ala Ile Thr Lys
    130                 135                 140

Ile Glu Pro Pro Glu Ile Phe Ser Val Lys Pro Val Leu Gly Val Lys
145                 150                 155                 160

Arg Met Val Gln Ile Lys Trp Ile Arg Pro Val Leu Ala Pro Val Ser
                165                 170                 175

Ser Thr Leu Lys Tyr Thr Leu Arg Phe Lys Thr Val Asn Ser Ala Tyr
            180                 185                 190
```

```
Trp Met Glu Val Asn Phe Thr Lys Glu Asp Ile Asp Arg Asp Glu Thr
            195                 200                 205
Tyr Asn Leu Thr Gly Leu Gln Ala Phe Thr Tyr Val Leu Ala Leu
        210                 215                 220
Arg Cys Ala Thr Lys Glu Ser Met Phe Trp Ser Gly Trp Ser Gln Glu
225                 230                 235                 240
Lys Met Gly Thr Thr Glu Glu Asp Lys Thr His Thr Cys Pro Pro Cys
                245                 250                 255
Pro Ala Pro Glu Leu Leu Gly Gly Pro Ser Val Phe Leu Phe Pro Pro
            260                 265                 270
Lys Pro Lys Asp Thr Leu Met Ile Ser Arg Thr Pro Glu Val Thr Cys
        275                 280                 285
Val Val Val Asp Val Ser His Glu Asp Pro Glu Val Lys Phe Asn Trp
290                 295                 300
Tyr Val Asp Gly Val Glu Val His Asn Ala Lys Thr Lys Pro Arg Glu
305                 310                 315                 320
Glu Gln Tyr Asn Ser Thr Tyr Arg Val Val Ser Val Leu Thr Val Leu
                325                 330                 335
His Gln Asp Trp Leu Asn Gly Lys Glu Tyr Lys Cys Lys Val Ser Asn
            340                 345                 350
Lys Ala Leu Pro Ala Pro Ile Glu Lys Thr Ile Ser Lys Ala Lys Gly
        355                 360                 365
Gln Pro Arg Glu Pro Gln Val Tyr Thr Leu Pro Pro Ser Arg Glu Glu
370                 375                 380
Met Thr Lys Asn Gln Val Ser Leu Thr Cys Leu Val Lys Gly Phe Tyr
385                 390                 395                 400
Pro Ser Asp Ile Ala Val Glu Trp Glu Ser Asn Gly Gln Pro Glu Asn
                405                 410                 415
Asn Tyr Lys Thr Thr Pro Pro Val Leu Asp Ser Asp Gly Ser Phe Phe
            420                 425                 430
Leu Tyr Ser Lys Leu Thr Val Asp Lys Ser Arg Trp Gln Gln Gly Asn
        435                 440                 445
Val Phe Ser Cys Ser Val Met His Glu Ala Leu His Asn His Tyr Thr
450                 455                 460
Gln Lys Ser Leu Ser Leu Ser Pro Gly Lys
465                 470
```

<210> SEQ ID NO 170
<211> LENGTH: 1422
<212> TYPE: DNA
<213> ORGANISM: Artificial Sequence
<220> FEATURE:
<223> OTHER INFORMATION: Nucleotide sequence encoding feline IL-31 Ra
      fused to human IgG1 Fc

<400> SEQUENCE: 170

```
atgatgtggc acaagtgtg gggcctggag atccagttca gcccccagcc tgcctgcatc      60
gatctgggca tgatgtgggc tcacgctctg tggaccctgc tgctgctgtg caagttttcc    120
ctggccgtgc tgcccgctaa gcctgagaac atcagctgcg tgttctacta tgaggagaac    180
ttcacctgta catggtcccc cgagaaggag gctagctata cctggtacaa ggtgaagaga    240
acatacagct atggctacaa gtctgatatc tgccccagcg acaactctac ccgcggcaat    300
cacacattct gttcttttct gcccccctacc atcacaaaacc tgataatta taccatccag    360 gtggaggccc agaacgctga tggcatcatc aagtctgaca tcacccattg gtccctggac    420
```

```
gccatcacaa agatcgagcc acccgagatt ttctccgtga agcccgtgct gggcgtgaag    480
aggatggtgc agatcaagtg gatcaggcct gtgctggctc cagtgtccag caccctgaag    540
tatacactga gattcaagac cgtgaactcc gcttactgga tggaggtgaa cttcaccaag    600
gaggacatcg atagggacga gacctataat ctgacaggcc tgcaggcctt caccgagtac    660
gtgctggccc tgaggtgcgc tacaaaggag tccatgtttt ggtccggctg gagccaggag    720
aagatgggca ccacagagga ggataagacc cacacatgcc ctccatgtcc agctccagag    780
ctgctgggag gaccaagcgt gttcctgttt ccacctaagc taaggacacc ctgatgatc    840 tctcgcaccc ctgaggtgac atgcgtggtg gtggacgtgt cccacgagga cccagaggtg    900
aagtttaact ggtatgtgga tggcgtggag gtgcataatg ccaagaccaa gcctagagag    960
gagcagtata acagcaccta ccgcgtggtg tctgtgctga cagtgctgca tcaggactgg    1020
ctgaacggca aggagtacaa gtgcaaggtg agcaataagg ccctgcctgc tccaatcgag    1080
aagaccatct ctaaggctaa gggacagcca agggagccac aggtgtatac actgccaccc    1140
agccgggagg agatgaccaa gaaccaggtg tctctgacat gtctggtgaa gggcttctac    1200
ccatctgata tcgctgtgga gtgggagtcc aatggccagc ccgagaacaa ttataagacc    1260
acacctccag tgctggattc tgacggctcc ttctttctgt actccaagct gaccgtggac    1320
aagagcaggt ggcagcaggg caacgtgttt tcttgctccg tgatgcatga ggctctgcac    1380
aatcattaca cacagaagag cctgtctctg tccccaggca ag                      1422
```

<210> SEQ ID NO 171
<211> LENGTH: 335
<212> TYPE: PRT
<213> ORGANISM: Felis catus

<400> SEQUENCE: 171

```
Ala Ser Thr Thr Ala Pro Ser Val Phe Pro Leu Ala Pro Ser Cys Gly
  1               5                  10                  15

Thr Thr Ser Gly Ala Thr Val Ala Leu Ala Cys Leu Val Leu Gly Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ala Ser Gly Leu Tyr Ser
     50                  55                  60

Leu Ser Ser Met Val Thr Val Pro Ser Ser Arg Trp Leu Ser Asp Thr
 65                  70                  75                  80

Phe Thr Cys Asn Val Ala His Pro Pro Ser Asn Thr Lys Val Asp Lys
                 85                  90                  95

Thr Val Arg Lys Thr Asp His Pro Pro Gly Pro Lys Pro Cys Asp Cys
            100                 105                 110

Pro Lys Cys Pro Pro Pro Glu Met Leu Gly Gly Pro Ser Ile Phe Ile
        115                 120                 125

Phe Pro Pro Lys Pro Lys Asp Thr Leu Ser Ile Ser Arg Thr Pro Glu
    130                 135                 140

Val Thr Cys Leu Val Val Asp Leu Gly Pro Asp Asp Ser Asp Val Gln
145                 150                 155                 160

Ile Thr Trp Phe Val Asp Asn Thr Gln Val Tyr Thr Ala Lys Thr Ser
                165                 170                 175

Pro Arg Glu Glu Gln Phe Asn Ser Thr Tyr Arg Val Val Ser Val Leu
            180                 185                 190
```

```
Pro Ile Leu His Gln Asp Trp Leu Lys Gly Lys Glu Phe Lys Cys Lys
        195                 200                 205
Val Asn Ser Lys Ser Leu Pro Ser Pro Ile Glu Arg Thr Ile Ser Lys
    210                 215                 220
Ala Lys Gly Gln Pro His Glu Pro Gln Val Tyr Val Leu Pro Pro Ala
225                 230                 235                 240
Gln Glu Glu Leu Ser Arg Asn Lys Val Ser Val Thr Cys Leu Ile Lys
                245                 250                 255
Ser Phe His Pro Pro Asp Ile Ala Val Glu Trp Glu Ile Thr Gly Gln
            260                 265                 270
Pro Glu Pro Glu Asn Asn Tyr Arg Thr Thr Pro Gln Leu Asp Ser
        275                 280                 285
Asp Gly Thr Tyr Phe Val Tyr Ser Lys Leu Ser Val Asp Arg Ser His
    290                 295                 300
Trp Gln Arg Gly Asn Thr Tyr Thr Cys Ser Val Ser His Glu Ala Leu
305                 310                 315                 320
His Ser His His Thr Gln Lys Ser Leu Thr Gln Ser Pro Gly Lys
                325                 330                 335

<210> SEQ ID NO 172
<211> LENGTH: 1005
<212> TYPE: DNA
<213> ORGANISM: Felis catus

<400> SEQUENCE: 172
gcctccacca cggcccccatc ggtgttccca ctggccccca gctgcgggac cacatctggc        60
gccaccgtgg ccctggcctg cctggtgtta ggctacttcc ctgagccggt gaccgtgtcc       120
tggaactccg gcgccctgac cagcggtgtg cacaccttcc cggccgtcct gcaggcctcg       180
gggctgtact ctctcagcag catggtgaca gtgccctcca gcaggtggct cagtgacacc       240
ttcacctgca acgtggccca cccgcccagc aacaccaagg tggacaagac cgtgcgcaaa       300
acagaccacc caccgggacc caaaccctgc gactgtccca atgcccaccc cctgagatg        360
cttggaggac cgtccatctt catcttcccc ccaaaaccca aggacaccct ctcgatttcc       420
cggacgcccg aggtcacatg cttggtggtg gacttgggcc agatgactc cgatgtccag        480
atcacatggt ttgtggataa cacccaggtg tacacagcca agacgagtcc gcgtgaggag       540
cagttcaaca gcacctaccg tgtggtcagt gtcctcccca tcctacacca ggactggctc       600
aagggggaagg agttcaagtg caaggtcaac agcaaatccc tcccctcccc catcgagagg       660
accatctcca aggccaaagg acagccccac gagcccagg tgtacgtcct gcctccagcc        720
caggaggagc tcagcaggaa caaagtcagt gtgacctgcc tgatcaaatc cttccacccg       780
cctgacattg ccgtcgagtg ggagatcacc ggacagccgg agccagagaa caactaccgg       840
acgaccccgc cccagctgga cagcgacggg acctacttcg tgtacagcaa gctctcggtg       900
gacaggtccc actggcagag ggaaacacc tacacctgct cggtgtcaca cgaagctctg        960
cacagccacc acacacagaa atccctcacc cagtctccgg gtaaa                     1005

<210> SEQ ID NO 173
<211> LENGTH: 335
<212> TYPE: PRT
<213> ORGANISM: Artificial Sequence
<220> FEATURE:
<223> OTHER INFORMATION: Amino acid sequence of feline heavy chain
      engineered with modifications to modulate antibody effector
      function
```

<400> SEQUENCE: 173

```
Ala Ser Thr Thr Ala Pro Ser Val Phe Pro Leu Ala Pro Ser Cys Gly
1               5                   10                  15

Thr Thr Ser Gly Ala Thr Val Ala Leu Ala Cys Leu Val Leu Gly Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ala Ser Gly Leu Tyr Ser
    50                  55                  60

Leu Ser Ser Met Val Thr Val Pro Ser Ser Arg Trp Leu Ser Asp Thr
65                  70                  75                  80

Phe Thr Cys Asn Val Ala His Pro Pro Ser Asn Thr Lys Val Asp Lys
                85                  90                  95

Thr Val Arg Lys Thr Asp His Pro Pro Gly Pro Lys Pro Cys Asp Cys
            100                 105                 110

Pro Lys Cys Pro Pro Pro Glu Ala Ala Gly Ala Pro Ser Ile Phe Ile
        115                 120                 125

Phe Pro Pro Lys Pro Lys Asp Thr Leu Ser Ile Ser Arg Thr Pro Glu
    130                 135                 140

Val Thr Cys Leu Val Val Asp Leu Gly Pro Asp Asp Ser Asp Val Gln
145                 150                 155                 160

Ile Thr Trp Phe Val Asp Asn Thr Gln Val Tyr Thr Ala Lys Thr Ser
                165                 170                 175

Pro Arg Glu Glu Gln Phe Asn Ser Thr Tyr Arg Val Val Ser Val Leu
            180                 185                 190

Pro Ile Leu His Gln Asp Trp Leu Lys Gly Lys Glu Phe Lys Cys Lys
        195                 200                 205

Val Asn Ser Lys Ser Leu Pro Ser Pro Ile Glu Arg Thr Ile Ser Lys
    210                 215                 220

Ala Lys Gly Gln Pro His Glu Pro Gln Val Tyr Val Leu Pro Pro Ala
225                 230                 235                 240

Gln Glu Glu Leu Ser Arg Asn Lys Val Ser Val Thr Cys Leu Ile Lys
                245                 250                 255

Ser Phe His Pro Pro Asp Ile Ala Val Glu Trp Glu Ile Thr Gly Gln
            260                 265                 270

Pro Glu Pro Glu Asn Asn Tyr Arg Thr Thr Pro Pro Gln Leu Asp Ser
        275                 280                 285

Asp Gly Thr Tyr Phe Val Tyr Ser Lys Leu Ser Val Asp Arg Ser His
    290                 295                 300

Trp Gln Arg Gly Asn Thr Tyr Thr Cys Ser Val Ser His Glu Ala Leu
305                 310                 315                 320

His Ser His His Thr Gln Lys Ser Leu Thr Gln Ser Pro Gly Lys
                325                 330                 335
```

<210> SEQ ID NO 174
<211> LENGTH: 1005
<212> TYPE: DNA
<213> ORGANISM: Artificial Sequence
<220> FEATURE:
<223> OTHER INFORMATION: Nucleotide sequence encoding feline heavy chain engineered with modifications to modulate antibody effector function

<400> SEQUENCE: 174

```
gcctccacca cggccccatc ggtgttccca ctggccccca gctgcgggac cacatctggc    60
gccaccgtgg ccctggcctg cctggtgtta ggctacttcc ctgagccggt gaccgtgtcc   120
tggaactccg gcgccctgac cagcggtgtg cacaccttcc cggccgtcct gcaggcctcg   180
gggctgtact ctctcagcag catggtgaca gtgccctcca gcaggtggct cagtgacacc   240
ttcacctgca acgtggccca cccgcccagc aacaccaagg tggacaagac cgtgcgcaaa   300
acagaccacc caccgggacc caaaccctgc gactgtccca aatgcccacc ccctgaggcg   360
gctggagcac cgtccatctt catcttcccc ccaaaaccca aggacaccct ctcgatttcc   420
cggacgcccg aggtcacatg cttggtggtg gacttgggcc agatgactc  cgatgtccag   480
atcacatggt ttgtggataa cacccaggtg tacacagcca agacgagtcc gcgtgaggag   540
cagttcaaca gcacctaccg tgtggtcagt gtcctcccca tcctacacca ggactggctc   600
aaggggaagg agttcaagtg caaggtcaac agcaaatccc tcccctcccc catcgagagg   660
accatctcca aggccaaagg acagccccac gagcccagg  tgtacgtcct gcctccagcc   720
caggaggagc tcagcaggaa caaagtcagt gtgacctgcc tgatcaaatc cttccacccg   780
cctgacattg ccgtcgagtg ggagatcacc ggacagccgg agccagagaa caactaccgg   840
acgaccccgc cccagctgga cagcgacggg acctacttcg tgtacagcaa gctctcggtg   900
gacaggtccc actggcagag gggaaacacc tacacctgct cggtgtcaca cgaagctctg   960
cacagccacc acacacagaa atccctcacc cagtctccgg gtaaa              1005
```

<210> SEQ ID NO 175
<211> LENGTH: 110
<212> TYPE: PRT
<213> ORGANISM: Artificial Sequence
<220> FEATURE:
<223> OTHER INFORMATION: Amino acid sequence of feline Kappa light chain engineered with glycosylation knockout (G-) at position 103

<400> SEQUENCE: 175

```
Arg Ser Asp Ala Gln Pro Ser Val Phe Leu Phe Gln Pro Ser Leu Asp
  1               5                  10                  15

Glu Leu His Thr Gly Ser Ala Ser Ile Val Cys Ile Leu Asn Asp Phe
             20                  25                  30

Tyr Pro Lys Glu Val Asn Val Lys Trp Lys Val Asp Gly Val Val Gln
         35                  40                  45

Asn Lys Gly Ile Gln Glu Ser Thr Thr Glu Gln Asn Ser Lys Asp Ser
     50                  55                  60

Thr Tyr Ser Leu Ser Ser Thr Leu Thr Met Ser Ser Thr Glu Tyr Gln
 65                  70                  75                  80

Ser His Glu Lys Phe Ser Cys Glu Val Thr His Lys Ser Leu Ala Ser
                 85                  90                  95

Thr Leu Val Lys Ser Phe Gln Arg Ser Glu Cys Gln Arg Glu
            100                 105                 110
```

<210> SEQ ID NO 176
<211> LENGTH: 330
<212> TYPE: DNA
<213> ORGANISM: Artificial Sequence
<220> FEATURE:
<223> OTHER INFORMATION: Nucleotide sequence encoding feline Kappa light chain engineered with glyosylation knockout (G-)

<400> SEQUENCE: 176

```
cggagtgatg ctcagccatc tgtctttctc ttccaaccat ctctggacga gttacataca    60
ggaagtgcct ctatcgtgtg catattgaat gacttctacc ccaaagaggt caatgtcaag   120
tggaaagtgg atggcgtagt ccaaaacaaa ggcatccagg agagcaccac agagcagaac   180
agcaaggaca gcacctacag cctcagcagc accctgacga tgtccagtac ggagtaccaa   240
agtcatgaaa agttctcctg cgaggtcact cacaagagcc tggcctccac cctcgtcaag   300
agcttccaga ggagcgagtg tcagagagag                                    330
```

<210> SEQ ID NO 177
<211> LENGTH: 335
<212> TYPE: PRT
<213> ORGANISM: Canis familiaris

<400> SEQUENCE: 177

```
Ala Ser Thr Thr Ala Pro Ser Val Phe Pro Leu Ala Pro Ser Cys Gly
1               5                   10                  15
Ser Thr Ser Gly Ser Thr Val Ala Leu Ala Cys Leu Val Ser Gly Tyr
            20                  25                  30
Phe Pro Glu Pro Val Thr Val Ser Trp Asn Ser Gly Ser Leu Thr Ser
        35                  40                  45
Gly Val His Thr Phe Pro Ser Val Leu Gln Ser Ser Gly Leu Tyr Ser
    50                  55                  60
Leu Ser Ser Met Val Thr Val Pro Ser Ser Arg Trp Pro Ser Glu Thr
65                  70                  75                  80
Phe Thr Cys Asn Val Ala His Pro Ala Ser Lys Thr Lys Val Asp Lys
                85                  90                  95
Pro Val Pro Lys Arg Glu Asn Gly Arg Val Pro Arg Pro Pro Asp Cys
            100                 105                 110
Pro Lys Cys Pro Ala Pro Glu Met Leu Gly Gly Pro Ser Val Phe Ile
        115                 120                 125
Phe Pro Pro Lys Pro Lys Asp Thr Leu Leu Ile Ala Arg Thr Pro Glu
    130                 135                 140
Val Thr Cys Val Val Val Asp Leu Asp Pro Glu Asp Pro Glu Val Gln
145                 150                 155                 160
Ile Ser Trp Phe Val Asp Gly Lys Gln Met Gln Thr Ala Lys Thr Gln
                165                 170                 175
Pro Arg Glu Glu Gln Phe Asn Gly Thr Tyr Arg Val Val Ser Val Leu
            180                 185                 190
Pro Ile Gly His Gln Asp Trp Leu Lys Gly Lys Gln Phe Thr Cys Lys
        195                 200                 205
Val Asn Asn Lys Ala Leu Pro Ser Pro Ile Glu Arg Thr Ile Ser Lys
    210                 215                 220
Ala Arg Gly Gln Ala His Gln Pro Ser Val Tyr Val Leu Pro Pro Ser
225                 230                 235                 240
Arg Glu Glu Leu Ser Lys Asn Thr Val Ser Leu Thr Cys Leu Ile Lys
                245                 250                 255
Asp Phe Phe Pro Pro Asp Ile Asp Val Glu Trp Gln Ser Asn Gly Gln
            260                 265                 270
Gln Glu Pro Glu Ser Lys Tyr Arg Thr Thr Pro Pro Gln Leu Asp Glu
        275                 280                 285
Asp Gly Ser Tyr Phe Leu Tyr Ser Lys Leu Ser Val Asp Lys Ser Arg
    290                 295                 300
```

Trp Gln Arg Gly Asp Thr Phe Ile Cys Ala Val Met His Glu Ala Leu
305                 310                 315                 320

His Asn His Tyr Thr Gln Glu Ser Leu Ser His Ser Pro Gly Lys
            325                 330                 335

<210> SEQ ID NO 178
<211> LENGTH: 1005
<212> TYPE: DNA
<213> ORGANISM: Canis familiaris

<400> SEQUENCE: 178

| | | | | | |
|---|---|---|---|---|---|
| gcctcaacaa | ctgctcctag | cgtgtttccc | ctggcccta | gctgcggaag | tacctcaggc | 60 |
| agcacagtgg | ccctggcttg | tctggtgtct | ggatatttcc | ctgagccagt | gaccgtgagt | 120 |
| tggaacagcg | gctctctgac | ctccggggtg | cacacatttc | catctgtgct | gcagtctagt | 180 |
| ggcctgtact | ccctgtcaag | catggtgact | gtgccttcct | ctaggtggcc | atcagaaact | 240 |
| ttcacctgca | acgtggccca | tcccgccagc | aagaccaaag | tggacaagcc | cgtgcctaaa | 300 |
| agggagaatg | gaagggtgcc | aagaccacct | gattgcccta | agtgtccagc | tccagaagcg | 360 |
| gcgggagcac | caagcgtgtt | catctttcca | cccaagccca | agacacact | gctgattgct | 420 |
| agaactcccg | aggtgacctg | cgtggtggtg | gacctggatc | cagaggaccc | cgaagtgcag | 480 |
| atctcctggt | tcgtggatgg | gaagcagatg | cagacagcca | aaactcagcc | tcggaggaa | 540 |
| cagtttaacg | aacctatag | agtggtgtct | gtgctgccaa | ttggacacca | ggactggctg | 600 |
| aagggcaaac | agtttacatg | caaggtgaac | aacaaggccc | tgcctagtcc | aatcgagagg | 660 |
| actatttcaa | aagctagggg | acaggctcat | cagccttccg | tgtatgtgct | gcctccatcc | 720 |
| cgggaggaac | tgtctaagaa | cacagtgagt | ctgacttgtc | tgatcaaaga | tttctttccc | 780 |
| cctgacattg | atgtggagtg | gcagagcaat | gggcagcagg | agccagaatc | caagtacaga | 840 |
| accacaccac | cccagctgga | cgaagatggc | tcctatttcc | tgtacagtaa | gctgtcagtg | 900 |
| gacaaatcta | ggtggcagcg | cggggatacc | tttatctgcg | ccgtgatgca | cgaggctctg | 960 |
| cacaatcatt | acacacaaga | aagtctgtca | catagccccg | gcaag | | 1005 |

<210> SEQ ID NO 179
<211> LENGTH: 106
<212> TYPE: PRT
<213> ORGANISM: Canis familiaris

<400> SEQUENCE: 179

Arg Asn Asp Ala Gln Pro Ala Val Tyr Leu Phe Gln Pro Ser Pro Asp
1               5                   10                  15

Gln Leu His Thr Gly Ser Ala Ser Val Val Cys Leu Leu Asn Ser Phe
            20                  25                  30

Tyr Pro Lys Asp Ile Asn Val Lys Trp Lys Val Asp Gly Val Ile Gln
        35                  40                  45

Asp Thr Gly Ile Gln Glu Ser Val Thr Glu Gln Asp Lys Asp Ser Thr
    50                  55                  60

Tyr Ser Leu Ser Ser Thr Leu Thr Met Ser Ser Thr Glu Tyr Leu Ser
65                  70                  75                  80

His Glu Leu Tyr Ser Cys Glu Ile Thr His Lys Ser Leu Pro Ser Thr
                85                  90                  95

Leu Ile Lys Ser Phe Gln Arg Ser Glu Cys
            100                 105

-continued

```
<210> SEQ ID NO 180
<211> LENGTH: 318
<212> TYPE: DNA
<213> ORGANISM: Canis familiaris

<400> SEQUENCE: 180
aggaacgacg cccagcctgc tgtgtatctg tttcagccct cccctgatca gctgcacact    60
ggctctgcta gtgtggtgtg tctgctgaac agcttctacc caaaggatat caatgtgaag   120
tggaaagtgg acggcgtgat ccaggatact gggattcagg agtccgtgac cgaacaggac   180
aaagattcaa catatagcct gagctccact ctgaccatgt ctagtaccga gtacctgagc   240
cacgaactgt attcctgcga gatcactcat aagtccctgc cctctaccct gatcaagagc   300
ttccagagat cagagtgt                                                 318

<210> SEQ ID NO 181
<211> LENGTH: 164
<212> TYPE: PRT
<213> ORGANISM: Homo sapiens

<400> SEQUENCE: 181

Met Ala Ser His Ser Gly Pro Ser Thr Ser Val Leu Phe Leu Phe Cys
1               5                   10                  15

Cys Leu Gly Gly Trp Leu Ala Ser His Thr Leu Pro Val Arg Leu Leu
                20                  25                  30

Arg Pro Ser Asp Asp Val Gln Lys Ile Val Glu Glu Leu Gln Ser Leu
            35                  40                  45

Ser Lys Met Leu Leu Lys Asp Val Glu Glu Lys Gly Val Leu Val
        50                  55                  60

Ser Gln Asn Tyr Thr Leu Pro Cys Leu Ser Pro Asp Ala Gln Pro Pro
65                  70                  75                  80

Asn Asn Ile His Ser Pro Ala Ile Arg Ala Tyr Leu Lys Thr Ile Arg
                85                  90                  95

Gln Leu Asp Asn Lys Ser Val Ile Asp Glu Ile Ile Glu His Leu Asp
            100                 105                 110

Lys Leu Ile Phe Gln Asp Ala Pro Glu Thr Asn Ile Ser Val Pro Thr
        115                 120                 125

Asp Thr His Glu Cys Lys Arg Phe Ile Leu Thr Ile Ser Gln Gln Phe
    130                 135                 140

Ser Glu Cys Met Asp Leu Ala Leu Lys Ser Leu Thr Ser Gly Ala Gln
145                 150                 155                 160

Gln Ala Thr Thr

<210> SEQ ID NO 182
<211> LENGTH: 111
<212> TYPE: PRT
<213> ORGANISM: Artificial Sequence
<220> FEATURE:
<223> OTHER INFORMATION: Caninized variable light chain mAb sequence,
      from Mus musculus and Canis

<400> SEQUENCE: 182

Asp Ile Val Met Thr Gln Thr Pro Leu Ser Leu Ser Val Ser Pro Gly
1               5                   10                  15

Glu Pro Ala Ser Ile Ser Cys Arg Ala Ser Glu Ser Val Asp Asn Tyr
                20                  25                  30

Gly Ile Ser Phe Met His Trp Phe Gln Gln Lys Pro Gly Gln Ser Pro
            35                  40                  45
```

```
Gln Arg Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Arg Ile Ser
65                  70                  75                  80

Arg Val Glu Ala Asp Asp Ala Gly Val Tyr Tyr Cys Gln Gln Ser Asn
                85                  90                  95

Lys Asp Pro Leu Thr Phe Gly Ala Gly Thr Lys Leu Glu Ile Lys
            100                 105                 110

<210> SEQ ID NO 183
<211> LENGTH: 333
<212> TYPE: DNA
<213> ORGANISM: Artificial Sequence
<220> FEATURE:
<223> OTHER INFORMATION: Nucleotide sequence encoding caninized variable
      light chain mAb sequence from Mus musculus and Canis

<400> SEQUENCE: 183
gacatcgtga tgacccagac ccccctgagc ctgagcgtgt cccctggcga gcctgccagc      60
atcagctgca gagccagcga gagcgtggac aactacggca tcagcttcat gcactggttc     120
cagcagaagc ccggccagag cccccagcgg ctgatctaca gagccagcaa cctggaaagc     180
ggcgtgcccg atcggtttag cggctctggc agcggcaccg acttcaccct gcggatctct     240
cgggtggaag ccgatgacgc cggagtgtac tactgccagc agagcaacaa ggaccccctg     300
acctttggcg ccggtaccaa gctggagatc aag                                  333

<210> SEQ ID NO 184
<211> LENGTH: 111
<212> TYPE: PRT
<213> ORGANISM: Artificial Sequence
<220> FEATURE:
<223> OTHER INFORMATION: Caninized variable light chain mAb sequence
      from Mus musculus and Canis

<400> SEQUENCE: 184

Asp Ile Val Met Thr Gln Thr Pro Leu Ser Leu Ser Val Ser Pro Gly
1               5                   10                  15

Glu Pro Ala Ser Ile Ser Cys Arg Ala Ser Glu Ser Val Asp Asn Tyr
            20                  25                  30

Gly Ile Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Arg Ile Ser
65                  70                  75                  80

Arg Val Glu Ala Asp Asp Ala Gly Val Tyr Tyr Cys Gln Gln Ser Asn
                85                  90                  95

Lys Asp Pro Leu Thr Phe Gly Ala Gly Thr Lys Leu Glu Ile Lys
            100                 105                 110

<210> SEQ ID NO 185
<211> LENGTH: 333
<212> TYPE: DNA
<213> ORGANISM: Artificial Sequence
<220> FEATURE:
<223> OTHER INFORMATION: Nucleotide sequence encoding caninized variable
      light chain mAb sequence from Mus musculus and Canis
```

<400> SEQUENCE: 185

```
gatatagtga tgacacaaac tcctctcagt ctttccgtat caccgggaga accggcttcc    60
atttcctgtc gggcctcaga gtctgtggac aactacggga tatccttcat gcactggtat   120
cagcagaaac ccggccagcc ccctaaactc cttatttaca gggccagtaa tctggaaagc   180
ggtgtgcccg atcgatttag cggttccggg agcggcacag atttcaccct gcgaatctct   240
agagttgaag cggatgatgc aggagtatat tactgccagc aatccaataa ggatccccttt  300
acattcggcg cgggtaccaa gctggagatc aag                                 333
```

<210> SEQ ID NO 186
<211> LENGTH: 107
<212> TYPE: PRT
<213> ORGANISM: Artificial Sequence
<220> FEATURE:
<223> OTHER INFORMATION: Amino acid sequence of feline Kappa light chain G minus with modified C-terminus

<400> SEQUENCE: 186

```
Arg Ser Asp Ala Gln Pro Ser Val Phe Leu Phe Gln Pro Ser Leu Asp
 1               5                  10                  15
Glu Leu His Thr Gly Ser Ala Ser Ile Val Cys Ile Leu Asn Asp Phe
             20                  25                  30
Tyr Pro Lys Glu Val Asn Val Lys Trp Lys Val Asp Gly Val Val Gln
         35                  40                  45
Asn Lys Gly Ile Gln Glu Ser Thr Thr Glu Gln Asn Ser Lys Asp Ser
     50                  55                  60
Thr Tyr Ser Leu Ser Ser Thr Leu Thr Met Ser Ser Thr Glu Tyr Gln
 65                  70                  75                  80
Ser His Glu Lys Phe Ser Cys Glu Val Thr His Lys Ser Leu Ala Ser
                 85                  90                  95
Thr Leu Val Lys Ser Phe Gln Arg Ser Glu Cys
            100                 105
```

<210> SEQ ID NO 187
<211> LENGTH: 324
<212> TYPE: DNA
<213> ORGANISM: Artificial Sequence
<220> FEATURE:
<223> OTHER INFORMATION: Nucleotide sequence encoding feline Kappa G minus with modified C-terminus

<400> SEQUENCE: 187

```
cggagtgatg ctcagccatc tgtctttctc ttccaaccat ctctggacga gttacataca    60
ggaagtgcct ctatcgtgtg catattgaat gacttctacc ccaaagaggt caatgtcaag   120
tggaaagtgg atggcgtagt ccaaaacaaa ggcatccagg agagcaccac agagcagaac   180
agcaaggaca gcacctacag cctcagcagc accctgacga tgtccagtac ggagtaccaa   240
agtcatgaaa agttctcctg cgaggtcact cacaagagcc tggcctccac cctcgtcaag   300
agcttccaga ggagcgagtg ttag                                           324
```

<210> SEQ ID NO 188
<211> LENGTH: 323
<212> TYPE: PRT
<213> ORGANISM: Mus musculus

<400> SEQUENCE: 188

| Lys | Thr | Thr | Pro | Pro | Ser | Val | Tyr | Pro | Leu | Ala | Pro | Gly | Ser | Ala | Ala |
|---|---|---|---|---|---|---|---|---|---|---|---|---|---|---|---|
| 1 | | | | 5 | | | | | 10 | | | | | 15 | |

| Gln | Thr | Asn | Ser | Met | Val | Thr | Leu | Gly | Cys | Leu | Val | Lys | Gly | Tyr | Phe |
|---|---|---|---|---|---|---|---|---|---|---|---|---|---|---|---|
| | | | 20 | | | | | 25 | | | | | 30 | | |

| Pro | Glu | Pro | Val | Thr | Val | Thr | Trp | Asn | Ser | Gly | Ser | Leu | Ser | Ser | Gly |
|---|---|---|---|---|---|---|---|---|---|---|---|---|---|---|---|
| | | 35 | | | | | 40 | | | | | 45 | | | |

| Val | His | Thr | Phe | Pro | Ala | Val | Leu | Glu | Ser | Asp | Leu | Tyr | Thr | Leu | Ser |
|---|---|---|---|---|---|---|---|---|---|---|---|---|---|---|---|
| | 50 | | | | | 55 | | | | | 60 | | | | |

| Ser | Ser | Val | Thr | Val | Pro | Ser | Ser | Pro | Arg | Pro | Ser | Glu | Thr | Val | Thr |
|---|---|---|---|---|---|---|---|---|---|---|---|---|---|---|---|
| 65 | | | | | 70 | | | | | 75 | | | | | 80 |

| Cys | Asn | Val | Ala | His | Pro | Ala | Ser | Ser | Thr | Lys | Val | Asp | Lys | Lys | Ile |
|---|---|---|---|---|---|---|---|---|---|---|---|---|---|---|---|
| | | | | 85 | | | | | 90 | | | | | 95 | |

| Val | Pro | Arg | Asp | Cys | Gly | Cys | Lys | Pro | Cys | Ile | Cys | Thr | Val | Pro | Glu |
|---|---|---|---|---|---|---|---|---|---|---|---|---|---|---|---|
| | | | 100 | | | | | 105 | | | | | 110 | | |

| Val | Ser | Ser | Val | Phe | Ile | Phe | Pro | Pro | Lys | Pro | Lys | Asp | Val | Leu | Thr |
|---|---|---|---|---|---|---|---|---|---|---|---|---|---|---|---|
| | | 115 | | | | | 120 | | | | | 125 | | | |

| Ile | Thr | Leu | Thr | Pro | Lys | Val | Thr | Cys | Val | Val | Val | Asp | Ile | Ser | Lys |
|---|---|---|---|---|---|---|---|---|---|---|---|---|---|---|---|
| | 130 | | | | | 135 | | | | | 140 | | | | |

| Asp | Asp | Pro | Glu | Val | Gln | Phe | Ser | Trp | Phe | Val | Asp | Asp | Val | Glu | Val |
|---|---|---|---|---|---|---|---|---|---|---|---|---|---|---|---|
| 145 | | | | | 150 | | | | | 155 | | | | | 160 |

| His | Thr | Ala | Gln | Thr | Gln | Pro | Arg | Glu | Glu | Gln | Phe | Asn | Ser | Thr | Phe |
|---|---|---|---|---|---|---|---|---|---|---|---|---|---|---|---|
| | | | | 165 | | | | | 170 | | | | | 175 | |

| Arg | Ser | Val | Ser | Glu | Leu | Pro | Ile | Met | His | Gln | Asp | Trp | Leu | Asn | Gly |
|---|---|---|---|---|---|---|---|---|---|---|---|---|---|---|---|
| | | | 180 | | | | | 185 | | | | | 190 | | |

| Lys | Glu | Phe | Lys | Cys | Arg | Val | Asn | Ser | Ala | Ala | Phe | Pro | Ala | Pro | Ile |
|---|---|---|---|---|---|---|---|---|---|---|---|---|---|---|---|
| | | 195 | | | | | 200 | | | | | 205 | | | |

| Glu | Lys | Thr | Ile | Ser | Lys | Thr | Lys | Gly | Arg | Pro | Lys | Ala | Pro | Gln | Val |
|---|---|---|---|---|---|---|---|---|---|---|---|---|---|---|---|
| | 210 | | | | | 215 | | | | | 220 | | | | |

| Tyr | Thr | Ile | Pro | Pro | Pro | Lys | Glu | Gln | Met | Ala | Lys | Asp | Lys | Val | Ser |
|---|---|---|---|---|---|---|---|---|---|---|---|---|---|---|---|
| 225 | | | | | 230 | | | | | 235 | | | | | 240 |

| Leu | Thr | Cys | Met | Ile | Thr | Asp | Phe | Phe | Pro | Glu | Asp | Ile | Thr | Val | Glu |
|---|---|---|---|---|---|---|---|---|---|---|---|---|---|---|---|
| | | | | 245 | | | | | 250 | | | | | 255 | |

| Trp | Gln | Trp | Asn | Gly | Gln | Pro | Ala | Glu | Asn | Tyr | Lys | Asn | Thr | Gln | Pro |
|---|---|---|---|---|---|---|---|---|---|---|---|---|---|---|---|
| | | | 260 | | | | | 265 | | | | | 270 | | |

| Ile | Met | Asn | Thr | Asn | Gly | Ser | Tyr | Phe | Val | Tyr | Ser | Lys | Leu | Asn | Val |
|---|---|---|---|---|---|---|---|---|---|---|---|---|---|---|---|
| | | 275 | | | | | 280 | | | | | 285 | | | |

| Gln | Lys | Ser | Asn | Trp | Glu | Ala | Gly | Asn | Thr | Phe | Thr | Cys | Ser | Val | Leu |
|---|---|---|---|---|---|---|---|---|---|---|---|---|---|---|---|
| | 290 | | | | | 295 | | | | | 300 | | | | |

| His | Glu | Gly | Leu | His | Asn | His | His | Thr | Glu | Lys | Ser | Leu | Ser | His | Ser |
|---|---|---|---|---|---|---|---|---|---|---|---|---|---|---|---|
| 305 | | | | | 310 | | | | | 315 | | | | | 320 |

Pro Gly Lys

<210> SEQ ID NO 189
<211> LENGTH: 971
<212> TYPE: DNA
<213> ORGANISM: Mus musculus

<400> SEQUENCE: 189
ccaaaacgac accccatct gtctatccac tggcccctgg atctgctgcc caaactaact        60
ccatggtgac cctgggatgc ctggtcaagg gctatttccc tgagccagtg acagtgacct      120
ggaactctgg atccctgtcc agcggtgtgc acaccttccc agctgtcctg gagtctgacc      180

```
tctacactct gagcagctca gtgactgtcc cctccagccc tcggcccagc gagaccgtca    240
cctgcaacgt tgcccacccg gccagcagca ccaaggtgga caagaaaatt gtgcccaggg    300
attgtggttg taagccttgc atatgtacag tcccagaagt atcatctgtc ttcatcttcc    360
ccccaaagcc caaggatgtg ctcaccatta ctctgactcc taaggtcacg tgtgttgtgg    420
tagacatcag caaggatgat cccgaggtcc agttcagctg gtttgtagat gatgtggagg    480
tgcacacagc tcagacgcaa ccccgggagg agcagttcaa cagcactttc cgctcagtca    540
gtgaacttcc catcatgcac caggactggc tcaatggcaa ggagttcaaa tgcagggtca    600
acagtgcagc tttccctgcc cccatcgaga aaaccatctc caaaaccaaa ggcagaccga    660
aggctccaca ggtgtacacc attccacctc ccaaggagca gatggccaag ataaagtca     720 gtctgacctg catgataaca gacttcttcc ctgaagacat tactgtggag tggcagtgga    780
atgggcagcc agcggagaac tacaagaaca ctcagcccat catgaacacg aatggctctt    840
acttcgtcta cagcaagctc aatgtgcaga gagcaactg ggaggcagga aatactttca    900
cctgctctgt gttacatgag ggcctgcaca accaccatac tgagaagagc ctctcccact    960
ctcctggtaa a                                                        971
```

<210> SEQ ID NO 190
<211> LENGTH: 106
<212> TYPE: PRT
<213> ORGANISM: Mus musculus

<400> SEQUENCE: 190

```
Ala Asp Ala Ala Pro Thr Val Ser Ile Phe Pro Pro Ser Ser Glu Gln
1               5                   10                  15

Leu Thr Ser Gly Gly Ala Ser Val Val Cys Phe Leu Asn Asn Phe Tyr
            20                  25                  30

Pro Lys Asp Ile Asn Val Lys Trp Lys Ile Asp Gly Ser Glu Arg Gln
        35                  40                  45

Asn Gly Val Leu Asn Ser Trp Thr Asp Gln Asp Ser Lys Asp Ser Thr
    50                  55                  60

Tyr Ser Met Ser Ser Thr Leu Thr Leu Thr Lys Asp Glu Tyr Glu Arg
65                  70                  75                  80

His Asn Ser Tyr Thr Cys Glu Ala Thr His Lys Thr Ser Thr Ser Pro
                85                  90                  95

Ile Val Lys Ser Phe Asn Arg Asn Glu Cys
            100                 105
```

<210> SEQ ID NO 191
<211> LENGTH: 321
<212> TYPE: DNA
<213> ORGANISM: Mus musculus

<400> SEQUENCE: 191

```
gctgatgctg caccaactgt atccatcttc ccaccatcca gtgagcagtt aacatctgga     60
ggtgcctcag tcgtgtgctt cttgaacaac ttctacccca agacatcaa tgtcaagtgg     120 aagattgatg gcagtgaacg acaaaatggc gtcctgaaca gttggactga tcaggacagc    180
aaagacagca cctacagcat gagcagcacc ctcacgttga ccaaggacga gtatgaacga    240
cataacagct atacctgtga ggccactcac aagacatcaa cttcacccat tgtcaagagc    300
ttcaacagga atgagtgtta g                                              321
```

<210> SEQ ID NO 192

<211> LENGTH: 106
<212> TYPE: PRT
<213> ORGANISM: Homo sapiens

<400> SEQUENCE: 192

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 193
<211> LENGTH: 321
<212> TYPE: DNA
<213> ORGANISM: Homo sapiens

<400> SEQUENCE: 193
actgtggctg caccatctgt cttcatcttc ccgccatctg atgagcagtt gaaatctgga      60
actgcctctg ttgtgtgcct gctgaataac ttctatccca gagaggccaa agtacagtgg     120
aaggtggata acgccctcca atcgggtaac tcccaggaga gtgtcacaga gcaggacagc     180
aaggacagca cctacagcct cagcagcacc ctgacgctga gcaaagcaga ctacgagaaa     240
cacaaagtct acgcctgcga agtcacccat cagggcctga gctcgcccgt cacaaagagc     300
ttcaacaggg gagagtgtta g                                               321

<210> SEQ ID NO 194
<211> LENGTH: 109
<212> TYPE: PRT
<213> ORGANISM: Canis familiaris

<400> SEQUENCE: 194

Asn Asp Ala Gln Pro Ala Val Tyr Leu Phe Gln Pro Ser Pro Asp Gln
1               5                   10                  15

Leu His Thr Gly Ser Ala Ser Val Val Cys Leu Leu Asn Ser Phe Tyr
            20                  25                  30

Pro Lys Asp Ile Asn Val Lys Trp Lys Val Asp Gly Val Ile Gln Asp
        35                  40                  45

Thr Gly Ile Gln Glu Ser Val Thr Glu Gln Asp Lys Asp Ser Thr Tyr
    50                  55                  60

Ser Leu Ser Ser Thr Leu Thr Met Ser Ser Thr Glu Tyr Leu Ser His
65                  70                  75                  80

Glu Leu Tyr Ser Cys Glu Ile Thr His Lys Ser Leu Pro Ser Thr Leu
                85                  90                  95

Ile Lys Ser Phe Gln Arg Ser Glu Cys Gln Arg Val Asp
            100                 105

<210> SEQ ID NO 195
<211> LENGTH: 330

-continued

```
<212> TYPE: DNA
<213> ORGANISM: Canis familiaris

<400> SEQUENCE: 195
aatgatgccc agccagccgt ctatttgttc caaccatctc cagaccagtt acacacagga      60
agtgcctctg ttgtgtgctt gctgaatagc ttctacccca aagacatcaa tgtcaagtgg     120
aaagtggatg gtgtcatcca agacacaggc atccaggaaa gtgtcacaga gcaggacaag     180
gacagtacct acagcctcag cagcaccctg acgatgtcca gtactgagta cctaagtcat     240
gagttgtact cctgtgagat cactcacaag agcctgccct ccaccctcat caagagcttc     300
caaaggagcg agtgtcagag agtggactaa                                      330

<210> SEQ ID NO 196
<211> LENGTH: 108
<212> TYPE: PRT
<213> ORGANISM: Sus scrofa

<400> SEQUENCE: 196

Ala Asp Ala Lys Pro Ser Val Phe Ile Phe Pro Ser Lys Glu Gln
1               5                   10                  15

Leu Glu Thr Gln Thr Val Ser Val Val Cys Leu Leu Asn Ser Phe Phe
            20                  25                  30

Pro Arg Glu Val Asn Val Lys Trp Lys Val Asp Gly Val Val Gln Ser
        35                  40                  45

Ser Gly Ile Leu Asp Ser Val Thr Glu Gln Asp Ser Lys Asp Ser Thr
    50                  55                  60

Tyr Ser Leu Ser Ser Thr Leu Ser Leu Pro Thr Ser Gln Tyr Leu Ser
65                  70                  75                  80

His Asn Leu Tyr Ser Cys Glu Val Thr His Lys Thr Leu Ala Ser Pro
                85                  90                  95

Leu Val Lys Ser Phe Ser Arg Asn Glu Cys Glu Ala
            100                 105

<210> SEQ ID NO 197
<211> LENGTH: 327
<212> TYPE: DNA
<213> ORGANISM: Sus scrofa

<400> SEQUENCE: 197
gctgatgcca agccatccgt cttcatcttc ccgccatcga aggagcagtt agagacccaa      60
actgtctctg tggtgtgctt gctcaatagc ttcttcccca gagaagtcaa tgtcaagtgg     120
aaagtggatg gggtggtcca aagcagtggc atcctggata gtgtcacaga gcaggacagc     180
aaggacagca cctacagcct cagcagcacc ctctcgctgc ccacgtcaca gtacctaagt     240
cataatttat attcctgtga ggtcacccac aagaccctgg cctcccctct ggtcaaaagc     300
ttcagcagga acgagtgtga ggcttag                                         327

<210> SEQ ID NO 198
<211> LENGTH: 108
<212> TYPE: PRT
<213> ORGANISM: Mustela vison

<400> SEQUENCE: 198

Arg Asn Asp Ala Gln Pro Ser Val Phe Leu Phe Gln Pro Ser Gln Asp
1               5                   10                  15

Gln Leu His Thr Gly Ser Ala Ser Val Val Cys Leu Leu Asn Gly Phe
            20                  25                  30
```

Tyr Pro Lys Glu Val Thr Val Lys Trp Met Val Asp Gly Val Thr Lys
        35                  40                  45

Asn Thr Gly Ile Leu Glu Ser Val Thr Glu Gln Asp Ser Lys Asp Ser
    50                  55                  60

Thr Tyr Ser Leu Ser Ser Thr Leu Thr Ile Pro Ser Thr Glu Tyr Leu
65                  70                  75                  80

Ser His Glu Thr Tyr Ser Cys Glu Val Thr His Lys Ser Leu Ser Ser
                85                  90                  95

Pro Leu Val Lys Ser Phe Gln Arg Ser Glu Cys Gln
            100                 105

<210> SEQ ID NO 199
<211> LENGTH: 327
<212> TYPE: DNA
<213> ORGANISM: Mustela vison

<400> SEQUENCE: 199
cggaatgatg cccagccatc cgtcttttg ttccaaccat ctcaggacca gttacatacc      60
ggcagtgcct ctgtcgtgtg cttgctgaat ggcttctacc ccaaagaagt cactgtcaaa     120
tggatggttg atggtgttac caaaaacaca ggcatcctag aaagtgtcac agaacaagac     180
agcaaggaca gcacctacag cctcagcagc accctgacga tccccagtac ggagtaccta     240
agtcatgaga cgtactcctg tgaggtcact cacaagagcc tgtcctcccc tcttgtcaag     300
agcttccaaa ggagcgagtg ccaatga                                          327

<210> SEQ ID NO 200
<211> LENGTH: 5
<212> TYPE: PRT
<213> ORGANISM: Mus musculus

<400> SEQUENCE: 200

Ser Tyr Trp Met Asn
1               5

<210> SEQ ID NO 201
<211> LENGTH: 17
<212> TYPE: PRT
<213> ORGANISM: Mus musculus

<400> SEQUENCE: 201

Met Ile Asp Pro Ser Asp Ser Glu Ile His Tyr Asn Gln Val Phe Lys
1               5                   10                  15

Asp

<210> SEQ ID NO 202
<211> LENGTH: 9
<212> TYPE: PRT
<213> ORGANISM: Mus musculus

<400> SEQUENCE: 202

Gln Asp Ile Val Thr Thr Val Asp Tyr
1               5

<210> SEQ ID NO 203
<211> LENGTH: 17
<212> TYPE: PRT
<213> ORGANISM: Mus musculus

<400> SEQUENCE: 203

Lys Ser Ser Gln Ser Leu Leu Tyr Ser Ile Asn Gln Lys Asn His Leu
1               5                   10                  15
Ala

<210> SEQ ID NO 204
<211> LENGTH: 7
<212> TYPE: PRT
<213> ORGANISM: Mus musculus

<400> SEQUENCE: 204

Trp Ala Ser Thr Arg Glu Ser
1               5

<210> SEQ ID NO 205
<211> LENGTH: 9
<212> TYPE: PRT
<213> ORGANISM: Mus musculus

<400> SEQUENCE: 205

Gln Gln Gly Tyr Thr Tyr Pro Phe Thr
1               5

<210> SEQ ID NO 206
<211> LENGTH: 5
<212> TYPE: PRT
<213> ORGANISM: Mus musculus

<400> SEQUENCE: 206

Ser Tyr Trp Met Asn
1               5

<210> SEQ ID NO 207
<211> LENGTH: 17
<212> TYPE: PRT
<213> ORGANISM: Mus musculus

<400> SEQUENCE: 207

Met Ile Asp Pro Ser Asp Ser Glu Thr His Tyr Asn Gln Ile Phe Arg
1               5                   10                  15
Asp

<210> SEQ ID NO 208
<211> LENGTH: 9
<212> TYPE: PRT
<213> ORGANISM: Mus musculus

<400> SEQUENCE: 208

Gln Asp Ile Val Thr Thr Val Asp Tyr
1               5

<210> SEQ ID NO 209
<211> LENGTH: 17
<212> TYPE: PRT
<213> ORGANISM: Mus musculus

<400> SEQUENCE: 209

Lys Ser Ser Gln Ser Leu Leu Tyr Ser Ile Asn Gln Lys Asn Phe Leu
1               5                   10                  15
Ala

-continued

<210> SEQ ID NO 210
<211> LENGTH: 7
<212> TYPE: PRT
<213> ORGANISM: Mus musculus

<400> SEQUENCE: 210

Trp Ala Ser Thr Arg Glu Ser
1               5

<210> SEQ ID NO 211
<211> LENGTH: 9
<212> TYPE: PRT
<213> ORGANISM: Mus musculus

<400> SEQUENCE: 211

Gln Gln His Tyr Gly Tyr Pro Phe Thr
1               5

<210> SEQ ID NO 212
<211> LENGTH: 118
<212> TYPE: PRT
<213> ORGANISM: Mus musculus

<400> SEQUENCE: 212

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Met Asn Trp Ala Lys Gln Arg Pro Gly Gln Gly Leu Glu Trp Ile
        35                  40                  45

Gly Met Ile Asp Pro Ser Asp Ser Glu Ile His Tyr Asn Gln Val Phe
    50                  55                  60

Lys Asp Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gln Asp Ile Val Thr Thr Val Asp Tyr Trp Gly Gln Gly Thr
            100                 105                 110

Thr Leu Thr Val Ser Ser
        115

<210> SEQ ID NO 213
<211> LENGTH: 354
<212> TYPE: DNA
<213> ORGANISM: Mus musculus

<400> SEQUENCE: 213
caggtccaac tgcagcagcc tggggctgag ctggtgaggc ctggggcttc agtgaagctg      60
tcctgcaagg cttctggcta caccttcacc agctactgga tgaactgggc gaagcagagg     120
cctggacaag gccttgaatg gattggtatg attgatcctt cagacagtga aattcactac     180
aatcaagtgt tcaaggacaa ggccacattg actgtagaca atcctccag cacagcctac      240 atgcagctca gcagcctgac atctgaggac tctgcggtct attactgtgc aagacaagat     300
atagtgacta cagttgacta ctggggccaa ggcaccactc tcacagtctc ctca           354

<210> SEQ ID NO 214
<211> LENGTH: 113
<212> TYPE: PRT
<213> ORGANISM: Mus musculus

<400> SEQUENCE: 214

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ile Asn Gln Lys Asn His Leu Ala Trp Phe Gln Gln Lys Pro Gly Gln
        35                  40                  45

Ser Pro Lys Leu Leu Ile Tyr Trp Ala Ser Thr Arg Glu Ser Gly Val
50                  55                  60

Pro Ala Arg Phe Thr Gly Ser Gly Ser Gly Thr Asp Phe Thr Leu Thr
65                  70                  75                  80

Ile Ser Ser Val Lys Thr Glu Asp Leu Ala Val Tyr Tyr Cys Gln Gln
                85                  90                  95

Gly Tyr Thr Tyr Pro Phe Thr Phe Gly Ser Gly Thr Lys Leu Glu Ile
                100                 105                 110

Lys

<210> SEQ ID NO 215
<211> LENGTH: 339
<212> TYPE: DNA
<213> ORGANISM: Mus musculus

<400> SEQUENCE: 215
gacattgtga tgtcacagtc tccatcctcc ctagctgtgt cagttggaga gaaggttaca      60
atgagctgca agtccagtca gagccttttta tatagtatca atcaaaagaa ccacttggcc     120
tggttccagc agaaaccagg gcagtctcct aaactgctga tttactgggc atccactagg     180
gaatctgggg tccctgctcg cttcacaggc agtggatctg gaacagattt cactctcacc     240
atcagcagtg tgaagactga agacctggca gtttattact gtcagcaagg ttatacctac     300
ccattcacgt tcggctcggg gacaaagttg gaaataaaa                            339

<210> SEQ ID NO 216
<211> LENGTH: 118
<212> TYPE: PRT
<213> ORGANISM: Mus musculus

<400> SEQUENCE: 216

Gln Val Gln Leu Gln Gln Pro Gly Ala Glu Leu Val Arg Pro Gly Ala
1               5                   10                  15

Ser Val Lys Leu Ser Cys Lys Ala Tyr Gly Tyr Thr Phe Thr Ser Tyr
            20                  25                  30

Trp Met Asn Trp Val Lys Gln Arg Pro Gly Gln Gly Leu Glu Trp Ile
        35                  40                  45

Gly Met Ile Asp Pro Ser Asp Ser Glu Thr His Tyr Asn Gln Ile Phe
50                  55                  60

Arg Asp Lys Ala Thr Leu Thr Ile Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gln Asp Ile Val Thr Thr Val Asp Tyr Trp Gly Gln Gly Thr
                100                 105                 110

Thr Leu Thr Val Ser Ser
        115

<210> SEQ ID NO 217

```
<211> LENGTH: 354
<212> TYPE: DNA
<213> ORGANISM: Mus musculus

<400> SEQUENCE: 217
caggtccaat tgcagcagcc tggggctgag ctggtgaggc ctggggcttc agtgaagctg     60
tcctgcaagg cctatggcta caccttcacc agttactgga tgaactgggt gaaacagagg    120
cctggacaag gccttgaatg gattggtatg attgatcctt cagacagtga aactcactac    180
aatcaaatat tcagggacaa ggccacattg actatagaca atcctccag cacagcctac     240 atgcagctca gcagcctgac atctgaggac tctgcggtct atttctgtgc aagacaagat    300
atagtgacta cagttgacta ctggggccag ggcaccactc tcacagtctc ctca          354

<210> SEQ ID NO 218
<211> LENGTH: 113
<212> TYPE: PRT
<213> ORGANISM: Mus musculus

<400> SEQUENCE: 218

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ile Asn Gln Lys Asn Phe Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ser Glu Asp Leu Ala Val Tyr Tyr Cys Gln Gln
                85                  90                  95

His Tyr Gly Tyr Pro Phe Thr Phe Gly Ser Gly Thr Lys Leu Glu Ile
            100                 105                 110

Lys

<210> SEQ ID NO 219
<211> LENGTH: 339
<212> TYPE: DNA
<213> ORGANISM: Mus musculus

<400> SEQUENCE: 219
gacattgtga tgtcacagtc tccatcctcc ctagctgtgt cagttggaga gaaggttact     60
atgagctgca agtccagtca gagcctttta tatagtatca tcaaaagaa cttcttggcc    120 tggtaccagc agaaaccagg gcagtctcct aaactgctga tttactgggc atccactagg    180
gaatctgggg tccctgatcg cttcacaggc agtggatctg gacagatttc actctcacc    240 atcagcagtg tgaagtctga agacctggca gtttattact gtcagcaaca ttatggctat    300
ccattcacgt tcggctcggg gacaaagttg gaaataaaa                            339

<210> SEQ ID NO 220
<211> LENGTH: 118
<212> TYPE: PRT
<213> ORGANISM: Artificial Sequence
<220> FEATURE:
<223> OTHER INFORMATION: Felinized variable heavy mAb sequence, from Mus
      musculus and Felis catus
```

<400> SEQUENCE: 220

Asp Val Gln Leu Val Glu Ser Gly Gly Asp Leu Val Lys Pro Gly Gly
1               5                   10                  15

Ser Leu Arg Leu Thr Cys Val Ala Ser Gly Phe Thr Tyr Ser Asn Tyr
            20                  25                  30

Trp Met His Trp Val Arg Gln Ala Pro Gly Lys Gly Leu Gln Trp Val
        35                  40                  45

Ala Arg Ile Asp Pro Tyr Gly Gly Thr Lys His Asn Glu Lys Phe
    50                  55                  60

Lys Arg Arg Phe Thr Ile Ser Arg Asp Asn Ala Lys Asn Thr Leu Tyr
65              70                  75                  80

Leu Gln Met Asn Ser Leu Lys Thr Glu Asp Thr Ala Thr Tyr Tyr Cys
                85                  90                  95

Val Arg Ser Gly Tyr Asp Tyr Tyr Phe Asp Val Trp Gly Gln Gly Thr
            100                 105                 110

Leu Val Thr Val Ser Ser
            115

<210> SEQ ID NO 221
<211> LENGTH: 354
<212> TYPE: DNA
<213> ORGANISM: Artificial Sequence
<220> FEATURE:
<223> OTHER INFORMATION: Nucleotide sequence encoding felinized variable
      heavy mAb sequence, from Mus musculus and Felis catus

<400> SEQUENCE: 221
gacgtgcaac tggtggagag tggaggggac cttgtaaagc caggcgggtc cctgcgcctg      60
acctgtgtag ccagcggctt cacttactcc aactattgga tgcactgggt cagacaggcc     120
cccggaaaag ggcttcagtg ggtggcaagg atcgatccct acggaggagg aacgaagcat     180
aacgagaagt tcaagcggag gtttactatc agtagagaca cgcgaaaaa tacactgtac      240
ctgcagatga atagtcttaa gacagaggat accgcgacct actattgcgt cagatccggc     300
tatgactatt actttgacgt ttggggacag ggcacactgg tcaccgtctc gagc            354

<210> SEQ ID NO 222
<211> LENGTH: 107
<212> TYPE: PRT
<213> ORGANISM: Artificial Sequence
<220> FEATURE:
<223> OTHER INFORMATION: Felinized variable light mAb sequence, from Mus
      musculus and Felis catus

<400> SEQUENCE: 222

Glu Ile Gln Met Thr Gln Ser Pro Ser Ser Leu Ser Ala Ser Pro Gly
1               5                   10                  15

Asp Arg Val Thr Ile Thr Cys Arg Ala Ser Glu Asn Ile Tyr Ser Phe
            20                  25                  30

Leu Ala Trp Tyr Gln Gln Lys Pro Gly Lys Val Pro Lys Leu Leu Ile
        35                  40                  45

Tyr Asn Ala Asn Thr Leu Ala Glu Gly Val Pro Ser Arg Phe Ser Gly
    50                  55                  60

Ser Gly Ser Gly Thr Asp Phe Thr Leu Thr Ile Ser Ser Leu Glu Pro
65              70                  75                  80

Glu Asp Ala Ala Thr Tyr Tyr Cys Gln His His Phe Gly Thr Pro Phe
                85                  90                  95

Thr Phe Gly Ser Gly Thr Lys Leu Glu Ile Lys
                100                 105

<210> SEQ ID NO 223
<211> LENGTH: 321
<212> TYPE: PRT
<213> ORGANISM: Artificial Sequence
<220> FEATURE:
<223> OTHER INFORMATION: Nucleotide sequence encoding felinized variable
      light mAb sequence, from Mus musculus and Felis catus

<400> SEQUENCE: 223

Gly Ala Ala Ala Thr Thr Cys Ala Ala Thr Gly Ala Cys Cys Cys
1               5                   10                  15

Ala Gly Thr Cys Ala Cys Cys Ala Gly Thr Thr Cys Cys Thr Thr
                20                  25                  30

Gly Thr Cys Cys Gly Cys Cys Ala Gly Thr Cys Cys Gly Gly Ala
                35                  40                  45

Gly Ala Thr Cys Gly Cys Gly Thr Cys Ala Cys Ala Thr Ala Ala
                50                  55                  60

Cys Cys Thr Gly Cys Cys Gly Gly Cys Cys Ala Gly Thr Gly Ala
65                  70                  75                  80

Ala Ala Ala Thr Ala Thr Thr Ala Thr Thr Cys Ala Thr Thr Cys
                85                  90                  95

Cys Thr Cys Gly Cys Gly Thr Gly Thr Ala Thr Cys Ala Gly Cys
                100                 105                 110

Ala Gly Ala Ala Gly Cys Cys Ala Gly Gly Cys Ala Ala Gly Gly
                115                 120                 125

Gly Cys Cys Gly Ala Ala Gly Cys Thr Gly Cys Thr Gly Ala Thr
                130                 135                 140

Thr Ala Cys Ala Ala Cys Gly Cys Thr Ala Ala Cys Ala Gly Thr
145                 150                 155                 160

Thr Gly Gly Cys Cys Gly Ala Gly Gly Gly Gly Thr Gly Cys Cys
                165                 170                 175

Cys Ala Gly Thr Ala Gly Ala Thr Thr Cys Ala Gly Cys Gly Gly
                180                 185                 190

Thr Cys Cys Gly Gly Cys Ala Gly Thr Gly Gly Ala Cys Cys Gly
                195                 200                 205

Ala Thr Thr Thr Cys Ala Cys Cys Cys Thr Gly Ala Cys Ala Thr
                210                 215                 220

Thr Thr Cys Ala Ala Gly Cys Cys Thr Gly Gly Ala Ala Cys Ala
225                 230                 235                 240

Gly Ala Ala Gly Ala Cys Gly Cys Cys Gly Cys Ala Cys Ala Thr
                245                 250                 255

Ala Cys Thr Ala Cys Thr Gly Cys Cys Ala Gly Cys Ala Cys Ala
                260                 265                 270

Cys Thr Thr Thr Gly Gly Ala Cys Cys Cys Thr Thr Thr Cys
                275                 280                 285

Ala Cys Thr Thr Thr Cys Gly Gly Ala Thr Cys Cys Gly Gly Ala
                290                 295                 300

Cys Cys Ala Ala Gly Cys Thr Gly Gly Ala Thr Cys Ala Ala
305                 310                 315                 320

Ala

<210> SEQ ID NO 224
<211> LENGTH: 118

```
<212> TYPE: PRT
<213> ORGANISM: Artificial Sequence
<220> FEATURE:
<223> OTHER INFORMATION: Felinized variable heavy mAb sequence, from Mus
      musculus and Felis catus

<400> SEQUENCE: 224

Asp Val Gln Leu Val Glu Ser Gly Gly Asp Leu Val Lys Pro Gly Gly
1               5                   10                  15

Ser Leu Arg Leu Thr Cys Val Ala Ser Gly Phe Thr Tyr Ser Asn Tyr
            20                  25                  30

Trp Met His Trp Val Arg Gln Ala Pro Gly Lys Gly Leu Gln Trp Val
        35                  40                  45

Ala Arg Ile Asp Pro Tyr Gly Gly Gly Thr Lys His Asn Glu Lys Phe
    50                  55                  60

Lys Arg Arg Phe Thr Ile Ser Arg Asp Asn Ala Lys Asn Thr Leu Tyr
65                  70                  75                  80

Leu Gln Met Asn Ser Leu Lys Thr Glu Asp Thr Ala Thr Tyr Tyr Cys
                85                  90                  95

Val Arg Ser Gly Tyr Asp Tyr Tyr Phe Asp Val Trp Gly Gln Gly Thr
            100                 105                 110

Leu Val Thr Val Ser Ser
            115

<210> SEQ ID NO 225
<211> LENGTH: 354
<212> TYPE: DNA
<213> ORGANISM: Artificial Sequence
<220> FEATURE:
<223> OTHER INFORMATION: Nucleotide sequence encoding felinized variable
      heavy mAb sequence, from Mus musculus and Felis catus

<400> SEQUENCE: 225
gacgtgcaac tggtggagag tggaggggac cttgtaaagc caggcgggtc cctgcgcctg      60
acctgtgtag ccagcggctt cacttactcc aactattgga tgcactgggt cagacaggcc     120
cccggaaaag ggcttcagtg ggtggcaagg atcgatccct acggaggagg aacgaagcat     180
aacgagaagt tcaagcggag gtttactatc agtagagaca cgcgaaaaa tacactgtac      240 ctgcagatga atagtcttaa gacagaggat accgcgacct actattgcgt cagatccggc     300
tatgactatt actttgacgt ttggggacag ggcacactgg tcaccgtctc gagc           354

<210> SEQ ID NO 226
<211> LENGTH: 107
<212> TYPE: PRT
<213> ORGANISM: Artificial Sequence
<220> FEATURE:
<223> OTHER INFORMATION: Felinized variable light mAb sequence, from Mus
      musculus and Felis catus

<400> SEQUENCE: 226

Glu Ile Gln Met Thr Gln Ser Pro Ser Ser Leu Ser Ala Ser Pro Gly
1               5                   10                  15

Asp Arg Val Thr Ile Thr Cys Arg Ala Ser Glu Asn Ile Tyr Ser Phe
            20                  25                  30

Leu Ala Trp Tyr Gln Gln Lys Pro Gly Lys Val Pro Lys Leu Leu Ile
        35                  40                  45

Tyr Asn Ala Asn Thr Leu Ala Glu Gly Val Pro Ser Arg Phe Ser Gly
    50                  55                  60
```

-continued

Ser Gly Ser Gly Thr Asp Phe Thr Leu Thr Ile Ser Ser Leu Glu Pro
 65                  70                  75                  80

Glu Asp Ala Ala Thr Tyr Tyr Cys Gln His His Phe Gly Thr Pro Phe
                 85                  90                  95

Thr Phe Gly Ser Gly Thr Lys Leu Glu Ile Lys
            100                 105

<210> SEQ ID NO 227
<211> LENGTH: 321
<212> TYPE: PRT
<213> ORGANISM: Artificial Sequence
<220> FEATURE:
<223> OTHER INFORMATION: Nucleotide sequence encoding felinized variable
      light mAb sequence, from Mus musculus and Felis catus

<400> SEQUENCE: 227

Gly Ala Ala Ala Thr Thr Cys Ala Ala Thr Gly Ala Cys Cys Cys
1               5                   10                  15

Ala Gly Thr Cys Ala Cys Cys Ala Gly Thr Thr Cys Cys Thr Thr
                20                  25                  30

Gly Thr Cys Cys Gly Cys Ala Gly Thr Cys Cys Gly Gly Ala
            35                  40                  45

Gly Ala Thr Cys Gly Cys Gly Thr Cys Ala Cys Ala Thr Ala Ala
    50                  55                  60

Cys Cys Thr Gly Cys Cys Gly Gly Cys Cys Ala Gly Thr Gly Ala
65                  70                  75                  80

Ala Ala Ala Thr Ala Thr Thr Thr Ala Thr Cys Ala Thr Cys
                85                  90                  95

Cys Thr Cys Gly Cys Gly Thr Gly Gly Thr Ala Thr Cys Ala Gly Cys
            100                 105                 110

Ala Gly Ala Ala Gly Cys Cys Ala Gly Gly Cys Ala Ala Gly Gly Thr
        115                 120                 125

Gly Cys Cys Gly Ala Ala Gly Cys Thr Gly Cys Thr Gly Ala Thr Ala
    130                 135                 140

Thr Ala Cys Ala Ala Cys Gly Cys Thr Ala Ala Cys Ala Cys Gly Thr
145                 150                 155                 160

Thr Gly Gly Cys Cys Gly Ala Gly Gly Gly Gly Thr Gly Cys Cys
            165                 170                 175

Cys Ala Gly Thr Ala Gly Ala Thr Thr Cys Ala Gly Cys Gly Gly Gly
        180                 185                 190

Thr Cys Cys Gly Gly Cys Ala Gly Thr Gly Gly Ala Ala Cys Cys Gly
    195                 200                 205

Ala Thr Thr Thr Cys Ala Cys Cys Thr Gly Ala Cys Ala Ala Thr
        210                 215                 220

Thr Thr Cys Ala Ala Gly Cys Thr Gly Gly Ala Ala Cys Cys Ala
225                 230                 235                 240

Gly Ala Ala Gly Ala Cys Gly Cys Cys Gly Cys Ala Cys Ala Thr
                245                 250                 255

Ala Cys Thr Ala Cys Thr Gly Cys Cys Ala Gly Cys Ala Thr Cys Ala
            260                 265                 270

Cys Thr Thr Thr Gly Gly Gly Ala Cys Cys Cys Thr Thr Thr Cys
        275                 280                 285

Ala Cys Thr Thr Thr Cys Gly Gly Ala Thr Cys Cys Gly Gly Thr Ala
    290                 295                 300

Cys Cys Ala Ala Gly Cys Thr Gly Gly Ala Gly Ala Thr Cys Ala Ala
305                 310                 315                 320

Ala

<210> SEQ ID NO 228
<211> LENGTH: 117
<212> TYPE: PRT
<213> ORGANISM: Artificial Sequence
<220> FEATURE:
<223> OTHER INFORMATION: Felinized variable heavy mAb sequence, from
      Canis familiaris and Felis catus

<400> SEQUENCE: 228

Asp Val Gln Leu Val Glu Ser Gly Gly Asp Leu Val Lys Pro Gly Gly
1               5                   10                  15

Ser Leu Arg Leu Thr Cys Val Ala Ser Gly Phe Thr Phe Ser Asp Tyr
            20                  25                  30

Ala Met Ser Trp Val Arg Gln Ala Pro Gly Lys Gly Leu Gln Trp Val
        35                  40                  45

Ala Gly Ile Asp Ser Val Gly Ser Gly Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Thr Glu Asp Thr Ala Thr Tyr Tyr Cys
                85                  90                  95

Ala Ser Gly Phe Pro Gly Ser Phe Glu His Trp Gly Gln Gly Ala Leu
            100                 105                 110

Val Thr Val Ser Ser
        115

<210> SEQ ID NO 229
<211> LENGTH: 351
<212> TYPE: DNA
<213> ORGANISM: Artificial Sequence
<220> FEATURE:
<223> OTHER INFORMATION: Nucleotide sequence encoding felinized variable
      heavy mAb sequence, Canis familiaris and Felis catus

<400> SEQUENCE: 229
gatgtgcagc tggtggaaag cggcggcgat ctggtgaaac cgggcggcag cctgcgcctg      60
acctgcgtgg cgagcggctt tacctttagc gattatgcga tgagctgggt gcgccaggcg     120
ccgggcaaag gcctgcagtg ggtggcgggc attgatagcg tgggcagcgg caccagctat     180
gcggatagcg tgaaaggccg ctttaccatt agccgcgata acgcgaaaaa cacccttgtat    240 ctgcagatga acagcctgaa aaccgaagat accgcgacct attattgcgc gagcggcttt     300
ccgggcagct ttgaacattg gggccagggc gcgctggtga ccgtgagcag c              351

<210> SEQ ID NO 230
<211> LENGTH: 132
<212> TYPE: PRT
<213> ORGANISM: Artificial Sequence
<220> FEATURE:
<223> OTHER INFORMATION: Felinized variable light mAb sequence, from
      Canis familiaris and Felis catus

<400> SEQUENCE: 230

Gln Ser Val Leu Thr Gln Pro Ser Ser Val Ser Gly Thr Leu Gly Gln
1               5                   10                  15

```
Arg Ile Thr Ile Ser Cys Thr Gly Ser Ser Asn Ile Gly Ser Gly
            20                  25                  30

Tyr Val Gly Trp Tyr Gln Gln Val Pro Gly Met Gly Pro Lys Thr Val
        35                  40                  45

Ile Tyr Tyr Asn Ser Asp Arg Pro Ser Gly Val Pro Asp Arg Phe Ser
    50                  55                  60

Gly Ser Lys Ser Gly Ser Ser Gly Thr Leu Thr Ile Thr Gly Leu Gln
65                  70                  75                  80

Ala Glu Asp Glu Ala Asp Tyr Tyr Cys Ser Val Tyr Asp Arg Thr Phe
                85                  90                  95

Asn Ala Val Phe Gly Gly Gly Thr His Leu Thr Val Leu Gly Gln Pro
            100                 105                 110

Lys Ser Ala Pro Pro Arg Ser His Ser Ser Arg Pro Ile Ser Tyr Ala
        115                 120                 125

Val Phe Cys Leu
    130
```

<210> SEQ ID NO 231
<211> LENGTH: 327
<212> TYPE: DNA
<213> ORGANISM: Artificial Sequence
<220> FEATURE:
<223> OTHER INFORMATION: Nucleotide sequence encoding felinized variable
      light mAb sequence, Canis familiaris and Felis catus

<400> SEQUENCE: 231

```
cagagcgtgc tgacccagcc gagcagcgtg agcggcaccc tgggccagcg cattaccatt      60
agctgcaccg gcagcagcag caacattggc agcggctatg tgggctggta tcagcaggtg     120
ccgggcatgg gccgaaaaac cgtgatttat tataacagcg atcgcccgag cggcgtgccg     180
gatcgcttta gcggcagcaa aagcggcagc agcggcaccc tgaccattac cggcctgcag     240
gcggaagatg aagcggatta ttattgcagc gtgtatgatc gcacctttaa cgcggtgttt     300
ggcggcggca cccatctgac cgtgctg                                         327
```

<210> SEQ ID NO 232
<211> LENGTH: 117
<212> TYPE: PRT
<213> ORGANISM: Artificial Sequence
<220> FEATURE:
<223> OTHER INFORMATION: Felinized variable heavy mAb sequence, from
      Canis familiaris and Felis catus

<400> SEQUENCE: 232

```
Asp Val Gln Leu Val Glu Ser Gly Gly Asp Leu Val Lys Pro Gly Gly
1               5                   10                  15

Ser Leu Arg Leu Thr Cys Val Ala Ser Gly Phe Thr Phe Ser Asp Tyr
            20                  25                  30

Ala Met Asn Trp Val Arg Gln Ala Pro Gly Lys Gly Leu Gln Trp Val
        35                  40                  45

Ala Gly Ile Asp Ser Val Gly Ser Gly Thr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Gly Leu Lys Thr Glu Asp Thr Ala Thr Tyr Tyr Cys
                85                  90                  95

Ala Ser Gly Phe Pro Gly Ser Phe Glu His Trp Gly Gln Gly Thr Leu
            100                 105                 110
```

Val Thr Val Ser Ser
        115

<210> SEQ ID NO 233
<211> LENGTH: 351
<212> TYPE: DNA
<213> ORGANISM: Artificial Sequence
<220> FEATURE:
<223> OTHER INFORMATION: Nucleotide sequence encoding felinized variable
      heavy mAb sequence, Canis familiaris and Felis catus

<400> SEQUENCE: 233
gatgtgcagc tggtggaaag cggcggcgat ctggtgaaac cgggcggcag cctgcgcctg      60
acctgcgtgg cgagcggctt tacctttagc gattatgcga tgaactgggt gcgccaggcg     120
ccgggcaaag gcctgcagtg gtggcgggc attgatagcg tgggcagcgg caccagctat      180
gcggatagcg tgaaaggccg ctttaccatt agccgcgata cgcgaaaaa caccctgtat      240 ctgcagatga gcggcctgaa accgaagat accgcgacct attattgcgc gagcggcttt      300
ccgggcagct ttgaacattg gggccagggc accctggtga ccgtgagcag c              351

<210> SEQ ID NO 234
<211> LENGTH: 132
<212> TYPE: PRT
<213> ORGANISM: Artificial Sequence
<220> FEATURE:
<223> OTHER INFORMATION: Felinized variable light mAb sequence, from
      Canis familiaris and Felis catus

<400> SEQUENCE: 234

Gln Ser Val Leu Thr Gln Pro Ser Ser Val Ser Gly Thr Leu Gly Gln
1               5                   10                  15

Arg Ile Thr Ile Ser Cys Thr Gly Ser Ser Ser Asn Ile Gly Ser Gly
            20                  25                  30

Tyr Val Gly Trp Tyr Gln Gln Val Pro Gly Met Gly Pro Lys Thr Val
        35                  40                  45

Ile Tyr Tyr Asn Ser Asp Arg Pro Ser Gly Val Pro Asp Arg Phe Ser
    50                  55                  60

Gly Ser Lys Ser Gly Ser Ser Gly Thr Leu Thr Ile Thr Gly Leu Gln
65                  70                  75                  80

Ala Glu Asp Glu Ala Asp Tyr Tyr Cys Ser Val Tyr Asp Arg Thr Phe
                85                  90                  95

Asn Ala Val Phe Gly Gly Gly Thr His Leu Thr Val Leu Gly Gln Pro
            100                 105                 110

Lys Ser Ala Pro Pro Arg Ser His Ser Ser Arg Pro Ile Ser Tyr Ala
        115                 120                 125

Val Phe Cys Leu
    130

<210> SEQ ID NO 235
<211> LENGTH: 327
<212> TYPE: DNA
<213> ORGANISM: Artificial Sequence
<220> FEATURE:
<223> OTHER INFORMATION: Nucleotide sequence encoding felinized variable
      light mAb sequence, Canis familiaris and Felis catus

<400> SEQUENCE: 235
cagagcgtgc tgacccagcc gagcagcgtg agcggcaccc tgggccagcg cattaccatt      60
agctgcaccg gcagcagcag caacattggc agcggctatg tgggctggta tcagcaggtg     120

```
ccgggcatgg gcccgaaaac cgtgatttat tataacagcg atcgcccgag cggcgtgccg      180
gatcgcttta gcggcagcaa aagcggcagc agcggcaccc tgaccattac cggcctgcag      240
gcggaagatg aagcggatta ttattgcagc gtgtatgatc gcacctttaa cgcggtgttt      300
ggcggcggca cccatctgac cgtgctg                                          327

<210> SEQ ID NO 236
<211> LENGTH: 106
<212> TYPE: PRT
<213> ORGANISM: Felis catus

<400> SEQUENCE: 236

Gly Gln Pro Lys Ser Ala Pro Ser Val Thr Leu Phe Pro Pro Ser Asn
1               5                   10                  15

Glu Glu Leu Ser Ala Asn Lys Ala Thr Leu Val Cys Leu Ile Ser Asp
            20                  25                  30

Phe Tyr Pro Ser Gly Leu Thr Val Ala Trp Lys Ala Asp Gly Thr Pro
        35                  40                  45

Ile Thr Gln Gly Val Glu Thr Thr Lys Pro Ser Lys Gln Ser Asn Asn
    50                  55                  60

Lys Tyr Ala Ala Ser Ser Tyr Leu Ser Leu Ser Pro Asn Glu Trp Lys
65                  70                  75                  80

Ser Arg Ser Arg Phe Thr Cys Gln Val Thr His Glu Gly Ser Thr Val
                85                  90                  95

Glu Lys Asn Val Val Pro Ala Glu Cys Ser
            100                 105

<210> SEQ ID NO 237
<211> LENGTH: 318
<212> TYPE: DNA
<213> ORGANISM: Felis catus

<400> SEQUENCE: 237
ggccagccca agagcgctcc ctccgtgacc ctgttccccc aagcaacga ggaactgagc       60 gccaacaagg ccaccctggt gtgcctgatc agcgacttct accccagcgg cctgaccgtg      120
gcctggaagg ccgatggcac ccctatcacc cagggcgtgg aaaccaccaa gcccagcaag      180
cagagcaaca caaatacgc cgccagcagc tacctgagcc tgagcccaa cgagtggaag        240 tcccggtccc ggttcacatg ccaggtgaca cacgagggca gcaccgtgga aaagaacgtg      300
gtgcccgccg agtgcagc                                                    318
```

INTERLEUKIN-31 MONOCLONAL ANTIBODIES FOR VETERINARY USE

CROSS-REFERENCE TO RELATED APPLICATIONS

This application is a continuation application of U.S. patent application Ser. No. 16/256,223, filed Jan. 24, 2019, which claims priority to and the benefit of U.S. Provisional Application No. 62/643,940, filed Mar. 16, 2018, the entire contents of all of which are incorporated herein by reference in their entirety.

FIELD OF THE INVENTION

The present invention relates to the field of recombinant monoclonal antibodies and their uses in clinical and scientific procedures, including diagnostic procedures. The present invention also provides isolated anti-IL31 antibodies in the form of veterinary compositions useful for treating an IL-31-mediated disorder in a mammal, such as a cat, dog, or horse.

BACKGROUND OF THE INVENTION

Atopic dermatitis has been defined by the American College of Veterinary Dermatology task force as "a genetically-predisposed inflammatory and pruritic allergic skin disease with characteristic clinical features" (Olivry, et al. Veterinary Immunology and Immunopathology 2001; 81: 143-146). The task force also recognized that the disease in canines has been associated with allergen-specific IgE (Olivry, et al. 2001 supra; Marsella & Olivry Clinics in Dermatology 2003; 21: 122-133). Severe pruritus, along with secondary alopecia and erythema, are the most noticeable and concerning symptoms to pet owners.

The potential factors involved in allergic dermatitis are numerous and poorly understood. Components in food may trigger atopic dermatitis (Picco, et al. Vet Dermatol. 2008; 19: 150-155), as well as environmental allergens such as fleas, dust mites, ragweed, plant extracts, etc. Genetic factors also play an important role. Although there is no confirmed breed predilection, some mode of inheritance is thought to increase predisposition to atopic dermatitis (Sousa & Marsella Veterinary Immunology and Immunopathology 2001; 81: 153-157; Schwartzman, et al. Clin. Exp. Immunol. 1971; 9: 549-569).

The prevalence of atopic dermatitis is estimated to be 10% of the total canine population (Marsella & Olivry 2003 supra; Scott, et al. Canadian Veterinary Journal 2002; 43: 601-603; Hillier Veterinary Immunology and Immunopathology 2001; 81: 147-151). Globally, about 4.5 million dogs are affected with this chronic and lifelong condition. Incidence appears to be increasing. Canine breed and sex predilections have been suspected, but may vary greatly depending on geographical region (Hillier, 2001 supra; Picco, et al. 2008 supra).

Feline allergic dermatitis is an inflammatory and pruritic skin condition thought to be caused by an abnormal response of the immune system to substances that do not induce a reaction in healthy cats. The most consistent feature of feline allergic dermatitis is chronic recurrent pruritus. Common clinical presentations of allergic dermatitis in cats include self-induced alopecia, miliary dermatitis, eosinophilic granuloma complex lesions (including plaques, granulomas, and indolent ulcer), and focused head and neck pruritus characterized by excoriations, erosions, and/or ulcers. Breed and sex predilections have not been demonstrated and young cats seem more prone to the disease (Hobi et al. Vet Dermatol 2011 22: 406-413; Ravens et al. Vet Dermatol 2014; 25: 95-102; Buckely In Practice 2017; 39: 242-254).

Current treatments for cats diagnosed with allergic dermatitis depend on the severity of the clinical signs, duration, and owner preferences and include allergen-specific immunotherapy and antipruritic drugs such as glucocorticoids and cyclosporines (Buckley, supra). Immunotherapy treatment is effective for some patients but requires frequent injections, and clinical improvement may not be seen for 6-9 months (Buckley, supra). Immunosuppressive drugs like glucocorticoids and cyclosporines are generally effective however long term use often results in undesirable adverse effects.

Atopic dermatitis in horses is recognized as a potential cause of pruritus. The role of environmental allergens in equine atopic dermatitis is becoming better appreciated. The disease may be seasonal or non-seasonal, depending on the allergen(s) involved. Age, breed, and sex predilections have not been extensively reported. In preliminary work at the School of Veterinary Medicine, University of California, Davis (SVM-UCD), the median age at onset was 6.5 years, Thoroughbreds were the most common breed, accounting for 25% of the horses, and males (usually geldings) were almost twice as prevalent as mares; however, these data are from only 24 horses, and have not yet been compared with the hospital population at large. Pruritus, often directed against the face, distal legs, or trunk, is the most common clinical sign of equine atopic dermatitis. Alopecia, erythema, urticaria, and papules may all be present. Urticarial lesions may be quite severe, yet nonpruritic. There may be a familial predisposition for urticarial atopic dermatitis in the horse. Horses may have a secondary pyoderma, typified by excess scaling, small epidermal collarettes, or encrusted papules ("miliary dermatitis"). Diagnosis of atopic dermatitis is based on clinical signs and the exclusion of other diagnoses, especially insect (Culicoides) hypersensitivity (White Clin Tech Equine Pract 2005; 4: 311-313; Fadok Vet Clin Equine 2013; 29 541-550). Currently, management of atopic dermatitis in horses is done both symptomatically, by suppressing the inflammation and the pruritus triggered by the allergic response, and by addressing the specific cause (i.e., by identifying the responsible allergens and by formulating an allergen-specific vaccine). The symptomatic approach is typically needed in the short term to make the patient comfortable and minimize self-trauma. This approach relies on the use of a combination of topical and systemic therapies including antihistamines, essential fatty acids, pentoxifylline, and glucocorticoids. The primary approach to environmental allergy control involves the identification of allergens that trigger the hypersensitivity reaction. It is commonly accepted by dermatologists that allergen-specific immunotherapy can be of help to atopic horses. However, as a general rule, most horses show improvement only after the first 6 months of immunotherapy (Marsella Vet Clin Equine 2013; 29: 551-557). Also, long term use of immunosuppressive drugs in horses can result in undesirable adverse effects.

Interleukin-31 (IL-31), a cytokine produced by T helper type 2 cells, has been shown to induce pruritus in humans, mice, and dogs (Bieber N Engl J Med 2008; 358: 1483-1494; Dillon et al. Nat Immunol 2004; 5:752-60; U.S. Pat. No. 8,790,651 to Bammert et al.; Gonzalez et al. Vet Dermatl. 2013; 24(1): 48-53). IL-31 binds a co-receptor composed of IL-31 receptor A (IL-31 RA) and the oncostatin M receptor (OSMR) (Dillon et al. 2004 supra and Bilsborough et al. J Allergy Clin Immunol. 2006 117(2):418-25). Receptor activation results in phosphorylation of STAT through JAK receptor(s). Expression of the co-receptor has been shown in macrophages, keratinocytes and in dorsal root ganglia.

Recently, it has been found that IL-31 is involved in dermatitis, pruritic skin lesions, allergy, and airway hypersensitivity. Cytopoint®, a canine anti-IL-31 monoclonal antibody produced by Zoetis Inc., Parsippany, NJ), has been shown to reduce pruritus and skin lesions in dogs with atopic dermatitis (Gonzalez et al. 2013 supra, Michels et al. Vet Dermatol. 2016; December; 27(6): 478-e129). It would be desirable to provide further anti-IL31 antibodies to prevent and treat IL-31-mediated disorders in veterinary mammals. Considering the currently unmet need for safe and effective alternative treatments for atopic and allergic dermatoses in cats and horses, it would be especially desirable to provide feline and equine anti-IL-31 antibodies to reduce pruritus and skin lesions in cats and horses with atopic dermatitis.

SUMMARY OF THE INVENTION

In one embodiment, the present invention provides a monoclonal antibody, or antigen-binding portion thereof that specifically binds to a region on a mammalian IL-31 protein involved with interaction of the IL-31 protein with its co-receptor, wherein the binding of said antibody to said region is impacted by mutations in a 15H05 epitope binding region selected from at least one of the following: a) a region between about amino acid residues 124 and 135 of a feline IL-31 sequence represented by SEQ ID NO: 157 (Feline_IL31_wildtype); b) a region between about amino acid residues 124 and 135 of a canine IL-31 sequence represented by SEQ ID NO: 155 (Canine_IL31); and c) a region between about amino acid residues 118 and 129 of an equine IL-31 sequence represented by SEQ ID NO: 165 (Equine_IL31).

In one embodiment, the aforementioned mutations in the 15H05 epitope binding region are selected from at least one of the following: (a) a mutant wherein positions 126 and 128 of SEQ ID NO: 157 are changed to Alanine; (b) a mutant wherein positions 126 and 128 of SEQ ID NO: 155 are changed to Alanine; and (c) a mutant wherein positions 120 and 122 of SEQ ID NO: 165 are changed to Alanine.

In one embodiment, a monoclonal antibody according to the present invention binds to the 15H05 epitope region. That is to say, in one embodiment, the present invention provides a monoclonal antibody, or antigen-binding portion thereof that specifically binds to a region on a mammalian IL-31 protein involved with interaction of the IL-31 protein with its co-receptor, wherein the binding region is a 15H05 epitope binding region selected from at least one of the following: a) a region between about amino acid residues 124 and 135 of a feline IL-31 sequence represented by SEQ ID NO: 157 (Feline_IL31_wildtype); b) a region between about amino acid residues 124 and 135 of a canine IL-31 sequence represented by SEQ ID NO: 155 (Canine_IL31); and c) a region between about amino acid residues 118 and 129 of an equine IL-31 sequence represented by SEQ ID NO: 165 (Equine_IL31).

In one embodiment, the mammalian IL-31 to which the antibody or antigen-binding portion thereof specifically binds is feline IL-31, wherein the antibody binds to a region between about amino acid residues 125 and 134 of a feline IL-31 sequence represented by SEQ ID NO: 157 (Feline_IL31_wildtype). In some embodiments, the antibody which binds to this region on feline IL-31 includes a VL chain comprising Framework 2 (FW2) changes selected from the following: an Asparagine in place of Lysine at position 42, an Isoleucine in place of Valine at position 43, a Valine in place of Leucine at position 46, an Asparagine in place of Lysine at position 49, and combinations thereof, wherein the positions are in reference to the numbering of SEQ ID NO: 127 (FEL_15H05_VL1).

In one embodiment, the mammalian IL-31 to which the antibody or antigen-binding portion thereof specifically binds is canine IL-31, wherein the antibody binds to a region between about amino acid residues 125 and 134 of a canine IL-31 sequence represented by SEQ ID NO: 155 (Canine_IL31).

In another embodiment, the mammalian IL-31 to which the antibody or antigen-binding portion thereof specifically binds is equine IL-31, wherein the antibody binds to a region between about amino acid residues 117 and 128 of an equine IL-31 sequence represented by SEQ ID NO: 165 (Equine_IL31).

In one embodiment, the monoclonal antibody or antigen-binding portion thereof includes the following combinations of complementary determining region (CDR) sequences:

```
1) antibody 15H05:
variable heavy
(VH)-CDR1 of
                                          (SEQ ID NO: 1)
SYTIH, VH-CDR2 of
                                          (SEQ ID NO: 2)
NINPTSGYTENNQRFKD, VH-CDR3 of
                                          (SEQ ID NO: 3)
WGFKYDGEWSFDV, variable light
(VL)-CDR1 of
                                          (SEQ ID NO: 4)
RASQGISIWLS, VL-CDR2 of
                                          (SEQ ID NO: 5)
KASNLHI,
and VL-CDR3 of
                                          (SEQ ID NO: 6)
LQSQTYPLT;
or 2) a variant of 1) that differs from the parent
antibody 15H05 by addition, deletion, and/or
substitution of one or more amino acid residues
in at least one of VH or VL CDR1, CDR2, or CDR3.
```

In one embodiment, a variant of antibody 15H05/1505 includes a substitution at one or more of the following positions within the CDRs: residue 4 (I) from SEQ ID NO 1; residues 1-3 (NIN), 5-7 (TSG), 9-11 (TEN) and 13 (Q) from SEQ ID NO 2; residues 4 (K), 6 (D) and 13 (V) from SEQ ID NO 3 in heavy chain CDR 1, 2 and 3, respectively, and residues 3-7 (SQGIS) from SEQ ID NO 4, residue 3 (S) and 5 (L) from SEQ ID NO 5, and residue 4 (Q), 5 (T) and 9 (T) in SEQ ID NO 6 from CDRL1, 2, and 3, respectively. In one embodiment, one or more of these substitutions are conservative amino acid substitutions.

In one embodiment, monoclonal antibody 15H05 above includes at least one of the following:

a) a variable light chain comprising FEL_15H05_VL1_FW2:
(SEQ ID NO: 135)
EIQMTQSPSSLSASPGDRVTITCRASQGISIWLSWYQQKPGNIPKVLINK

ASNLHIGVPSRFSGSGSGTDFTLTISSLEPEDAATYYCLQSQTYPLTFGG

GTKLEIK,
and b) a variable heavy chain comprising FEL_15H05_VH1:
(SEQ ID NO: 121)
QVLLVQSGAEVRTPGASVKIFCKASGYSFTSYTIHWLRQAPAQGLEWMGN

INPTSGYTENNQRFKDRLTLTADTSTNTAYMELSSLRSADTAMYYCARWG

FKYDGEWSFDVWGAGTTVTVSS.

The present invention also provides a monoclonal antibody or antigen-binding portion thereof which includes the following combinations of complementary determining region (CDR) sequences:

1) antibody ZIL1:
variable heavy
(VH)-CDR1 of
(SEQ ID NO: 13)
SYGMS,

VH-CDR2 of
(SEQ ID NO: 14)
HINSGGSSTYYADAVKG,

VH-CDR3 of
(SEQ ID NO: 15)
VYTTLAAFWTDNFDY, variable light
(VL)-CDR1 of
(SEQ ID NO: 16)
SGSTNNIGILAAT, VL-CDR2 of
(SEQ ID NO: 17)
SDGNRPS,
and VL-CDR3 of
(SEQ ID NO: 18)
QSFDTTLDAYV;

2) antibody ZIL8:
VH-CDR1 of
(SEQ ID NO: 19)
DYAMS,

VH-CDR2 of
(SEQ ID NO: 20)
GIDSVGSGTSYADAVKG,

VH-CDR3 of
(SEQ ID NO: 21)
GFPGSFEH,

VL-CDR1 of
(SEQ ID NO: 22)
TGSSSNIGSGYVG,

VL-CDR2 of
(SEQ ID NO: 23)
YNSDRPS,

VL-CDR3 of
(SEQ ID NO: 24)
SVYDRTFNAV;

3) antibody ZIL9:
VH-CDR1 of
(SEQ ID NO: 25)
SYDMT,

VH-CDR2 of
(SEQ ID NO: 26)
DVNSGGTGTAYAVAVKG,

VH-CDR3 of
(SEQ ID NO: 27)
LGVRDGLSV,

VL-CDR1 of
(SEQ ID NO: 28)
SGESLNEYYTQ,

VL-CDR2 of
(SEQ ID NO: 29)
RDTERPS,

VL-CDR3 of
(SEQ ID NO: 30)
ESAVDTGTLV;

4) antibody ZIL11:
VH-CDR1 of
(SEQ ID NO: 31)
TYVMN,

VH-CDR2 of
(SEQ ID NO: 32)
SINGGGSSPTYADAVRG,

VH-CDR3 of
(SEQ ID NO: 33)
SMVGPFDY,

VL-CDR1 of
(SEQ ID NO: 34)
SGESLSNYYAQ,

VL-CDR2 of
(SEQ ID NO: 35)
KDTERPS,

VL-CDR3 of
(SEQ ID NO: 36)
ESAVSSDTIV;

5) antibody ZIL69:
VH-CDR1 of
(SEQ ID NO: 37)
SYAMK,

VH-CDR2 of
(SEQ ID NO: 38)
TINNDGTRTGYADAVRG,

VH-CDR3 of
(SEQ ID NO: 39)
GNAESGCTGDHCPPY,

VL-CDR1 of
(SEQ ID NO: 40)
SGESLNKYYAQ,

VL-CDR2 of
(SEQ ID NO: 41)
KDTERPS,

VL-CDR3 of
(SEQ ID NO: 42)
ESAVSSETNV;

-continued 6) antibody ZIL94:
VH-CDR1 of
TYFMS, (SEQ ID NO: 43)

VH-CDR2 of
LISSDGSGTYYADAVKG, (SEQ ID NO: 44)

VH-CDR3 of
FWRAFND, (SEQ ID NO: 45)

VL-CDR1 of
GLNSGSVSTSNYPG, (SEQ ID NO: 46)

VL-CDR2 of
DTGSRPS, (SEQ ID NO: 47)

VL-CDR3 of
SLYTDSDILV; (SEQ ID NO: 48)

7) antibody ZIL154:
VH-CDR1 of
DRGMS, (SEQ ID NO: 49)

VH-CDR2 of
YIRYDGSRTDYADAVEG, (SEQ ID NO: 50)

VH-CDR3 of
WDGSSFDY, (SEQ ID NO: 51)

VL-CDR1 of
KASQSLLHSDGNTYLD, (SEQ ID NO: 52)

VL-CDR2 of
KVSNRDP, (SEQ ID NO: 53)

VL-CDR3 of
MQAIHFPLT; (SEQ ID NO: 54)

8) antibody ZIL159:
VH-CDR1 of
SYVMT, (SEQ ID NO: 55)

VH-CDR2 of
GINSEGSRTAYADAVKG, (SEQ ID NO: 56)

VH-CDR3 of
GDIVATGTSY, (SEQ ID NO: 57)

VL-CDR1 of
SGETLNRFYTQ, (SEQ ID NO: 58)

VL-CDR2 of
KDTERPS, (SEQ ID NO: 59)

VL-CDR3 of
KSAVSIDVGV; (SEQ ID NO: 60)

9) antibody ZIL171:
VH-CDR1 of
TYVMN, (SEQ ID NO: 61)

VH-CDR2 of
SINGGGSSPTYADAVRG, (SEQ ID NO: 62)

VH-CDR3 of
SMVGPFDY, (SEQ ID NO: 63)

VL-CDR1 of
SGKSLSYYYAQ, (SEQ ID NO: 64)

VL-CDR2 of
KDTERPS, (SEQ ID NO: 65)

VL-CDR3 of
ESAVSSDTIV; (SEQ ID NO: 66)

10) antibody 04H07:
VH-CDR1 of
SYWMN, (SEQ ID NO: 200)

VH-CDR2 of
MIDPSDSEIHYNQVFKD, (SEQ ID NO: 201)

VH-CDR3 of
QDIVTTVDY, (SEQ ID NO: 202)

VL-CDR1 of
KSSQSLLYSINQKNHLA, (SEQ ID NO: 203)

VL-CDR2 of
WASTRES, (SEQ ID NO: 204)

VL-CDR3 of
QQGYTYPFT; (SEQ ID NO: 205)

11) antibody 06A09:
VH-CDR1 of
SYWMN, (SEQ ID NO: 206)

VH-CDR2 of
MIDPSDSETHYNQIFRD, (SEQ ID NO: 207)

VH-CDR3 of
QDIVTTVDY, (SEQ ID NO: 208)

VL-CDR1 of
KSSQSLLYSINQKNFLA, (SEQ ID NO: 209)

VL-CDR2 of
WASTRES, (SEQ ID NO: 210)

VL-CDR3 of
QQHYGYPFT; (SEQ ID NO: 211)
or 12) a variant of 1) to 11) that differs from respective parent antibody ZIL1, ZIL8, ZIL9, ZIL11, ZIL69, ZIL94, ZIL154, ZIL159, ZIL171, 04H07, or 06A09 by addition, deletion, and/or substitution of one or more amino acid residues in at least oneof VH or VL CDR1, CDR2, or CDR3.

In some embodiments of the present invention, 1) antibody ZIL1 includes at least one of the following:

a) a variable light chain comprising CAN-ZIL1_VL:
(SEQ ID NO: 77)
QSVLTQPTSVSGSLGQRVTISCSGSTNNIGILAATWYQQLPGKAPKVLVY
SDGNRPSGVPDRFSGSKSGNSATLTITGLQAEDEADYYCQSFDTTLDAYV
FGSGTQLTVL,
and b) a variable heavy chain comprising CAN-ZIL1_VH:
(SEQ ID NO: 75)
EVQLVESGGDLVKPGGSLRLSCVASGFTFSSYGMSWVRQAPGKGLQWVAH
INSGGSSTYYADAVKGRFTISRDNAKNTLYLQMNSLRAEDTAVYYCVEVY
TTLAAFWTDNFDYWGQGTLVTVSS;

2) antibody ZIL8 includes at least one of the following:

a) a variable light chain comprising CAN-ZIL8_VL:
(SEQ ID NO: 81)
QSVLIQPASVSGSLGQKVTISCIGSSSNIGSGYVGWYQQLPGTGPRTLIY
YNSDRPSGVPDRFSGSRSGTTATLTISGLQAEDEADYYCSVYDRTFNAVF
GGGT,
and b) a variable heavy chain comprising CAN-ZIL8_VH:
(SEQ ID NO: 79)
EVQLVESGGDLVKPAGSLRLSCVASGFTFSDYAMSWVRQAPGRGLQWVAG
IDSVGSGTSYADAVKGRFTISRDDAKNTLYLQMFNLRAEDTAIYYCASGF
PGSFEHWGQGTLVTVSS;

or includes at least one of the following:

c) a variable light chain comprising ZTS_5864_VL:
(SEQ ID NO: 230)
QSVLTQPSSVSGTLGQRITISCTGSSSNIGSGYVGWYQQVPGMGPKTVIY
YNSDRPSGVPDRFSGSKSGSSGTLTITGLQAEDEADYYCSVYDRTFNAVF
GGGTHLTVLGQPKSAPPRSHSSRPISYAVFCL,
and d) a variable heavy chain comprising ZTS_5864_VH:
(SEQ ID NO: 228)
DVQLVESGGDLVKPGGSLRLTCVASGFTFSDYAMSWVRQAPGKGLQWVAG
IDSVGSGTSYADSVKGRFTISRDNAKNTLYLQMNSLKTEDTATYYCASGF
PGSFEHWGQGALVTVSS;

or includes at least one of the following:

e) a variable light chain comprising ZTS_5865_VL:
(SEQ ID NO: 234)
SVLTQPSSVSGTLGQRITISCTGSSSNIGSGYVGWYQQVPGMGPKTVIYY
NSDRPSGVPDRFSGSKSGSSGTLTITGLQAEDEADYYCSVYDRTFNAVFG
GGTHLTVLGQPKSAPPRSHSSRPISYAVFCL,
and f) a variable heavy chain comprising ZTS_5865_VH:
(SEQ ID NO: 232)
DVQLVESGGDLVKPGGSLRLTCVASGFTFSDYAMNWVRQAPGKGLQWVAG
IDSVGSGTSYADSVKGRFTISRDNAKNTLYLQMSGLKTEDTATYYCASGF
PGSFEHWGQGTLVTVSS.

3) antibody ZIL9 includes at least one of the following:

a) a variable light chain comprising CAN-ZIL9_VL:
(SEQ ID NO: 85)
SSVLTQPPSVSVSLGQTATISCSGESLNEYYTQWFQQKAGQAPVLVIYRD
TERPSGIPDRFSGSSSGNTHTLTISGARAEDEADYYCESAVDTGTLVFGG
GTHLAVL,
and b) a variable heavy chain comprising CAN-ZIL9_VH:
(SEQ ID NO: 83)
EVQLVESGGDLVKPPGSLRLSCVASGFTFSSYDMTWVRQAPGKGLQWVAD
VNSGGTGTAYAVAVKGRFTISRDNAKKTLYLQMNSLRAEDTAVYYCAKLG
VRDGLSVWGQGTLVTVSS;

4) antibody ZIL11 includes at least one of the following:

a) a variable light chain comprising CAN-ZIL11_VL:
(SEQ ID NO: 89)
SSVLTQPPSVSVSLGQTATISCSGESLSNYYAQWFQQKAGQAPVLVIYKD
TERPSGIPDRFSGSSSGNTHTLTISGARAEDEADYYCESAVSSDTIVFGG
GT,
and b) a variable heavy chain comprising CAN-ZIL11_VH:
(SEQ ID NO: 87)
EVQLVESGGDLVKPAGSLRLSCVASGFTFRTYVMNWVRQAPGKGLQWVAS
INGGGSSPTYADAVRGRFTVSRDNAQNSLFLQMNSLRAEDTAVYFCVVSM
VGPFDYWGQGTLVTVSS;

5) antibody ZIL69 includes at least one of the following:

a) a variable light chain comprising CAN-ZIL69_VL:
(SEQ ID NO: 93)
SSVLTQPPSVSVSLGQTATISCSGESLNKYYAQWFQQKAGQAPVLVIYKD
TERPSGIPDRFSGSSAGNTHTLTISGARAEDEADYYCESAVSSETNVFGS
GTQLTVL,
and b) a variable heavy chain comprising CAN-ZIL69_VH:
(SEQ ID NO: 91)
EVQLVESGGDLVKPAGSLRLSCVASGFTFSSYAMKWVRQAPGKGLQWVAT
INNDGTRTGYADAVRGRFTISKDNAKNTLYLQMDSLRADDTAVYYCTKGN
AESGCTGDHCPPYWGQGTLVTVSS;

6) antibody ZIL94 includes at least one of the following:

a) a variable light chain comprising
CAN-ZIL94_VL:
(SEQ ID NO: 97)
QTVVIQEPSLSVSPGGTVTLTCGLNSGSVSTSNYPGWYQQTRGRTPRTII

YDTGSRPSGVPNRFSGSISGNKAALTITGAQPEDEADYYCSLYTDSDILV

FGGGTHLTVL,
and b) a variable heavy chain comprising
CAN-ZIL94_VH:
(SEQ ID NO: 95)
EVQLVDSGGDLVKPGGSLRLSCVASGFTFSTYFMSWVRQAPGRGLQWVAL

ISSDGSGTYYADAVKGRFTISRDNAKNTLYLQMNSLRAEDTAMYYCAIFW

RAFNDWGQGTLVTVSS;

7) antibody ZIL154 includes at least one of the following:

a) a variable light chain comprising
CAN-ZIL154_VL:
(SEQ ID NO: 101)
DIVVTQTPLSLSVSPGETASFSCKASQSLLHSDGNTYLDWFRQKPGQSPQ

RLIYKVSNRDPGVPDRFSGSGSGTDFTLRISGVEADDAGLYYCMQAIHFP

LTFGAGTKVELK,
and b) a variable heavy chain comprising
CAN-ZIL154_VH:
(SEQ ID NO: 99)
EVHLVESGGDLVKPWGSLRLSCVASGFTFSDRGMSWVRQSPGKGLQWVAY

IRYDGSRTDYADAVEGRFTISRDNAKNTLYLQMNSLRAEDTAVYYCARWD

GSSFDYWGQGTLVTVSS;

8) antibody ZIL159 includes at least one of the following:

a) a variable light chain comprising
CAN-ZIL159_VL:
(SEQ ID NO: 105)
SNVLTQPPSVSVSLGQTATISCSGETLNRFYTQWFQQKAGQAPVLVIYKD

TERPSGIPDRFSGSSSGNIHTLTISGARAEDEAAYYCKSAVSIDVGVFGG

GTHLTVF,
and b) a variable heavy chain comprising
CAN-ZIL159_VH:
(SEQ ID NO: 103)
EVQLVESGGDLVKPAGSLRLSCVASGFTFSSYVMTWVRQAPGKGLQWVAG

INSEGSRTAYADAVKGRFTISRDNAKNTLYLQIDSLRAEDTAIYYCATGD

IVATGTSYWGQGTLVTVSS;

and 9) antibody ZIL171 includes at least one of the following:

a) a variable light chain comprising
CAN-ZIL171_VL:
(SEQ ID NO: 109)
SSVLTQPPSVSVSLGQTATISCSGKSLSYYYAQWFQQKAGQAPVLVIYKD

TERPSGIPDRFSGSSSGNTHTLTISGARAEDEADYYCESAVSSDTIVFGG

GTHLTVL, and b) a variable heavy chain comprising
CAN-ZIL171_VH:
(SEQ ID NO: 107)
EVQLVESGGDLVKPAGSLRLSCVASGFTFRTYVMNWVRQAPGKGLQWVAS

INGGGSSPTYADAVRGRFTVSRDNAQNSLFLQMNSLRAEDTAIYFCVVSM

VGPFDYWGHGTLVTVSS 10) antibody 04H07 includes at least one of the following:

a) a variable light chain comprising
Mu_04H07_VL:
(SEQ ID NO: 214)
DIVMSQSPSSLAVSVGEKVTMSCKSSQSLLYSINQKNHLAWFQQKPGQSP

KLLIYWASTRESGVPARFTGSGSGTDFTLTISSVKTEDLAVYYCQQGYTY

PFTFGSGTKLEIK,
and b) a variable heavy chain comprising
Mu_04H07_VH:
(SEQ ID NO: 212)
QVQLQQPGAELVRPGASVKLSCKASGYTFTSYWMNWAKQRPGQGLEWIGM

IDPSDSEIHYNQVFKDKATLTVDKSSSTAYMQLSSLTSEDSAVYYCARQD

IVTTVDYWGQGTTLTVSS;

and 11) antibody 06A09 includes at least one of the following:

a) a variable light chain comprising
Mu_06A09_VL:
(SEQ ID NO: 218)
DIVMSQSPSSLAVSVGEKVTMSCKSSQSLLYSINQKNFLAWYQQKPGQSP

KLLIYWASTRESGVPDRFTGSGSGTDFTLTISSVKSEDLAVYYCQQHYGY

PFTFGSGTKLEIK,
and b) a variable heavy chain comprising
Mu_06A09_VH:
(SEQ ID NO: 216)
QVQLQQPGAELVRPGASVKLSCKAYGYTFTSYWMNWVKQRPGQGLEWIGM

IDPSDSETHYNQIFRDKATLTIDKSSSTAYMQLSSLTSEDSAVYFCARQD

IVTTVDYWGQGTTLTVSS.

In one embodiment, a monoclonal antibody or antigen-binding portion thereof according to the present invention reduces, inhibits, or neutralizes an IL-31-mediated pruritic or allergic condition in a mammal. In one embodiment, such a mammal is selected from a dog, a cat, or a horse.

In some embodiments, the monoclonal antibody is chimeric. In further embodiments, the antibody is caninized, felinized, equinized, fully canine, fully feline, or fully equine.

The present invention also provides a veterinary composition including a therapeutically effective amount of at least one antibody or antigen-binding portion thereof described above.

Also provided is a method of treating an IL-31 mediated disorder in a subject, the method including administering a therapeutically effective amount of at least one antibody or antigen-binding portion thereof described above to the subject.

In one embodiment, the IL-31-mediated disorder is a pruritic or allergic condition. In some embodiments, the pruritic or allergic condition is a pruritic condition selected from atopic dermatitis, eczema, psoriasis, scleroderma, and pruritus. In other embodiments, the pruritic or allergic condition is an allergic condition selected from allergic dermatitis, summer eczema, urticaria, heaves, inflammatory airway disease, recurrent airway obstruction, airway hyper-responsiveness, chronic obstruction pulmonary disease, and inflammatory processes resulting from autoimmunity.

In other embodiments, the IL-31 mediated disorder is tumor progression. In some embodiments, the IL-31 mediated disorder is eosinophilic disease or mastocytomas.

Further provided is a method of inhibiting IL-31 activity in a mammal by administering an antibody or antigen-binding portion thereof as described above to the mammal.

Also provided is an antibody or antigen-binding portion thereof described above for use in treating a mammal with an IL-31-mediated disorder.

Further provided is the use of the antibody or antigen-binding portion thereof described above for treating a mammal with an IL-31-mediated disorder.

Also provided is a method of detecting IL-31, the method including: incubating a sample comprising IL-31 in the presence of an antibody or antigen-binding portion thereof described above; and detecting the antibody which is bound to IL-31 in the sample. In one embodiment, the method further includes quantitating the IL-31 in the sample.

The present invention also provides a host cell that produces a monoclonal antibody or antigen-binding portion thereof including at least one of the following combinations of complementary determining region (CDR) sequences:

```
1) antibody 15H05: variable heavy (VH)-CDR1 of SYTIH (SEQ ID NO: 1), VH-CDR2
   of NINPTSGYTENNQRFKD (SEQ ID NO: 2), VH-CDR3 of WGFKYDGEWSFDV (SEQ
   ID NO: 3), variable light (VL)-CDR1 of RASQGISIWLS (SEQ ID NO: 4), VL-CDR2
   of KASNLHI (SEQ ID NO: 5), and VL-CDR3 of LQSQTYPLT (SEQ ID NO: 6);

2) antibody ZIL1: variable heavy (VH)-CDR1 of SYGMS (SEQ ID NO: 13), VH-CDR2
   of HINSGGSSTYYADAVKG (SEQ ID NO:14), VH-CDR3 of VYTTLAAFWTDNFDY (SEQ
   ID NO: 15), variable light (VL)-CDR1 of SGSTNNIGILAAT (SEQ ID NO: 16),
   VL-CDR2 of SDGNRPS (SEQ ID NO: 17, and VL-CDR3 of QSFDTTLDAYV (SEQ ID
   NO: 18);

3) antibody ZIL8: VH-CDR1 of DYAMS (SEQ ID NO: 19), VH-CDR2 of
   GIDSVGSGTSYADAVKG (SEQ ID NO: 20), VH-CDR3 of GFPGSFEH (SEQ ID NO:
   21), VL-CDR1 of TGSSSNIGSGYVG (SEQ ID NO: 22), VL-CDR2 of YNSDRPS
   (SEQ ID NO: 23), VL-CDR3 of SVYDRTFNAV (SEQ ID NO: 24);

4) antibody ZIL9: VH-CDR1 of SYDMT (SEQ ID NO: 25), VH-CDR2 of
   DVNSGGTGTAYAVAVKG (SEQ ID NO: 26), VH-CDR3 of LGVRDGLSV (SEQ ID
   NO: 27), VL-CDR1 of SGESLNEYYTQ (SEQ ID NO: 28), VL-CDR2 of RDTERPS
   (SEQ ID NO: 29), VL-CDR3 of ESAVDTGTLV (SEQ ID NO: 30);

5) antibody ZIL11: VH-CDR1 of TYVMN (SEQ ID NO: 31), VH-CDR2 of
   SINGGGSSPTYADAVRG (SEQ ID NO: 32), VH-CDR3 of SMVGPFDY (SEQ ID NO:
   33), VL-CDR1 of SGESLSNYYAQ (SEQ ID NO: 34), VL-CDR2 of KDTERPS (SEQ
   ID NO: 35), VL-CDR3 of ESAVSSDTIV (SEQ ID NO: 36);

6) antibody ZIL69: VH-CDR1 of SYAMK (SEQ ID NO: 37), VH-CDR2 of
   TINNDGTRTGYADAVRG (SEQ ID NO: 38), VH-CDR3 of GNAESGCTGDHCPPY
   (SEQ ID NO: 39), VL-CDR1 of SGESLNKYYAQ (SEQ ID NO: 40), VL-CDR2 of
   KDTERPS (SEQ ID NO: 41), VL-CDR3 of ESAVSSETNV (SEQ ID NO: 42);

7) antibody ZIL94: VH-CDR1 of TYFMS (SEQ ID NO: 43), VH-CDR2 of
   LISSDGSGTYYADAVKG (SEQ ID NO: 44), VH-CDR3 of FWRAFND (SEQ ID NO:
   45), VL-CDR1 of GLNSGSVSTSNYPG (SEQ ID NO: 46), VL-CDR2 of DTGSRPS
   (SEQ ID NO: 47), VL-CDR3 of SLYTDSDILV (SEQ ID NO: 48);

8) antibody ZIL154: VH-CDR1 of DRGMS (SEQ ID NO: 49), VH-CDR2 of
   YIRYDGSRTDYADAVEG (SEQ ID NO: 50), VH-CDR3 of WDGSSFDY (SEQ ID NO:
   51), VL-CDR1 of KASQSLLHSDGNTYLD (SEQ ID NO: 52), VL-CDR2 of KVSNRDP
   (SEQ ID NO: 53), VL-CDR3 of MQAIHFPLT (SEQ ID NO: 54);

9) antibody ZIL159: VH-CDR1 of SYVMT (SEQ ID NO: 55), VH-CDR2 of
   GINSEGSRTAYADAVKG (SEQ ID NO: 56), VH-CDR3 of GDIVATGTSY (SEQ ID
   NO: 57), VL-CDR1 of SGETLNRFYTQ (SEQ ID NO: 58), VL-CDR2 of KDTERPS
   (SEQ ID NO: 59), VL-CDR3 of KSAVSIDVGV (SEQ ID NO: 60);

10) antibody ZIL171: VH-CDR1 of TYVMN (SEQ ID NO: 61), VH-CDR2 of
    SINGGGSSPTYADAVRG (SEQ ID NO: 62), VH-CDR3 of SMVGPFDY (SEQ ID NO:
    63), VL-CDR1 of SGKSLSYYYAQ (SEQ ID NO: 64), VL-CDR2 of KDTERPS (SEQ
    ID NO: 65), VL-CDR3 of ESAVSSDTIV (SEQ ID NO: 66);

11) antibody 04H07: VH-CDR1 of SYWMN (SEQ ID NO: 200), VH-CDR2 of
    MIDPSDSEIHYNQVFKD (SEQ ID NO: 201), VH-CDR3 of QDIVTTVDY (SEQ ID NO:
    202), VL-CDR1 of KSSQSLLYSINQKNHLA (SEQ ID NO: 203), VL-CDR2 of
    WASTRES (SEQ ID NO: 204), VL-CDR3 of QQGYTYPFT (SEQ ID NO: 205);

12) antibody 06A09: VH-CDR1 of SYWMN (SEQ ID NO: 206), VH-CDR2 of
    MIDPSDSETHYNQIFRD (SEQ ID NO: 207), VH-CDR3 of QDIVTTVDY (SEQ ID NO:
    208), VL-CDR1 of KSSQSLLYSINQKNFLA (SEQ ID NO: 209), VL-CDR2 of
    WASTRES (SEQ ID NO: 210), VL-CDR3 of QQHYGYPFT (SEQ ID NO: 211); or
```

13) a variant of 1) to 12) that differs from respective parent antibody 15H05, ZIL1, ZIL8, ZIL9, ZIL11, ZIL69, ZIL94, ZIL154, ZIL159, ZIL171, 04H07, or 06A09 by addition, deletion, and/or substitution of one or more amino acid residues in at least one of VH or VL CDR1, CDR2, or CDR3.

Also provided is a method of producing an antibody, including culturing the host cell described above under conditions which result in the production of the antibody, and isolating the antibody from the host cell or culture medium of the host cell.

Described below are isolated nucleic acids according to the present invention. Such nucleic acids may contain a nucleic acid sequence encoding the above-described variable heavy or variable light CDR sequences. Alternatively, an isolated nucleic acid according to the present invention may contain nucleic acid sequence encoding both the variable heavy and variable light CDRs.

In one embodiment, the invention provides an isolated nucleic acid comprising a nucleic acid sequence encoding at least one of the following combinations of variable heavy complementary determining region (CDR) sequences:

1) 15H05:
variable heavy
(VH)-CDR1 of
SYTIH, (SEQ ID NO: 1)

VH-CDR2 of
NINPTSGYTENNQRFKD, (SEQ ID NO: 2)
and

VH-CDR3 of
WGFKYDGEWSFDV; (SEQ ID NO: 3)

2) ZIL1:
VH-CDR1 of
SYGMS, (SEQ ID NO: 13)

VH-CDR2 of
HINSGGSSTYYADAVKG, (SEQ ID NO: 14)
and

VH-CDR3 of
VYTTLAAFWTDNFDY; (SEQ ID NO: 15)

3) ZIL8:
VH-CDR1 of
DYAMS, (SEQ ID NO: 19)

VH-CDR2 of
GIDSVGSGTSYADAVKG, (SEQ ID NO: 20)
and

VH-CDR3 of
GFPGSFEH; (SEQ ID NO: 21)

4) ZIL9:
VH-CDR1 of
SYDMT, (SEQ ID NO: 25)

VH-CDR2 of
DVNSGGTGTAYAVAVKG, (SEQ ID NO: 26)
and

VH-CDR3 of
LGVRDGLSV; (SEQ ID NO: 27)

5) ZIL11:
VH-CDR1 of
TYVMN, (SEQ ID NO: 31)

VH-CDR2 of
SINGGGSSPTYADAVRG, (SEQ ID NO: 32)
and

VH-CDR3 of
SMVGPFDY; (SEQ ID NO: 33)

6) ZIL69:
VH-CDR1 of
SYAMK, (SEQ ID NO: 37)

VH-CDR2 of
TINNDGTRTGYADAVRG, (SEQ ID NO: 38)
and

VH-CDR3 of
GNAESGCTGDHCPPY; (SEQ ID NO: 39)

7) ZIL94:
VH-CDR1 of
TYFMS, (SEQ ID NO: 43)
VH-CDR2 of
LISSDGSGTYYADAVKG, (SEQ ID NO: 44)
and VH-CDR3 of
FWRAFND; (SEQ ID NO: 45)

8) ZIL154:
VH-CDR1 of
DRGMS, (SEQ ID NO: 49)

VH-CDR2 of
YIRYDGSRTDYADAVEG, (SEQ ID NO: 50)
and

VH-CDR3 of
WDGSSFDY; (SEQ ID NO: 51)

9) ZIL159:
VH-CDR1 of
SYVMT, (SEQ ID NO: 55)

VH-CDR2 of

GINSEGSRTAYADAVKG, (SEQ ID NO: 56)
and

VH-CDR3 of

GDIVATGTSY; (SEQ ID NO: 57)

10) ZIL171:
VH-CDR1 of

TYVMN, (SEQ ID NO: 61)

VH-CDR2 of

SINGGGSSPTYADAVRG, (SEQ ID NO: 62)
and

VH-CDR3 of

SMVGPFDY; (SEQ ID NO: 63)

11) 04H07:
VH-CDR1 of

SYWMN, (SEQ ID NO: 200)

VH-CDR2 of

MIDPSDSEIHYNQVFKD, (SEQ ID NO: 201)
and

VH-CDR3 of

QDIVTTVDY; (SEQ ID NO: 202)

12) 06A09:
VH-CDR1 of

SYWMN, (SEQ ID NO: 206)

VH-CDR2 of

MIDPSDSETHYNQIFRD, (SEQ ID NO: 207)
and

VH-CDR3 of

QDIVTTVDY; (SEQ ID NO: 208)
or 13) a variant of 1) to 12) that differs from the CDRs of respective parent antibody 15H05, ZIL1, ZIL8, ZIL9, ZIL11, ZIL69, ZIL94, ZIL154, ZIL159, ZIL171, 04H07, or 06A09 by addition, deletion, and/or substitution of one or more amino acid residues in at least one of VH CDR1, CDR2, or CDR3.

In one embodiment, the isolated nucleic acid described above may further include a nucleic acid sequence encoding at least one of the following combinations of variable light complementary determining region (CDR) sequences:

1) 15H05:
variable light
(VL)-CDR1 of

RASQGISIWLS, (SEQ ID NO: 4)

VL-CDR2 of

KASNLHI, (SEQ ID NO: 5)
and

VL-CDR3 of

LQSQTYPLT; (SEQ ID NO: 6)

2) ZIL1:
VL-CDR1 of

SGSTNNIGILAAT, (SEQ ID NO: 16)

VL-CDR2 of

SDGNRPS, (SEQ ID NO: 17)

and VL-CDR3 of

QSFDTTLDAYV; (SEQ ID NO: 18)

3) ZIL8:
VL-CDR1 of

TGSSSNIGSGYVG, (SEQ ID NO: 22)

VL-CDR2 of

YNSDRPS, (SEQ ID NO: 23)
and

VL-CDR3 of

SVYDRTFNAV; (SEQ ID NO: 24)

4) ZIL9:
VL-CDR1 of

SGESLNEYYTQ, (SEQ ID NO: 28)

VL-CDR2 of

RDTERPS, (SEQ ID NO: 29)
and

VL-CDR3 of

ESAVDTGTLV; (SEQ ID NO: 30)

5) ZIL11:
VL-CDR1 of

SGESLSNYYAQ, (SEQ ID NO: 34)

VL-CDR2 of

KDTERPS, (SEQ ID NO: 35)
and

VL-CDR3 of

ESAVSSDTIV; (SEQ ID NO: 36)

6) ZIL69:
VL-CDR1 of

SGESLNKYYAQ, (SEQ ID NO: 40)

VL-CDR2 of

KDTERPS, (SEQ ID NO: 41)
and

VL-CDR3 of

ESAVSSETNV; (SEQ ID NO: 42)

7) ZIL94:
VL-CDR1 of

GLNSGSVSTSNYPG, (SEQ ID NO: 46)

VL-CDR2 of

DTGSRPS, (SEQ ID NO: 47)

and

VL-CDR3 of

SLYTDSDILV; (SEQ ID NO: 48)

8) ZIL154:
VL-CDR1 of

KASQSLLHSDGNTYLD, (SEQ ID NO: 52)

VL-CDR2 of

KVSNRDP, (SEQ ID NO: 53)
and

VL-CDR3 of

MQAIHFPLT; (SEQ ID NO: 54)

9) ZIL159:
VL-CDR1 of

SGETLNRFYTQ, (SEQ ID NO: 58)

VL-CDR2 of

KDTERPS, (SEQ ID NO: 59)
and

VL-CDR3 of

KSAVSIDVGV; (SEQ ID NO: 60)

10) ZIL171:
VL-CDR1 of

SGKSLSYYYAQ, (SEQ ID NO: 64)

VL-CDR2 of

KDTERPS, (SEQ ID NO: 65)
and

VL-CDR3 of

ESAVSSDTIV; (SEQ ID NO: 66)

11) 04H07:
VL-CDR1 of

KSSQSLLYSINQKNHLA, (SEQ ID NO: 203)

VL-CDR2 of

WASTRES, (SEQ ID NO: 204)

VL-CDR3 of

QQGYTYPFT; (SEQ ID NO: 205)

12) 06A09:
VL-CDR1 of

KSSQSLLYSINQKNFLA, (SEQ ID NO: 209)

VL-CDR2 of

WASTRES, (SEQ ID NO: 210)

VL-CDR3 of

QQHYGYPFT; (SEQ ID NO: 211)
or 13) a variant of 1) to 12) that differs from the CDRs of respective parent antibody 15H05, ZIL1, ZIL8, ZIL9, ZIL11, ZIL69, ZIL94, ZIL154, ZIL159, ZIL171, 04H07, or 06A09 by addition, deletion, and/or substitution of one or more amino acid residues in at least one of VH or VL CDR1, CDR2, or CDR3.

In one embodiment, the invention provides an isolated nucleic acid comprising a nucleic acid sequence encoding at least one of the following combinations of variable light complementary determining region (CDR) sequences:

1) 15H05:
variable light
(VL)-CDR1 of

RASQGISIWLS, (SEQ ID NO: 4)

VL-CDR2 of

KASNLHI, (SEQ ID NO: 5)
and

VL-CDR3 of

LQSQTYPLT; (SEQ ID NO: 6)

2) ZIL1:
VL-CDR1 of

SGSTNNIGILAAT, (SEQ ID NO: 16)

VL-CDR2 of

SDGNRPS, (SEQ ID NO: 17)

and VL-CDR3 of

QSFDTTLDAYV; (SEQ ID NO: 18)

3) ZIL8:
VL-CDR1 of

TGSSSNIGSGYVG, (SEQ ID NO: 22)

VL-CDR2 of

YNSDRPS, (SEQ ID NO: 23)
and

VL-CDR3 of

SVYDRTFNAV; (SEQ ID NO: 24)

4) ZIL9:
VL-CDR1 of

SGESLNEYYTQ, (SEQ ID NO: 28)

VL-CDR2 of

RDTERPS, (SEQ ID NO: 29)
and

VL-CDR3 of

ESAVDTGTLV; (SEQ ID NO: 30)

5) ZIL11:
VL-CDR1 of

SGESLSNYYAQ, (SEQ ID NO: 34)

VL-CDR2 of

KDTERPS, (SEQ ID NO: 35)
and

VL-CDR3 of

ESAVSSDTIV; (SEQ ID NO: 36)

6) ZIL69:
VL-CDR1 of
(SEQ ID NO: 40)
SGESLNKYYAQ,

VL-CDR2 of
(SEQ ID NO: 41)
KDTERPS,
and

VL-CDR3 of
(SEQ ID NO: 42)
ESAVSSETNV;

7) ZIL94:
VL-CDR1 of
(SEQ ID NO: 46)
GLNSGSVSTSNYPG,

VL-CDR2 of
(SEQ ID NO: 47)
DTGSRPS,
and

VL-CDR3 of
(SEQ ID NO: 48)
SLYTDSDILV;

8) ZIL154:
VL-CDR1 of
(SEQ ID NO: 52)
KASQSLLHSDGNTYLD,

VL-CDR2 of
(SEQ ID NO: 53)
KVSNRDP,
and

VL-CDR3 of
(SEQ ID NO: 54)
MQAIHFPLT;

9) ZIL159:
VL-CDR1 of
(SEQ ID NO: 58)
SGETLNRFYTQ,

VL-CDR2 of
(SEQ ID NO: 59)
KDTERPS,
and

VL-CDR3 of
(SEQ ID NO: 60)
KSAVSIDVGV;

10) ZIL171:
VL-CDR1 of
(SEQ ID NO: 64)
SGKSLSYYYAQ,

VL-CDR2 of
(SEQ ID NO: 65)
KDTERPS,
and

VL-CDR3 of
(SEQ ID NO: 66)
ESAVSSDTIV;

11) 04H07:
VL-CDR1 of
(SEQ ID NO: 203)
KSSQSLLYSINQKNHLA,

VL-CDR2 of
(SEQ ID NO: 204)
WASTRES,

VL-CDR3 of
(SEQ ID NO: 205)
QQGYTYPFT;

12) 06A09:
VL-CDR1 of
(SEQ ID NO: 209)
KSSQSLLYSINQKNFLA,

VL-CDR2 of
(SEQ ID NO: 210)
WASTRES,

VL-CDR3 of
(SEQ ID NO: 211)
QQHYGYPFT;
or 13) a variant of 1) to 12) that differs from the CDRs of respective parent antibody 15H05, ZIL1, ZIL8, ZIL9, ZIL11, ZIL69, ZIL94, ZIL154, ZIL159, ZIL171, 04H07, or 06A09 by addition, deletion, and/or substitution of one or more amino acid residues in at least one of VH or VL CDR1, CDR2, or CDR3.

The present invention further provides a vector including at least one of the nucleic acids described above.

The present also provides a method of improving the consistency and/or quality of a feline antibody, the method including: expressing nucleotide sequence encoding a feline IgG kappa light chain and nucleotide sequence encoding a feline IgG heavy chain in a host cell to produce a feline antibody, wherein the nucleotide sequence encoding the feline IgG kappa light chain comprises a kappa light chain constant nucleotide sequence in which sequence encoding a C-terminal QRE sequence otherwise present in a wild-type feline IgG kappa light chain constant region has been modified and/or deleted. Such modifications can include modifications to the nucleotide sequence such that, for example, deletions, substitutions, or additions of one or more amino acids to the c-terminus occur.

In on embodiment, the method of improving the consistency and/or quality of a feline antibody includes:
a) providing nucleotide sequence encoding a wild-type feline IgG kappa light chain constant region of a feline antibody, wherein said wild-type feline kappa light chain constant region comprises a C-terminal amino acid sequence of QRE;
b) removing and/or modifying sequence encoding the C-terminal QRE in the nucleotide sequence in a) to form a revised kappa light chain constant nucleotide sequence;
c) combining the revised kappa light chain constant nucleotide sequence from b) with nucleotide sequence encoding a feline IgG kappa light chain variable region to form nucleotide sequence encoding a complete feline IgG kappa light chain; and
d) expressing the nucleotide sequence encoding the complete feline IgG kappa light chain from c) and nucleotide sequence encoding a feline IgG heavy chain in a host cell to produce a feline antibody in which the C-terminal QRE sequence which would otherwise be present in the wild-type feline IgG kappa light chain constant region is modified and/or deleted.

In one embodiment, improving the consistency and/or quality of the feline antibody includes reducing the levels of free IgG kappa light chain, thereby increasing the percentage of intact feline IgG antibody monomer.

In one embodiment, the nucleotide sequence encoding the feline IgG kappa light chain and the nucleotide sequence encoding the feline IgG heavy chain are carried on the same vector used to transform the host cell. In another embodiment, the nucleotide sequence encoding the feline IgG kappa light chain and the nucleotide sequence encoding the feline IgG heavy chain are carried on separate vectors used to transform the host cell.

In on embodiment of the method of improving the consistency and/or quality of a feline antibody, the feline antibody specifically binds to a target involved in a cytokine and/or growth factor-mediated disorder. In one specific embodiment, the feline antibody specifically binds to feline IL-31 or feline NGF.

In one embodiment, the feline antibody comprises a kappa light chain constant region having the sequence: RSDAQPSVFLFQPSLDELHTGSASIVCILNDFYPKEVNVKWKVDGVVQNKGIQESTTEQNSKD STYSLSSTLTMSSTEYQSHEKFSCEVTHKSLASTLVKSFQRSEC (SEQ ID NO: 186) or a variant thereof. Such variants can include, for example, an addition or modification of one or more amino acid residue(s) to the c-terminus of SEQ ID NO: 186.

The present invention further provides a method of improving the consistency and/or quality of a canine antibody, the method including: expressing nucleotide sequence encoding a canine IgG kappa light chain and nucleotide sequence encoding a canine IgG heavy chain in a host cell to produce a canine antibody, wherein the nucleotide sequence encoding the canine IgG kappa light chain comprises a kappa light chain constant nucleotide sequence in which sequence encoding a C-terminal QRVD sequence otherwise present in a wild-type canine IgG kappa light chain (Canine LC Kappa wt, SEQ ID NO: 194) constant region has been modified and/or deleted. Such modifications can include modifications to the nucleotide sequence such that, for example, deletions, substitutions, or additions of one or more amino acids to the c-terminus occur.

In one embodiment, the method of improving the consistency and/or quality of a canine antibody includes:
  a) providing nucleotide sequence encoding a wild-type canine IgG kappa light chain constant region of a canine antibody, wherein said wild-type canine kappa light chain constant region comprises a C-terminal amino acid sequence of QRVD;
  b) removing and/or modifying sequence encoding the C-terminal QRVD in the nucleotide sequence in a) to form a revised kappa light chain constant nucleotide sequence;
  c) combining the revised kappa light chain constant nucleotide sequence from b) with nucleotide sequence encoding a canine IgG kappa light chain variable region to form nucleotide sequence encoding a complete canine IgG kappa light chain; and
  d) expressing the nucleotide sequence encoding the complete canine IgG kappa light chain from c) and nucleotide sequence encoding a canine IgG heavy chain in a host cell to produce a canine antibody in which the C-terminal QRVD sequence which would otherwise be present in the wild-type canine IgG kappa light chain constant region is modified and/or deleted.

In one embodiment, improving the consistency and/or quality of the canine antibody includes reducing the levels of free IgG kappa light chain, thereby increasing the percentage of intact canine IgG antibody monomer.

In one embodiment, the nucleotide sequence encoding the canine IgG kappa light chain and the nucleotide sequence encoding the canine IgG heavy chain are carried on the same vector used to transform the host cell. In another embodiment, the nucleotide sequence encoding the canine IgG kappa light chain and the nucleotide sequence encoding the canine IgG heavy chain are carried on separate vectors used to transform the host cell.

In one embodiment of the method of improving the consistency and/or quality of a canine antibody, the canine antibody specifically binds to a target involved in a cytokine and/or growth factor-mediated disorder. In one specific embodiment, the canine antibody specifically binds to canine IL-31.

In one embodiment of the method of improving the consistency and/or quality of a canine antibody, the canine antibody comprises a kappa light chain constant region having the sequence: RNDAQPAVYLFQPSPDQLHTGSASVVCLLNSFYPKDINVKWKVDGVIQDTGIQESVTEQDKDS TYSLSSTLTMSSTEYLSHELYSCEITHKSLPSTLI KSFQRSEC (SEQ ID NO: 179) or a variant thereof. Such variants can include, for example, an addition or modification of one or more amino acid residue(s) to the c-terminus of SEQ ID NO: 179.

The revised kappa light chain constant regions described herein can be used in conjunction with any number of feline and canine antibodies, such as including, but not limited to, any of the canine or feline antibodies described in the specification and claims of this invention. Canine and feline antibodies having targets other than IL-31 are also envisioned to be suitably combined with the revised kappa light chain constant regions disclosed herein. The present invention includes any feline or canine antibody comprising such revised kappa light chain constant regions disclosed herein as such antibodies are reasonably expected to have improved consistency and/or quality on the basis of the disclosure in the instant specification and claims.

BRIEF DESCRIPTION OF THE DRAWINGS

FIG. 1A is an alignment showing amino acid sequence conservation between IL-31 from different species. In particular, a comparison between SEQ ID NO: 155 (canine IL-31), SEQ ID NO: 157 (feline IL-31), SEQ ID NO: 165 (equine IL-31), and SEQ ID NO: 181 (human IL-31) is shown. In FIG. 1B, the percent amino acid sequence identity between canine, feline, horse and human IL-31 is also indicated.

FIG. 2 details the affinity with which candidate antibodies with CDRs derived from mouse origin bind feline and canine IL-31 using surface plasmon resonance (SPR) on a Biacore system (Biacore Life Sciences (GE Healthcare), Uppsala, Sweden).

FIG. 3 is a table showing potency (IC50 (µg/ml)) of candidate antibodies with CDRs derived from mouse origin as measured by canine and feline cellular assays. In particular, the candidate antibodies were assessed for their ability to inhibit IL-31-mediated STAT phosphorylation in canine DH-82 or feline FCWF4 macrophage-like cells.

FIG. 4 shows the results obtained for binding of candidate monoclonal antibodies with CDRs of dog origin to various proteins using both an indirect ELISA and Biacore methods. For the indirect ELISA, binding (ELISA OD) to wildtype feline IL-31 and a feline IL-31 15H05 mutant which had mutations in the monoclonal antibody 15H05 epitope region was assessed. To confirm binding, biacore analysis was performed using canine, feline, equine, human, the feline 15H05 mutant, and feline 11 E12 mutant IL-31 proteins as surfaces and a single test concentration of antibody. The feline IL-31 11E12 mutant had mutations in the monoclonal antibody 11E12 epitope region.

FIG. 6A shows the alignment of wildtype feline IL-31 (SEQ ID NO: 157) with mutants 15H05 (SEQ ID NO: 163) and 11E12 (SEQ ID NO: 161) highlighting the positions where the alanine substitutions occur.

FIG. 7A shows the competition binding data for mouse 15H05 and 11E12 antibodies to canine IL-31. FIG. 7B shows the competition binding data for antibodies 15H05 and 11E12 on a feline IL-31 surface.

FIG. 10A shows the baseline pre-challenge pruritic behavior for the T01 vehicle placebo and T02 antibody ZTS-361 groups from day −7 through day 28 with day zero being the day of antibody administration to group T02. FIG. 10B shows the efficacy of antibody ZTS-361 demonstrating a significant reduction in pruritus observed on days 7 (p<0.0001), 21 (p<0.0027), and 28 (p<0.0238) following IL-31 challenge when compared to vehicle placebo control.

FIG. 11A is of a graph showing the plasma levels of IL-31 in client owned animals among dogs with atopic and allergic dermatitis compared to normal laboratory FIG. 11B is of a graph showing the results of a recent study to determine serum IL-31 levels in cats with a presumptive diagnosis of allergic dermatitis (AD) from several different geographic regions in the USA. FIG. 11C is of a graph showing the pharmacokinetic profile of canine IL-31 in dogs following administration of a subcutaneous dose of 1.75 µg/kg canine IL-31.

FIG. 15 shows the amino acids on the c-terminal end of the Ig kappa light chain constant protein for the depicted species. Canine LC kappa wt, the depicted C-terminal amino acid residues are positions 103 to109 of SEQ ID NO: 194, with the depicted nucleotide residue nos. being residue nos. 307 to 330 of SEQ ID NO: 195; Feline LC kappa G minus (G−), the depicted C-terminal amino acid residues are positions 105 to 110 of SEQ ID NO: 175, with the depicted nucleotide residue nos. being residue nos. 313 to 330 of SEQ ID NO: 176; Pig LC kappa, the depicted C-terminal amino acid residues are positions 104 to108 of SEQ ID NO: 196, with the depicted nucleotide residue nos. being residue nos. 310 to 327 of SEQ ID NO: 197; Mink LC kappa, the depicted C-terminal amino acid residues are positions 105 to108 of SEQ ID NO: 198, with the depicted nucleotide residue nos. being residue nos. 313 to 327 of SEQ ID NO: 199; Human LC kappa, the depicted C-terminal amino acid residues are positions 102 to106 of SEQ ID NO: 192, with the depicted nucleotide residue nos. being residue nos. 304 to 321 of SEQ ID NO: 193; Mouse LC kappa, the depicted C-terminal amino acid residues are positions 102 to106 of SEQ ID NO: 190, with the depicted nucleotide residue nos. being residue nos. 304 to 321 of SEQ ID NO: 191. The grey rectangle outlines the position of the c-terminal cysteine that forms an interchain disulphide bond with the IgG heavy constant chain necessary for an intact antibody. The grey triangle highlights the increasing percentage of kappa light chain utilization by IgGs from the species depicted according to; Canine, Feline, and Pig (Arun et al. 1996 Zentralbl Veterinarmed. November; 43(9):573-6), Mink (Bovkun et al. 1993 Eur J Immunol. August; 23(8):1929-34), Mouse (Woloschak et al. 1987 Mol Immunol. July; 24(7):751-7), Human (Barandun et al. 1976 Blood. January; 47(1):79-89). Nucleotides depicted in light grey highlight those codons in which a single nucleotide change at that position will result in a stop codon.

FIG. 16A is a pictoral representation of a feline IgG highlighting relative positions of the expected inter and intra-disulphide bonds. CYS15, the depicted amino acid residue is position 15 of Feline HC AlleleA wt (SEQ ID NO: 171) and Feline HC AlleleA 1 (SEQ ID NO: 173), with the depicted nucleotide residue nos. being residue nos. 43-45 of Feline HC AlleleA wt (SEQ ID NO: 172) and 43-45 of Feline HC AlleleA 1 (SEQ ID NO: 174) respectively. CYS107, the depicted amino acid residue is position 107 of Feline LC Kappa G minus (SEQ ID NO: 175), with the depicted nucleotide residue nos. being residue nos. 319-321 of Feline LC Kappa G minus (SEQ ID NO: 176). FIG. 16B is a homology model of ZTS-361 highlighting the positions of CYS15 and CYS107 described above. FIG. 16C is an enlarged picture of the area encircled in 16B again highlighting the positions of the two cysteines responsible for interchain pairing of feline heavy and light chains. The wire surface shells depicted are the calculated electrostatic contributions for the kappa light chain constant residues QRE that immediately follow CYS107 described in FIG. 15 for the feline LC kappa G−.

FIG. 17A describes the sequence ID numbers corresponding to the heavy and light chains used to create stable CHO cell lines producing antibodies ZTS-361 and ZTS-1505 (described above and/or in section 1.9 of example section). Highlighted is feline LC Kappa G minus QRE minus (SEQ ID NO: 186), the corresponding nucleotide sequence for which is feline LC Kappa G minus QRE minus (SEQ ID NO: 187). FIG. 17B shows the results for non-reducing capillary gel electrophoresis (NR-CGE) comparing IgG from individual stable CHO clones of ZTS-1505. The time corrected area (TCA) is defined as the individual peak area from the instrument output divided by the migration time. Total TCA is defined as the sum of the TCAs for all peaks greater than or equal to 0.3%. Percent monomer intact IgG (% Monomer) and percent fragments (% Fragments) are calculated based on their individual TCAs as a percent of the total TCA. % Fragments are the sum of all the peak areas migrating with a lower molecular weight than that of intact IgG. FIG. 17C shows the comparison of a single stable CHO clone producing antibody ZTS-361 compared to a single stable CHO clone producing ZTS-1505. Comparison of the two stable clones was made across 8 independent culture conditions labeled A through G. The percent viability of each culture following 14 days of culture is indicated. The titer indicates the amount of antibody produced after 14 days of culture by each stable clone under the respective culture condition. The percent monomer calculated from NR-CGE from each clone grown using various culture conditions is indicated.

FIG. 19 shows the results from the NR CGE comparing anti feline IL-31 and anti feline NGF antibodies with and without the modified kappa constant C-terminus.

FIG. 20 shows a ClustallW sequence alignment of feline to equine IL-31.

FIGS. 21A and 21B show an alignment of the variable heavy (FIG. 21A) and light (FIG. 21B) chains of antibodies 04H07 and 06A09 compared to mouse antibody 15H05 using ClustallW. For comparison, the location of each of the six CDRs are outlined with boxes.

FIG. 23 shows the results of Alanine substitution mutagenesis of the heavy chain CDRs of antibody ZTS-1505 comparing bindingi and IL-31 mediated pSTAT signalling inhibition to the wildtype antibody.

FIG. 24 shows the results of Alanine substitution mutagenesis of the light chain CDRs of antibody ZTS-1505 comparing bindingi and IL-31 mediated pSTAT signalling inhibition to the wildtype antibody.

Figure 5A:
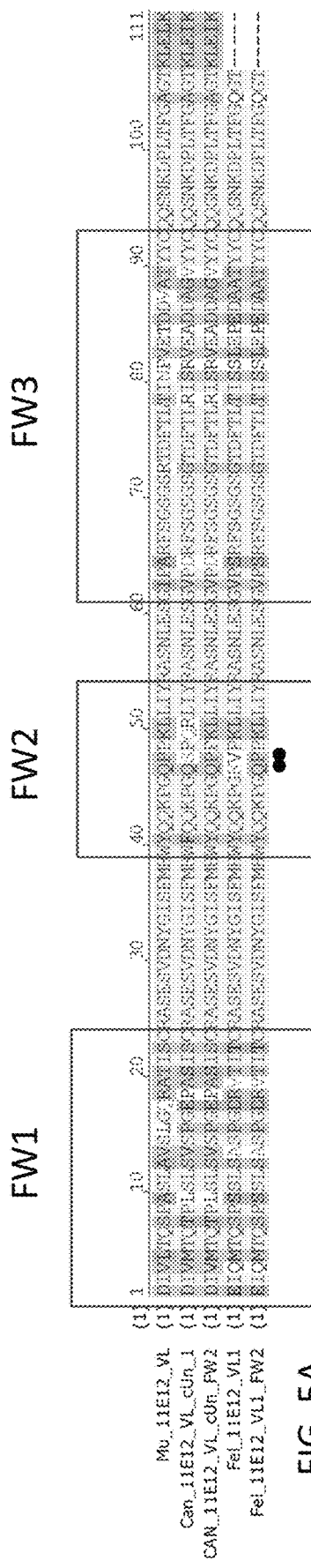
FIG. 5A shows an alignment of mouse antibody 11 E1 2 VL sequence (SEQ ID NO: 73) comparing previously disclosed caninized 11E12 sequences designated as Can_11E12_VL_cUn_1 (SEQ ID NO: 182) and CAN_11E12_VL_cUn_FW2 (SEQ ID NO: 184) to the felinized versions designated as FEL_11E12_VL1 (SEQ ID NO: 113) and FEL_11E12_VL1_FW2 (SEQ ID NO: 117). Noted below the alignment in FIG. 5A are dots showing the positons of relevant changes to Fel_11E12_VL1 that were necessary to restore affinity of this antibody to the IL-31 protein.

Antibodies described in FIGS. 12, 13A and 13B, and 14A and 14B were grown in culture conditions equivalent to culture condition A from FIG. 17C.

BRIEF DESCRIPTION OF THE SEQUENCES

SEQ ID NO: 1 is a variable heavy chain CDR1 referred to herein as MU_15H05_VH_CDR1;
SEQ ID NO: 2 is a variable heavy chain CDR2 referred to herein as MU_15H05_VH_CDR2;
SEQ ID NO: 3 is a variable heavy chain CDR3 referred to herein as MU_15H05_VH_CDR3;
SEQ ID NO: 4 is a variable light CDR1 referred to herein as MU_15H05_VL_CDR1;

SEQ ID NO: 5 is a variable light CDR2 referred to herein as MU_15H05_VL_CDR2;
SEQ ID NO: 6 is a variable light CDR3 referred to herein as MU_15H05_VL_CDR3;
SEQ ID NO: 7 is a variable heavy chain CDR1 referred to herein as 11E12-VH-CDR1;
SEQ ID NO: 8 is a variable heavy chain CDR2 referred to herein as 11E12-VH-CDR2;
SEQ ID NO: 9 is a variable heavy chain CDR3 referred to herein as 11E12-VH-CDR3;
SEQ ID NO: 10 is a variable light chain CDR1 referred to herein as 11E12-VL-CDR1;
SEQ ID NO: 11 is a variable light chain CDR2 referred to herein as 11E12-VL-CDR2;
SEQ ID NO: 12 is a variable light chain CDR3 referred to herein as 11E12-VL-CDR3;
SEQ ID NO: 13 is a variable heavy chain CDR1 referred to herein as CAN_ZIL1_VH_CDR1;
SEQ ID NO: 14 is a variable heavy chain CDR2 referred to herein as CAN_ZIL1_VH_CDR2;
SEQ ID NO: 15 is a variable heavy chain CDR3 referred to herein as CAN_ZIL1_VH_CDR3;
SEQ ID NO: 16 is a variable light chain CDR1 referred to herein as CAN_ZIL1_VL_CDR1;
SEQ ID NO: 17 is a variable light chain CDR2 referred to herein as CAN_ZIL1_VL_CDR2;
SEQ ID NO: 18 is a variable light chain CDR3 referred to herein as CAN_ZIL1_VL_CDR3;
SEQ ID NO: 19 is a variable heavy chain CDR1 referred to herein as CAN_ZIL8_VH_CDR1;
SEQ ID NO: 20 is a variable heavy chain CDR2 referred to herein as CAN_ZIL8_VH_CDR2;
SEQ ID NO: 21 is a variable heavy chain CDR3 referred to herein as CAN_ZIL8_VH_CDR3;
SEQ ID NO: 22 is a variable light chain CDR1 referred to herein as CAN_ZIL8_VL_CDR1;
SEQ ID NO: 23 is a variable light chain CDR2 referred to herein as CAN_ZIL8_VL_CDR2;
SEQ ID NO: 24 is a variable light chain CDR3 referred to herein as CAN_ZIL8_VL_CDR3;
SEQ ID NO: 25 is a variable heavy chain CDR1 referred to herein as CAN_ZIL9_VH_CDR1;
SEQ ID NO: 26 is a variable heavy chain CDR2 referred to herein as CAN_ZIL9_VH_CDR2;
SEQ ID NO: 27 is a variable heavy chain CDR3 referred to herein as CAN_ZIL9_VH_CDR3;
SEQ ID NO: 28 is a variable light chain CDR1 referred to herein as CAN_ZIL9_VL_CDR1;
SEQ ID NO: 29 is a variable light chain CDR2 referred to herein as CAN_ZIL9_VL_CDR2;
SEQ ID NO: 30 is a variable light chain CDR3 referred to herein as CAN_ZIL9_VL_CDR3;
SEQ ID NO: 31 is a variable heavy chain CDR1 referred to herein as CAN_ZIL11_VH_CDR1;
SEQ ID NO: 32 is a variable heavy chain CDR2 referred to herein as CAN_ZIL11_VH_CDR2;
SEQ ID NO: 33 is a variable heavy chain CDR3 referred to herein as CAN_ZIL11_VH_CDR3;
SEQ ID NO: 34 is a variable light chain CDR1 referred to herein as CAN_ZIL11_VL_CDR1;
SEQ ID NO: 35 is a variable light chain CDR2 referred to herein as CAN_ZIL11_VL_CDR2;
SEQ ID NO: 36 is a variable light chain CDR3 referred to herein as CAN_ZIL11_VL_CDR3;
SEQ ID NO: 37 is a variable heavy chain CDR1 referred to herein as CAN_ZIL69_VH_CDR1;
SEQ ID NO: 38 is a variable heavy chain CDR2 referred to herein as CAN_ZIL69_VH_CDR2;
SEQ ID NO: 39 is a variable heavy chain CDR3 referred to herein as CAN_ZIL69_VH_CDR3;
SEQ ID NO: 40 is a variable light chain CDR1 referred to herein as CAN_ZIL69_VL_CDR1;
SEQ ID NO: 41 is a variable light chain CDR2 referred to herein as CAN_ZIL69_VL_CDR2;
SEQ ID NO: 42 is a variable light chain CDR3 referred to herein as CAN_ZIL69_VL_CDR3;
SEQ ID NO: 43 is a variable heavy chain CDR1 referred to herein as CAN_ZIL94_VH_CDR1;
SEQ ID NO: 44 is a variable heavy chain CDR2 referred to herein as CAN_ZIL94_VH_CDR2;
SEQ ID NO: 45 is a variable heavy chain CDR3 referred to herein as CAN_ZIL94_VH_CDR3;
SEQ ID NO: 46 is a variable light chain CDR1 referred to herein as CAN_ZIL94_VL_CDR1;
SEQ ID NO: 47 is a variable light chain CDR2 referred to herein as CAN_ZIL94_VL_CDR2;
SEQ ID NO: 48 is a variable light chain CDR3 referred to herein as CAN_ZIL94_VL_CDR3;
SEQ ID NO: 49 is a variable heavy chain CDR1 referred to herein as CAN_ZIL154_VH_CDR1;
SEQ ID NO: 50 is a variable heavy chain CDR2 referred to herein as CAN_ZIL154_VH_CDR2;
SEQ ID NO: 51 is a variable heavy chain CDR3 referred to herein as CAN_ZIL154_VH_CDR3;
SEQ ID NO: 52 is a variable light chain CDR1 referred to herein as CAN_ZIL154_VL_CDR1;
SEQ ID NO: 53 is a variable light chain CDR2 referred to herein as CAN_ZIL154_VL_CDR2;
SEQ ID NO: 54 is a variable light chain CDR3 referred to herein as CAN_NIL154_VL_CDR3;
SEQ ID NO: 55 is a variable heavy chain CDR1 referred to herein as CAN_ZIL159_VH_CDR1;
SEQ ID NO: 56 is a variable heavy chain CDR2 referred to herein as CAN_ZIL159_VH_CDR2;
SEQ ID NO: 57 is a variable heavy chain CDR3 referred to herein as CAN_ZIL159_VH_CDR3;
SEQ ID NO: 58 is a variable light chain CDR1 referred to herein as CAN_ZIL159_VL_CDR1;
SEQ ID NO: 59 is a variable light chain CDR2 referred to herein as CAN_ZIL159_VL_CDR2;
SEQ ID NO: 60 is a variable light chain CDR3 referred to herein as CAN_ZIL159_VL_CDR3;
SEQ ID NO: 61 is a variable heavy chain CDR1 referred to herein as CAN_ZIL171_VH_CDR1;
SEQ ID NO: 62 is a variable heavy chain CDR2 referred to herein as CAN_ZIL171_VH_CDR2;
SEQ ID NO: 63 is a variable heavy chain CDR3 referred to herein as CAN_ZIL171_VH_CDR3;
SEQ ID NO: 64 is a variable light chain CDR1 referred to herein as CAN_ZIL171_VL_CDR1;
SEQ ID NO: 65 is a variable light chain CDR2 referred to herein as CAN_ZIL171_VL_CDR2;
SEQ ID NO: 66 is a variable light chain CDR3 referred to herein as CAN_ZIL171_VL_CDR3;
SEQ ID NO: 67 is a variable heavy chain referred to herein as MU_15H05_VH;
SEQ ID NO: 68 is a nucleotide sequence encoding the variable heavy chain referred to herein as MU_15H05_VH;
SEQ ID NO: 69 is a variable light chain referred to herein as MU_15H05_VL;
SEQ ID NO: 70 is a nucleotide sequence encoding the variable light chain referred to herein as MU_15H05_VL;

SEQ ID NO: 71 is a variable heavy chain referred to herein as MU-11E12-VH;

SEQ ID NO: 72 is a nucleotide sequence encoding the variable heavy chain referred to herein as MU-11E12-VH;

SEQ ID NO: 73 is a variable light chain referred to herein as MU-11E12-VL;

SEQ ID NO: 74 is a nucleotide sequence encoding the variable light chain referred to herein as MU-11E12-VL;

SEQ ID NO: 75 is a variable heavy chain referred to herein as CAN-ZIL1_VH;

SEQ ID NO: 76 is a nucleotide sequence encoding the variable heavy chain referred to herein as CAN-ZIL1_VH;

SEQ ID NO: 77 is a variable light chain referred to herein as CAN-ZIL1_VL;

SEQ ID NO: 78 is a nucleotide sequence encoding the variable light chain referred to herein as CAN-ZIL1_VL;

SEQ ID NO: 79 is a variable heavy chain referred to herein as CAN-ZIL8_VH;

SEQ ID NO: 80 is a nucleotide sequence encoding the variable heavy chain referred to herein as CAN-ZIL8_VH;

SEQ ID NO: 81 is a variable light chain referred to herein as CAN-ZIL8_VL;

SEQ ID NO: 82 is a nucleotide sequence encoding the variable light chain referred to herein as CAN-ZIL8_VL;

SEQ ID NO: 83 is a variable heavy chain referred to herein as CAN-ZIL9_VH;

SEQ ID NO: 84 is a nucleotide sequence encoding the variable heavy chain referred to herein as CAN-ZIL9_VH;

SEQ ID NO: 85 is a variable light chain referred to herein as CAN-ZIL9_VL;

SEQ ID NO: 86 is a nucleotide sequence encoding the variable light chain referred to herein as CAN-ZIL9_VL;

SEQ ID NO: 87 is a variable heavy chain referred to herein as CAN-ZIL11_VH;

SEQ ID NO: 88 is a nucleotide sequence encoding the variable heavy chain referred to herein as CAN-ZIL11_VH;

SEQ ID NO: 89 is a variable light chain referred to herein as CAN-ZIL11_VL;

SEQ ID NO: 90 is a nucleotide sequence encoding the variable light chain referred to herein as CAN-ZIL11_VL;

SEQ ID NO: 91 is a variable heavy chain referred to herein as CAN-ZIL69_VH;

SEQ ID NO: 92 is a nucleotide sequence encoding the variable heavy chain referred to herein as CAN-ZIL69_VH;

SEQ ID NO: 93 is a variable light chain referred to herein as CAN-ZIL69_VL;

SEQ ID NO: 94 is a nucleotide sequence encoding the variable light chain referred to herein as CAN-ZIL69_VL;

SEQ ID NO: 95 is a variable heavy chain referred to herein as CAN-ZIL94_VH;

SEQ ID NO: 96 is a nucleotide sequence encoding the variable heavy chain referred to herein as CAN-ZIL94_VH;

SEQ ID NO: 97 is a variable light chain referred to herein as CAN-ZIL94_VL;

SEQ ID NO: 98 is a nucleotide sequence encoding the variable light chain referred to herein as CAN-ZIL94_VL;

SEQ ID NO: 99 is a variable heavy chain referred to herein as CAN-ZIL154_VH;

SEQ ID NO: 100 is a nucleotide sequence encoding the variable heavy chain referred to herein as CAN-ZIL154_VH;

SEQ ID NO: 101 is a variable light chain referred to herein as CAN-ZIL154_VL;

SEQ ID NO: 102 is a nucleotide sequence encoding the variable light chain referred to herein as CAN-ZIL154_VL;

SEQ ID NO: 103 is a variable heavy chain referred to herein as CAN-ZIL159_VH;

SEQ ID NO: 104 is a nucleotide sequence encoding the variable heavy chain referred to herein as CAN-ZIL159_VH;

SEQ ID NO: 105 is a variable light chain referred to herein as CAN-ZIL159_VL;

SEQ ID NO: 106 is a nucleotide sequence encoding the variable light chain referred to herein as CAN-ZIL159_VL;

SEQ ID NO: 107 is a variable heavy chain referred to herein as CAN-ZIL171_VH;

SEQ ID NO: 108 is a nucleotide sequence encoding the variable heavy chain referred to herein as CAN-ZIL171_VH;

SEQ ID NO: 109 is a variable light chain referred to herein as CAN-ZIL171_VL;

SEQ ID NO: 110 is a nucleotide sequence encoding the variable light chain referred to herein as CAN-ZIL171_VL;

SEQ ID NO: 111 is a variable heavy chain referred to herein as FEL_11E12_VH1;

SEQ ID NO: 112 is a nucleotide sequence encoding the variable heavy chain referred to herein as FEL_11E12_VH1;

SEQ ID NO: 113 is a variable light chain referred to herein as FEL_11E12_VL1;

SEQ ID NO: 114 is a nucleotide sequence encoding the variable light chain referred to herein as FEL_11E12_VL1;

SEQ ID NO: 115 is a variable light chain referred to herein as FEL_11E12_VL2;

SEQ ID NO: 116 is a nucleotide sequence encoding the variable light chain referred to herein as FEL_11E12_VL2;

SEQ ID NO: 117 is a variable light chain referred to herein as FEL_11E12_VL1_FW2;

SEQ ID NO: 118 is a nucleotide sequence encoding the variable light chain referred to herein as FEL_11E12_VL1_FW2;

SEQ ID NO: 119 is a variable light chain referred to herein as FEL_11E12_VL1_K46Q;

SEQ ID NO: 120 is a nucleotide sequence encoding the variable light chain referred to herein as FEL_11E12_VL1_K46Q;

SEQ ID NO: 121 is a variable heavy chain referred to herein as FEL_15H05_VH1;

SEQ ID NO: 122 is a nucleotide sequence encoding the variable heavy chain referred to herein as FEL_15H05_VH1;

SEQ ID NO: 123 is a variable heavy chain referred to herein as FEL_15H05_VH2;

SEQ ID NO: 124 is a nucleotide sequence encoding the variable heavy chain referred to herein as FEL_15H05_VH2;

SEQ ID NO: 125 is a variable heavy chain referred to herein as FEL_15H05_VH3;

SEQ ID NO: 126 is a nucleotide sequence encoding the variable heavy chain referred to herein as FEL_15H05_VH3;

SEQ ID NO: 127 is a variable light chain referred to herein as FEL_15H05_VL1;

SEQ ID NO: 128 is a nucleotide sequence encoding the variable light chain referred to herein as FEL_15H05_VL1;

SEQ ID NO: 129 is a variable light chain referred to herein as FEL_15H05_VL2;

SEQ ID NO: 130 is a nucleotide sequence encoding the variable light chain referred to herein as FEL_15H05_VL2;

SEQ ID NO: 131 is a variable light chain referred to herein as FEL_15H05_VL3;

SEQ ID NO: 132 is a nucleotide sequence encoding the variable light chain referred to herein as FEL_15H05_VL3;

SEQ ID NO: 133 is a variable light chain referred to herein as FEL_15H05_VL1_FW1;

SEQ ID NO: 134 is a nucleotide sequence encoding the variable light chain referred to herein as FEL_15H05_VL1_FW1;

SEQ ID NO: 135 is a variable light chain referred to herein as FEL_15H05_VL1_FW2;

SEQ ID NO: 136 is a nucleotide sequence encoding the variable light chain referred to herein as FEL_15H05_VL1_FW2;

SEQ ID NO: 137 is a variable light chain referred to herein as FEL_15H05_VL1_FW3;

SEQ ID NO: 138 is a nucleotide sequence encoding the variable light chain referred to herein as FEL_15H05_VL1_FW3;

SEQ ID NO: 139 is a variable light chain referred to herein as FEL_15H05_VL1_FW1_FW2;

SEQ ID NO: 140 is a nucleotide sequence encoding the variable light chain referred to herein as FEL_15H05_VL1_FW1_FW2;

SEQ ID NO: 141 is a variable light chain referred to herein as FEL_15H05_VL1_FW1_FW3;

SEQ ID NO: 142 is a nucleotide sequence encoding the variable light chain referred to herein as FEL_15H05_VL1_FW1_FW3;

SEQ ID NO: 143 is a variable light chain referred to herein as FEL_15H05_VL1_FW2_FW3;

SEQ ID NO: 144 is a nucleotide sequence encoding the variable light chain referred to herein as FEL_15H05_VL1_FW2_FW3;

SEQ ID NO: 145 is a variable light chain referred to herein as FEL_15H05_VL1_FW2_K42N;

SEQ ID NO: 146 is a nucleotide sequence encoding the variable light chain referred to herein as FEL_15H05_VL1_FW2_K42N;

SEQ ID NO: 147 is a variable light chain referred to herein as FEL_15H05_VL1_FW2_V43I;

SEQ ID NO: 148 is a nucleotide sequence encoding the variable light chain referred to herein as FEL_15H05_VL1_FW2_V43I;

SEQ ID NO: 149 is a variable light chain referred to herein as FEL_15H05_VL1_FW2_L46V;

SEQ ID NO: 150 is a nucleotide sequence encoding the variable light chain referred to herein as FEL_15H05_VL1_FW2_L46V;

SEQ ID NO: 151 is a variable light chain referred to herein as FEL_15H05_VL1_FW2_Y49N;

SEQ ID NO: 152 is a nucleotide sequence encoding the variable light chain referred to herein as FEL_15H05_VL1_FW2_Y49N;

SEQ ID NO: 153 is a variable light chain referred to herein as FEL_15H05_VL1_FW2_K42N_V43I;

SEQ ID NO: 154 is a nucleotide sequence encoding the variable light chain referred to herein as FEL_15H05_VL1_FW2_K42N_V43I;

SEQ ID NO: 155 is the amino acid sequence of canine IL-31 protein referred to herein as Canine_IL31;

SEQ ID NO: 156 is the nucleotide sequence encoding the canine IL-31 protein referred to herein as Canine_IL31;

SEQ ID NO: 157 is an amino acid sequence referred to herein as Feline_IL31_wildtype which represents wild-type feline IL-31 protein with a C-terminal His tag;

SEQ ID NO: 158 is a nucleotide sequence encoding the amino acid sequence referred to herein as Feline_IL31_wildtype;

SEQ ID NO: 159 is an amino acid sequence referred to herein as Feline_IL31E_coli which represents feline IL-31 protein with an N-terminal His tag;

SEQ ID NO: 160 is a nucleotide sequence encoding the amino acid sequence referred to herein as Feline_IL31_E_coli;

SEQ ID NO: 161 is an amino acid sequence referred to herein as Feline_IL31_11E12_mutant which represents mutant Feline IL-31 11E12 protein with a C-terminal His tag;

SEQ ID NO: 162 is a nucleotide sequence encoding the amino acid sequence referred to herein as Feline_IL31_11E12_mutant;

SEQ ID NO: 163 is an amino acid sequence referred to herein as Feline_IL31_15H05_mutant which represents mutant Feline IL-31 15H05 protein with a C-terminal His tag;

SEQ ID NO: 164 is a nucleotide sequence encoding the amino acid sequence referred to herein as Feline_IL31_15H05_mutant;

SEQ ID NO: 165 is the amino acid of equine IL-31 protein referred to herein as Equine_IL31;

SEQ ID NO: 166 is the nucleotide sequence encoding the equine IL-31 protein referred to herein as Equine_IL31;

SEQ ID NO: 167 is an amino acid sequence referred to herein as Feline_OSMR_hIgG1_Fc which represents the extracellular domain of feline OSMR fused to human IgG1 Fc;

SEQ ID NO: 168 is a nucleotide sequence encoding the amino acid sequence referred to herein as Feline_OSMR_hIgG1_Fc;

SEQ ID NO: 169 is an amino acid sequence referred to herein as Feline_IL31Ra_HIgG1_Fc_X1_Fn3 which represents feline IL-31 Ra fused to human IgG1 Fc;

SEQ ID NO: 170 is a nucleotide sequence encoding the amino acid sequence referred to herein as Feline_IL31Ra_HIgG1_Fc_X1_Fn3;

SEQ ID NO: 171 is a feline heavy chain referred to herein as Feline_HC_AlleleA_wt;

SEQ ID NO: 172 is a nucleotide sequence encoding the feline heavy chain referred to herein as Feline_HC_AlleleA_wt;

SEQ ID NO: 173 is a feline heavy chain referred to herein as Feline_HC_AlleleA_1, which was engineered to replace the M, L, and G at positions 120, 121, and 123, repectively, of the wild-type sequence of SEQ ID NO: 171 with Alanines (A) in order to elminate antibody effector function;

SEQ ID NO: 174 is a nucleotide sequence encoding the feline heavy chain referred to herein as Feline_HC_AlleleA_1;

SEQ ID NO: 175 is a feline kappa light chain referred to herein as Feline_LC_Kappa_G_minus, which was engineered with a glycosylation knockout (G−) at position 103 such that an N normally present in the wild-type feline kappa light chain at this position was changed to Q;

SEQ ID NO: 176 is a nucleotide sequence encoding the amino acid sequence of a feline kappa light chain referred to herein as Feline_LC_Kappa_G_minus;

SEQ ID NO: 177 is a canine heavy chain referred to herein as Canine_HC_65_1;

SEQ ID NO: 178 is a nucleotide sequence encoding the canine heavy chain referred to herein as Canine_HC_65_1;

SEQ ID NO: 179 is a canine kappa light chain referred to herein as Canine_LC_Kappa;

SEQ ID NO: 180 is a nucleotide sequence encoding the canine kappa light chain referred to herein as Canine_LC_Kappa;

SEQ ID NO: 181 is the amino acid sequence of human IL-31.

SEQ ID NO: 182 is a variable light chain mAb sequence referred to herein as Can_11E12_VL_cUn_1;

SEQ ID NO: 183 is a nucleotide sequence encoding the variable light chain mAb sequence referred to herein as Can_11E12_VL_cUn_1;

SEQ ID NO: 184 is a variable light chain mAb sequence referred to herein as Can_11E12_VL_cUn_FW2;

SEQ ID NO: 185 is a nucleotide sequence encoding the variable light chain mAb sequence referred to herein as Can_11E12_VL_cUn_FW2;

SEQ ID NO: 186 is a feline kappa light chain referred to herein as Feline_LC_Kappa_G_minus_QRE_minus, which was engineered with i) a glycosylation knockout (G−) at position 103 such that an N normally present in the wild-type feline kappa light chain at this position was changed to Q, and ii) a deletion of the C-terminus QRE relative to the wild-type;

SEQ ID NO: 187 is a nucleotide sequence encoding the feline kappa light chain referred to herein as Feline_LC_Kappa_G_minus_QRE_minus;

SEQ ID NO: 188 is a mouse heavy chain designated herein as Mouse_HC_IgG1;

SEQ ID NO: 189 is a nucleotide sequence encoding the mouse heavy chain designated herein as Mouse_HC_IgG1;

SEQ ID NO: 190 is a mouse kappa light chain designated herein as Mouse_LC_Kappa;

SEQ ID NO: 191 is a nucleotide sequence encoding the mouse kappa light chain designated herein as Mouse_LC_Kappa;

SEQ ID NO: 192 is a human kappa light chain designated herein as Human_LC_Kappa;

SEQ ID NO: 193 is a nucleotide sequence encoding the human kappa light chain designated herein as Human_LC_Kappa;

SEQ ID NO: 194 is a wild-type canine kappa light chain designated herein as Canine_LC_Kappa_wt;

SEQ ID NO: 195 is a nucleotide sequence encoding the wild-type canine kappa light chain designated herein as Canine_LC_Kappa_wt;

SEQ ID NO: 196 is a pig kappa light chain designated herein as Pig_LC_Kappa;

SEQ ID NO: 197 is a nucleotide sequence encoding the pig kappa light chain designated herein as Pig_LC_Kappa;

SEQ ID NO: 198 is a mink kappa light chain designated herein as Mink_LC_Kappa;

SEQ ID NO: 199 is a nucleotide sequence encoding the mink kappa light chain designated herein as Mink_LC_Kappa;

SEQ ID NO: 200 is a variable heavy chain CDR1 referred to herein as Mu_04H07_VH_CDR1;

SEQ ID NO: 201 is a variable heavy chain CDR2 referred to herein as Mu_04H07_VH_CDR2;

SEQ ID NO: 202 is a variable heavy chain CDR3 referred to herein as Mu_04H07_VH_CDR3;

SEQ ID NO: 203 is a variable light CDR1 referred to herein as Mu_04H07_VL_CDR1;

SEQ ID NO: 204 is a variable light CDR2 referred to herein as Mu_04H07_VL_CDR2;

SEQ ID NO: 205 is a variable light CDR3 referred to herein as Mu_04H07_VL_CDR3;

SEQ ID NO: 206 is a variable heavy chain CDR1 referred to herein as Mu_06A09_VH_CDR1;

SEQ ID NO: 207 is a variable heavy chain CDR2 referred to herein as Mu_06A09_VH_CDR2;

SEQ ID NO: 208 is a variable heavy chain CDR3 referred to herein as Mu_06A09_VH_CDR3;

SEQ ID NO: 209 is a variable light CDR1 referred to herein as Mu_06A09_VL_CDR1;

SEQ ID NO: 210 is a variable light CDR2 referred to herein as Mu_06A09_VL_CDR2;

SEQ ID NO: 211 is a variable light CDR3 referred to herein as Mu_06A09_VL_CDR3;

SEQ ID NO: 212 is a variable heavy chain referred to herein as Mu_04H07_VH;

SEQ ID NO: 213 is a nucleotide sequence encoding the variable heavy chain referred to herein as Mu_04H07_VH;

SEQ ID NO: 214 is a variable light chain referred to herein as Mu_04H07_VL;

SEQ ID NO: 215 is a nucleotide sequence encoding the variable light chain referred to herein as Mu_04H07_VL;

SEQ ID NO: 216 is a variable heavy chain referred to herein as Mu_06A09_VH;

SEQ ID NO: 217 is a nucleotide sequence encoding the variable heavy chain referred to herein as Mu_06A09_VH;

SEQ ID NO: 218 is a variable light chain referred to herein as Mu_06A09_VL;

SEQ ID NO: 219 is a nucleotide sequence encoding the variable light chain referred to herein as Mu_06A09_VL;

SEQ ID NO: 220 is a variable heavy chain referred to herein as ZTS_768_VH;

SEQ ID NO: 221 is a nucleotide sequence encoding the variable heavy chain referred to herein as ZTS_768_VH;

SEQ ID NO: 222 is a variable light chain referred to herein as ZTS_768_VL;

SEQ ID NO: 223 is a nucleotide sequence encoding the variable light chain referred to herein as ZTS_768_VL;

SEQ ID NO: 224 is a variable heavy chain referred to herein as ZTS_943_VH;

SEQ ID NO: 225 is a nucleotide sequence encoding the variable heavy chain referred to herein as ZTS_943_VH;

SEQ ID NO: 226 is a variable light chain referred to herein as ZTS_943_VL;

SEQ ID NO: 227 is a nucleotide sequence encoding the variable light chain referred to herein as ZTS_943_VL;

SEQ ID NO: 228 is a variable heavy chain referred to herein as ZTS_5864_VH;

SEQ ID NO: 229 is a nucleotide sequence encoding the variable heavy chain referred to herein as ZTS_5864_VH;

SEQ ID NO: 230 is a variable light chain referred to herein as ZTS_5864_VL;

SEQ ID NO: 231 is a nucleotide sequence encoding the variable light chain referred to herein as ZTS_5864_VL;

SEQ ID NO: 232 is a variable heavy chain referred to herein as ZTS_5865_VH;

SEQ ID NO: 233 is a nucleotide sequence encoding the variable heavy chain referred to herein as ZTS_5865_VH;

SEQ ID NO: 234 is a variable light chain referred to herein as ZTS_5865_VL;

SEQ ID NO: 235 is a nucleotide sequence encoding the variable light chain referred to herein as ZTS_5865_VL;

SEQ ID NO: 236 is the amino acid sequence of a feline kappa light chain referred to herein as Feline_LC_Lambda;

SEQ ID NO: 237 is a nucleotide sequence encoding the feline kappa light chain referred to herein as Feline_LC_Lambda.

Definitions

Before describing the present invention in detail, several terms used in the context of the present invention will be defined. In addition to these terms, others are defined elsewhere in the specification, as necessary. Unless otherwise expressly defined herein, terms of art used in this specification will have their art-recognized meanings.

As used in the specification and claims, the singular form "a", "an" and "the" include plural references unless the context clearly dictates otherwise. For example, reference to "an antibody" includes a plurality of such antibodies.

As used herein, the term "comprising" is intended to mean that the compositions and methods include the recited elements, but not excluding others.

Epitope, as used herein, refers to the antigenic determinant recognized by the CDRs of the antibody. In other words, epitope refers to that portion of any molecule capable of being recognized by, and bound by, an antibody. Unless indicated otherwise, the term "epitope" as used herein, refers to the region of IL-31 to which an anti-IL-31 agent is reactive to.

An "antigen" is a molecule or a portion of a molecule capable of being bound by an antibody which is additionally capable of being recognized by, and bound by, an antibody (the corresponding antibody binding region may be referred to as a paratope). In general, epitopes consist of chemically active surface groupings of molecules, for example, amino acids or sugar side chains, and have specific three-dimensional structural characteristics as well as specific charge characteristics. Epitopes are the antigenic determinant on a protein that is recognized by the immune system. The components of the immune system recognizing epitopes are antibodies, T-cells, and B-cells. T-cell epitopes are displayed on the surface of antigen-presenting cells (APCs) and are typically 8-11 (MHC class I) or 15 plus (MHC class II) amino acids in length. Recognition of the displayed MHC-peptide complex by T-cells is critical to their activation. These mechanisms allow for the appropriate recognition of self versus "non-self" proteins such as bacteria and viruses. Independent amino acid residues that are not necessarily contiguous contribute to interactions with the APC binding cleft and subsequent recognition by the T-Cell receptor (Janeway, Travers, Walport, Immunobiology: The Immune System in Health and Disease. 5$^{th}$ edition New York: Garland Science; 2001). Epitopes that are recognized by soluble antibodies and cell surface associated B-cell receptors vary greatly in length and degree of continuity (Sivalingam and Shepherd, Immunol. 2012; 51(3-4): 304-309). Again even linear epitopes or epitopes found in a continuous stretch of protein sequence will often have discontiguous amino acids that represent the key points of contact with the antibody paratopes or B-cell receptor. Epitopes recognized by antibodies and B-cells can be conformational with amino acids comprising a common area of contact on the protein in three dimensional space and are dependent on tertiary and quaternary structural features of the protein. These residues are often found in spatially distinct areas of the primary amino acid sequence.

A "mimotope" as used herein is a linear or constrained peptide which mimics an antigen's epitope. A mimotope may have a primary amino acid sequence capable of eliciting a T-cell effector response and/or a three dimensional structure necessary to bind B-cells resulting in maturation of an acquired immunological response in an animal. An antibody for a given epitope antigen will recognize a mimotope which mimics that epitope.

The term "specifically" in the context of antibody binding, refers to high avidity and/or high affinity binding of an antibody to a specific antigen, i.e., a polypeptide, or epitope. In many embodiments, the specific antigen is an antigen (or a fragment or subfraction of an antigen) used to immunize the animal host from which the antibody-producing cells were isolated. Antibody specifically binding an antigen is stronger than binding of the same antibody to other antigens. Antibodies which bind specifically to a polypeptide may be capable of binding other polypeptides at a weak, yet detectable level (e.g., 10% or less of the binding shown to the polypeptide of interest). Such weak binding, or background binding, is readily discernible from the specific antibody binding to a subject polypeptide, e.g. by use of appropriate controls. In general, specific antibodies bind to an antigen with a binding affinity with a $K_D$ of $10^{-7}$ M or less, e.g., $10^{-8}$ M or less (e.g., $10^{-9}$ M or less, $10^{-10}$ or less, $10^{-11}$ or less, $10^{-12}$ or less, or $10^{-13}$ or less, etc.).

As used herein, the term "antibody" refers to an intact immunoglobulin having two light and two heavy chains. Thus a single isolated antibody or fragment may be a polyclonal antibody, a monoclonal antibody, a synthetic antibody, a recombinant antibody, a chimeric antibody, a heterochimeric antibody, a caninized antibody, a felinized antibody, a fully canine antibody, a fully feline antibody, or a fully equine antibody. The term "antibody" preferably refers to monoclonal antibodies and fragments thereof, and immunologic binding equivalents thereof that can bind to the IL-31 protein and fragments thereof. The term antibody is used both to refer to a homogeneous molecular, or a mixture such as a serum product made up of a plurality of different molecular entities.

"Native antibodies" and "native immunoglobulins" are usually heterotetrameric glycoproteins of about 150,000 Daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The term "antibody fragment" refers to less than an intact antibody structure, including, without limitation, an isolated single antibody chain, an Fv construct, a Fab construct, an Fc construct, a light chain variable or complementarity determining region (CDR) sequence, etc.

The term "variable" region comprises framework and CDRs (otherwise known as hypervariables) and refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework region (FR). The variable domains of native heavy and light chains each comprise multiple FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat, et al., Sequences of Proteins of Immunological Interest, 5th Ed. Public Health Service, National Institutes of Health, Bethesda, Md. (1991), pages 647-669). The constant domains are not involved directly in binding an antibody to an antigen, but exhibit various effector functions, such as participation of the antibody in antibody-dependent cellular toxicity.

The term "hypervariable region" when used herein refers to the amino acid residues of an antibody which are responsible for antigen binding. The hypervariable region comprises amino acid residues from a "complementarity determining region" or "CDR" (Kabat, et al. (1991), above) and/or those residues from a "hypervariable loop" (Chothia and Lesk J. Mol. Biol. 196:901-917 (1987). "Framework" or "FR" residues are those variable domain residues other than the hypervariable region residues as herein defined.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment that contains a complete antigen-recognition and binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (K) and lambda (A), based on the amino acid sequences of their constant domains.

Depending on the amino acid sequence of the constant domain of their heavy chains, immunoglobulins can be assigned to different classes. Presently there are five major classes of immunoglobulins: IgA, IgD, IgE, IgG, and IgM, and several of these may be further divided into subclasses (isotypes), e.g., IgG1, IgG2, IgG3, IgG4, IgA, and IgA2 (as defined by mouse and human designation). The heavy-chain constant domains that correspond to the different classes of immunoglobulins are called alpha, delta, epsilon, gamma, and mu, respectively. The subunit structures and three-dimensional configurations of different classes of immunoglobulins are well known in multiple species. The prevalence of individual isotypes and functional activities associated with these constant domains are species-specific and must be experimentally defined.

"Monoclonal antibody" as defined herein is an antibody produced by a single clone of cells (specifically, a single clone of cells, such as hybridoma cells) and therefore a single pure homogeneous type of antibody. All monoclonal antibodies produced from the same clone are identical and have the same antigen specificity. The term "monoclonal" pertains to a single clone of cells, a single cell, and the progeny of that cell.

"Fully canine antibody" as defined herein is a monoclonal antibody produced by a clone of cells (typically a CHO cell line) and therefore a single pure homogeneous type of antibody. Antibodies identified from single B cells of immunized mammals, such as dogs are created as recombinant IgG proteins following identification of their variable domain sequences. Grafting of these variable domains onto canine constant domains (heavy chain and light chain kappa or lambda constant) results in the generation of recombinant fully canine antibodies. All fully canine monoclonal antibodies produced from the same clone are identical and have the same antigen specificity. The term "monoclonal" pertains to a single clone of cells, a single cell, and the progeny of that cell.

"Fully feline antibody" as defined herein is a monoclonal antibody produced by a clone of cells (typically a CHO cell line) and therefore a single pure homogeneous type of antibody. Antibodies identified from single B cells of immunized mammals, such as dogs are created as recombinant IgG proteins following identification of their variable domain sequences. Grafting of these variable domains onto feline constant domains (heavy chain and light chain kappa or lambda constant) results in the generation of recombinant fully feline antibodies. All fully feline monoclonal antibodies produced from the same clone are identical and have the same antigen specificity. The term "monoclonal" pertains to a single clone of cells, a single cell, and the progeny of that cell.

"Fully equine antibody" as defined herein is a monoclonal antibody produced by a clone of cells (typically a CHO cell line) and therefore a single pure homogeneous type of antibody. Antibodies identified from single B cells of immunized mammals, such as dogs are created as recombinant IgG proteins following identification of their variable domain sequences. Grafting of these variable domains onto equine constant domains (heavy chain and light chain kappa or lambda constant) results in the generation of recombinant fully equine antibodies. All fully equine monoclonal antibodies produced from the same clone are identical and have the same antigen specificity. The term "monoclonal" pertains to a single clone of cells, a single cell, and the progeny of that cell.

The monoclonal antibodies herein specifically include "chimeric" antibodies (immunoglobulins) in which a portion of the heavy and/or light chain is identical with or homologous to corresponding sequences in antibodies derived from a particular species, while the remainder of the chain(s) is identical with or homologous to corresponding sequences in antibodies derived from another species, as well as fragments of such antibodies, so long as they exhibit the desired biological activity. Typically, chimeric antibodies are antibodies whose light and heavy chain genes have been constructed, typically by genetic engineering, from antibody variable and constant region genes belonging to different species. For example, the variable segments of the genes from a mouse monoclonal antibody may be joined to canine constant segments. In one embodiment of a chimeric mouse: canine IgG, the antigen binding site is derived from mouse while the $F_C$ portion is canine.

"Caninized" forms of non-canine (e.g., murine) antibodies are genetically engineered antibodies that contain minimal sequence derived from non-canine immunoglobulin. Caninized antibodies are canine immunoglobulin sequences (recipient antibody) in which hypervariable region residues of the recipient are replaced by hypervariable region residues from a non-canine species (donor antibody) such as mouse having the desired specificity, affinity, and capacity. In some instances, framework region (FR) residues of the canine immunoglobulin sequences are replaced by corresponding non-canine residues. Furthermore, caninized antibodies may include residues that are not found in the recipient antibody or in the donor antibody. These modifications are made to further refine antibody performance. In general, the caninized antibody will include substantially all of at least one, and typically two, variable domains, in which all or substantially all of the hypervariable regions correspond to those of a non-canine immunoglobulin sequence and all or substantially all of the FRs are those of a canine immunoglobulin sequence. The caninized antibody optionally also will comprise a complete, or at least a portion of an immunoglobulin constant region (Fc), typically that of a canine immunoglobulin sequence. In one embodiment of speciation or caninization of a mouse IgG, mouse CDRs are grafted onto canine frameworks.

"Felinized" forms of non-feline (e.g., murine) antibodies are genetically engineered antibodies that contain minimal sequence derived from non-feline immunoglobulin. Felinized antibodies are feline immunoglobulin sequences (recipient antibody) in which hypervariable region residues of the recipient are replaced by hypervariable region residues from a non-feline species (donor antibody) such as mouse having the desired specificity, affinity, and capacity. In some instances, framework region (FR) residues of the feline immunoglobulin sequences are replaced by corresponding non-feline residues. Furthermore, felinized antibodies may include residues that are not found in the recipient antibody or in the donor antibody. These modifications are made to further refine antibody performance. In general, the felinized antibody will include substantially all of at least one, and typically two, variable domains, in which all or substantially all of the hypervariable regions correspond to those of a non-feline immunoglobulin sequence and all or substantially all of the FRs are those of a feline immunoglobulin sequence. The felinized antibody optionally also will comprise a complete, or at least a portion of an immunoglobulin constant region (Fc), typically that of a feline immunoglobulin sequence.

"Equinized" forms of non-equine (e.g., murine) antibodies are genetically engineered antibodies that contain minimal sequence derived from non-equine immunoglobulin. Equinized antibodies are equine immunoglobulin sequences (recipient antibody) in which hypervariable region residues of the recipient are replaced by hypervariable region residues from a non-equine species (donor antibody) such as mouse having the desired specificity, affinity, and capacity. In some instances, framework region (FR) residues of the equine immunoglobulin sequences are replaced by corresponding non-equine residues. Furthermore, equinized antibodies may include residues that are not found in the recipient antibody or in the donor antibody. These modifications are made to further refine antibody performance. In general, the equinized antibody will include substantially all of at least one, and typically two, variable domains, in which all or substantially all of the hypervariable regions correspond to those of a non-equine immunoglobulin sequence and all or substantially all of the FRs are those of an equine immunoglobulin sequence. The equinized antibody optionally also will comprise a complete, or at least a portion of an immunoglobulin constant region (Fc), typically that of an equine immunoglobulin sequence.

"Fully Canine" antibodies are genetically engineered antibodies that contain no sequence derived from non-canine immunoglobulin. Fully canine antibodies are canine immunoglobulin sequences (recipient antibody) in which hypervariable region residues are derived from a naturally occurring canine antibody (donor antibody) having the desired specificity, affinity, and capacity. In some instances, framework region (FR) residues of the canine immunoglobulin sequences are replaced by corresponding non-canine residues. Furthermore, fully canine antibodies may include residues that are not found in the recipient antibody or in the donor antibody, such as including, but not limited to changes in the CDRs to modify affinity. These modifications are made to further refine antibody performance. In general, the fully canine antibody will include substantially all of at least one, and typically two, variable domains, in which all or substantially all of the hypervariable regions correspond to those of a canine immunoglobulin sequence and all or substantially all of the FRs are those of an canine immunoglobulin sequence. The fully canine antibody optionally also will comprise a complete, or at least a portion of an immunoglobulin constant region (Fc), typically that of canine immunoglobulin sequence.

"Fully Feline" antibodies are genetically engineered antibodies that contain no sequence derived from non-feline immunoglobulin. Fully feline antibodies are feline immunoglobulin sequences (recipient antibody) in which hypervariable region residues are derived from a naturally occurring feline antibody (donor antibody) having the desired specificity, affinity, and capacity. In some instances, framework region (FR) residues of the feline immunoglobulin sequences are replaced by corresponding non-feline residues. Furthermore, fully feline antibodies may include residues that are not found in the recipient antibody or in the donor antibody, such as including, but not limited to changes in the CDRs to modify affinity. These modifications are made to further refine antibody performance. In general, the fully feline antibody will include substantially all of at least one, and typically two, variable domains, in which all or substantially all of the hypervariable regions correspond to those of a feline immunoglobulin sequence and all or substantially all of the FRs are those of an feline immunoglobulin sequence. The fully feline antibody optionally also will comprise a complete, or at least a portion of an immunoglobulin constant region (Fc), typically that of feline immunoglobulin sequence.

"Fully Equine" antibodies are genetically engineered antibodies that contain no sequence derived from non-equine immunoglobulin. Fully equine antibodies are equine immunoglobulin sequences (recipient antibody) in which hypervariable region residues are derived from a naturally occurring equine antibody (donor antibody) having the desired specificity, affinity, and capacity. In some instances, framework region (FR) residues of the equine immunoglobulin sequences are replaced by corresponding non-equine residues. Furthermore, fully equine antibodies may include residues that are not found in the recipient antibody or in the donor antibody, such as including, but not limited to changes in the CDRs to modify affinity. These modifications are made to further refine antibody performance. In general, the fully equine antibody will include substantially all of at least one, and typically two, variable domains, in which all or substantially all of the hypervariable regions correspond to those of a equine immunoglobulin sequence and all or substantially all of the FRs are those of an equine immunoglobulin sequence. The fully equine antibody optionally also will comprise a complete, or at least a portion of an immunoglobulin constant region (Fc), typically that of equine immunoglobulin sequence.

The term "heterochimeric" as defined herein, refers to an antibody in which one of the antibody chains (heavy or light) is caninized, felinized, or equinized while the other is chimeric. In one embodiment, a felinized variable heavy chain (where all of the CDRs are mouse and all FRs are feline) is paired with a chimeric variable light chain (where all of the CDRs are mouse and all FRs are mouse. In this embodiment, both the variable heavy and variable light chains are fused to a feline constant region.

A "variant" anti-IL-31 antibody, refers herein to a molecule which differs in amino acid sequence from a "parent" anti-IL-31 antibody amino acid sequence by virtue of addition, deletion, and/or substitution of one or more amino acid residue(s) in the parent antibody sequence and retains at least one desired activity of the parent anti-IL-31-antibody. Desired activities can include the ability to bind the antigen specifically, the ability to reduce, inhibit or neutralize IL-31 activity in an animal, and the ability to inhibit IL-31-mediated pSTAT signaling in a cell-based assay. In one embodiment, the variant comprises one or more amino acid substitution(s) in one or more hypervariable and/or framework region(s) of the parent antibody. For example, the variant may comprise at least one, e.g. from about one to about ten, and preferably from about two to about five, substitutions in one or more hypervariable and/or framework regions of the parent antibody. Ordinarily, the variant will have an amino acid sequence having at least 50% amino acid sequence identity with the parent antibody heavy or light chain variable domain sequences, more preferably at least 65%, more preferably at least 75%, more preferably at least 80%, more preferably at least 85%, more preferably at least 90%, and most preferably at least 95% sequence identity. Identity or homology with respect to this sequence is defined herein as the percentage of amino acid residues in the candidate sequence that are identical with the parent antibody residues, after aligning the sequences and introducing gaps, if necessary, to achieve the maximum percent sequence identity. None of N-terminal, C-terminal, or internal extensions, deletions, or insertions into the antibody sequence shall be construed as affecting sequence identity or homology. The variant retains the ability to bind an IL-31 and preferably has desired activities which are superior to those of the parent antibody. For example, the variant may have a stronger binding affinity, enhanced ability to reduce, inhibit or neutralize IL-31 activity in an animal, and/or enhanced ability to inhibit IL-31-mediated pSTAT signaling in a cell-based assay.

A "variant" nucleic acid refers herein to a molecule which differs in sequence from a "parent" nucleic acid. Polynucleotide sequence divergence may result from mutational changes such as deletions, substitutions, or additions of one or more nucleotides. Each of these changes may occur alone or in combination, one or more times in a given sequence.

The "parent" antibody herein is one that is encoded by an amino acid sequence used for the preparation of the variant. In one embodiment, the parent antibody has a canine framework region and, if present, has canine antibody constant region(s). For example, the parent antibody may be a caninized or canine antibody. As another example, the parent antibody may be a felinized or feline antibody. As yet another example, the parent antibody may be an equinized or equine antibody. In a still further example, the parent antibody is a murine monoclonal antibody.

The term "antigen binding region", "antigen-binding portion", and the like as used throughout the specification and claims refers to that portion of an antibody molecule which contains the amino acid residues that interact with an antigen and confer on the antibody its specificity and affinity for the antigen. The antibody binding region includes the "framework" amino acid residues necessary to maintain the proper conformation of the antigen-binding residues. The antigen-binding portion of an antibody according to the present invention may alternatively be referred to herein as an IL-31-specific peptide or polypeptide or as an anti-IL-31 peptide or polypeptide, for example.

The term "isolated" means that the material (e.g., antibody or nucleic acid) is separated and/or recovered from a component of its natural environment. Contaminant components of its natural environment are materials that would interfere with diagnostic or therapeutic uses for the material, and may include enzymes, hormones, and other proteinaceous or nonproteinaceous solutes. With respect to nucleic acid, an isolated nucleic acid may include one that is separated from the 5' to 3' sequences with which it is normally associated in the chromosome. In preferred embodiments, the material will be purified to greater than 95% by weight of the material, and most preferably more than 99% by weight. Isolated material includes the material in situ within recombinant cells since at least one component of the material's natural environment will not be present. Ordinarily, however, isolated material will be prepared by at least one purification step.

The word "label" when used herein refers to a detectable compound or composition that is conjugated directly or indirectly to the antibody or nucleic acid. The label may itself be detectable by itself (e.g., radioisotope labels or fluorescent labels) or, in the case of an enzymatic label, may catalyze chemical alteration of a substrate compound or composition that is detectable.

The terms "nucleic acid", "polynucleotide", "nucleic acid molecule" and the like may be used interchangeably herein and refer to a series of nucleotide bases (also called "nucleotides") in DNA and RNA. The nucleic acid may contain deoxyribonucleotides, ribonucleotides, and/or their analogs. The term "nucleic acid" includes, for example, single-stranded and double-stranded molecules. A nucleic acid can be, for example, a gene or gene fragment, exons, introns, a DNA molecule (e.g., cDNA), an RNA molecule (e.g., mRNA), recombinant nucleic acids, plasmids, and other vectors, primers and probes. Both 5' to 3' (sense) and 3' to 5' (antisense) polynucleotides are included.

A "subject" or "patient" refers to an animal in need of treatment that can be affected by molecules of the invention. Animals that can be treated in accordance with the invention include vertebrates, with mammals such as canine, feline, and equine animals being particularly preferred examples.

A "therapeutically effective amount" (or "effective amount") refers to an amount of an active ingredient, e.g., an agent according to the invention, sufficient to effect beneficial or desired results when administered to a subject or patient. An effective amount can be administered in one or more administrations, applications or dosages. A therapeutically effective amount of a composition according to the invention may be readily determined by one of ordinary skill in the art. In the context of this invention, a "therapeutically effective amount" is one that produces an objectively measured change in one or more parameters associated with treatment of a pruritic condition or an allergic condition including clinical improvement in symptoms. Of course, the therapeutically effective amount will vary depending upon the particular subject and condition being treated, the weight and age of the subject, the severity of the disease condition, the particular compound chosen, the dosing regimen to be followed, timing of administration, the manner of administration and the like, all of which can readily be determined by one of ordinary skill in the art.

As used herein, the term "therapeutic" encompasses the full spectrum of treatments for a disease or disorder. A "therapeutic" agent of the invention may act in a manner that is prophylactic or preventive, including those that incorporate procedures designed to target animals that can be identified as being at risk (pharmacogenetics); or in a manner that is ameliorative or curative in nature; or may act to slow the rate or extent of the progression of at least one symptom of a disease or disorder being treated.

"Treatment", "treating", and the like refers to both therapeutic treatment and prophylactic or preventative measures. Animals in need of treatment include those already with the disorder as well as those in which the disorder is to be prevented. The term "treatment" or "treating" of a disease or disorder includes preventing or protecting against the disease or disorder (that is, causing the clinical symptoms not to develop); inhibiting the disease or disorder (i.e., arresting or suppressing the development of clinical symptoms; and/ or relieving the disease or disorder (i.e., causing the regression of clinical symptoms). As will be appreciated, it is not always possible to distinguish between "preventing" and "suppressing" a disease or disorder since the ultimate inductive event or events may be unknown or latent. Accordingly, the term "prophylaxis" will be understood to constitute a type of "treatment" that encompasses both "preventing" and "suppressing." The term "treatment" thus includes "prophylaxis".

The term "allergic condition" is defined herein as a disorder or disease caused by an interaction between the immune system and a substance foreign to the body. This foreign substance is termed "an allergen". Common allergens include aeroallergens, such as pollens, dust, molds, dust mite proteins, injected saliva from insect bites, etc. Examples of allergic conditions include, but are not limited to, the following: allergic dermatitis, summer eczema, urticaria, heaves, inflammatory airway disease, recurrent airway obstruction, airway hyper-responsiveness, chronic obstructive pulmonary disease, and inflammatory processes resulting from autoimmunity, such as Irritable bowel syndrome (IBS).

The term "pruritic condition" is defined herein as a disease or disorder characterized by an intense itching sensation that produces the urge to rub or scratch the skin to obtain relief. Examples of pruritic conditions include, but are not limited to the following: atopic dermatitis, allergic dermatitis, eczema, psoriasis, scleroderma, and pruritus.

As used herein, the terms "cell", "cell line", and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell (e.g., bacterial cells, yeast cells, mammalian cells, and insect cells) whether located in vitro or in vivo. For example, host cells may be located in a transgenic animal. Host cell can be used as a recipient for vectors and may include any transformable organism that is capable of replicating a vector and/or expressing a heterologous nucleic acid encoded by a vector.

A "composition" is intended to mean a combination of active agent and another compound or composition which can be inert (e.g., a label), or active, such as an adjuvant.

As defined herein, pharmaceutically acceptable carriers suitable for use in the invention are well known to those of skill in the art. Such carriers include, without limitation, water, saline, buffered saline, phosphate buffer, alcoholic/aqueous solutions, emulsions or suspensions. Other conventionally employed diluents, adjuvants and excipients, may be added in accordance with conventional techniques. Such carriers can include ethanol, polyols, and suitable mixtures thereof, vegetable oils, and injectable organic esters. Buffers and pH adjusting agents may also be employed. Buffers include, without limitation, salts prepared from an organic acid or base. Representative buffers include, without limitation, organic acid salts, such as salts of citric acid, e.g., citrates, ascorbic acid, gluconic acid, histidine-HCl, carbonic acid, tartaric acid, succinic acid, acetic acid, or phthalic acid, Tris, trimethanmine hydrochloride, or phosphate buffers. Parenteral carriers can include sodium chloride solution, Ringer's dextrose, dextrose, trehalose, sucrose, and sodium chloride, lactated Ringer's or fixed oils. Intravenous carriers can include fluid and nutrient replenishers, electrolyte replenishers, such as those based on Ringer's dextrose and the like. Preservatives and other additives such as, for example, antimicrobials, antioxidants, chelating agents (e.g., EDTA), inert gases and the like may also be provided in the pharmaceutical carriers. The present invention is not limited by the selection of the carrier. The preparation of these pharmaceutically acceptable compositions, from the above-described components, having appropriate pH isotonicity, stability and other conventional characteristics is within the skill of the art. See, e.g., texts such as Remington: The Science and Practice of Pharmacy, 20th ed, Lippincott Williams & Wilkins, publ., 2000; and The Handbook of Pharmaceutical Excipients, 4.sup.th edit., eds. R. C. Rowe et al, APhA Publications, 2003.

The term "conservative amino acid substitution" indicates any amino acid substitution for a given amino acid residue, where the substitute residue is so chemically similar to that of the given residue that no substantial decrease in polypeptide function (e.g., enzymatic activity) results.

Conservative amino acid substitutions are commonly known in the art and examples thereof are described, e.g., in U.S. Pat. Nos. 6,790,639, 6,774,107, 6,194,167, or 5,350,576. In a preferred embodiment, a conservative amino acid substitution will be any one that occurs within one of the following six groups
1. Small aliphatic, substantially non-polar residues: Ala, Gly, Pro, Ser, and Thr;
2. Large aliphatic, non-polar residues: Ile, Leu, and Val; Met;
3. Polar, negatively charged residues and their amides: Asp and Glu;
4. Amides of polar, negatively charged residues: Asn and Gln; His;
5. Polar, positively charged residues: Arg and Lys; His; and
6. Large aromatic residues: Trp and Tyr; Phe.

In a preferred embodiment, a conservative amino acid substitution will be any one of the following, which are listed as Native Residue (Conservative Substitutions) pairs: Ala (Ser); Arg (Lys); Asn (Gln; His); Asp (Glu); Gln (Asn); Glu (Asp); Gly (Pro); His (Asn; Gln); Ile (Leu; Val); Leu (Ile; Val); Lys (Arg; Gln; Glu); Met (Leu; Ile); Phe (Met; Leu; Tyr); Ser (Thr); Thr (Ser); Trp (Tyr); Tyr (Trp; Phe); and Val (Ile; Leu).

Just as a polypeptide may contain conservative amino acid substitution(s), a polynucleotide hereof may contain conservative codon substitution(s). A codon substitution is considered conservative if, when expressed, it produces a conservative amino acid substitution, as described above. Degenerate codon substitution, which results in no amino acid substitution, is also useful in polynucleotides according to the present invention. Thus, e.g., a polynucleotide encoding a selected polypeptide useful in an embodiment of the present invention may be mutated by degenerate codon substitution in order to approximate the codon usage frequency exhibited by an expression host cell to be transformed therewith, or to otherwise improve the expression thereof.

DETAILED DESCRIPTION OF THE INVENTION

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Unless otherwise defined, scientific and technical terms used in connection with the antibodies described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art.

Standard techniques are used for recombinant DNA, oligonucleotide synthesis, and tissue culture and transfection (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification, See e.g., Sambrook et al. *MOLECULAR CLONING: LAB. MANUAL* (3rd ed., Cold Spring Harbor Lab. Press, Cold Spring Harbor, N.Y., 2001) and Ausubel et al. Current Protocols in Molecular Biology (New York: Greene Publishing Association/Wiley Interscience), 1993. The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application.

The present invention provides for recombinant monoclonal antibodies and peptides and their uses in clinical and scientific procedures, including diagnostic procedures. With the advent of methods of molecular biology and recombinant technology, it is possible to produce antibody and antibody-like molecules by recombinant means and thereby generate gene sequences that code for specific amino acid sequences found in the polypeptide structure of the antibodies. Such antibodies can be produced by either cloning the gene sequences encoding the polypeptide chains of said antibodies or by direct synthesis of said polypeptide chains, with assembly of the synthesized chains to form active tetrameric ($H_2L_2$) structures with affinity for specific epitopes and antigenic determinants. This has permitted the ready production of antibodies having sequences characteristic of neutralizing antibodies from different species and sources.

Regardless of the source of the antibodies, or how they are recombinantly-constructed, or how they are synthesized, in vitro or in vivo, using transgenic animals, large cell cultures of laboratory or commercial size, using transgenic plants, or by direct chemical synthesis employing no living organisms at any stage of the process, all antibodies have a similar overall 3 dimensional structure. This structure is often given as $H_2L_2$ and refers to the fact that antibodies commonly comprise two light (L) amino acid chains and 2 heavy (H) amino acid chains. Both chains have regions capable of interacting with a structurally complementary antigenic target. The regions interacting with the target are referred to as "variable" or "V" regions and are characterized by differences in amino acid sequence from antibodies of different antigenic specificity. The variable regions of either H or L chains contain the amino acid sequences capable of specifically binding to antigenic targets.

As noted above, the term "antigen binding region", "antigen-binding portion" and the like as used throughout the specification and claims refers to that portion of an antibody molecule which contains the amino acid residues that interact with an antigen and confer on the antibody its specificity and affinity for the antigen. The antibody binding region includes the "framework" amino acid residues necessary to maintain the proper conformation of the antigen-binding residues. The antigen-binding portion of an antibody according to the present invention may be referred to herein as an IL-31-specific peptide or polypeptide or as an anti-IL-31 peptide or polypeptide, for example.

Within the variable regions of the H or L chains that provide for the antigen binding regions are smaller sequences dubbed "hypervariable" because of their extreme variability between antibodies of differing specificity. Such hypervariable regions are also referred to as "complementarity determining regions" or "CDR" regions. These CDR regions account for the basic specificity of the antibody for a particular antigenic determinant structure.

The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The variable heavy and light chains of all antibodies each have three CDR regions, each non-contiguous with the others.

In all mammalian species, antibody peptides contain constant (i.e., highly conserved) and variable regions, and, within the latter, there are the CDRs and the so-called "framework regions" made up of amino acid sequences within the variable region of the heavy or light chain but outside the CDRs.

Regarding the antigenic determinate recognized by the CDR regions of the antibody, this is also referred to as the "epitope." In other words, epitope refers to that portion of any molecule capable of being recognized by, and bound by, an antibody (the corresponding antibody binding region may be referred to as a paratope).

An "antigen" is a molecule or a portion of a molecule capable of being bound by an antibody which is additionally capable of inducing an animal to produce an antibody capable of binding to an epitope of that antigen. An antigen may have one or more than one epitope. The specific reaction referred to above is meant to indicate that the antigen will react, in a highly selective manner, with its corresponding antibody and not with the multitude of other antibodies which may be evoked by other antigens.

The antibodies of the present invention are meant to include both intact immunoglobulin molecules as well as portions, fragments, peptides and derivatives thereof such as, for example, Fab, Fab', F(ab')$_2$, Fv, Fse, CDR regions, paratopes, or any portion (e.g., a polypeptide) or peptide sequence of the antibody that is capable of binding an antigen or epitope. An antibody is said to be "capable of binding" a molecule if it is capable of specifically reacting with the molecule to thereby bind the molecule to the antibody.

The antibodies of the present invention also includes chimeric antibodies, heterochimeric antibodies, caninized antibodies, felinized antibodies, or equinized antibodies, as well as fragments, portions, regions, peptides or derivatives thereof, provided by any known technique, such as, but not limited to, enzymatic cleavage, peptide synthesis, or recombinant techniques. Such antibodies of the present invention are capable of specifically binding at least one of canine IL-31 or feline IL-31. Antibody fragments or portions may lack the Fc fragment of intact antibody, clear more rapidly from the circulation, and may have less non-specific tissue binding than an intact antibody. Examples of antibody fragments may be produced from intact antibodies using methods well known in the art, for example by proteolytic cleavage with enzymes such as papain (to produce Fab fragments) or pepsin (to produce F(ab')$._2$ fragments). See, e.g., Wahl et al., 24 J. Nucl. Med. 316-25 (1983). Portions of antibodies may be made by any of the above methods, or may be made by expressing a portion of the recombinant molecule. For example, the CDR region(s) of a recombinant antibody may be isolated and subcloned into the appropriate expression vector. See, e.g., U.S. Pat. No. 6,680,053.

The term "antigen binding region", "antigen-binding portion", and the like as used throughout the specification and claims refers to that portion of an antibody molecule which contains the amino acid residues that interact with an antigen and confer on the antibody its specificity and affinity for the antigen. The antibody binding region includes the "framework" amino acid residues necessary to maintain the proper conformation of the antigen-binding residues. The antigen-binding portion of an antibody according to the present invention may alternatively be referred to herein as an IL-31-specific peptide or polypeptide or as an anti-IL-31 peptide or polypeptide, for example.

Clones 15H05, ZIL1, ZIL8, ZIL9, ZIL11, ZIL69, ZIL94, ZIL154, ZIL159, ZIL171, 04H07, and 06A09 Nucleotide and Amino Acid Sequences In some embodiments, the present invention provides novel monoclonal antibodies that specifically bind to at least one of canine IL-31, feline IL-31, or equine IL-31. In one embodiment, a monoclonal antibody of the invention binds to canine IL-31, feline IL-31, or equine IL-31 and prevents its binding to, and activation of, its co-receptor complex comprising IL-31 receptor A (IL-31 Ra) and Oncostatin-M-specific receptor (OsmR or IL-31 Rb). The monoclonal antibodies of the present invention are identified herein as "15H05", "ZIL1", "ZIL8", "ZIL9", "ZIL11", "ZIL69", "ZIL94", "ZIL154", "ZIL159", "ZIL171", 04H07, and 06A09 which refers to the number assigned to its clone. Herein, "15H05", "ZIL1", "ZIL8", "ZIL9", "ZIL11", "ZIL69", "ZIL94", "ZIL154", "ZIL159", "ZIL171", "04H07", and "06A09" also refers to the portion of the monoclonal antibody, the paratope or CDRs, that bind specifically with an IL-31 epitope identified as 15H05, ZIL1, ZIL8, ZIL9, ZIL11, ZIL69, ZIL94, ZIL154, ZIL159, ZIL171, 04H07, and 06A09 because of its ability to bind the 15H05, ZIL1, ZIL8, ZIL9, ZIL11, ZIL69, ZIL94, ZIL154, ZIL159, ZIL171, 04H07, and 06A09 antibodies, respectively. The several recombinant, chimeric, heterochimeric, caninized, felinized, equinized, fully canine, fully feline, and/or fully equine forms of 15H05, ZIL1, ZIL8, ZIL9, ZIL11, ZIL69, ZIL94, ZIL154, ZIL159, ZIL171, 04H07, and 06A09 described herein may be referred to by the same name. In some embodiments, 15H05 may be alternatively referred to herein as 1505 at least because they share the same CDRs.

In one embodiment, the present invention provides a monoclonal antibody, or antigen-binding portion thereof that specifically binds to a region on a mammalian IL-31 protein involved with interaction of the IL-31 protein with its co-receptor, wherein the binding of said antibody to said region is impacted by mutations in a 15H05 epitope binding region selected from at least one of the following: a) a region between about amino acid residues 124 and 135 of a feline IL-31 sequence represented by SEQ ID NO: 157 (Feline_IL31_wildtype); b) a region between about amino acid residues 124 and 135 of a canine IL-31 sequence represented by SEQ ID NO: 155 (Canine_IL31); and c) a region between about amino acid residues 118 and 129 of an equine IL-31 sequence represented by SEQ ID NO: 165 (Equine_IL31). In one embodiment, the mutations in the 15H05 epitope binding region are selected from at least one of the following: (a) a mutant wherein positions 126 and 128 of SEQ ID NO: 157 are changed to Alanine; (b) a mutant wherein positions 126 and 128 of SEQ ID NO: 155 are changed to Alanine; and (c) a mutant wherein positions 120 and 122 of SEQ ID NO: 165 are changed to Alanine.

In one particular embodiment, an antibody according to the present invention binds to the 15H05 epitope binding region described above. That is to say, in one embodiment, the present invention provides a monoclonal antibody, or antigen-binding portion thereof that specifically binds to a region on a mammalian IL-31 protein involved with interaction of the IL-31 protein with its co-receptor, wherein the binding region is selected from at least one of the following: a) a region between about amino acid residues 124 and 135 of a feline IL-31 sequence represented by SEQ ID NO: 157 (Feline_IL31_wildtype); b) a region between about amino acid residues 124 and 135 of a canine IL-31 sequence represented by SEQ ID NO: 155 (Canine_IL31); and c) a region between about amino acid residues 118 and 129 of an equine IL-31 sequence represented by SEQ ID NO: 165 (Equine_IL31).

In one embodiment, the mammalian IL-31 to which the antibody or antigen-binding portion thereof specifically binds is feline IL-31, wherein the antibody binds to a region between about amino acid residues 125 and 134 of a feline IL-31 sequence represented by SEQ ID NO: 157 (Feline_IL31_wildtype). In some embodiments, the antibody which binds to feline IL31 includes a VL chain comprising Framework 2 (FW2) changes selected from the following: an Asparagine in place of Lysine at position 42, an Isoleucine in place of Valine at position 43, a Valine in place of Leucine at position 46, an Asparagine in place of Lysine at position 49, and combinations thereof, wherein the positions are in reference to the numbering of SEQ ID NO: 127 (FEL_15H05_VL1).

In one embodiment, the monoclonal antibody or antigen-binding portion thereof includes the following combinations of complementary determining region (CDR) sequences:

```
1) antibody 15H05:
variable heavy
(VH)-CDR1 of
                                         (SEQ ID NO: 1)
SYTIH, VH-CDR2 of
                                         (SEQ ID NO: 2)
NINPTSGYTENNQRFKD, VH-CDR3 of
                                         (SEQ ID NO: 3)
WGFKYDGEWSFDV, variable light
(VL)-CDR1 of
                                         (SEQ ID NO: 4)
RASQGISIWLS, VL-CDR2 of
                                         (SEQ ID NO: 5)
KASNLHI,
and VL-CDR3 of
                                         (SEQ ID NO: 6)
LQSQTYPLT;
or 2) a variant of 1) that differs from the parent
antibody 15H05 by addition, deletion, and/or
substitution of one or more amino acid residues
in at least one of VH or VL CDR1, CDR2, or CDR3.
```

In one embodiment, antibody 15H05 above includes at least one of the following variable heavy and/or variable light chains:

```
a) a variable light chain comprising FEL_15H05_
VL1_FW2:
                                       (SEQ ID NO: 135)
EIQMTQSPSSLSASPGDRVTITCRASQGISIWLSWYQQKPGNIPKVLIN

KASNLHIGVPSRFSGSGSGTDFTLTISSLEPEDAATYYCLQSQTYPLTF

GGGTKLEIK,
and b) a variable heavy chain comprising FEL_15H05_
VH1:
                                       (SEQ ID NO: 121)
QVLLVQSGAEVRTPGASVKIFCKASGYSFTSYTIHWLRQAPAQGLEWMG

NINPTSGYTENNQRFKDRLTLTADTSTNTAYMELSSLRSADTAMYYCAR

WGFKYDGEWSFDVWGAGTTVTVSS.
```

In another embodiment, the monoclonal antibody or antigen-binding portion thereof includes the following combinations of complementary determining region (CDR) sequences:

```
1) antibody ZIL1:
variable heavy
(VH)-CDR1 of
                                        (SEQ ID NO: 13)
SYGMS, VH-CDR2 of
                                        (SEQ ID NO: 14)
HINSGGSSTYYADAVKG, VH-CDR3 of
                                        (SEQ ID NO: 15)
VYTTLAAFWTDNFDY, variable light
(VL)-CDR1 of
                                        (SEQ ID NO: 16)
SGSTNNIGILAAT, VL-CDR2 of
                                        (SEQ ID NO: 17
SDGNRPS,
and VL-CDR3 of
                                        (SEQ ID NO: 18)
QSFDTTLDAYV;

2) antibody ZIL8:
VH-CDR1 of
                                        (SEQ ID NO: 19)
DYAMS, VH-CDR2 of
                                        (SEQ ID NO: 20)
GIDSVGSGTSYADAVKG, VH-CDR3 of
                                        (SEQ ID NO: 21)
GFPGSFEH, VL-CDR1 of
                                        (SEQ ID NO: 22)
TGSSSNIGSGYVG, VL-CDR2 of
                                        (SEQ ID NO: 23)
YNSDRPS, VL-CDR3 of
                                        (SEQ ID NO: 24)
SVYDRTFNAV;

3) antibody ZIL9:
VH-CDR1 of
                                        (SEQ ID NO: 25)
SYDMT, VH-CDR2 of
                                        (SEQ ID NO: 26)
DVNSGGTGTAYAVAVKG, VH-CDR3 of
                                        (SEQ ID NO: 27)
LGVRDGLSV, VL-CDR1 of
                                        (SEQ ID NO: 28)
SGESLNEYYTQ, VL-CDR2 of
                                        (SEQ ID NO: 29)
RDTERPS, VL-CDR3 of
                                        (SEQ ID NO: 30)
ESAVDTGTLV;
```

4) antibody ZIL11:
VH-CDR1 of

TYVMN, (SEQ ID NO: 31)

VH-CDR2 of

SINGGGSSPTYADAVRG, (SEQ ID NO: 32)

VH-CDR3 of

SMVGPFDY, (SEQ ID NO: 33)

VL-CDR1 of

SGESLSNYYAQ, (SEQ ID NO: 34)

VL-CDR2 of

KDTERPS, (SEQ ID NO: 35)

VL-CDR3 of

ESAVSSDTIV; (SEQ ID NO: 36)

5) antibody ZIL69:
VH-CDR1 of

SYAMK, (SEQ ID NO: 37)

VH-CDR2 of

TINNDGTRTGYADAVRG, (SEQ ID NO: 38)

VH-CDR3 of

GNAESGCTGDHCPPY, (SEQ ID NO: 39)

VL-CDR1 of

SGESLNKYYAQ, (SEQ ID NO: 40)

VL-CDR2 of

KDTERPS, (SEQ ID NO: 41)

VL-CDR3 of

ESAVSSETNV; (SEQ ID NO: 42)

6) antibody ZIL94:
VH-CDR1 of

TYFMS, (SEQ ID NO: 43)

VH-CDR2 of

LISSDGSGTYYADAVKG, (SEQ ID NO: 44)

VH-CDR3 of

FWRAFND, (SEQ ID NO: 45)

VL-CDR1 of

GLNSGSVSTSNYPG, (SEQ ID NO: 46)

VL-CDR2 of

DTGSRPS, (SEQ ID NO: 47)

VL-CDR3 of

SLYTDSDILV; (SEQ ID NO: 48)

7) antibody ZIL154:
VH-CDR1 of

DRGMS, (SEQ ID NO: 49)

VH-CDR2 of

YIRYDGSRTDYADAVEG, (SEQ ID NO: 50)

VH-CDR3 of

WDGSSFDY, (SEQ ID NO: 51)

VL-CDR1 of

KASQSLLHSDGNTYLD, (SEQ ID NO: 52)

VL-CDR2 of

KVSNRDP, (SEQ ID NO: 53)

VL-CDR3 of

MQAIHFPLT; (SEQ ID NO: 54)

8) antibody ZIL159:
VH-CDR1 of

SYVMT, (SEQ ID NO: 55)

VH-CDR2 of

GINSEGSRTAYADAVKG, (SEQ ID NO: 56)

VH-CDR3 of

GDIVATGTSY, (SEQ ID NO: 57)

VL-CDR1 of

SGETLNRFYTQ, (SEQ ID NO: 58)

VL-CDR2 of

KDTERPS, (SEQ ID NO: 59)

VL-CDR3 of

KSAVSIDVGV; (SEQ ID NO: 60)

9) antibody ZIL171:
VH-CDR1 of

TYVMN, (SEQ ID NO: 61)

VH-CDR2 of

SINGGGSSPTYADAVRG, (SEQ ID NO: 62)

VH-CDR3 of

SMVGPFDY, (SEQ ID NO: 63)

VL-CDR1 of

SGKSLSYYYAQ, (SEQ ID NO: 64)

VL-CDR2 of

KDTERPS, (SEQ ID NO: 65)

VL-CDR3 of

ESAVSSDTIV; (SEQ ID NO: 66)

10) antibody 04H07:
VH-CDR1 of

SYWMN, (SEQ ID NO: 200)

VH-CDR2 of

MIDPSDSEIHYNQVFKD, (SEQ ID NO: 201)

-continued

VH-CDR3 of
QDIVTTVDY, (SEQ ID NO: 202)

VL-CDR1 of
KSSQSLLYSINQKNHLA, (SEQ ID NO: 203)

VL-CDR2 of
WASTRES, (SEQ ID NO: 204)

VL-CDR3 of
QQGYTYPFT; (SEQ ID NO: 205)

11) antibody 06A09:
VH-CDR1 of
SYWMN, (SEQ ID NO: 206)

VH-CDR2 of
MIDPSDSETHYNQIFRD, (SEQ ID NO: 207)

VH-CDR3 of
QDIVTTVDY, (SEQ ID NO: 208)

VL-CDR1 of
KSSQSLLYSINQKNFLA, (SEQ ID NO: 209)

VL-CDR2 of
WASTRES, (SEQ ID NO: 210)

VL-CDR3 of
QQHYGYPFT; (SEQ ID NO: 211)
or 12) a variant of 1) to 11) that differs from respective parent antibody ZIL1, ZIL8, ZIL9, ZIL11, ZIL69, ZIL94, ZIL154, ZIL159, ZIL171, 04H07, or 06A09 by addition, deletion, and/or substitution of one or more amino acid residues in at least oneof VH or VL CDR1, CDR2, or CDR3.

In some embodiments of the present invention, 1) antibody ZIL1 includes at least one of the following:

a) a variable light chain comprising CAN-ZIL1_VL:
(SEQ ID NO: 77)
QSVLTQPTSVSGSLGQRVTISCSGSTNNIGILAATWYQQLPGKAPKVLV

YSDGNRPSGVPDRFSGSKSGNSATLTITGLQAEDEADYYCQSFDTTLDA

YVFGSGTQLTVL,
and b) a variable heavy chain comprising CAN-ZIL1_VH:
(SEQ ID NO: 75)
EVQLVESGGDLVKPGGSLRLSCVASGFTFSSYGMSWVRQAPGKGLQWVA

HINSGGSSTYYADAVKGRFTISRDNAKNTLYLQMNSLRAEDTAVYYCVE

VYTTLAAFWTDNFDYWGQGTLVTSS;

2) antibody ZIL8 includes at least one of the following:

a) a variable light chain comprising CAN-ZIL8_VL:
(SEQ ID NO: 81)
QSVLIQPASVSGSLGQKVTISCIGSSSNIGSGYVGWYQQLPGTGPRTLI

YYNSDRPSGVPDRFSGSRSGTTATLTISGLQAEDEADYYCSVYDRTFNA

VFGGGT,
and b) a variable heavy chain comprising CAN-ZIL8_VH:
(SEQ ID NO: 79)
EVQLVESGGDLVKPAGSLRLSCVASGFTFSDYAMSWVRQAPGRGLQWVA

GIDSVGSGTSYADAVKGRFTISRDDAKNTLYLQMFNLRAEDTAIYYCAS

GFPGSFEHWGQGTLVTVSS;

or antibody ZIL8 includes at least one of the following:

c) a variable light chain comprising ZTS_5864_VL:
(SEQ ID NO: 230)
QSVLTQPSSVSGTLGQRITISCTGSSSNIGSGYVGWYQQVPGMGPKTVI

YYNSDRPSGVPDRFSGSKSGSSGTLTITGLQAEDEADYYCSVYDRTFNA

VFGGGTHLTVLGQPKSAPPRSHSSRPISYAVFCL,
and d) a variable heavy chain comprising ZTS_5864_VH:
(SEQ ID NO: 228)
DVQLVESGGDLVKPGGSLRLTCVASGFTFSDYAMSWVRQAPGKGLQWVA

GIDSVGSGTSYADSVKGRFTISRDNAKNTLYLQMNSLKTEDTATYYCAS

GFPGSFEHWGQGALVTVSS;

or antibody ZIL8 includes at least one of the following:

e) a variable light chain comprising ZTS_5865_VL:
(SEQ ID NO: 234)
SVLTQPSSVSGTLGQRITISCTGSSSNIGSGYVGWYQQVPGMGPKTVIY

YNSDRPSGVPDRFSGSKSGSSGTLTITGLQAEDEADYYCSVYDRTFNAV

FGGGTHLTVLGQPKSAPPRSHSSRPISYAVFCL,
and f) a variable heavy chain comprising ZTS_5865_VH:
(SEQ ID NO: 232)
DVQLVESGGDLVKPGGSLRLTCVASGFTFSDYAMNWVRQAPGKGLQWVA

GIDSVGSGTSYADSVKGRFTISRDNAKNTLYLQMSGLKTEDTATYYCAS

GFPGSFEHWGQGTLVTVSS;

3) antibody ZIL9 includes at least one of the following:

a) a variable light chain comprising CAN-ZIL9_VL:
(SEQ ID NO: 85)
SSVLTQPPSVSVSLGQTATISCSGESLNEYYTQWFQQKAGQAPVLVIYR

DTERPSGIPDRFSGSSSGNTHTLTISGARAEDEADYYCESAVDTGTLVF

GGGTHLAVL,
and b) a variable heavy chain comprising CAN-ZIL9_VH:
(SEQ ID NO: 83)
EVQLVESGGDLVKPPGSLRLSCVASGFTFSSYDMTWVRQAPGKGLQWVA

DVNSGGTGTAYAVAVKGRFTISRDNAKKTLYLQMNSLRAEDTAVYYCAK

LGVRDGLSVWGQGTLVTVSS;

4) antibody ZIL11 includes at least one of the following:

a) a variable light chain comprising CAN-ZIL11_VL:
(SEQ ID NO: 89)
SSVLTQPPSVSVSLGQTATISCSGESLSNYYAQWFQQKAGQAPVLVIYKDTERPSGIPDRFSGSSSGNTHTLTISGARAEDEADYYCESAVSSDTIVFGGGT,
and b) a variable heavy chain comprising CAN-ZIL11_VH:
(SEQ ID NO: 87)
EVQLVESGGDLVKPAGSLRLSCVASGFTFRTYVMNWVRQAPGKGLQWVASINGGGSSPTYADAVRGRFTVSRDNAQNSLFLQMNSLRAEDTAVYFCVVSMVGPFDYWGQGTLVTVSS;

5) antibody ZIL69 includes at least one of the following:

a) a variable light chain comprising CAN-ZIL69_VL:
(SEQ ID NO: 93)
SSVLTQPPSVSVSLGQTATISCSGESLNKYYAQWFQQKAGQAPVLVIYKDTERPSGIPDRFSGSSAGNTHTLTISGARAEDEADYYCESAVSSETNVFGSGTQLTVL,
and b) a variable heavy chain comprising CAN-ZIL69_VH:
(SEQ ID NO: 91)
EVQLVESGGDLVKPAGSLRLSCVASGFTFSSYAMKWVRQAPGKGLQWVATINNDGTRTGYADAVRGRFTISKDNAKNTLYLQMDSLRADDTAVYYCTKGNAESGCTGDHCPPYWGQGTLVTVSS;

6) antibody ZIL94 includes at least one of the following:

a) a variable light chain comprising CAN-ZIL94_VL:
(SEQ ID NO: 97)
QTVVIQEPSLSVSPGGTVTLTCGLNSGSVSTSNYPGWYQQTRGRTPRTIIYDTGSRPSGVPNRFSGSISGNKAALTITGAQPEDEADYYCSLYTDSDILVFGGGTHLTVL,
and b) a variable heavy chain comprising CAN-ZIL94_VH:
(SEQ ID NO: 95)
EVQLVDSGGDLVKPGGSLRLSCVASGFTFSTYFMSWVRQAPGRGLQWVALISSDGSGTYYADAVKGRFTISRDNAKNTLYLQMNSLRAEDTAMYYCAIFWRAFNDWGQGTLVTVSS;

7) antibody ZIL154 includes at least one of the following:

a) a variable light chain comprising CAN-ZIL154_VL:
(SEQ ID NO: 101)
DIVVTQTPLSLSVSPGETASFSCKASQSLLHSDGNTYLDWFRQKPGQSPQRLIYKVSNRDPGVPDRFSGSGSGTDFTLRISGVEADDAGLYYCMQAIHFPLTFGAGTKVELK,
and b) a variable heavy chain comprising CAN-ZIL154_VH:
(SEQ ID NO: 99)
EVHLVESGGDLVKPWGSLRLSCVASGFTFSDRGMSWVRQSPGKGLQWVAYIRYDGSRTDYADAVEGRFTISRDNAKNTLYLQMNSLRAEDTAVYYCARWDGSSFDYWGQGTLVTVSS;

8) antibody ZIL159 includes at least one of the following:

a) a variable light chain comprising CAN-ZIL159_VL:
(SEQ ID NO: 105)
SNVLTQPPSVSVSLGQTATISCSGETLNRFYTQWFQQKAGQAPVLVIYKDTERPSGIPDRFSGSSSGNIHTLTISGARAEDEAAYYCKSAVSIDVGVFGGGTHLTVF,
and b) a variable heavy chain comprising CAN-ZIL159_VH:
(SEQ ID NO: 103)
EVQLVESGGDLVKPAGSLRLSCVASGFTFSSYVMTWVRQAPGKGLQWVAGINSEGSRTAYADAVKGRFTISRDNAKNTLYLQIDSLRAEDTAIYYCATGDIVATGTSYWGQGTLVTVSS;

9) antibody ZIL171 includes at least one of the following:

a) a variable light chain comprising CAN-ZIL171_VL:
(SEQ ID NO: 109)
SSVLTQPPSVSVSLGQTATISCSGKSLSYYYAQWFQQKAGQAPVLVIYKDTERPSGIPDRFSGSSSGNTHTLTISGARAEDEADYYCESAVSSDTIVFGGGTHLTVL,
and b) a variable heavy chain comprising CAN-ZIL171_VH:
(SEQ ID NO: 107)
EVQLVESGGDLVKPAGSLRLSCVASGFTFRTYVMNWVRQAPGKGLQWVASINGGGSSPTYADAVRGRFTVSRDNAQNSLFLQMNSLRAEDTAIYFCVVSMVGPFDYWGHGTLVTVSS;

and 10) antibody 04H07 includes at least one of the following:

a) a variable light chain comprising Mu_04H07_VL:
(SEQ ID NO: 214)
DIVMSQSPSSLAVSVGEKVTMSCKSSQSLLYSINQKNHLAWFQQKPGQSPKLLIYWASTRESGVPARFTGSGSGTDFTLTISSVKTEDLAVYYCQQGYTYPFTFGSGTKLEIK,
and b) a variable heavy chain comprising Mu_04H07_VH:
(SEQ ID NO: 212)
QVQLQQPGAELVRPGASVKLSCKASGYTFTSYWMNWAKQRPGQGLEWIGMIDPSDSEIHYNQVFKDKATLTVDKSSSTAYMQLSSLTSEDSAVYYCARQDIVTTVDYWGQGTTLTVSS;

and 11) antibody 06A09 includes at least one of the following:

a) a variable light chain comprising Mu_06A09_VL:
(SEQ ID NO: 218)
DIVMSQSPSSLAVSVGEKVTMSCKSSQSLLYSINQKNFLAWYQQKPGQS

PKLLIYWASTRESGVPDRFTGSGSGTDFTLTISSVKSEDLAVYYCQQHY

GYPFTFGSGTKLEIK,
and b) a variable heavy chain comprising Mu_06A09_VH:
(SEQ ID NO: 216)
QVQLQQPGAELVRPGASVKLSCKAYGYTFTSYWMNWVKQRPGQGLEWIG

MIDPSDSETHYNQIFRDKATLTIDKSSSTAYMQLSSLTSEDSAVYFCAR

QDIVTTVDYWGQGTTLTVSS.

In other embodiments, the invention provides a host cell that produces an antibody described above.

The present invention also includes, within its scope, nucleotide sequences encoding the variable regions of the light and heavy chains of the anti-IL-31 antibody of the present invention.

Included also within the scope of the invention is any nucleotide sequence that encodes the amino acid sequence of 15H05, ZIL1, ZIL8, ZIL9, ZIL11, ZIL69, ZIL94, ZIL154, ZIL159, ZIL171, 04H07, 06A09, or IL-31-specific polypeptides or peptides thereof.

In some embodiments, the invention provides an isolated nucleic acid including a nucleic acid sequence encoding at least one of the following combinations of variable heavy complementary determining region (CDR) sequences:

1) 15H05: variable heavy
(VH)-CDR1 of
(SEQ ID NO: 1)
SYTIH,

VH-CDR2 of
(SEQ ID NO: 2)
NINPTSGYTENNQRFKD,
and

VH-CDR3 of
(SEQ ID NO: 3)
WGFKYDGEWSFDV;

2) ZIL1:
VH-CDR1 of
(SEQ ID NO: 13)
SYGMS,

VH-CDR2 of
(SEQ ID NO: 14)
HINSGGSSTYYADAVKG,
and

VH-CDR3 of
(SEQ ID NO: 15)
VYTTLAAFWTDNFDY;

3) ZIL8:
VH-CDR1 of
(SEQ ID NO: 19)
DYAMS,

VH-CDR2 of
(SEQ ID NO: 20)
GIDSVGSGTSYADAVKG,
and

VH-CDR3 of
(SEQ ID NO: 21)
GFPGSFEH;

4) ZIL9:
VH-CDR1 of
(SEQ ID NO: 25)
SYDMT,

VH-CDR2 of
(SEQ ID NO: 26)
DVNSGGTGTAYAVAVKG,
and

VH-CDR3 of
(SEQ ID NO: 27)
LGVRDGLSV;

5) ZIL11:
VH-CDR1 of
(SEQ ID NO: 31)
TYVMN,

VH-CDR2 of
(SEQ ID NO: 32)
SINGGGSSPTYADAVRG,
and

VH-CDR3 of
(SEQ ID NO: 33)
SMVGPFDY;

6) ZIL69:
VH-CDR1 of
(SEQ ID NO: 37)
SYAMK,

VH-CDR2 of
(SEQ ID NO: 38)
TINNDGTRTGYADAVRG,
and

VH-CDR3 of
(SEQ ID NO: 39)
GNAESGCTGDHCPPY;

7) ZIL94:
VH-CDR1 of
(SEQ ID NO: 43)
TYFMS,

VH-CDR2 of
(SEQ ID NO: 44)
LISSDGSGTYYADAVKG,
and

VH-CDR3 of
(SEQ ID NO: 45)
FWRAFND

8) ZIL154:
VH-CDR1 of
(SEQ ID NO: 49)
DRGMS,

VH-CDR2 of
(SEQ ID NO: 50)
YIRYDGSRTDYADAVEG,
and

VH-CDR3 of
(SEQ ID NO: 51)
WDGSSFDY;

9) ZIL159:
VH-CDR1 of
(SEQ ID NO: 55)
SYVMT,

-continued

VH-CDR2 of
(SEQ ID NO: 56)
GINSEGSRTAYADAVKG,
and

VH-CDR3 of
(SEQ ID NO: 57)
GDIVATGTSY;

10) ZIL171:
VH-CDR1 of
(SEQ ID NO: 61)
TYVMN,

VH-CDR2 of
(SEQ ID NO: 62)
SINGGGSSPTYADAVRG,
and

VH-CDR3 of
(SEQ ID NO: 63)
SMVGPFDY, 11) 04H07:
VH-CDR1 of
(SEQ ID NO: 200)
SYWMN,

VH-CDR of
(SEQ ID NO: 201)
MIDPSDSEIHYNQVFKD,
and

VH-CDR3 of
(SEQ ID NO: 202)
QDIVTTVDY;

12) 06A09:
VH-CDR1 of
(SEQ ID NO: 206)
SYWMN,

VH-CDR2 of
(SEQ ID NO: 207)
MIDPSDSETHYNQIFRD,
and

VH-CDR3 of
(SEQ ID NO: 208)
QDIVTTVDY;
or 13) a variant of 1) to 12) that differs from the CDRs of respective parent antibody 15H05, ZIL1, ZIL8, ZIL9, ZIL11, ZIL69, ZIL94, ZIL154, ZIL159, ZIL171, 04H07, or 06A09 by addition, deletion, and/or substitution of one or more amino acid residues in at least one of VH CDR1, CDR2, or CDR3.

In one embodiment, the isolated nucleic acid described above may further include a nucleic acid sequence encoding at least one of the following combinations of variable light complementary determining region (CDR) sequences:

1) 15H05: variable light
(VL)-CDR1 of
(SEQ ID NO: 4)
RASQGISIWLS,

VL-CDR2 of
(SEQ ID NO: 5)
KASNLHI,
and

VL-CDR3 of
(SEQ ID NO: 6)
LQSQTYPLT;

2) ZIL1:
VL-CDR1 of
(SEQ ID NO: 16)
SGSTNNIGILAAT,

VL-CDR2 of
(SEQ ID NO: 17)
SDGNRPS,
and

VL-CDR3 of
(SEQ ID NO: 18)
QSFDTTLDAYV;

3) ZIL8:
VL-CDR1 of
(SEQ ID NO: 22)
TGSSSNIGSGYVG,

VL-CDR2 of
(SEQ ID NO: 23)
YNSDRPS,
and

VL-CDR3 of
(SEQ ID NO: 24)
SVYDRTFNAV;

4) ZIL9:
VL-CDR1 of
(SEQ ID NO: 28)
SGESLNEYYTQ,

VL-CDR2 of
(SEQ ID NO: 29)
RDTERPS,
and

VL-CDR3 of
(SEQ ID NO: 30)
ESAVDTGTLV;

5) ZIL11:
VL-CDR1 of
(SEQ ID NO: 34)
SGESLSNYYAQ,

VL-CDR2 of
(SEQ ID NO: 35)
KDTERPS,
and

VL-CDR3 of
(SEQ ID NO: 36)
ESAVSSDTIV;

6) ZIL69:
VL-CDR1 of
(SEQ ID NO: 40)
SGESLNKYYAQ,

VL-CDR2 of
(SEQ ID NO: 41)
KDTERPS,
and

VL-CDR3 of
(SEQ ID NO: 42)
ESAVSSETNV;

7) ZIL94:
VL-CDR1 of
(SEQ ID NO: 46)
GLNSGSVSTSNYPG,

VL-CDR2 of
(SEQ ID NO: 47)
DTGSRPS,

-continued and

VL-CDR3 of
SLYTDSDILV;                                    (SEQ ID NO: 48)

8) ZIL154:
VL-CDR1 of
KASQSLLHSDGNTYLD,                              (SEQ ID NO: 52)

VL-CDR2 of
KVSNRDP,                                       (SEQ ID NO: 53)
and

VL-CDR3 of
MQAIHFPLT;                                     (SEQ ID NO: 54)

9) ZIL159:
VL-CDR1 of
SGETLNRFYTQ,                                   (SEQ ID NO: 58)

VL-CDR2 of
KDTERPS,                                       (SEQ ID NO: 59)
and

VL-CDR3 of
KSAVSIDVGV;                                    (SEQ ID NO: 60)

10) ZIL171:
VL-CDR1 of
SGKSLSYYYAQ,                                   (SEQ ID NO: 64)

VL-CDR2 of
KDTERPS,                                       (SEQ ID NO: 65)
and

VL-CDR3 of
ESAVSSDTIV;                                    (SEQ ID NO: 66)

11) 04H07:
VL-CDR1 of
KSSQSLLYSINQKNHLA,                             (SEQ ID NO: 203)

VL-CDR2 of
WASTRES,                                       (SEQ ID NO: 204)

VL-CDR3 of
QQGYTYPFT;                                     (SEQ ID NO: 205)

12) 06A09:
VL-CDR1 of
KSSQSLLYSINQKNFLA,                             (SEQ ID NO: 209)

VL-CDR2 of
WASTRES,                                       (SEQ ID NO: 210)

VL-CDR3 of
QQHYGYPFT;                                     (SEQ ID NO: 211)
or 13) a variant of 1) to 12) that differs from the CDRs of respective parent antibody 15H05, ZIL1, ZIL8, ZIL9, ZIL11, ZIL69, ZIL94, ZIL154, ZIL159, ZIL171, 04H07, or 06A09 by addition, deletion, -continued and/or substitution of one or more amino acid residues in at least one of VH or VL CDR1, CDR2, or CDR3.

In one embodiment, the invention provides an isolated nucleic acid comprising a nucleic acid sequence encoding at least one of the following combinations of variable light complementary determining region (CDR) sequences:

1) 15H05: variable light
(VL)-CDR1 of
RASQGISIWLS,                                   (SEQ ID NO: 4)

VL-CDR2 of
KASNLHI,                                       (SEQ ID NO: 5)
and

VL-CDR3 of
LQSQTYPLT;                                     (SEQ ID NO: 6)

2) ZIL1:
VL-CDR1 of
SGSTNNIGILAAT,                                 (SEQ ID NO: 16)

VL-CDR2 of
SDGNRPS,                                       (SEQ ID NO: 17)
and

VL-CDR3 of
QSFDTTLDAYV;                                   (SEQ ID NO: 18)

3) ZIL8:
VL-CDR1 of
TGSSSNIGSGYVG,                                 (SEQ ID NO: 22)

VL-CDR2 of
YNSDRPS,                                       (SEQ ID NO: 23)
and

VL-CDR3 of
SVYDRTFNAV;                                    (SEQ ID NO: 24)

4) ZIL9:
VL-CDR1 of
SGESLNEYYTQ,                                   (SEQ ID NO: 28)

VL-CDR2 of
RDTERPS,                                       (SEQ ID NO: 29)
and

VL-CDR3 of
ESAVDTGTLV;                                    (SEQ ID NO: 30)

5) ZIL11:
VL-CDR1 of
SGESLSNYYAQ,                                   (SEQ ID NO: 34)

VL-CDR2 of
KDTERPS,                                       (SEQ ID NO: 35)
and

VL-CDR3 of
ESAVSSDTIV;                                    (SEQ ID NO: 36)

6) ZIL69:
VL-CDR1 of
(SEQ ID NO: 40)
SGESLNKYYAQ,

VL-CDR2 of
(SEQ ID NO: 41)
KDTERPS,
and

VL-CDR3 of
(SEQ ID NO: 42)
ESAVSSETNV;

7) ZIL94:
VL-CDR1 of
(SEQ ID NO: 46)
GLNSGSVSTSNYPG,

VL-CDR2 of
(SEQ ID NO: 47)
DTGSRPS,
and

VL-CDR3 of
(SEQ ID NO: 48)
SLYTDSDILV;

8) ZIL154:
VL-CDR1 of
(SEQ ID NO: 52)
KASQSLLHSDGNTYLD,

VL-CDR2 of
(SEQ ID NO: 53)
KVSNRDP,
and

VL-CDR3 of
(SEQ ID NO: 54)
MQAIHFPLT;

9) ZIL159:
VL-CDR1 of
(SEQ ID NO: 58)
SGETLNRFYTQ,

VL-CDR2 of
(SEQ ID NO: 59)
KDTERPS,
and

VL-CDR3 of
(SEQ ID NO: 60)
KSAVSIDVGV;

10) ZIL171:
VL-CDR1 of
(SEQ ID NO: 64)
SGKSLSYYYAQ,

VL-CDR2 of
(SEQ ID NO: 65)
KDTERPS,
and

VL-CDR3 of
(SEQ ID NO: 66)
ESAVSSDTIV;

11) 04H07:
VL-CDR1 of
(SEQ ID NO: 203)
KSSQSLLYSINQKNHLA,

VL-CDR2 of
(SEQ ID NO: 204)
WASTRES,

VL-CDR3 of
(SEQ ID NO: 205)
QQGYTYPFT;

12) 06A09:
VL-CDR1 of
(SEQ ID NO: 209)
KSSQSLLYSINQKNFLA,

VL-CDR2 of
(SEQ ID NO: 210)
WASTRES,

VL-CDR3 of
(SEQ ID NO: 211)
QQHYGYPFT;
or 13) a variant of 1) to 12) that differs from the CDRs of respective parent antibody 15H05, ZIL1, ZIL8, ZIL9, ZIL11, ZIL69, ZIL94, ZIL154, ZIL159, ZIL171, 04H07, or 06A09 by addition, deletion, and/or substitution of one or more amino acid residues in at least one of VH or VL CDR1, CDR2, or CDR3.

The present invention further provides a vector including at least one of the nucleic acids described above.

As will be described in further detail below, the nucleic acid sequence encoding at least one of the above-described combinations of variable heavy complementary determining region (CDR) sequences may be contained on the same vector together with the nucleic acid sequence encoding at least one of the above-described combinations of variable light CDR sequences. Alternatively, the nucleic acid sequence encoding at least one of the above-described combinations of variable light CDR sequences and the nucleic acid sequence encoding at least one of the above-described combinations of variable heavy CDR sequences may each be contained on separate vectors.

Because the genetic code is degenerate, more than one codon can be used to encode a particular amino acid. Using the genetic code, one or more different nucleotide sequences can be identified, each of which would be capable of encoding the amino acid. The probability that a particular oligonucleotide will, in fact, constitute the actual XXX-encoding sequence can be estimated by considering abnormal base pairing relationships and the frequency with which a particular codon is actually used (to encode a particular amino acid) in eukaryotic or prokaryotic cells expressing an anti-IL-31 antibody or IL-31-specific portion thereof. Such "codon usage rules" are disclosed by Lathe, et al., 183 J. Molec. Biol. 1-12 (1985). Using the "codon usage rules" of Lathe, a single nucleotide sequence, or a set of nucleotide sequences that contains a theoretical "most probable" nucleotide sequence capable of encoding anti-IL-31 sequences can be identified. It is also intended that the antibody coding regions for use in the present invention could also be provided by altering existing antibody genes using standard molecular biological techniques that result in variants (agonists) of the antibodies and peptides described herein. Such variants include, but are not limited to deletions, additions and substitutions in the amino acid sequence of the anti-IL-31 antibodies or IL-31-specific polypeptides or peptides, including in the CDR regions of the antibody. For example, residues which are found to be non-critical for antigen binding within the CDR regions or other regions of the antibody can be substituted. Examples of the types of experimentation used to assess whether particular residues are non-critical for antigen binding are described in section 1.21 of the example section below. In one embodiment, one or more of the substitutions are conservative amino acid substitutions, which are described in further detail herein. However, antibody variants according to the present invention, including CDR variants are not limited to conservative amino acid substitutions.

For example, one class of substitutions is conservative amino acid substitutions. Such substitutions are those that substitute a given amino acid in an anti-IL-31antibody peptide by another amino acid of like characteristics. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg, replacements among the aromatic residues Phe, Tyr, and the like. Guidance concerning which amino acid changes are likely to be phenotypically silent is found in Bowie et al., 247 Science 1306-10 (1990).

Variant or agonist anti-IL-31 antibodies or IL-31-specific polypeptides, or peptides may be fully functional or may lack function in one or more activities. Fully functional variants typically contain only conservative variations or variations in non-critical residues or in non-critical regions. Functional variants can also contain substitution of similar amino acids that result in no change or an insignificant change in function. Alternatively, such substitutions may positively or negatively affect function to some degree. Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis. Cunningham et al., 244 Science 1081-85 (1989). The latter procedure introduces single alanine mutations at every residue in the molecule. The resulting mutant molecules are then tested for biological activity such as epitope binding or in vitro ADCC activity. Sites that are critical for ligand-receptor binding can also be determined by structural analysis such as crystallography, nuclear magnetic resonance, or photoaffinity labeling. Smith et al., 224 J. Mol. Biol. 899-904 (1992); de Vos et al., 255 Science 306-12 (1992).

Moreover, polypeptides often contain amino acids other than the twenty "naturally occurring" amino acids. Further, many amino acids, including the terminal amino acids, may be modified by natural processes, such as processing and other post-translational modifications, or by chemical modification techniques well known in the art. Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as Proteins—Structure and Molecular Properties (2nd ed., T. E. Creighton, W. H. Freeman & Co., NY, 1993). Many detailed reviews are available on this subject, such as by Wold, Posttranslational Covalent Modification of proteins, 1-12 (Johnson, ed., Academic Press, NY, 1983); Seifter et al. 182 Meth. Enzymol. 626-46 (1990); and Rattan et al. 663 Ann. NY Acad. Sci. 48-62 (1992).

Accordingly, the IL-31-specific antibodies, polypeptides, and peptides of the present invention also encompass derivatives or analogs in which a substituted amino acid residue is not one encoded by the genetic code.

Similarly, the additions and substitutions in the amino acid sequence as well as variations, and modifications just described may be equally applicable to the amino acid sequence of the IL-31 antigen and/or epitope or peptides thereof, and are thus encompassed by the present invention. As mentioned above, the genes encoding a monoclonal antibody according to the present invention is specifically effective in the recognition of IL-31.

Antibody Derivatives

Included within the scope of this invention are antibody derivatives. A "derivative" of an antibody contains additional chemical moieties not normally a part of the protein. Covalent modifications of the protein are included within the scope of this invention. Such modifications may be introduced into the molecule by reacting targeted amino acid residues of the antibody with an organic derivatizing agent that is capable of reacting with selected side chains or terminal residues. For example, derivatization with bifunctional agents, well-known in the art, is useful for cross-linking the antibody or fragment to a water-insoluble support matrix or to other macromolecular carriers.

Derivatives also include radioactively labeled monoclonal antibodies that are labeled. For example, with radioactive iodine ($^{125}$I, $^{131}$I), carbon ($^{14}$C), sulfur ($^{35}$S), indium ($^{111}$In), tritium ($^{3}$H) or the like; conjugates of monoclonal antibodies with biotin or avidin, with enzymes, such as horseradish peroxidase, alkaline phosphatase, beta-D-galactosidase, glucose oxidase, glucoamylase, carboxylic acid anhydrase, acetylcholine esterase, lysozyme, malate dehydrogenase or glucose 6-phosphate dehydrogenase; and also conjugates of monoclonal antibodies with bioluminescent agents (such as luciferase), chemoluminescent agents (such as acridine esters) or fluorescent agents (such as phycobiliproteins).

Another derivative bifunctional antibody of the present invention is a bispecific antibody, generated by combining parts of two separate antibodies that recognize two different antigenic groups. This may be achieved by crosslinking or recombinant techniques. Additionally, moieties may be added to the antibody or a portion thereof to increase half-life in vivo (e.g., by lengthening the time to clearance from the blood stream. Such techniques include, for example, adding PEG moieties (also termed PEGylation), and are well-known in the art. See U.S. Patent. Appl. Pub. No. 20030031671.

Recombinant Expression of Antibodies

In some embodiments, the nucleic acids encoding a subject monoclonal antibody are introduced directly into a host cell, and the cell is incubated under conditions sufficient to induce expression of the encoded antibody. After the subject nucleic acids have been introduced into a cell, the cell is typically incubated, normally at 37° C., sometimes under selection, for a period of about 1-24 hours in order to allow for the expression of the antibody. In one embodiment, the antibody is secreted into the supernatant of the media in which the cell is growing.

Traditionally, monoclonal antibodies have been produced as native molecules in murine hybridoma lines. In addition to that technology, the present invention provides for recombinant DNA expression of monoclonal antibodies. This allows the production of caninized, felinized, equinized, fully canine, fully feline, and fully equine antibodies, as well as a spectrum of antibody derivatives and fusion proteins in a host species of choice.

A nucleic acid sequence encoding at least one anti-IL-31 antibody, portion or polypeptide of the present invention may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, e.g., by Maniatis et al., MOLECULAR CLONING, LAB. MANUAL, (Cold Spring Harbor Lab. Press, N.Y., 1982 and 1989), and Ausubel et al. 1993 supra, may be used to construct nucleic acid sequences which encode a monoclonal antibody molecule or antigen binding region thereof.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression as anti-IL-31 peptides or antibody portions in recoverable amounts. The precise nature of the regulatory regions needed for gene expression may vary from organism to organism, as is well known in the analogous art. See, e.g., Sambrook et al., 2001 supra; Ausubel et al., 1993 supra.

The present invention accordingly encompasses the expression of an anti-IL-31 antibody or IL-31-specific polypeptide or peptide, in either prokaryotic or eukaryotic cells. Suitable hosts include bacterial or eukaryotic hosts including bacteria, yeast, insects, fungi, bird and mammalian cells either in vivo, or in situ, or host cells of mammalian, insect, bird or yeast origin. The mammalian cell or tissue may be of human, primate, hamster, rabbit, rodent, cow, pig, sheep, horse, goat, dog or cat origin, but any other mammalian cell may be used.

In one embodiment, the introduced nucleotide sequence will be incorporated into a plasmid or viral vector capable of autonomous replication in the recipient host. Any of a wide variety of vectors may be employed for this purpose. See, e.g., Ausubel et al., 1993 supra. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Example prokaryotic vectors known in the art include plasmids such as those capable of replication in E. coli (such as, for example, pBR322, ColE1, pSC101, pACYC 184, .pi.VX). Such plasmids are, for example, disclosed by Maniatis et al., 1989 supra; Ausubel et al, 1993 supra. Bacillus plasmids include pC194, pC221, pT127, etc. Such plasmids are disclosed by Gryczan, in THE MOLEC. BIO. OF THE BACILLI 307-329 (Academic Press, NY, 1982). Suitable Streptomyces plasmids include pIJ101 (Kendall et al., 169 J. Bacteriol. 4177-83 (1987)), and Streptomyces bacteriophages such as .phi.C31 (Chater et al., in SIXTH INT'L SYMPOSIUM ON ACTINOMYCETALES BIO. 45-54 (Akademiai Kaido, Budapest, Hungary 1986). Pseudomonas plasmids are reviewed in John et al., 8 Rev. Infect. Dis. 693-704 (1986); Izaki, 33 Jpn. J. Bacteriol. 729-42 (1978); and Ausubel et al., 1993 supra.

Alternatively, gene expression elements useful for the expression of cDNA encoding anti-IL-31antibodies or peptides include, but are not limited to (a) viral transcription promoters and their enhancer elements, such as the SV40 early promoter (Okayama et al., 3 Mol. Cell. Biol. 280 (1983)), Rous sarcoma virus LTR (Gorman et al., 79 Proc. Natl. Acad. Sci., USA 6777 (1982)), and Moloney murine leukemia virus LTR (Grosschedl et al., 41 Cell 885 (1985)); (b) splice regions and polyadenylation sites such as those derived from the SV40 late region (Okayarea et al., MCB, 3: 280 (1983), and (c) polyadenylation sites such as in SV40 (Okayama et al., 1983, supra).

Immunoglobulin cDNA genes can be expressed as described by Weidle et al., 51(1) Gene 21-29 (1987), using as expression elements the SV40 early promoter and its enhancer, the mouse immunoglobulin H chain promoter enhancers, SV40 late region mRNA splicing, rabbit S-globin intervening sequence, immunoglobulin and rabbit S-globin polyadenylation sites, and SV40 polyadenylation elements.

For immunoglobulin genes comprised of part cDNA, part genomic DNA (Whittle et al., 1 Protein Engin. 499-505 (1987)), the transcriptional promoter can be human cytomegalovirus, the promoter enhancers can be cytomegalovirus and mouse/human immunoglobulin, and mRNA splicing and polyadenylation regions can be the native chromosomal immunoglobulin sequences.

In one embodiment, for expression of cDNA genes in rodent cells, the transcriptional promoter is a viral LTR sequence, the transcriptional promoter enhancers are either or both the mouse immunoglobulin heavy chain enhancer and the viral LTR enhancer, the splice region contains an intron of greater than 31 bp, and the polyadenylation and transcription termination regions are derived from the native chromosomal sequence corresponding to the immunoglobulin chain being synthesized. In other embodiments, cDNA sequences encoding other proteins are combined with the above-recited expression elements to achieve expression of the proteins in mammalian cells.

Each fused gene can be assembled in, or inserted into, an expression vector. Recipient cells capable of expressing the chimeric immunoglobulin chain gene product are then transfected singly with an anti-IL-31 peptide or chimeric H or chimeric L chain-encoding gene, or are co-transfected with a chimeric H and a chimeric L chain gene. The transfected recipient cells are cultured under conditions that permit expression of the incorporated genes and the expressed immunoglobulin chains or intact antibodies or fragments are recovered from the culture.

In one embodiment, the fused genes encoding the anti-IL-31 peptide or chimeric H and L chains, or portions thereof are assembled in separate expression vectors that are then used to co-transfect a recipient cell. Alternatively the fused genes encoding the chimeric H and L chains can be assembled on the same expression vector.

For transfection of the expression vectors and production of the chimeric antibody, the recipient cell line may be a myeloma cell. Myeloma cells can synthesize, assemble and secrete immunoglobulins encoded by transfected immunoglobulin genes and possess the mechanism for glycosylation of the immunoglobulin. Myeloma cells can be grown in culture or in the peritoneal cavity of a mouse, where secreted immunoglobulin can be obtained from ascites fluid. Other suitable recipient cells include lymphoid cells such as B lymphocytes of human or non-human origin, hybridoma cells of human or non-human origin, or interspecies heterohybridoma cells.

The expression vector carrying a chimeric, caninized, felinized, equinized, fully canine, fully feline, or fully equine anti-IL-31 antibody construct or IL-31-specific polypeptide or peptide (e.g., antigen-binding portion of the antibodies described herein) of the present invention can be introduced into an appropriate host cell by any of a variety of suitable means, including such biochemical means as transformation, transfection, conjugation, protoplast fusion, calcium phosphate-precipitation, and application with polycations such as diethylaminoethyl (DEAE) dextran, and such mechanical means as electroporation, direct microinjection, and microprojectile bombardment. Johnston et al., 240 Science 1538-1541 (1988).

Yeast can provide substantial advantages over bacteria for the production of immunoglobulin H and L chains. Yeasts carry out post-translational peptide modifications including glycosylation. A number of recombinant DNA strategies now exist which utilize strong promoter sequences and high copy number plasmids which can be used for production of the desired proteins in yeast. Yeast recognizes leader sequences of cloned mammalian gene products and secretes peptides bearing leader sequences (i.e., pre-peptides). Hitzman et al., 11th Int'l Conference on Yeast, Genetics & Molec. Biol. (Montpelier, France, 1982).

Yeast gene expression systems can be routinely evaluated for the levels of production, secretion and the stability of anti-IL-31 peptides, antibody and assembled murine and chimeric, heterochimeric, caninized, felinized, equinized, fully canine, fully feline, or fully equine antibodies, fragments and regions thereof. Any of a series of yeast gene expression systems incorporating promoter and termination elements from the actively expressed genes coding for glycolytic enzymes produced in large quantities when yeasts are grown in media rich in glucose can be utilized. Known glycolytic genes can also provide very efficient transcription control signals. For example, the promoter and terminator signals of the phosphoglycerate kinase (PGK) gene can be utilized. A number of approaches can be taken for evaluating optimal expression plasmids for the expression of cloned immunoglobulin cDNAs in yeast. See Vol. II DNA Cloning, 45-66, (Glover, ed.,) IRL Press, Oxford, UK 1985).

Bacterial strains can also be utilized as hosts for the production of antibody molecules or peptides described by this invention. Plasmid vectors containing replicon and control sequences which are derived from species compatible with a host cell are used in connection with these bacterial hosts. The vector carries a replication site, as well as specific genes which are capable of providing phenotypic selection in transformed cells. A number of approaches can be taken for evaluating the expression plasmids for the production of murine, chimeric, heterochimeric, caninized, felinized, equinized, fully canine, fully feline, or fully equine antibodies, fragments and regions or antibody chains encoded by the cloned immunoglobulin cDNAs in bacteria (see Glover, 1985 supra; Ausubel, 1993 supra; Sambrook, 2001 supra; Colligan et al., eds. Current Protocols in Immunology, John Wiley & Sons, NY, NY (1994-2001); Colligan et al., eds. Current Protocols in Protein Science, John Wiley & Sons, NY, NY (1997-2001).

Host mammalian cells may be grown in vitro or in vivo. Mammalian cells provide post-translational modifications to immunoglobulin protein molecules including leader peptide removal, folding and assembly of H and L chains, glycosylation of the antibody molecules, and secretion of functional antibody protein.

Mammalian cells which can be useful as hosts for the production of antibody proteins, in addition to the cells of lymphoid origin described above, include cells of fibroblast origin, such as Vero (ATCC CRL 81) or CHO-K1 (ATCC CRL 61) cells.

Many vector systems are available for the expression of cloned anti-IL-31 peptides H and L chain genes in mammalian cells (see Glover, 1985 supra). Different approaches can be followed to obtain complete $H_2L_2$ antibodies. It is possible to co-express H and L chains in the same cells to achieve intracellular association and linkage of H and L chains into complete tetrameric $H_2L_2$ antibodies and/or anti-IL-31 peptides. The co-expression can occur by using either the same or different plasmids in the same host. Genes for both H and L chains and/or anti-IL-31 peptides can be placed into the same plasmid, which is then transfected into cells, thereby selecting directly for cells that express both chains. Alternatively, cells can be transfected first with a plasmid encoding one chain, for example the L chain, followed by transfection of the resulting cell line with an H chain plasmid containing a second selectable marker. Cell lines producing anti-IL-31 peptides and/or $H_2L_2$ molecules via either route could be transfected with plasmids encoding additional copies of peptides, H, L, or H plus L chains in conjunction with additional selectable markers to generate cell lines with enhanced properties, such as higher production of assembled $H_2L_2$ antibody molecules or enhanced stability of the transfected cell lines.

For long-term, high-yield production of recombinant antibodies, stable expression may be used. For example, cell lines, which stably express the antibody molecule may be engineered. Rather than using expression vectors which contain viral origins of replication, host cells can be transformed with immunoglobulin expression cassettes and a selectable marker. Following the introduction of the foreign DNA, engineered cells may be allowed to grow for 1-2 days in enriched media, and then are switched to a selective media. The selectable marker in the recombinant plasmid confers resistance to the selection and allows cells to stably integrate the plasmid into a chromosome and grow to form foci which in turn can be cloned and expanded into cell lines. Such engineered cell lines may be particularly useful in screening and evaluation of compounds/components that interact directly or indirectly with the antibody molecule.

Once an antibody of the invention has been produced, it may be purified by any method known in the art for purification of an immunoglobulin molecule, for example, by chromatography (e.g., ion exchange, affinity, particularly affinity for the specific antigen after Protein A, and sizing column chromatography), centrifugation, differential solubility, or by any other standard technique for the purification of proteins. In many embodiments, antibodies are secreted from the cell into culture medium and harvested from the culture medium.

Pharmaceutical Applications

The anti-IL-31 antibodies or IL-31-specific polypeptides or peptides of the present invention can be used for example in the treatment of pruritic and/or allergic conditions in companion animals, such as dogs, cats, and horses. In one embodiment, such polypeptides or peptides comprise the antigen-binding portion of the anti-IL-31 antibodies described herein. More specifically, the invention further provides for a pharmaceutical composition comprising a pharmaceutically acceptable carrier or diluent and, as active ingredient, an antibody or polypeptide or peptide according to the invention. The antibody can be a chimeric, heterochimeric, caninized, felinized, equinized, fully canine, fully feline, or fully equine antibody according to the present invention. Intact immunoglobulins or their binding fragments, such as Fab, are also envisioned. The antibody and pharmaceutical compositions thereof of this invention are useful for parenteral administration, e.g., subcutaneously, intramuscularly or intravenously.

Anti-IL-31 antibodies and/or IL-31-specific polypeptides and/or IL-31-specific peptides of the present invention can be administered either as individual therapeutic agents or in combination with other therapeutic agents. They can be administered alone, but are generally administered with a pharmaceutical carrier selected on the basis of the chosen route of administration and standard pharmaceutical practice.

Administration of the antibodies disclosed herein may be carried out by any suitable means, including parenteral injection (such as intraperitoneal, subcutaneous, or intramuscular injection), orally, or by topical administration of the antibodies (typically carried in a pharmaceutical formulation) to an airway surface. Topical administration to an airway surface can be carried out by intranasal administration (e.g., by use of dropper, swab, or inhaler). Topical administration of the antibodies to an airway surface can also be carried out by inhalation administration, such as by creating respirable particles of a pharmaceutical formulation (including both solid and liquid particles) containing the antibodies as an aerosol suspension, and then causing the subject to inhale the respirable particles. Methods and apparatus for administering respirable particles of pharmaceutical formulations are well known, and any conventional technique can be employed. Oral administration may be, for example, in the form of an ingestable liquid or solid formulation.

In some desired embodiments, the antibodies are administered by parenteral injection. For parenteral administration, anti-IL-31 antibodies or polypeptides or peptides can be formulated as a solution, suspension, emulsion or lyophilized powder in association with a pharmaceutically acceptable parenteral vehicle. For example the vehicle may be a solution of the antibody or a cocktail thereof dissolved in an acceptable carrier, such as an aqueous carrier such vehicles are water, saline, Ringer's solution, dextrose solution, trehalose or sucrose solution, or 5% serum albumin, 0.4% saline, 0.3% glycine and the like. Liposomes and nonaqueous vehicles such as fixed oils can also be used. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjustment agents and the like, for example sodium acetate, sodium chloride, potassium chloride, calcium chloride, sodium lactate, etc. The concentration of antibody in these formulations can vary widely, for example from less than about 0.5%, usually at or at least about 1% to as much as 15% or 20% by weight and will be selected primarily based on fluid volumes, viscosities, etc., in accordance with the particular mode of administration selected. The vehicle or lyophilized powder can contain additives that maintain isotonicity (e.g., sodium chloride, mannitol) and chemical stability (e.g., buffers and preservatives). The formulation is sterilized by commonly used techniques.

Actual methods for preparing parenterally administrable compositions will be known or apparent to those skilled in the art and are described in more detail in, for example, *REMINGTON'S PHARMA. SCI.* (15th ed., Mack Pub. Co., Easton, Pa., 1980).

The antibodies of this invention can be lyophilized for storage and reconstituted in a suitable carrier prior to use. This technique has been shown to be effective with conventional immune globulins. Any suitable lyophilization and reconstitution techniques can be employed. It will be appreciated by those skilled in the art that lyophilization and reconstitution can lead to varying degrees of antibody activity loss and that use levels may have to be adjusted to compensate.

The compositions containing the present antibodies or a cocktail thereof can be administered for prevention of recurrence and/or therapeutic treatments for existing disease. Suitable pharmaceutical carriers are described in the most recent edition of *REMINGTON'S PHARMACEUTICAL SCIENCES*, a standard reference text in this field of art.

In therapeutic application, compositions are administered to a subject already suffering from a disease, in an amount sufficient to cure or at least partially arrest or alleviate the disease and its complications. An amount adequate to accomplish this is defined as a "therapeutically effective dose" or a "therapeutically effective amount". Amounts effective for this use will depend upon the severity of the disease and the general state of the subject's own immune system, but generally range from about 0.1 mg antibody per kg body weight to about 15 mg antibody per kg body weight, preferably about 0.3 mg antibody per kg of body weight to about 12 mg of antibody per kg of body weight. In one embodiment, the therapeutically effective amount will provide at least one month duration of efficacy with a dose up to 12 mg/kg of body weight. In view of the minimization of extraneous substances and the lower probability of "foreign substance" rejections which are achieved by the present canine-like, feline-like, and equine-like antibodies of this invention, it may be possible to administer substantial excesses of these antibodies.

The dosage administered will, of course, vary depending upon known factors such as the pharmacodynamic characteristics of the particular agent, and its mode and route of administration; age, health, and weight of the recipient; nature and extent of symptoms kind of concurrent treatment, frequency of treatment, and the effect desired.

As a non-limiting example, treatment of IL-31-related pathologies in dogs, cats, or horses can be provided as a biweekly or monthly dosage of anti-IL-31 antibodies of the present invention in the dosage range described above.

Example antibodies for canine, feline, or equine therapeutic use are high affinity (these may also be high avidity) antibodies, and fragments, regions and derivatives thereof having potent in vivo anti-IL-31 activity, according to the present invention. The antibody fragments and regions may be alternatively referred to herein as polypeptides or peptides of the present invention which include the antigen-binding portion of the anti-II-31 antibodies.

Single or multiple administrations of the compositions can be carried out with dose levels and pattern being selected by the treating veterinarian. In any event, the pharmaceutical formulations should provide a quantity of the antibody or antibodies of this invention sufficient to effectively treat the subject.

Diagnostic Applications

The present invention also provides the above anti-IL-31 antibodies, polypeptides, and/or peptides for use in diagnostic methods for detecting IL-31 in companion animals known to be or suspected of having a puritic and/or allergic condition.

Anti-IL-31 antibodies, polypeptides, and/or peptides of the present invention are useful for immunoassays which detect or quantitate IL-31, or anti-IL-31 antibodies, in a sample. An immunoassay for IL-31 typically comprises incubating a clinical or biological sample in the presence of a detectably labeled high affinity (or high avidity) anti-IL-31 antibody, polypeptide, or peptide of the present invention capable of selectively binding to IL-31, and detecting the labeled polypeptide, peptide or antibody which is bound in a sample. Various clinical assay procedures are well known in the art. See, e.g., *IMMUNOASSAYS FOR THE 80'S* (Voller et al., eds., Univ. Park, 1981). Such samples include tissue biopsy, blood, serum, and fecal samples, or liquids collected from animal subjects and subjected to ELISA analysis as described below.

In some embodiments, the binding of antigen to antibody is detected without the use of a solid support. For example, the binding of antigen to antibody can be detected in a liquid format.

In other embodiments, an anti-IL-31 antibody, polypeptide, or peptide can, for example, be fixed to nitrocellulose, or another solid support which is capable of immobilizing cells, cell particles or soluble proteins. The support can then be washed with suitable buffers followed by treatment with the detectably labeled IL-31-specific polypeptide, peptide or antibody. The solid phase support can then be washed with the buffer a second time to remove unbound polypeptide, peptide or antibody. The amount of bound label on the solid support can then be detected by known method steps.

"Solid phase support" or "carrier" refers to any support capable of binding polypeptide, peptide, antigen, or antibody. Well-known supports or carriers, include glass, polystyrene, polypropylene, polyethylene, polyvinylidenefluoride (PVDF), dextran, nylon, amylases, natural and modified celluloses, polyacrylamides, agaroses, and magnetite. The nature of the carrier can be either soluble to some extent or insoluble for the purposes of the present invention. The support material can have virtually any possible structural configuration so long as the coupled molecule is capable of binding to IL-31 or an anti-IL-31 antibody. Thus, the support configuration can be spherical, as in a bead, or cylindrical, as in the inside surface of a test tube, or the external surface of a rod. Alternatively, the surface can be flat, such as a sheet, culture dish, test strip, etc. For example, supports may include polystyrene beads. Those skilled in the art will know many other suitable carriers for binding antibody, polypeptide, peptide or antigen, or can ascertain the same by routine experimentation.

Well known method steps can determine binding activity of a given lot of anti-IL-31 polypeptide, peptide and/or antibody. Those skilled in the art can determine operative and optimal assay conditions by routine experimentation.

Detectably labeling an IL-31-specific polypeptide, peptide and/or antibody can be accomplished by linking to an enzyme for use in an enzyme immunoassay (EIA), or enzyme-linked immunosorbent assay (ELISA). The linked enzyme reacts with the exposed substrate to generate a chemical moiety which can be detected, for example, by spectrophotometric, fluorometric or by visual means. Enzymes which can be used to detectably label the IL-31-specific antibodies of the present invention include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase.

By radioactively labeling the IL-31-specific antibodies, it is possible to detect IL-31 through the use of a radioimmunoassay (RIA). See Work et al., *LAB. TECHNIQUES & BIOCHEM. 1N MOLEC.* Bio. (No. Holland Pub. Co., NY, 1978). The radioactive isotope can be detected by such means as the use of a gamma counter or a scintillation counter or by autoradiography. Isotopes which are particularly useful for the purpose of the present invention include: $^3$H, $^{125}$I, $^{131}$I, $^{35}$S, $^{14}$O, and $^{125}$I.

It is also possible to label the IL-31-specific antibodies with a fluorescent compound. When the fluorescent labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The IL-31-specific antibodies can also be delectably labeled using fluorescence-emitting metals such a $^{125}$Eu, or others of the lanthanide series. These metals can be attached to the IL-31-specific antibody using such metal chelating groups as diethylenetriaminepentaacetic acid (DTPA) or ethylenediamine-tetraacetic acid (EDTA).

The IL-31-specific antibodies also can be detectably labeled by coupling to a chemiluminescent compound. The presence of the chemiluminescently labeled antibody is then determined by detecting the presence of luminescence that arises during the course of a chemical reaction. Examples of useful chemiluminescent labeling compounds are luminol, isoluminol, theromatic acridinium ester, imidazole, acridinium salt and oxalate ester.

Likewise, a bioluminescent compound can be used to label the IL-31-specific antibody, portion, fragment, polypeptide, or derivative of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Detection of the IL-31-specific antibody, portion, fragment, polypeptide, or derivative can be accomplished by a scintillation counter, for example, if the detectable label is a radioactive gamma emitter, or by a fluorometer, for example, if the label is a fluorescent material. In the case of an enzyme label, the detection can be accomplished by colorometric methods which employ a substrate for the enzyme. Detection can also be accomplished by visual comparison of the extent of enzymatic reaction of a substrate in comparison with similarly prepared standards.

For the purposes of the present invention, the IL-31 which is detected by the above assays can be present in a biological sample. Any sample containing IL-31 may be used. For example, the sample is a biological fluid such as, for example, blood, serum, lymph, urine, feces, inflammatory exudate, cerebrospinal fluid, amniotic fluid, a tissue extract or homogenate, and the like. The invention is not limited to assays using only these samples, however, it being possible for one of ordinary skill in the art, in light of the present specification, to determine suitable conditions which allow the use of other samples.

In situ detection can be accomplished by removing a histological specimen from an animal subject, and providing the combination of labeled antibodies of the present invention to such a specimen. The antibody (or portion thereof) may be provided by applying or by overlaying the labeled antibody (or portion) to a biological sample. Through the use of such a procedure, it is possible to determine not only the presence of IL-31 but also the distribution of IL-31 in the examined tissue. Using the present invention, those of ordinary skill will readily perceive that any of a wide variety of histological methods (such as staining procedures) can be modified in order to achieve such in situ detection.

The antibody, fragment or derivative of the present invention can be adapted for utilization in an immunometric assay, also known as a "two-site" or "sandwich" assay. In a typical immunometric assay, a quantity of unlabeled antibody (or fragment of antibody) is bound to a solid support that is insoluble in the fluid being tested and a quantity of detectably labeled soluble antibody is added to permit detection and/or quantification of the ternary complex formed between solid-phase antibody, antigen, and labeled antibody.

The antibodies may be used to quantitatively or qualitatively detect the IL-31 in a sample or to detect presence of cells that express the IL-31. This can be accomplished by immunofluorescence techniques employing a fluorescently labeled antibody (see below) coupled with fluorescence microscopy, flow cytometric, or fluorometric detection. For diagnostic purposes, the antibodies may either be labeled or unlabeled. Unlabeled antibodies can be used in combination with other labeled antibodies (second antibodies) that are reactive with the antibody, such as antibodies specific for canine or feline immunoglobulin constant regions. Alternatively, the antibodies can be directly labeled. A wide variety of labels may be employed, such as radionuclides, fluors, enzymes, enzyme substrates, enzyme cofactors, enzyme inhibitors, ligands (particularly haptens), etc. Numerous types of immunoassays, such as those discussed previously are available and are well known to those skilled in the art.

In one embodiment, the diagnostic method for detecting IL-31 is a lateral flow immunoassay test. This is also known as the immunochromatographic assay, Rapid ImmunoMigration (RIM™) or strip test. Lateral flow immunoassays are essentially immunoassays adapted to operate along a single axis to suit the test strip format. A number of variations of the technology have been developed into commercial products, but they all operate according to the same basic principle. A typical test strip consists of the following components: (1) sample pad—an absorbent pad onto which the test sample is applied; (2) conjugate or reagent pad—this contains antibodies specific to the target analyte conjugated to colored particles (usually colloidal gold particles, or latex microspheres); (3) reaction membrane—typically a hydrophobic nitrocellulose or cellulose acetate membrane onto which anti-target analyte antibodies are immobilized in a line across the membrane as a capture zone or test line (a control zone may also be present, containing antibodies specific for the conjugate antibodies); and (4) wick or waste reservoir—a further absorbent pad designed to draw the sample across the reaction membrane by capillary action and collect it. The components of the strip are usually fixed to an inert backing material and may be presented in a simple dipstick format or within a plastic casing with a sample port and reaction window showing the capture and control zones.

There are two main types of lateral flow immunoassay used in microbiological testing: double antibody sandwich assays and competitive assays. In the double antibody sandwich format, the sample migrates from the sample pad through the conjugate pad where any target analyte present will bind to the conjugate. The sample then continues to migrate across the membrane until it reaches the capture zone where the target/conjugate complex will bind to the immobilized antibodies producing a visible line on the membrane. The sample then migrates further along the strip until it reaches the control zone, where excess conjugate will bind and produce a second visible line on the membrane. This control line indicates that the sample has migrated across the membrane as intended. Two clear lines on the membrane is a positive result. A single line in the control zone is a negative result. Competitive assays differ from the double antibody sandwich format in that the conjugate pad contains antibodies that are already bound to the target analyte, or to an analogue of it. If the target analyte is present in the sample it will therefore not bind with the conjugate and will remain unlabelled. As the sample migrates along the membrane and reaches the capture zone an excess of unlabelled analyte will bind to the immobilized antibodies and block the capture of the conjugate, so that no visible line is produced. The unbound conjugate will then bind to the antibodies in the control zone producing a visible control line. A single control line on the membrane is a positive result. Two visible lines in the capture and control zones is a negative result. However, if an excess of unlabelled target analyte is not present, a weak line may be produced in the capture zone, indicating an inconclusive result. There are a number of variations on lateral flow technology. The capture zone on the membrane may contain immobilized antigens or enzymes—depending on the target analyte—rather than antibodies. It is also possible to apply multiple capture zones to create a multiplex test. For example, commercial test strips able to detect both EHEC Shiga toxins ST1 and ST2 separately in the same sample have been developed.

Importantly, the antibodies of the present invention may be helpful in diagnosing a pruritic and/or allergic in dogs, cats, or horses. More specifically, the antibody of the present invention may identify the overexpression of IL-31 in companion animals. Thus, the antibody of the present invention may provide an important immunohistochemistry tool. In one embodiment, an assay design is conceived here whereby an IL-31 mimotope (peptide) is used to capture an antibody of the present invention that is labeled for detection in an assay. This captured antibody would have an affinity to the attached mimotope that is lower that the affinity of native circulating IL-31 in a host species. In this embodiment, incubation of the fluid derived from the host species is incubated with the labeled antibody: mimotope complex that is tethered to a solid surface. The presence of IL-31 in the test fluid derived from the host species will have a higher affinity to the antibody, thus liberating the labeled antibody from the solid surface where it can be removed during wash steps. The level of IL-31 in the test fluid can thus be correlated to the lack of signal that appears on the mimotope-bound surface. It is conceived that such an assay would have utility to measure IL-31 in a research or clinical setting for use as a diagnostic test.

The antibodies of the present invention may be used on antibody arrays, highly suitable for measuring gene expression profiles.

Kits

Also included within the scope of the present invention are kits for practicing the subject methods. The kits at least include one or more of the antibodies of the present invention, a nucleic acid encoding the same, or a cell containing the same. In one embodiment, an antibody of the present invention may be provided, usually in a lyophilized form, in a container. The antibodies, which may be conjugated to a label or toxin, or unconjugated, are typically included in the kits with buffers, such as Tris, phosphate, carbonate, etc., stabilizers, biocides, inert proteins, e.g., serum albumin, or the like. Generally, these materials will be present in less than 5% wt. based on the amount of active antibody, and usually present in total amount of at least about 0.001% wt. based again on the antibody concentration. Frequently, it will be desirable to include an inert extender or excipient to dilute the active ingredients, where the excipient may be present in from about 1% to 99% wt. of the total composition. Where a second antibody capable of binding to the primary antibody is employed in an assay, this will usually be present in a separate vial. The second antibody is typically conjugated to a label and formulated in an analogous manner with the antibody formulations described above. The kit will generally also include a set of instructions for use.

In one embodiment, a kit according to the present invention is a test strip kit (lateral flow immunoassay kit) useful for detecting canine, feline, or equine IL-31 protein in a sample. Such a test strip will typically include a sample pad onto which the test sample is applied; a conjugate or reagent pad containing an antibody specific to canine, feline, or equine IL-31, wherein the antibody is conjugated to colored particles (usually colloidal gold particles); a reaction membrane onto which anti-IL-31 antibodies are immobilized in a line across the membrane as a capture zone or test line (a control zone may also be present, containing antibodies specific for the conjugate antibodies); and a further absorbent pad designed to draw the sample across the reaction membrane by capillary action and collect it. The test strip kit will generally also include directions for use.

Methods of Improving the Consistency and/or Quality of a Feline or Canine Antibody Such methods are described above in the Summary of the Invention section, as well as in the Examples and figures of the present application.

The present inventors have surprisingly discovered that the removal, or modification of the c-terminal end of the kappa light chain constant from those animal species whose native germline encodes additional residues beyond the terminal light chain Cysteine is beneficial to both the production of homogeneous recombinant antibody for these species and beneficial to the amount of antibody produced from a stable cell line (e.g., yield improvement). The results described herein support that additional amino acid residues beyond the terminal cysteine in the kappa light chain of feline (and canine) is detrimental to efficient pairing with the heavy chain leading to mispairing and poor production of the antibody.

In one embodiment, the present invention provides a method of improving the consistency and/or quality of a feline antibody. This method includes expressing nucleotide sequence encoding a feline IgG kappa light chain and nucleotide sequence encoding a feline IgG heavy chain in a host cell to produce a feline antibody, wherein the nucleotide sequence encoding the feline IgG kappa light chain comprises a kappa light chain constant nucleotide sequence in which sequence encoding a C-terminal QRE sequence otherwise present in a wild-type feline IgG kappa light chain constant region has been modified and/or deleted. With reference to the C-terminal amino acid residues of the feline Ig Kappa light chain constant domain shown in FIG. 15, in one embodiment, the present invention provides for removal of the c-terminal "QRE" that immediately follows CYS107 of the feline light chain kappa sequence of SEQ ID NO: 175. This modification was found to improve the production of monomeric recombinant feline IgG. However, the present invention is not limited in this regard. For example, even three additional amino acids added contiguously to the c-terminal end of the Cysteine at position 107 in place of the native QRE may be tolerated if the amino acids have a minimal electrostatic charge influence.

The present invention further provides a method of improving the consistency and/or quality of a canine antibody. This method includes expressing nucleotide sequence encoding a canine IgG kappa light chain and nucleotide sequence encoding a canine IgG heavy chain in a host cell to produce a canine antibody, wherein the nucleotide sequence encoding the canine IgG kappa light chain comprises a kappa light chain constant nucleotide sequence in which sequence encoding a C-terminal QRVD sequence otherwise present in a wild-type canine IgG kappa light chain constant region has been modified and/or deleted. With reference to the C-terminal amino acid residues of the canine Ig Kappa light chain constant domain shown in FIG. 15, in one embodiment, the present invention provides for removal of the c-terminal "QRVD" that immediately follows CYS105 of the canine light chain kappa sequence of SEQ ID NO: 194. However, the present invention is not limited in this regard. For example, even three additional amino acids added contiguously to the c-terminal end of the Cysteine at position 105 in place of the native QRVD may be tolerated if the amino acids have a minimal electrostatic charge influence.

The results herein clearly demonstrate that the above methods apply to structurally disparate antibodies which recognize completely distinct targets and therefore these modifications will likely be applicable to the broad genus of feline antibodies, including but not limited to anti-IL31 and anti-NGF antibodies, as well as other mammalian antibodies possessing additional C-terminal amino acids on the kappa light chain constant region. While not wishing to be bound by any one theory, this light chain modification appears to result in a higher fidelity of immunoglobulin chain pairing during the induced production from stable CHO cell lines resulting in a higher amount of monomeric IgG and potentially a higher overall antibody yield. Both of these attributes are highly desirable from the standpoint of manufacturing commercial grade antibody therapeutics.

In one embodiment, any of the anti-IL-31 antibodies disclosed herein can comprise the kappa light chain constant deletions and/or modifications disclosed herein. For example, in one embodiment, a feline antibody according to the present invention comprises a kappa light chain constant region wherein the "ORE" normally present at the c-terminal of the kappa light chain constant region has been removed and optionally replaced with up to three additional amino acids which have a minimal electrostatic charge influence. In a particular embodiment, a feline antibody according to the present invention comprises a feline kappa light chain having the sequence:

(SEQ ID NO: 186)
RSDAQPSVFLFQPSLDELHTGSASIVCILNDFYPKEVNVKWKVDGVVQN

KGIQESTTEQNSKDSTYSLSSTLTMSSTEYQSHEKFSCEVTHKSLASTL

VKSFQRSEC or a variant thereof.

The invention will now be described further by the non-limiting examples below. In the example section below and in the Figures, any data presented for antibodies containing "11E12" in their designation is for purposes of comparison with the antibodies of the present invention.

EXAMPLES 1.1. Production of Canine Interleukin 31 (cIL-31) from Chinese Hamster Ovary (CHO) Cells The Interleukin 31 protein varies in amino acid sequence conservation among homologous species (FIGS. 1A and 1B) but is believed to have common structural architecture with other members of the type I cytokine family (Boulay et al. 2003, Immunity. August; 19(2):159-632003; Dillon et al. 2004 Nat Immunol. July; 5(7):752-60). This up-down bundle topology is significant to the mode of receptor recognition shared by these cytokines (Dillon et al. supra, Cornelissen et al. 2012 Eur J Cell Biol. June-July; 91(6-7): 552-66). With variation in IL-31 protein sequence identities between different species, it is not possible to predict if antibodies raised against one species will cross-react with others given different epitope propensities and local amino acid compositions. As a consequence, multiple forms of IL-31 protein were considered for this work representing multiple species and expression systems. The canine IL-31 protein (cIL-31) was produced to use as an immunogen and a reagent to test affinity and potency of antibody hits. Recombinant cIL-31 was created in CHO cells using the CHROMOS ACE (Artificial Chromosome Expression) system (Chromos Molecular Systems, Inc., Burnaby, British Columbia) to generate the secreted canine IL-31 protein having the sequence of (SEQ ID NO: 155; Canine_IL31), the corresponding nucleotide sequence for which is (SEQ ID NO: 156; Canine_IL31). Conditioned medium from 400 ml of cell culture (CHO cell line) was obtained and dialyzed against 10 volumes of QA buffer (20 mM Tris pH 8.0, 20 mM NaCl) for 4.5 hours. Dialyzed medium was 0.2 µm filtered and loaded at 1 ml/min onto a SOURCE™ Q column (GE Healthcare, Uppsala, Sweden) pre-equilibrated with QA buffer. Protein was eluted using a multi-step linear gradient. The majority of cIL-31 remained in the flow through (FT) fraction, a small amount of cIL-31 eluted early in the gradient. Identity of the protein was previously confirmed by Western immunoblotting, and Mass-Spectrometry (MS) analysis of a tryptic digest. Protein in the FT fraction was concentrated 4-5 fold and dialyzed overnight against Phosphate Buffered Saline (PBS) at 4° C. Stability of the protein was checked following dialysis into PBS. No precipitation was observed, and no proteolysis was observed after several days at 4° C. De-glycosylation experiments using N-glycosidase F resulted in the protein condensing down to a single band of ~15 kDa on SDS-PAGE. Protein concentration was determined using a bicinchoninic assay (BCA assay) with Bovine Serum Albumin (BSA) as a standard (ThermoFisher Scientific, Inc., Rockford, IL). The protein solution was split into aliquots, snap frozen (liquid N2) and stored at −80° C.

1.2. Transient Expression of Wildtype and Mutant Feline Interleukin 31 (fIL-31) from CHO Cells To aid in the identification of antibodies with the appropriate epitope binding property, wildtype and mutant feline IL-31 proteins were expressed in a mammalian expression system for production, purification, and assessment in affinity and cell-based assays. The binding site of antibody 11E12 on IL-31 was described previously (U.S. Pat. No. 8,790,651 to Bammert, et al.). Characterization of the novel binding site on IL-31 recognized by antibody 15H05 is described herein. The wildtype designation is full length feline IL-31 protein with no changes to the native amino acid residues. Mutant proteins were designated by their corresponding antibodies name (11E12 and 15H05) referring to mutations in amino acids in the IL-31 protein that (when altered) affect the binding to each respective antibody. Identification of the appropriate mutations required for the feline IL-31 15H05 protein are described below in section 1.10. The objective was to change amino acids in the IL-31 epitope and observe a loss of binding phenotype to each respective antibody. A comparison can then be made during screening to see if new candidate antibodies bind to the wildtype protein and not to the mutant. New antibody hits can then be binned according to binding to the same or similar epitope as antibody 11E12 or 15H05.

Expression constructs were codon optimized and synthesized for expression in Chinese Hamster Ovarian (CHO) cells. The synthesized genes were cloned into pD2529 (ATUM vector) for transient expression use. Wildtype feline IL-31 protein is represented by (SEQ ID NO: 157; Feline_IL31_wildtype), the corresponding nucleotide sequence for which is (SEQ ID NO: 158; Feline_IL31_wildtype). Mutant feline IL-31 11 E12 protein is represented by (SEQ ID NO: 161; Feline_IL31_11E12_mutant), the corresponding nucleotide sequence for which is (SEQ ID NO: 162; Feline_IL31_11E12_mutant). Mutant feline IL-31 15H05 protein is represented by (SEQ ID NO: 163; Feline_IL31_15H05_mutant), the corresponding nucleotide sequence for which is (SEQ ID NO: 164; Feline_IL31_15H05_mutant). Recombinant feline IL-31 proteins were expressed in ExpiCHO-S™ cells (ThermoFisher Scientific, Inc., Rockford, IL) by following the manufacturer's maximum titer protocol for transient CHO expression. Twelve days post transfection the cells were centrifuged and filtered to capture the secreted protein in the conditioned media. For each construct (wild type and mutants), 120 mL of conditioned media (from CHO cell culture, 0.2 μm filtered) was adjusted to 30 mS/cm with the addition of NaCl, 5 mM imidazole, and pH 7.4. Each media sample was combined with 5 mL of HisPur Cobalt resin (ThermoFisher Scientific, Inc., Rockford, IL) which had been equilibrated with 5 mM imidazole, 20 mM sodium phosphate, 300 mM NaCl, pH 7.4. Each sample and resin was allowed to mix at 4° C., overnight. Resins were collected (and separated from the unbound fraction) by pouring through BioRad Econcolumns (Bio-Rad, Hercules, CA). Resins were washed with 5×5 mL of buffer (as above) and then eluted with 5×5 mL of 500 mM imidazole in the same buffer. Fractions were evaluated by SDS-PAGE. Concentration was measured by a BCA protein assay using standard methods.

1.3. Production of Feline Interleukin 31 (fIL-31) from *E. coli*

Recombinant feline IL-31 protein was generated in an *E. coli* expression host to use as an assay reagent and for in vivo challenge studies to induce a pruritic response in cats. The gene representing feline IL-31 was synthesized for optimal expression in *E. coli*. Expression constructs were created with the full length feline IL-31 gene containing an N-terminal 6-His tag for detection and purification. This feline IL-31 protein is represented by (SEQ ID NO: 159; Feline_IL-31_E_coli), the corresponding nucleotide sequence for which is (SEQ ID NO: 160; Feline_IL-31_E_coli). Sequence confirmed plasmids were used to transform *E. coli* BL21 DE3 (Invitrogen Corp., Carlsbad, CA) and subsequent protein expression carried out.

Cell paste (262.3 g) from *E. coli* was lysed as follows: The cell paste was resuspended in 500 mL of 50 mM Tris pH 8, filtered through a stainless mesh filter to remove particles, and then lysed via two passes through a microfluidizer at 1300 psi. The lysate (~1200 mL volume) was divided into four bottles, centrifuged at 12,000 g for 20 minutes at 10° C. The supernatant was decanted and discarded. Each pellet was washed by suspension in 300 mL of 5 mM EDTA, 0.5% Triton X-100, pH 9.0, and then centrifugation at 12,000 g, 50 minutes, at 10° C. The supernatant was decanted and discarded. The washed pellets were stored at −20° C. until folding and isolation.

Prior to isolation, one of the pellets was washed with water to remove the residual detergent, and then centrifuged at 10,000 g, 20 minutes, at 4° C. Again, the supernatant was decanted. Finally, the washed pellet was solubilized in 60 mL of 50 mM sodium phosphate, 300 mM NaCl, 6 M guanidine-HCl, 5 mM imidazole, pH 7.4. The pellet was allowed to mix at room temperature for approximately 25 minutes before centrifuging again at 10,000 g, 20 minutes, and 4° C. This time, the supernatant was decanted and kept for further processing. The pellet (resuspended in water to original volume) was set aside for SDS-PAGE only. Crude IMAC (immobilized metal affinity chromatography) was performed to increase purity prior to folding. In this case, 15 mL of Ni-NTA Superflow (Qiagen Inc, Germantown, MD, Cat #30450, pre-equilibrated in the same buffer) was added to the clarified supernatant and allowed to mix at room temperature for approximately 90 minutes. The unbound fraction was decanted and set aside for SDS-PAGE. The IMAC resin was washed with 5 mM imidazole, 50 mM sodium phosphate, 300 mM NaCl, 6 M guanidine-HCl, pH 7.4 (same as solubilization buffer). The resin was eluted with (first 7.5 mL and then multiples of 15 mL, monitoring protein elution by Bradford assay) 200 mM imidazole, 50 mM sodium phosphate, 300 mM NaCl, 6 M guanidine-HCl, pH 7.4. Elution fractions containing protein (as per Bradford) were pooled (125 mL) for further processing.

The IL-31 protein was folded as follows. The IL-31 was reduced by the addition of dithiothreitol to a final of 10 mM, and allowed to mix at room temperature for 2 hours. The diluted sample was then diluted drop-wise into 2500 mL (20× volume) of PBS+1 M NaCl with rapid stirring. The theoretical concentration of urea should have been approximately 0.4 M at this point. The remainder of the urea was removed slowly by dialysis against 3 exchanges (4 L each) of PBS, at 4° C. overnight. Following dialysis, the sample was 0.2 μm filtered to remove any unfolded/precipitated protein.

The sample was further purified by a second round of IMAC, this time with a linear gradient elution. Fifteen mL of Ni-NTA Superflow resin was added to the sample and allowed to bind batch-wise by stirring (with a suspended stir bar) overnight at 4° C. Again, the unbound fraction was decanted and set aside. The Ni-NTA Superflow resin was packed in an XK16 column (GE Healthcare Lifesciences, Marlborough, MA) and hooked up to an AKTA brand chromatography system (GE Healthcare Lifesciences, Marlborough, MA). The column was then washed with 50 mM Tris, 300 mM NaCl, pH 8.2 and the eluted via a 150 mL linear gradient from 0 to 500 mM imidazole, each in wash buffer. Fractions were analyzed by SDS-PAGE. Fractions having sufficient purity of IL-31 were pooled and buffer exchanged again by dialysis against 3 exchanges (2 L each) of PBS, at 4° C., overnight. Finally, the folded and purified sample was collected from dialysis, sterile filtered, concentration measured aliquoted, snap-froze in a dry-ice/isopropanol bath, and stored at −80° C.

1.4. Method to Determine Affinity of Anti-IL-31 Antibodies for IL-31 Using Surface Plasmon Resonance The affinity with which candidate mAbs bind canine and feline IL-31 was determined using surface plasmon resonance (SPR) on a Biacore system (Biocore Life Sciences (GE Healthcare), Uppsala, Sweden). To avoid affinity differences associated with differential surface preparation that can occur when immobilizing antibodies to surfaces; a strategy was employed where IL-31 was directly conjugated to the surface. Immobilization was obtained by amine coupling 5 μg/mL IL-31 using N-hydroxysuccinimide (NHS)/1-Ethyl-3-(3-dimethylaminopropyl) carbodiimide (EDC) chemistry. Chips were quenched with ethanolamine and the affinity with which all candidate mAbs bound to the immobilized IL-31 was evaluated. All curves were fit to a 1:1 model. Affinity constants (KD) less than $1\times10^{-11}$M (1E-11 M) are below the lower limit of quantitation of detection for the instrument. Results for affinity measurements are described herein.

1.5. Method to Determine Potency of Anti-IL-31 Antibodies Assessed by Inhibition of Canine and Feline IL-31 Induced pSTAT3 Signaling in Canine and Feline Macrophage Cells To identify candidates with inhibitory activity, antibodies were assessed for their ability to affect IL-31-mediated STAT3 phosphorylation in either a canine or feline cell-based assay. STAT3 phosphorylation was determined in canine DH-82 (ATCC® CRL-10389™) or feline FCWF4 macrophage-like cells (ATCC CRL-2787). DH82 and FCWF4 cells were primed with canine interferon gamma (R&D Systems, Minneapolis, MN) at 10 ng/mL for 24 hours or feline interferon gamma (R&D Systems, Minneapolis, MN) at 125 ng/mL for 96 hours, respectively, to increase receptor expression. Both cell types were serum starved for 2 hours prior to IL-31 and mAb treatment. Using two independent methods, all candidate mAbs were evaluated for their ability to inhibit either 1 μg/mL canine or 0.2 μg/mL feline IL-31 induced STAT3 phosphorylation. Assays were also run to demonstrate cross-reactivity of canine and feline cytokines and cross-functionality of the antibodies ability to inhibit signaling in both species. To ensure complex formation, a one hour co-incubation of mAb and IL-31 cytokine prior to cell stimulation was completed. IL-31 cell stimulation was carried out for five minutes. STAT3 phosphorylation was measured using AlphaLISA SureFire ULTRA™ technology (Perkin Elmer, Waltham, MA). In the case where antibody concentration and purity are unknown, hybridoma supernatants were qualitatively measured for their ability to inhibit STAT3 phosphorylation following a 1 hour co-incubation with 1 mg/ml canine or 0.2 mg/ml feline IL-31. The potency of individual monoclonal antibodies defined by their ability to inhibit IL-31 mediated STAT3 phosphorylation in these assays was considered the key selection criteria for further advancement of select antibodies. The term potency refers to the IC50 value calculated from these assays and is the concentration of the antibody where signaling induced by IL-31 is reduced to one half its maximal value. Increased potency described herein correlates to a lower IC50 value.

1.6. Identification of Mouse and Canine Monoclonal Antibodies Recognizing Canine and Feline Interleukin 31

Mice and dogs were immunized with recombinant canine IL-31 (SEQ ID No. 155) for the purpose of identifying antibodies. Serum antibody titers from immunized animals were determined using an enzyme linked immunosorbent assay (ELISA). Canine or feline IL-31 (50 ng/well) was immobilized to polystyrene microplates and used as a capture antigen. Serum from immunized animals was diluted in phosphate buffered saline with 0.05% tween-20 (PBST). The presence of anti-IL-31 antibodies was detected with an appropriate secondary HRP labeled antibody. Following addition of a chromogenic substrate (SureBlue Reserve TMB 1-Component Microwell Peroxidase Substrate, KPL, Inc., Gaithersburg, MD) and a ten minute incubation at room temperature (RT) the reaction was stopped with the addition of 100 μL of 0.1 N HCl. The absorbance of each well was determined at an optical density (OD) of 450 nm. Antibodies were selected for their ability to bind canine and feline IL-31 using an ELISA. In some cases, further characterization was performed at the time of selection using an ELISA with a mutant form of the feline IL-31 protein as a capture antigen. Cells producing antibodies with desired binding and inhibitory properties were chosen for sequence analysis of RNA transcripts representing the variable heavy (VH) and variable light (VL) IgG chains.

In the case of mouse antibodies, donor splenocytes from a single responsive CF-1 mouse were used for fusion and hybridoma supernatants were screened for antibodies that bind to either canine or feline IL-31 proteins by ELISA. This resulted in the identification of a single mouse antibody, Mu-15H05, having a sub-nanomolar affinity to both species of IL-31 (FIG. 2, Section A). Mouse anti IL-31 15H05 was further subcloned to generate a hybridoma producing homogeneous antibody and for sequencing of the variable heavy and light chains. The mouse anti IL-31 variable sequences determined for antibody 15H05 are as follows, 15H05 variable heavy chain (SEQ ID NO: 67; MU-15H05-VH), the corresponding nucleotide sequence for which is (SEQ ID NO: 68; MU-15H05-VH), 15H05 variable light chain (SEQ ID NO: 69; MU-15H05-VL), the corresponding nucleotide sequence for which is (SEQ ID NO: 70; MU-15H05-VL). In addition to mouse antibody 15H05, further consideration was given to mouse-derived antibody 11E12 that was previously described in U.S. Pat. No. 8,790,651 to Bammert, et al. Described herein are data showing the ability of antibody 11 E12 to bind both canine and feline IL-31 proteins with high affinity. The ability of 11E12 to bind feline IL-31 made this antibody a suitable candidate for felinization and potential therapeutic use in cats. The mouse anti IL-31 variable sequences previously determined for antibody 11E12 are as follows, 11E12 variable heavy chain (SEQ ID NO: 71; MU-11E12-VH), the corresponding nucleotide sequence for which is (SEQ ID NO: 72; MU-11E12-VH), 11E12 variable light chain (SEQ ID NO: 73; MU-11E12-VL), the corresponding nucleotide sequence for which is (SEQ ID NO: 74; MU-11E12-VL).

Dogs having elevated anti IL-31 titers following vaccination were selected for analysis of B-cell populations producing antibodies with desired phenotypes. B-cells were derived from PBMCs, bone marrow, spleen, or lymph nodes for further analysis. Single B-cells were segregated into individual wells and assayed for presence of secreted IgGs capable of binding wildtype, 11E12 mutant, and 15H05 mutant forms of canine IL-31 (AbCellera, Vancouver, BC) using methods described in US2012/0009671A1, US2016/0252495A1, U.S. Pat. No. 9,188,593, WO 2015/176162 A9, and WO 2016/123692 A1.

This screening strategy is based on known regions of the IL-31 protein that are critical for binding and signal transduction through its co-receptor complex. Selection of these mutant proteins for screening is described in section 1.2 of this application. Sequencing of the variable heavy and light IgG domains was carried following an RT-PCR reaction from individual candidate B-cells. These screens resulted in the identification of nine canine antibodies selected for further evaluation. These canine anti IL-31 variable sequences are as follows, ZIL1 variable heavy chain (SEQ ID NO:75; CAN-ZIL1_VH), the corresponding nucleotide sequence for which is (SEQ ID NO: 76; CAN-ZIL1_VH), ZIL1 variable light chain (SEQ ID NO: 77; CAN-ZIL1_VL), the corresponding nucleotide sequence for which is (SEQ ID NO: 78; CAN-ZIL1_VL); ZIL8 variable heavy chain (SEQ ID NO:79; CAN-ZIL8_VH), the corresponding nucleotide sequence for which is (SEQ ID NO: 80; CAN-ZIL8_VH), ZIL8 variable light chain (SEQ ID NO: 81; CAN-ZIL8_VL), the corresponding nucleotide sequence for which is (SEQ ID NO: 82; CAN-ZIL8_VL); ZIL9 variable heavy chain (SEQ ID NO:83; CAN-ZIL9_VH), the corresponding nucleotide sequence for which is (SEQ ID NO: 84; CAN-ZIL9_VH), ZIL9 variable light chain (SEQ ID NO: 85; CAN-ZIL9_VL), the corresponding nucleotide sequence for which is (SEQ ID NO: 86; CAN-ZIL9_VL); ZIL11 variable heavy chain (SEQ ID NO:87; CAN-ZIL11_VH), the corresponding nucleotide sequence for which is (SEQ ID NO: 88; CAN-ZIL11_VH), ZIL11 variable light chain (SEQ ID NO: 89; CAN-ZIL11_VL), the corresponding nucleotide sequence for which is (SEQ ID NO: 90; CAN-ZIL11_VL); ZIL69 variable heavy chain (SEQ ID NO:91; CAN-ZIL69_VH), the corresponding nucleotide sequence for which is (SEQ ID NO: 92; CAN-ZIL69_VH), ZIL69 variable light chain (SEQ ID NO: 93; CAN-ZIL69_VL), the corresponding nucleotide sequence for which is (SEQ ID NO: 94; CAN-ZIL69_VL); ZIL94 variable heavy chain (SEQ ID NO:95; CAN-ZIL94_VH), the corresponding nucleotide sequence for which is (SEQ ID NO: 96; CAN-ZIL94_VH), ZIL94 variable light chain (SEQ ID NO: 97; CAN-ZIL94_VL), the corresponding nucleotide sequence for which is (SEQ ID NO: 98; CAN-ZIL94_VL); ZIL154 variable heavy chain (SEQ ID NO:99; CAN-ZIL154_VH), the corresponding nucleotide sequence for which is (SEQ ID NO: 100; CAN-ZIL154_VH), ZIL154 variable light chain (SEQ ID NO: 101; CAN-ZIL154_VL), the corresponding nucleotide sequence for which is (SEQ ID NO: 102; CAN-ZIL154_VL); ZIL159 variable heavy chain (SEQ ID NO:103; CAN-ZIL159_VH), the corresponding nucleotide sequence for which is (SEQ ID NO: 104; CAN-ZIL159_VH), ZIL159 variable light chain (SEQ ID NO: 105; CAN-ZIL159_VL), the corresponding nucleotide sequence for which is (SEQ ID NO: 106; CAN-ZIL159_VL); ZIL171 variable heavy chain (SEQ ID NO:107; CAN-ZIL171_VH), the corresponding nucleotide sequence for which is (SEQ ID NO: 108; CAN-ZIL171_VH), ZIL171 variable light chain (SEQ ID NO: 109; CAN-ZIL171_VL), the corresponding nucleotide sequence for which is (SEQ ID NO: 110; CAN-ZIL171_VL).

The aforementioned nine monoclonal antibodies which were selected for further characterization may be referred to elsewhere in the specification, Figures, or claims as ZIL1, ZIL8, ZIL8, ZIL11, ZIL69, ZIL94, ZIL154, ZIL159, and ZIL171.

1.7. Construction of Recombinant Chimeric and Fully Canine Antibodies

Antibody variable domains are responsible for antigen binding. Grafting of the full variable domain onto respective constant region is expected to have little or no impact on the antibody's ability to bind the IL-31 immunogen. To simultaneously confirm that the correct sequence of the heavy and light chain variable regions were identified and to produce homogenous material, expression vectors were designed to produce recombinant chimeric or fully canine antibodies in mammalian expression systems. Chimeric antibodies described here consist of the variable sequence (both CDR and framework) from the host species antibody grafted onto the respective heavy and light constant regions of a feline or canine IgG molecule (for example; mouse variable: canine constant is referred to as mouse:canine chimera). Fully canine antibodies described here consist of the variable sequence (both CDR and framework) from the host species antibody (canine) grafted on to the respective heavy and light chain constant regions of the canine IgG molecule. Synthetic DNA sequences were constructed for the variable heavy (VH) and variable light (VL) sequences of selected antibodies. These sequences contain unique restriction endonuclease sites, a Kozak consensus sequence and, an N-terminal secretion leader to facilitate expression and secretion of the recombinant antibody from a mammalian cell line.

For mouse: feline chimeras, each respective variable region was cloned into a mammalian expression plasmid containing either the feline IgG heavy (SEQ ID NO: 173; Feline_HC_AlleleA_1) the corresponding nucleotide sequence for which is (SEQ ID NO: 174; Feline_HC_AlleleA_1) or light chain (SEQ ID NO: 175; Feline_LC_Kappa_G_minus) the corresponding nucleotide sequence for which is (SEQ ID NO: 176; Feline_LC_Kappa_G_minus) constant regions. For mouse: canine chimeras or fully canine antibodies, each mouse or canine variable region was cloned into a mammalian expression plasmid containing either the canine IgG heavy (SEQ ID NO: 177; Canine_HC_65_1) the corresponding nucleotide sequence for which is (SEQ ID NO: 178; Canine_HC_65_1) or light chain (SEQ ID NO: 179; Canine_LC_Kappa) the corresponding nucleotide sequence for which is (SEQ ID NO: 180; Canine_LC_Kappa) constant regions. The plasmids encoding each heavy and light chain, under the control of the CMV promoter, were co-transfected into HEK 293 cells using standard methods. Following six days of expression, chimeric mAbs were purified from 50 ml of transiently transfected HEK293FS cell supernatants using MabSelect Sure protein A resin (GE Healthcare, Uppsala, Sweden) according to standard methods for protein purification. Eluted fractions were pooled, concentrated to ~500 µl using a 10,000 nominal MW cutoff Nanosep Omega centrifugal device (Pall Corp., Port Washington, NY), dialyzed overnight at 4° C. in 1× PBS, pH 7.2 and stored at 4° C. for further use. Affinity and cell based potency of select recombinant antibodies are described below.

FIG. 2 details the affinity of antibodies with CDRs derived from mouse origin using biacore. FIG. 2, Section A shows the affinity of mouse anti IL-31 antibodies 11E12 and 15H05 and the corresponding affinities of the feline and canine chimeric forms to both feline and canine IL-31 surfaces. These observations confirm the correct sequence for both mouse antibodies and indicate conversion to the chimeric form results in antibodies with equivalent or higher affinity when compared to the mouse parent with the exception of the mouse:feline 15H05 chimera which lost some affinity to both IL-31 species as a result of its conversion to the chimeric form. Fully mouse and chimeric forms of antibodies 11E12 and 15H05 were also tested for activity in the canine and feline cellular assays described in section 1.5. FIG. 3 shows the results for these assays. Mouse antibodies 11E12 and 15H05 were tested for activity against canine and feline cell types using both canine and feline IL-31 to stimulate signaling. The potency of both mouse antibodies was comparable against both canine and feline cells using the feline cytokine with the exception of 15H05 against feline IL-31 in feline FCWF4 cells that shows a slight increase in IC50. Mouse 15H05 was capable of blocking canine IL-31 signaling in both feline and canine cells with the potency in the canine assay being slightly higher. These results indicate that the respective epitopes recognized by these antibodies exists on both canine and feline IL-31 and binding of these antibodies is capable of neutralizing receptor-mediated cellular signaling in a relevant cell line from both species.

FIG. 3 also describes the potency of select chimeras in both cellular assays. Conversion of mouse antibodies to feline and canine chimeras had minimal impact on the potency against feline IL-31 in the feline potency assay (IC50 range 1.15-3.45 µg/ml). Similar results were observed when these chimeras were tested against feline IL-31 signaling on the canine DH82 cell line with a slight increase in potency (IC50=0.71 µg/ml) observed for the 15H05 mouse: canine chimera. In general there was an increase in IC50 values against canine IL-31 in both canine and feline cell types. The mouse: feline 15H05 chimera was slightly less potent in this assay format compared to the mouse: canine form (IC50 28.61 vs. 12.49 µg/ml). Consistent with observations for the mouse antibodies, conversion to canine and feline chimeric forms resulted in minimal changes in potency.

Antibodies described above that were identified from single B cells of immunized dogs were constructed as recombinant IgG proteins following identification of their variable domain sequences. Grafting of these variable domains onto the canine heavy chain Fc (65_1 isotype) resulted in the generation of recombinant fully canine antibodies. It was of interest to identify additional canine antibodies that bound wildtype feline IL-31 and who's binding was decreased to the feline IL-31 15H05 mutant (i.e. are directed at the 15H05 epitope). These antibodies obtained from this alternate source (canine vs. mouse) provide additional paratopes (the portion of the antibody which recognizes the IL-31 protein, includes CDRs) recognizing the 15H05 epitope thus increasing the diversity of antibodies with different physical properties to select from.

FIG. 4 shows the results obtained for binding of these recombinant canine antibodies to various proteins using both ELISA and Biacore methods. For the indirect ELISA method, antibody binding to wildtype and feline IL-31 15H05 mutant proteins was assessed. All nine canine monoclonal antibodies (ZIL1, ZIL8, ZIL8, ZIL11, ZIL69, ZIL94, ZIL154, ZIL159, and ZIL1 71) were capable of binding to wildtype feline IL-31 and binding was impacted by mutations in the mAb 15H05 epitope region confirming the correct binding phenotype determined during the initial screening used to identify them. In comparison, the 11E12 antibody bound to the wild-type feline IL-31 and its binding was not impacted by the mutations in the 15H05 epitope region as evidenced by the data in FIG. 4. To confirm binding, biacore analysis was performed using canine, feline, equine, human, feline 15H05 mutant, and feline 11E12 mutant IL-31 proteins as surfaces and a single test concentration of antibody. Similar to ELISA observations, all antibodies tested bound to wildtype feline IL-31. In agreement with the data described above in this section, mouse antibodies 11E12 and 15H05 both bound to canine and feline IL-31 surfaces. Three additional antibodies where shown to have this dual binding property, ZIL69 (partial canine binding), ZIL94, and ZIL159. From this group of nine fully canine antibodies, only ZIL1 and ZIL9 cross-reacted with equine IL-31. Of note, antibody 15H05 was the only one of all assayed herein that bound to canine, feline, and equine IL-31 indicating some level of epitope conservation across the three species. In contrast, none of the antibodies described herein bound to human IL-31. Additional biacore surfaces were used to verify ELISA observations showing differential binding of antibodies to wildtype feline IL-31 and two proteins with mutations in the 15H05 (15H05 mutant) or 11E12 (11E12 mutant) epitopes. As expected, control mouse antibody 11E12 bound to the 15H05 IL-31 mutant and did not bind to the 11E12 IL-31 mutant due to mutations in the epitope. Likewise mouse 15H05 did not bind to the 15H05 mutant and retained binding to the 11E12 IL-31 mutant further distinguishing the separate binding epitopes recognized by these two antibodies. In agreement with the ELISA results, all fully canine antibodies were impacted by the 15H05 mutation with the exception of ZIL94, ZIL154, and ZIL171 (partially affected). Differing results can be attributed to differences in the two assay methodologies. In addition, binding of three antibodies was also shown to be impacted by the 11E12 mutation; ZIL1 (partially effected), ZIL8, and ZIL159. These results indicate the epitope recognized by these antibodies is impacted by changes in both regions of the IL-31 protein. Taken together these results support the characterization nine antibodies derived from canine B cells sharing binding to a region on the feline IL-31 protein that is recognized by antibody 15H05.

1.8. Felinization of the Murine 11E12 and 15H05 Antibodies and Optimization of Binding Affinities The generation of anti-drug antibodies (ADAs) can been associated with loss of efficacy for any biotherapeutic protein including monoclonal antibodies. Comprehensive evaluation of the literature has shown that speciation of monoclonal antibodies can reduce the propensity for mAbs to be immunogenic although examples of immunogenic fully human mAbs and non-immunogenic chimeric mAbs can be found. To help mitigate risks associated with ADA formation for the anti-IL-31 monoclonal antibodies provided herein, a felinization strategy was employed. This felinization strategy is based on identifying the most appropriate feline germline antibody sequence for CDR grafting. Following extensive analysis of all available feline germline sequences for both the variable heavy and light chain, germline candidates were selected based on their homology to the mouse mAbs, and the CDRs from the mouse progenitor mAbs were used to replace native feline CDRs. The objective was to retain high affinity and cell-based activity using feline antibody frameworks to minimize the potential of immunogenicity in vivo. Felinized mAbs were expressed and characterized for their affinity to feline IL-31 and their potency in cell-based assays. In the event that a felinized antibody loses its ability to bind IL-31, a systematic dissection was undertaken to identify; 1) the chain responsible for the loss of function, 2) the framework responsible for the loss of function and 3) the amino acid(s) responsible for the loss function.

Synthetic nucleotide constructs representing the felinized variable heavy and light chains of mAbs 11E12 and 15H05 were made. Following subcloning of each variable chain into plasmids containing the respective feline heavy or kappa constant region, plasmids were co-transfected for antibody expression in HEK 293 cells. Initial attempts at felinization of antibody 11E12 focused on utilization of a single feline VH framework (SEQ ID NO: 111; FEL_11E12_VH1) the corresponding nucleotide sequence for which is (SEQ ID NO: 112; FEL_11E12_VH1) paired independently with VL frameworks (SEQ ID NO: 113; FEL_11E12_VL1) the corresponding nucleotide sequence for which is (SEQ ID NO: 114; FEL_11E12_VL1) and (SEQ ID NO: 115; FEL_11E12_VL2) the corresponding nucleotide sequence for which is (SEQ ID NO: 116; FEL_11E12_VL2) to form Feline 11E12 1.1 and Feline 11 E12 1.2 respectively. This attempt at speciation resulted in a loss of affinity with Feline 11E12 1.1 to both the feline and canine IL-31 proteins and a total loss of binding with the Feline 11E12 1.2 mAb when compared to the mouse form of the antibody (FIG. 2, Section B). Potency of these speciated antibodies was tested in the canine DH82 and Feline FCWF4 cell assays using the feline IL-31 cytokine. Felinized 11E12 1.1 had approximately a two-fold decrease in potency against feline IL-31 in the feline FCWF assay when compared to the mouse version of the antibody. In agreement with the loss of affinity for felinized 11E12 1.2, a complete loss of cellular potency was observed for this antibody (FIG. 3). Based on previous experience during caninization of the mAb 11E12 ortholog, a similar strategy was undertaken in attempt to restore the affinity loss to felinization (U.S. Pat. No. 8,790,651 to Bammert, et al.). Substitution of the felinized framework 2 (FW2) region of Feline 11E12 VL1 with the mouse FW2 from (SEQ ID NO: 73; Mu_11E12_VL) the corresponding nucleotide sequence for which is (SEQ ID NO: 74; Mu_11E12_VL) was done to generate Feline 11E12 VL1 FW2. In addition, a single substitution at position 46 of the feline VL (K46Q) was performed to generate (SEQ ID NO: 119; FEL_11E12_VL1_K46Q) the corresponding nucleotide sequence for which is (SEQ ID NO: 120; FEL_11E12_VL1_K46Q). Pairing of the above VLs with Fel_11E12_VH1 resulted in Feline 11E12 1.1 FW2 and Feline 11E12 1.1 K46Q respectively. Changing FW2 resulted in a restoration of affinity for Feline 11E12 1.1 FW2 to the feline IL-31 protein resulting in a KD equivalent to that of the mouse and chimeric form (FIG. 2, Sections A and B). These changes however had a detrimental effect on Feline 11E12 1.1 FW2s affinity to the canine IL-31 protein indicating a clear distinction in the nature of antibody 11E12s ability to bind this epitope on the feline and canine cytokine. The single amino acid substitution in Feline 11E12 1.1 K46Q was unable to influence affinity of this antibody. Increased affinity of antibody 11E12 1.1 FW2 for the feline IL-31 protein resulted in increased potency against the feline cytokine in the canine DH82 assay (FIG. 3).

Felinization efforts with mouse antibody 15H05 focused on the combinations of three feline VH frameworks with three feline VL frameworks for a total of 9 felinized mAbs. FEL 15H05 VH1 (SEQ ID NO: 121; FEL_15H05_VH1), the corresponding nucleotide sequence for which is (SEQ ID NO: 122; FEL_15H05_VH1) was combined with (SEQ ID NO: 127; FEL_15H05_VL1), the corresponding nucleotide sequence for which is (SEQ ID NO: 128; FEL_15H05_VL1), (SEQ ID NO: 129; FEL_15H05_VL2), the corresponding nucleotide sequence for which is (SEQ ID NO: 130; FEL_15H05_VL2), and (SEQ ID NO: 131;

FEL_15H05_VL3), the corresponding nucleotide sequence for which is (SEQ ID NO: 132; FEL_15H05_VL3) were used to create Feline 15H05 1.1, Feline 15H05 1.2, and Feline 15H05 1.3 respectively. FEL_15H05_VH2 (SEQ ID NO: 123; FEL_15H05_VH2), the corresponding nucleotide sequence for which is (SEQ ID NO: 124; FEL_15H05_VH2) was combined with (SEQ ID NO: 127; FEL_15H05_VL1), the corresponding nucleotide sequence for which is (SEQ ID NO: 128; FEL_15H05_VL1), (SEQ ID NO: 129; FEL_15H05_VL2), the corresponding nucleotide sequence for which is (SEQ ID NO: 130; FEL_15H05_VL2), and (SEQ ID NO: 131; FEL_15H05_VL3), the corresponding nucleotide sequence for which is (SEQ ID NO: 132; FEL_15H05_VL3) were used to create Feline 15H05 2.1, Feline 15H05 2.2, and Feline 15H05 2.3 respectively. FEL_15H05_VH3 (SEQ ID NO: 125; FEL_15H05_VH3), the corresponding nucleotide sequence for which is (SEQ ID NO: 126; FEL_15H05_VH3) was combined with (SEQ ID NO: 127; FEL_15H05_VL1), the corresponding nucleotide sequence for which is (SEQ ID NO: 128; FEL_15H05_VL1), (SEQ ID NO: 129; FEL_15H05_VL2), the corresponding nucleotide sequence for which is (SEQ ID NO: 130; FEL_15H05_VL2), and (SEQ ID NO: 131; FEL_15H05_VL3), the corresponding nucleotide sequence for which is (SEQ ID NO: 132; FEL_15H05_VL3) were used to create Feline 15H05 3.1, Feline 15H05 3.2, and Feline 15H05 3.3 respectively. Similar to observations with antibody 11E12, the first attempt at felinization of antibody 15H05 resulted in a loss of affinity to the feline IL-31 protein when compared to mouse 15H05 and a neutral affect when compared to the 15H05 mouse feline chimera (FIG. 2, Sections A and C). Similar to observations with felinized antibody 11E12 binding to canine IL-31, certain combinations of feline 15H05 VH and VL frameworks had a neutral to positive impact on affinity to canine IL-31 (See FIG. 2, Section C: Feline 15H05 1.1, 2.2, and 3.2).

In an effort to restore the affinity of felinized antibody 15H05, each felinized 15H05 VH was paired with the mouse 15H05 VL to generate heterochimeric antibodies. FEL_15H05_VH1 (SEQ ID NO: 121; FEL_15H05_VH1), the corresponding nucleotide sequence for which is (SEQ ID NO: 122; FEL_15H05_VH1) was combined with MU_15H05_VL (SEQ ID NO: 69; MU_15H05_VL), the corresponding nucleotide sequence for which is (SEQ ID NO: 70; MU_15H05_VL) to generate Feline 15H05 VH1 mouse VL. FEL_15H05_VH2 (SEQ ID NO: 123; FEL_15H05_VH2), the corresponding nucleotide sequence for which is (SEQ ID NO: 124; FEL_15H05_VH2) was combined with MU_15H05_VL (SEQ ID NO: 69; MU_15H05_VL), the corresponding nucleotide sequence for which is (SEQ ID NO: 70; MU_15H05_VL) to generate Feline 15H05 VH2 mouse VL. FEL_15H05_VH3 (SEQ ID NO: 125; FEL_15H05_VH3), the corresponding nucleotide sequence for which is (SEQ ID NO: 126; FEL_15H05_VH3) was combined with MU_15H05_VL (SEQ ID NO: 69; MU_15H05_VL), the corresponding nucleotide sequence for which is (SEQ ID NO: 70; MU_15H05_VL) to generate Feline 15H05 VH3 mouse VL. These felinized VH mouse VL heterochimeras were analyzed for their affinity to canine and feline IL-31. Pairing of felinized 15H05 VH1 and VH3 with mouse 15H05 VL restored the affinity to feline IL-31 to equivalent or better than the mouse and chimeric forms. This trend in improved affinity was also observed to the canine IL-31 protein (FIG. 2, Sections A and C).

To further dissect the positions in the 15H05 frameworks responsible for affinity loss, a single felinized VH of 15H05 (FEL_15H05_VH1) was used to pair with individual framework substitutions from mouse 15H05 VL. FEL_15H05_VH1 (SEQ ID NO: 122; FEL_15H05_VH1), the corresponding nucleotide sequence for which is (SEQ ID NO: 123; FEL_15H05_VH1) was combined independently with FEL_15H05_VL1_FW1 (SEQ ID NO: 133; FEL_15H05_VL1_FW1), the corresponding nucleotide sequence for which is (SEQ ID NO: 134; FEL_15H05_VL1_FW1), FEL_15H05_VL1_FW2 (SEQ ID NO: 135; FEL_15H05_VL1_FW2), the corresponding nucleotide sequence for which is (SEQ ID NO: 136; FEL_15H05_VL1_FW2), and FEL_15H05_VL1_FW3 (SEQ ID NO: 137; FEL_15H05_VL1_FW3), the corresponding nucleotide sequence for which is (SEQ ID NO: 138; FEL_15H05_VL1_FW3) to create Feline 15H05 1.1 FW1, Feline 15H05 1.1 FW2, and Feline 15H05 1.1 FW3 respectively. Substitution of mouse 15H05 FW1 onto Feline 15H05 1.1 was detrimental to the affinity to both feline and canine IL-31, however, when mouse FW2 or FW3 were substituted on Feline 15H05 1.1, excellent affinity was achieved to canine and feline IL-31 with the FW2 being superior for both species (FIG. 2, Section C). Additional pairwise framework substitutions were performed to determine the extent of affinity modulation by this approach. FEL_15H05_VH1 (SEQ ID NO: 121; FEL_15H05_VH1), the corresponding nucleotide sequence for which is (SEQ ID NO: 122; FEL_15H05_VH1) was combined independently with FEL_15H05_VL1_FW1_2 (SEQ ID NO: 139; FEL_15H05_VL1_FW1_FW2), the corresponding nucleotide sequence for which is (SEQ ID NO: 140; FEL_15H05_VL1_FW1_FW2), FEL_15H05_VL1_FW2_3 (SEQ ID NO: 143; FEL_15H05_VL1_FW2_FW3), the corresponding nucleotide sequence for which is (SEQ ID NO: 144; FEL_15H05VL1_FW2_FW3), and FEL_15H05_VL1_FW1_3 (SEQ ID NO: 141; FEL_15H05_VL1_FW1_FW3), the corresponding nucleotide sequence for which is (SEQ ID NO: 142; FEL_15H05_VL1_FW1_FW3) to give Feline 15H05 1.1 FW1_2, Feline 15H05 1.1 FW2_3, and Feline 15H05 1.1 FW1_3 respectively. Interestingly, the substitution of mouse FW1 alone was detrimental to affinity while combinations of FW1 with FW2 or FW3 resulted in good affinity to both feline and canine IL-31 (FIG. 2, Section C).

Finally, an attempt was made to minimize the number of backmutations in the feline frameworks beginning with the most promising combinations of felinized VH and VL sequences. For this, FEL_15H05_VH1 (SEQ ID NO: 121; FEL_15H05_VH1), the corresponding nucleotide sequence for which is (SEQ ID NO: 122; FEL_15H05_VH1) was combined independently with FEL_15H05_VL1_FW2_K42N (SEQ ID NO: 145; FEL_15H05_VL1_FW2_K42N), the corresponding nucleotide sequence for which is (SEQ ID NO: 146; FEL_15H05_VL1FW2_K42N), FEL_15H05_VL1_FW2_V43I (SEQ ID NO: 147; FEL_15H05_VL1_FW2_V43I), the corresponding nucleotide sequence for which is (SEQ ID NO: 148; FEL_15H05_VL1_FW2_V43I), FEL_15H05_VL1_FW2_L46V (SEQ ID NO: 149; FEL_15H05_VL1_FW2_L46V), the corresponding nucleotide sequence for which is (SEQ ID NO: 150; FEL_15H05_VL1_FW2_L46V), FEL_15H05_VL1_FW2_Y49N (SEQ ID NO: 151; FEL_15H05_VL1_FW2_Y49N), the corresponding nucleotide sequence for which is (SEQ ID NO: 152;

FEL_15H05_VL1_FW2_Y49N), and FEL_15H05_VL1_FW2_K42N_V43I (SEQ ID NO: 153; FEL_15H05_VL1_FW2_K42N_V43I), the corresponding nucleotide sequence for which is (SEQ ID NO: 154; FEL_15H05_VL1_FW2_K42N_V43I) to give Feline 15H05 1.1 K42N, Feline 15H05 1.1 V43I, Feline 15H05 1.1 L46V, Feline 15H05 1.1 Y49N, and Feline 15H05 1.1 K42N_V43I respectively. While the substitution of the entire mouse FW2 framework onto Felinized 15H05 VL1 resulted in an antibody with excellent affinity to canine and feline IL-31 (FIG. 2, Section C, Feline 15H05 1.1 FW2), the individual backmutations of FW2 amino acid residues had a neutral or detrimental effect indicating all 4 substitutions are necessary to maintain the optimal tertiary structure for positioning of the CDRs on the IL-31 epitope. Increased affinity of felinized 15H05 1.1 FW2 to feline and canine IL-31 lead to the selection of this antibody for further work.

Figure 5B:
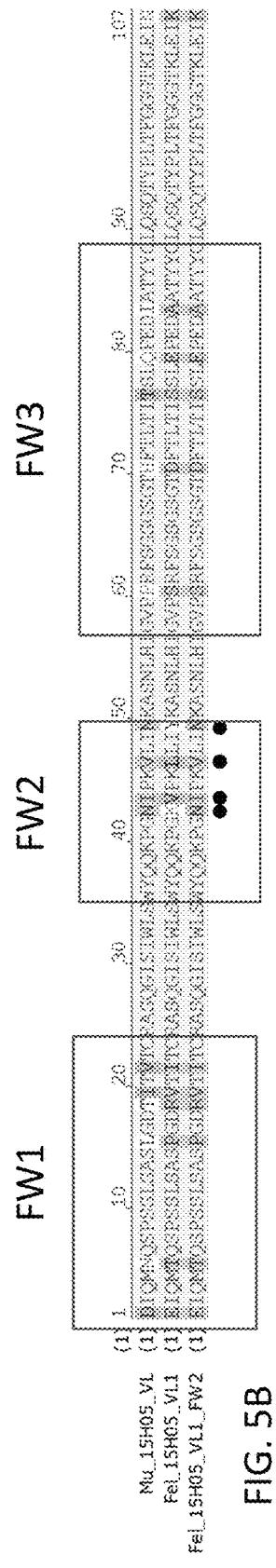
FIG. 5B shows an alignment of the mouse antibody 15H05 VL sequence designated herein as MU_15H05_VL (SEQ ID NO: 69) with the felinized 15H05 VL sequences designated herein as FEI_15H05_VL1 (SEQ ID NO: 127) and FEI_15H05_VL_FW2 (SEQ ID NO: 135). The dots below the alignment in FIG. 5B indicate the necessary changes to the felinized 15H05 VL (FeI_15H05_VL1) that were required to not only restore, but improve, its affinity to canine and feline IL-31 when compared to the mouse and chimeric forms of this antibody.

FIG. 5A shows an alignment of mouse antibody 11E12 VL sequence comparing previously referenced caninized 11E12 sequence to the felinized versions. Noted below the alignment are dots showing the positons of relevant changes to Fel_11E12_VL1 that were necessary to restore affinity of this antibody to the IL-31 protein. Likewise FIG. 5B shows the necessary changes to the felinized 15H05 VL (Fel_15H05_VL1) that were required to not only restore, but improve, its affinity to canine and feline IL-31 when compared to the mouse and chimeric forms of this antibody.

1.9. Generation of Cell Lines Expressing Felinized Anti IL-31 Antibodies from Glutamine Synthetase (GS) Plasmids Felinized 15H05 1.1 FW2 was chosen as a candidate for the generation of stable cell lines that will produce a homogenous supply of the antibody for further characterization. The genes encoding the felinized heavy and light chains for cell line production were cloned into GS plasmids pEE 6.4 and pEE 12.4 respectively (Lonza, Basel, Switzerland). The resulting plasmids were digested according to the manufacturer's protocol and ligated together to form a single mammalian expression plasmid. For ZTS-927, the heavy chain is (SEQ ID NO: 121; FEL_15H05_VH1), the corresponding nucleotide sequence for which is (SEQ ID NO: 122; FEL_15H05_VH1) combined with feline IgG heavy chain constant (SEQ ID NO: 171; Feline_HC_AlleleA_wt), the corresponding nucleotide sequence for which is (SEQ ID NO: 172; Feline_HC_AlleleA_wt). For ZTS-927, the light chain is (SEQ ID NO: 135; FEL-15H05-VL1_FW2), the corresponding nucleotide sequence for which is (SEQ ID NO: 136; FEL-15H05-VL1_FW2) combined with feline IgG light chain constant (SEQ ID NO: 175; Feline_LC_Kappa_G_minus), the corresponding nucleotide sequence for which is (SEQ ID NO: 176; Feline_LC_Kappa_G_minus). For ZTS-361, the heavy chain is (SEQ ID NO: 121; FEL_15H05_VH1), the corresponding nucleotide sequence for which is (SEQ ID NO: 122; FEL_15H05_VH1) combined with feline IgG heavy chain constant (SEQ ID NO: 173; Feline_HC_AlleleA_1), the corresponding nucleotide sequence for which is (SEQ ID NO: 174; Feline_HC_AlleleA_1). For ZTS-361, the light chain is (SEQ ID NO: 135; FEL-15H05-VL1_FW2), the corresponding nucleotide sequence for which is (SEQ ID NO: 136; FEL-15H05-VL1_FW2) combined with feline IgG light chain constant (SEQ ID NO: 175; Feline_LC_Kappa_G_minus), the corresponding nucleotide sequence for which is (SEQ ID NO: 176; Feline_LC_Kappa_G minus). For ZTS-1505, the heavy chain is (SEQ ID NO: 121; FEL_15H05_VH1), the corresponding nucleotide sequence for which is (SEQ ID NO: 122; FEL_15H05_VH1) combined with feline IgG heavy chain constant (SEQ ID NO: 173; Feline_HC_AlleleA_1), the corresponding nucleotide sequence for which is (SEQ ID NO: 174; Feline_HC_AlleleA_1). For ZTS-1505, the light chain is (SEQ ID NO: 135; FEL-15H05-VL1_FW2), the corresponding nucleotide sequence for which is (SEQ ID NO: 136; FEL-15H05-VL1_FW2) combined with feline IgG light chain constant (SEQ ID NO: 186; Feline_LC_Kappa_G_minus_QRE_minus), the corresponding nucleotide sequence for which is (SEQ ID NO: 187; Feline_LC_Kappa_G_minus_QRE_minus). The affinity and potency data for ZTS-1505 is described below in section 1.18 of this example section.

To demonstrate transient production of antibody, each plasmid was used to transfect HEK 293 cells and expression was carried out in various size cultures. Protein was isolated from conditioned HEK medium using Protein A affinity chromatography according to standard protein purification methods. Medium was loaded onto chromatographic resin and eluted by pH shift. Eluted protein was pH adjusted, dialyzed, and sterile filtered prior to use. ZTS-361 was subsequently used for evaluation in the cat pruritus model to evaluate in vivo efficacy. Antibodies produced from a single GS plasmid, ZTS-927 and ZTS-361, were tested for affinity and potency. FIG. 2, Section D shows the results for the affinity assessment of these antibodies using biacore. The affinity of ZTS-927 and ZTS-361 to feline IL-31 is highly consistent with that of the mouse and chimeric form of the progenitor mouse mAb 15H05. The potency of these two antibodies was determined against canine and feline IL-31 using both canine and feline cell assays (FIG. 3). Consistent with previous observations the IC50 values were proportionally higher when using the canine form of IL-31 with both cell types. The IC50 values for ZTS-927 and ZTS-361 against feline IL-31 were also highly consistent with values derived from the chimeric and mouse form of the antibody indicating the final felinized version of mAb 15H05 produced form a single GS plasmid was suitable for cell line development.

For generation of a stable cell line producing candidate antibodies, the GS plasmid was linearized prior to transfection with the restriction enzyme, Pvul, which cuts at a single site in the plasmid backbone. GS-CHOK1SV (clone 144E12) cells were transfected with linearized plasmid DNA via electroporation. Following transfection, cells were plated in 48-well plates (48WP) in order to generate stable pools. When pools were at least 50% confluent in the 48WPs, 100 µl of supernatant was analyzed for IgG expression using the ForteBio Octet and protein A biosensors (Pall ForteBio, Fremont, CA). The best expressing clones were scaled up into 6 well-plates (6 WP) and then into 125 mL shake flasks (SF). Once cells adapted to suspension culture in 125 mL flasks, 2 vials of each cell line pool were banked for LN storage. Since manufacturing cell lines must be clonal, the top 3 highest expressing pools were subcloned by limiting dilution in 96 well culture plates. In order to prove clonality and avoid a second round of limiting dilution, 96 well plates were imaged using Molecular Devices CloneSelect Imager (CSI) (Molecular Devices LLC, San Jose, CA) which captures images of single-cells and their subsequent growth. Clones were selected based on successful CSI images, growth and production in 96WPs.

In order to assess cell culture growth and productivity, the top expressing pools were further evaluated in a 14-day fed batch in 125 mL SFs. Cells were seeded in platform media and feeds consisting of Life Technologies' CD CHO plus 4 amino acids, proprietary feed CDF v6.2, and 10% glucose. Following the 14-day Fed-Batch, pools were centrifuged and the CD CHO produced mAB was isolated by filtering the supernatant via a 0.20 μm Polyethersulfone (PES) membrane prior to purification.

A typical purification consists of two liters of conditioned medium (from CHO cell culture, 0.2 μm filtered) loaded onto a 235 mL column of MabSelect (GE healthcare, cat #17-5199-02). The column had been pre-equilibrated with PBS. The sample was loaded at a residence time of >2.5 minutes. Following load, the column was washed again with PBS, and then with 25 mM sodium acetate, pH neutral. The column was eluted with 25 mM acetic acid, pH 3.6, and then stripped with 250 mM acetic acid, 250 mM sodium chloride, pH ~2.2. Fractions (50 mL) were collected during the elution and strip steps. UV absorbance at A280 was monitored throughout. Peak fractions were pooled, pH adjusted to ~5.5 with the addition of 20 mM sodium acetate, and then dialyzed against three exchanges of buffer. The dialysate was collected, sterile filtered, and stored at 4° C.

1.10. Identification of the Epitope on IL-31 Recognized by Antibody 15H05

Knowledge of the epitope on IL-31 that is recognized by an antibody is critical to understanding the mechanism by which it neutralizes the cytokine from binding to the IL-31 Ra: OSMR co-receptor. In addition, knowing the epitope enables (but is not limited to) optimization of antibody binding affinity and design of peptide epitope mimetics (mimotopes) which can have great utility as analytical capture reagents and as a subunit vaccines to elicit a relevant focused immune response. A multistep process using CLIPS (Chemical Linkage of Peptides onto Scaffolds) technology (Timmerman et al. J Mol Recognit. 2007; 20(5): 283-299) was used to identify and optimize a peptide capable of binding to the paratope of mAb 15H05 (Pepscan, Lelystad Netherlands). The affinity of mAb 15H05 to both canine and feline IL-31 proteins is high (FIG. 2A, MU-15H05) so the primary sequence of both IL-31 species was considered relevant to this effort. A peptide microarray library representing the canine IL-31 protein was created and used to identify peptides capable of binding mAb 15H05 using an indirect ELISA. Following identification of peptides whose primary amino acid sequences represent the binding region of mAb 15H05 on IL-31, a focused full replacement analysis was performed using peptides representing a segment of IL-31 and replacing each of the 12 amino acids in this mAb 15H05 binding region with the 19 other possible amino acid residues at each position. This analysis was essential to identify the key amino acid residues on IL-31 involved with mAb 15H05 binding and also demonstrated where substitutions on the canine primary sequence lead to an enhancement of antibody binding.

The amino acids on the canine IL-31 protein that are recognized by antibody 11E12 were described previously (U.S. Pat. No. 8,790,651 to Bammert, et al.). Therein were described the mutational analysis of the canine IL-31 protein showing positions on the canine IL-31 protein that affect binding of mAb 11E12 when converted to alanine. Based on the full replacement analysis described for mAb 15H05 above and previous knowledge of the binding epitope of 11E12, mutant forms of the feline IL-31 protein were created by substituting alanine for two key residues on the epitope recognized by each antibody (mutants described in section 1.2 above). Mutations for each epitope were named according to the antibody that recognizes the site of the mutation (mutant 11E12 and 15H05 vs. the native wt protein sequence).

FIG. 6A shows the alignment of wildtype feline IL-31 (SEQ ID NO: 157) with mutants 15H05 (SEQ ID NO: 163) and 11E12 (SEQ ID NO: 161) highlighting the positions where the alanine substitutions occur. IL-31 belongs to the IL-6 family of cytokines with the four helical bundles possessing an up and down architecture (CATH database, Dawson et al. 2017 Nucleic Acids Res. 2017 Jan. 4; 45 (Database issue): D289-D295). A homology model was generated based on the human IL-6 structure 1P9M (Boulanger et al. 2003 Science. June 27; 300(5628):2101-4) using the MOE software (Chemical Computing Group, Montreal, QC, Canada). FIG. 6B shows the feline IL-31 homology model highlighting the positions of the amino acids involved with binding of antibodies 11E12 (site 1) and 15H05 (site 2). The binding sites for each antibody appear to be located at separate positions on the IL-31 protein.

To determine the impact of mAbs 11E12 and 15H05 ability to bind these mutant forms of feline IL-31, an indirect ELISA was run using the mutants directly coated on to an immunoassay plate. FIG. 6C shows the results for this ELISA demonstrating that mAbs 11E12 and 15H05 are capable of binding to wiltype feline IL-31 in this assay format. When mutant 11E12 is used as a capture protein, binding of mAb 11E12 is highly attenuated and binding of mAb 15H05 is partially attenuated. Previous analysis of the 11E12 epitope on canine IL-31 (described in U.S. Pat. No. 8,790,651 to Bammert et al.) indicated that 4 amino acid residues impact binding of the mAb when mutated to alanine so the mutation of 2 residues, in this case, may not be enough to completely eliminate the high affinity binding of mAb 11E12 using this ELISA format. The minor attenuation of mAb 15H05s binding to the 11E12 mutant is likely due to translational effects of the mutations from movement of the two front helices effecting the 15H05 binding site. The mutations designed to affect mAb 15H05s binding (mutant 15H05) show a complete loss of mAb 1505s ability to bind this IL-31 mutant by ELISA. Unlike the 11E12 mutant, the changes in the random coil recognized by mAb 15H05 (mutant 15H05) had no impact on mAb 11E12 binding further supporting the distinction between the two epitopes (FIG. 6C).

1.11. Competition Binding Assessment of mAbs 15H05 and 11E12 Using Biacore

To further characterize the IL-31 epitopes bound by mAbs 15H05 and 11E12, blocking experiments were performed using biacore where the surface containing the IL-31 protein was generated followed by sequential addition of antibodies. FIGS. 7A and FIG. 7B show the relative binding of each antibody to IL-31 following capture of 11E12 or 15H05. The columns labeled HBS-EP (assay buffer) indicate the maximum signal obtained from each antibody binding to the IL-31 surface alone without competition. FIG. 7A shows the competition binding data for mouse 15H05 and 11E12 antibodies to canine IL-31. These results clearly indicate that antibodies 15H05 and 11E12 are capable of binding to canine IL-31 in the presence of one another indicating they recognized distinct epitopes on the protein. The sensorgrams related to FIG. 7A show the disassociation kinetics of both antibodies are very slow on this newly formed biacore surface therefore no additional occupation of binding sites can occur with addition of the same antibody (data not shown).

FIG. 7B shows the competition binding data for antibodies 15H05 and 11E12 on a feline IL-31 surface again showing no overlap in the epitope recognized. Binding of additional antibody in the presence of the same antibody is a result of the increased off rate due to the poorer quality of the surface used. Increased off rates can be seen and compared to the KD values from newly formed feline IL-31 surfaces in FIG. 2.

These results further support the epitope mapping data in section 1.10 indicating a distinct epitope is recognized by the CDRs contained in antibody MU-15H05 when compared to MU-11E12. The epitope recognized by antibody 15H05 is distinct from antibody 11E12 described in (U.S. Pat. No. 8,790,651 to Bammert, et al.) and is a novel target on the IL-31 protein for neutralization of this cytokines activity in multiple species. These findings highlight the distinct spatial relationship of binding sites described in the feline IL-31 homology model (FIG. 6B) and support the hypothesis that this face of the cytokine is critical for interaction with the IL-31 Ra:OSMR receptor complex.

1.12. Synthesis and Characterization of Soluble Feline IL-31 Co-Receptor (IL-31 RA and OSMR)

The human IL-31 heteromeric receptor co-complex, consisting of IL31 Ra and OSMR subunits, was shown to be required for IL31-mediated intercellular activation of the JAK-STAT pathway and having involvement in atopic skin disease (Dillon et al. 2004 Nat Immunol. July; 5(7):752-60, Dreuw et al. 2004 J Biol Chem. 279:36112-36120; and Diveu et al. 2004 Eur Cytokine Netw. 15:291-302). The human IL-31 Ra subunit was later described as the initial binding event that occurs when IL-31 is in contact with cell surface receptors and this event is a pre-requisite for the recruitment of OSMR with subsequent formation of a high affinity co-receptor complex (Le Saux et al. 2010 J Biol Chem. January 29; 285(5):3470-7). We describe here evidence that the feline IL-31 protein is capable of binding to both OSMR and the IL-31 Ra independently. This observation is novel and has important implications to understanding how the IL-31 protein interacts with the IL-31 Ra:OSMR co-receptor and to the biological role of IL-31 as it interacts independently with individual subunits.

To enable understanding of how IL-31 binds to its co-receptor and to characterize the inhibitory properties of identified antibodies, two receptor forms were synthesized. The individual IL-31 receptor subunit IL-31 Ra (SEQ ID NO: 169; Feline_IL31Ra_HIgG1_Fc_X1_Fn3) the corresponding nucleotide sequence for which is (SEQ ID NO: 170; Feline_IL31Ra_HIgG1_Fc_X1_Fn3), and OSMR-(SEQ ID NO: 167; Feline_OSMR_hIgG1_Fc) the corresponding nucleotide sequence for which is (SEQ ID NO: 168; Feline_OSMR_hIgG1_Fc) were both constructed as human IgG1 Fc fusions. By homology to the human homologs, the cytokine binding, fibronectin III, and Ig-like domains were identified. To evaluate the individual receptor subunits, the extracellular domains of OSMR and the IL-31 Ra (with its expected N-terminal proximal fibronectin III domain) were generated as human IgG1 Fc fusions, both employing their native signal peptides. All synthetic cassettes were cloned into pcDNA3.1, expressed in the ExpiCHO system and purified as described above.

Figure 8:
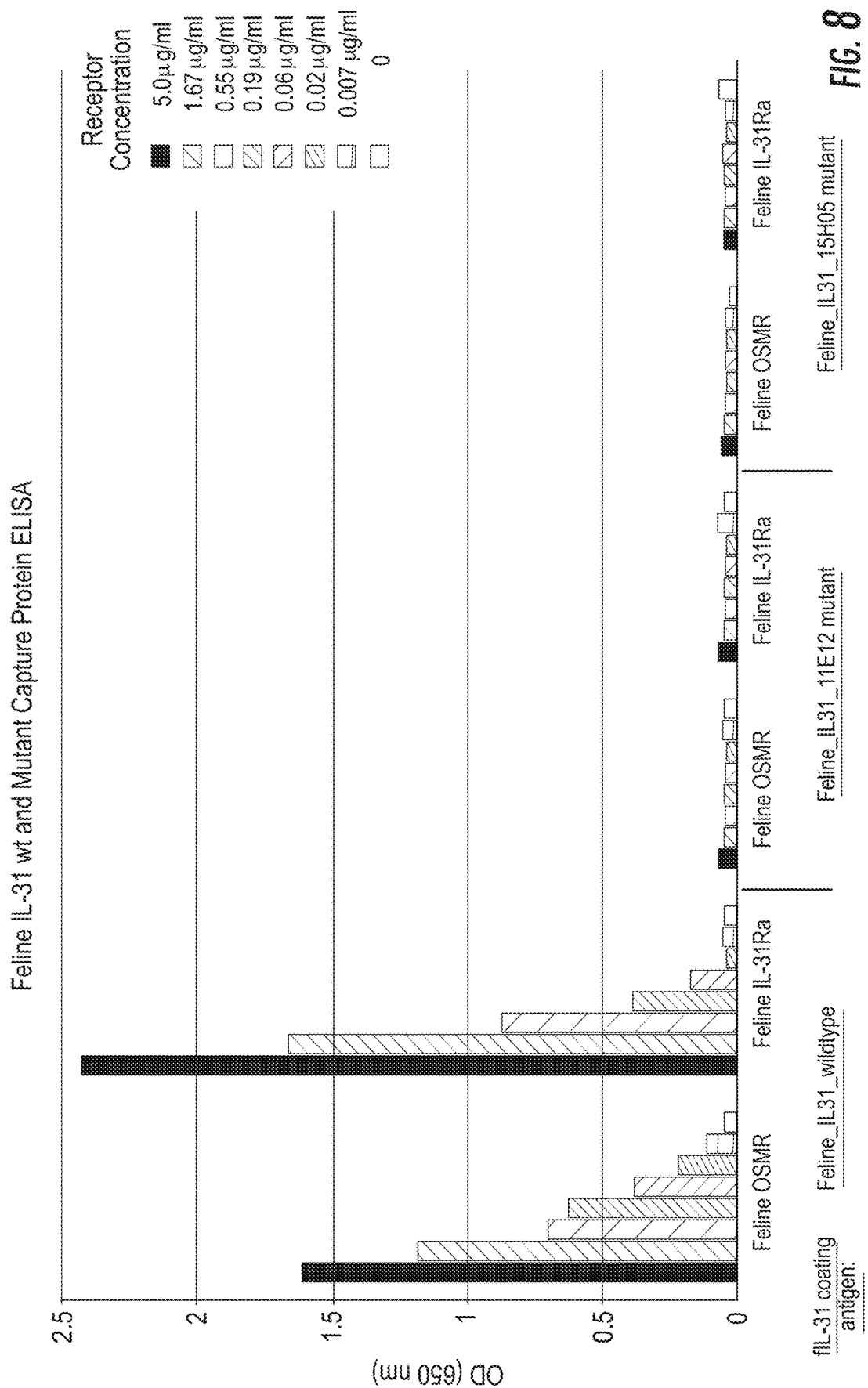
FIG. 8 is of a graph showing the results obtained for binding of the individual receptor subunits of OSMR and IL-31 Ra to wild-type feline IL-31 and to mutant IL-31 proteins 15H05 (SEQ ID NO: 163) and 11E12 (SEQ ID NO: 161) when the wild-type and these mutants are used as the coating antigens.

To analyze the ability of these receptor forms to bind wildtype and mutant IL-31 proteins, and indirect ELISA was run by coating 100 ul of each respective protein on an immulon 2HB plate (1 µg/ml) overnight in carb/bicarb buffer (sigma C3041-100CAP) at 4C. The ELISA plates were then blocked with 5% NFDM blocking buffer in PBST for 1 hour at room temperature followed by binding of multiple concentrations of each receptor construct at room for 1 hour. Following washing with PBST, the presence of the bound receptor (Fc fusion) was identified using mouse anti-human IgG1 (Lifetech A10684, 1:500 dilution) for 1 hour at room temperature. The wells were again washed with PBST and developed with KPL sureblue 3,3',5,5'-tetramethylbenzidene (TMB) microwell substrate. FIG. 8 shows the results for this indirect ELISA using wildtype and mutant forms of the feline IL-31 protein as a capture. These data demonstrate the ability of the wildtype feline IL-31 to independently bind to the IL-31 Ra and OSMR receptor subunits. These observations are in contrast to previous reports indicating the IL-31 protein initially binds to the IL-31Ra subunit and further recruits OSMR to the site. As the biological role of IL-31 is still being determined, it is of great importance to understand the dynamics of receptor binding and the potential consequences to attenuation of its role in diseases such as atopic dermatitis. For this reason, consideration was further given to these observations when characterizing antibodies the bind to epitopes capable of disrupting the ability of IL-31 to recognize IL-31 Ra and OSMR.

In section 1.2 we describe the attenuated binding of antibodies 11E12 and 15H05 to mutants with key amino acids in their binding sites converted to alanine (mutant 11E12 and 15H05 respectively). It was therefore of great interest to understand the impact of these mutations on the ability to bind to the individual IL-31 Ra and OSMR receptor subunits. FIG. 8 shows that mutation in either the 11E12 or 15H05 binding site completely disrupts IL-31 Ra and OSMRs ability to bind indicating both antibodies bind epitopes that are necessary for interaction of IL-31 with both receptor subunits. Lack of binding could also be due to changes in the confirmation of IL-31 resulting from mutation however these mutants are still capable of binding to antibody which suggests this is not the case. This key finding supports the ability of both antibodies 11E12 and 15H05 (and derivatives) recognizing epitopes on IL-31 that neutralize the cytokines ability to signal through its co-receptor and further block cell association of the cytokine to either receptor during this process. These data support the identification of antibodies that are capable of removing IL-31 from circulation and rendering it unable to bind to cell surface or soluble receptor forms.

1.13. In Vivo Evaluation of Chimeric Antibodies in a Feline IL-31 Pruritus Challenge Model The ability of an antibody to effectively neutralize its target can be assessed in vitro through examination of binding to a relevant epitope on the target protein with the appropriate affinity and potency in a cell based assays that allow extrapolation to in vivo potency. Described above are the steps taken to characterize two series of antibodies generated from the mouse progenitor mAbs 11E12 and 15H05. Section 1.7 describes the generation of mouse: feline chimeric forms of mAbs 11E12 and 15H05 with a resulting affinity to canine and feline IL-31 that are comparable to the original mouse monoclonal antibody (FIG. 2, Section A). The mouse: feline chimeric forms of 11E12 and 15H05 also had comparable IC50 values showing inhibition of feline IL-31 induced pSTAT3 signaling in canine and feline macrophage cells (FIG. 3). During the felinization process in section 1.8, mouse mAb 11E12 was converted to the felinized version (Feline 11E12 1.1) with subsequent loss of affinity to canine and feline IL-31 (FIG. 3) and loss of potency against feline IL-31 signaling in canine and feline cells (FIG. 3). Prior to optimization of the felinized 11E12 and 15H05 antibodies described in section 1.8, it was of interest to understand the ability of these preliminary felinized and chimeric forms to neutralize the pruritic activity of feline IL-31 in a cat challenge model. Of interest was the pharmacodynamic effect of these different antibodies on neutralization of pruritus and to understand any correlation to affinity, cellular potency, or epitope recognition that may influence efficacy. Going forward a range of cellular potency that correlates to in vivo efficacy in the pruritus challenge model could be predictive of further optimization necessary using in vitro assays.

Figure 9:
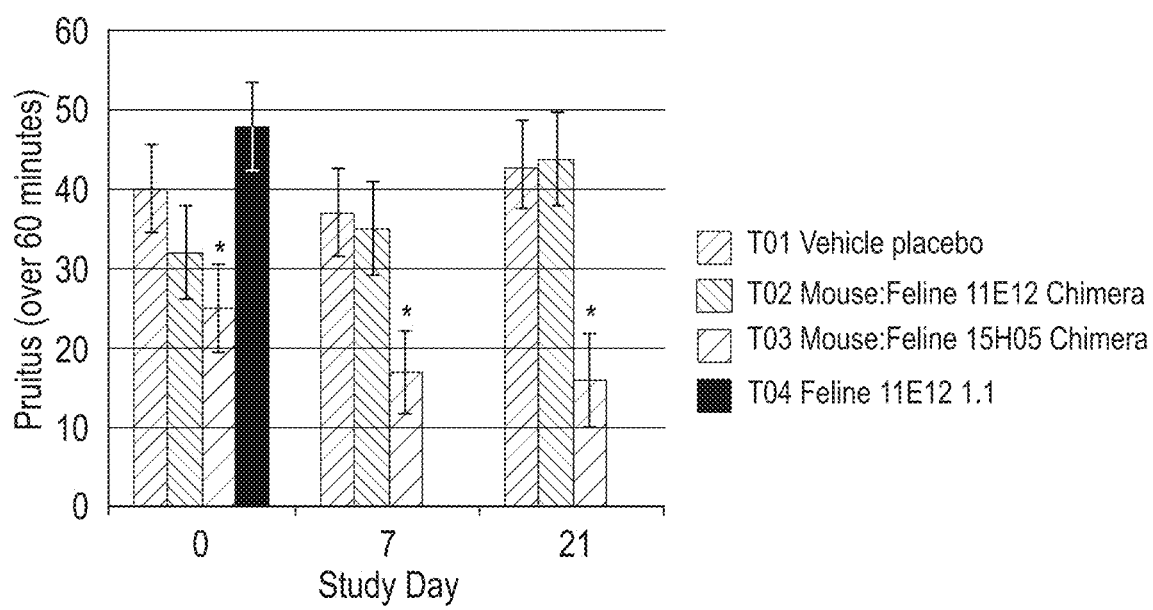
FIG. 9 is of a graph showing the preliminary efficacy of mouse: feline 11E12 chimera, mouse: feline 15H05 chimera, and felinized 11E12 (Feline 11E12 1.1) in an IL-31 induced pruritus model in cats.

To test the preliminary efficacy of mouse: feline 11E12 chimera, mouse: feline 15H05 chimera, and felinized 11E12 (Feline 11E12 1.1), an IL-31 induced pruritus model in cats was developed. Following an intravenous dose of 0.5 µg/kg feline IL-31 (SEQ ID NO: 159; Feline_IL-31_E_coli), the corresponding nucleotide sequence for which is (SEQ ID NO: 160; Feline_IL-31_E_coli), cats will portray transient pruritic behavior that includes (but is not limited to) licking, chewing, scratching, and head or body shaking. Rubbing up against the cage was not considered a pruritic activity. Pruritic observations take place by a trained investigator for 30 minutes prior to administration of the IL-31 protein and for 1 hour following. For this study, a baseline challenge with feline IL-31 was performed up to 1 month prior to dosing with antibody. On day zero, a 0.5 mg/kg antibody dose was combined with 0.5 µg/kg of feline IL-31 at room temperature for 60 minutes prior to injecting the pre-bound complex into each animal. A "no mAb" control was included for a control. The dose of mAb represents a gross molar excess of antibody to cytokine. Pruritic activity was monitored as described on days 0, 7, and 21. Results in FIG. 9 show significant improvement (p<0.05) in pruritus scores with mAb mouse: feline 15H05 chimera at days 0, 7, and 21 when compared to the placebo control. Although the mouse: feline 11E12 chimera showed an initial trend in efficacy at day zero, it did not achieve a significant reduction in pruritus at any timepoint when compared to vehicle placebo. Feline 11E12 1.1 did not reduce pruritus at day zero and showed no trend in efficacy when compared to vehicle placebo so further IL-31 challenges on days 7 and 21 were not performed.

Taken together these results show a clear delineation between the activities of these antibodies with the lack of efficacy for feline 11E12 1.1 at preventing pruritic behavior in the cat induced by IL-31. The loss of affinity and potency of feline 11E12 1.1 likely resulted in the lack of in vivo efficacy. When comparing the efficacy outcome of mouse: feline 11E12 chimera and mouse: feline 15H05 chimera the distinction is more subtle. The chimeric forms of both mAbs have a comparable KD value to their mouse progenitor with the affinity of mouse: feline 11E12 being slightly superior to both feline and canine IL-31 (FIG. 2, Section A). This increased affinity however does not translate directly to increased potency as the mouse: feline 15H05 chimera has an approximately 2-fold increased IC50 to that of mouse: feline 11E12 chimera against feline IL-31 induced pSTAT3 signaling in feline FCWF4 cells (FIG. 3). These data suggest that the manner in which antibody 15H05 CDRs recognize feline IL-31 is superior at neutralizing the cytokines ability to signal through its co-receptor in turn making it more effective at blocking pruritus in cats. The differences in IC50s observed in these cellular assays offers a promising means to predict in vivo potency and to discriminate subtle differences in epitope recognition both within and between series of antibodies.

1.14. In Vivo Evaluation of the Efficacy of Felinized 15H05 anti IL-31 Antibodies in a Cat Pruritus Challenge Model Based on the positive efficacy outcome using the mouse: feline 15H05 chimera described above, further work was done to increase the affinity and potency of felinized 15H05 (described above in section 1.8). Systematic substitution of the variable light chain feline frameworks in antibody feline 15H05 1.1 lead to the identification of Feline 15H05 1.1 FW2 having increased affinity to both feline and canine IL-31 compared to mouse 15H05 (FIG. 2). Combination of the heavy and light chains of Feline 15H05 1.1 FW2 into a single plasmid lead to the formation of ZTS-927 and ZTS-361 antibodies following production from HEK and CHO expression systems. The affinity and potency of both antibodies resulting from expression from a single plasmid are also described in FIGS. 2 and 3 respectively.

Figure 10A:
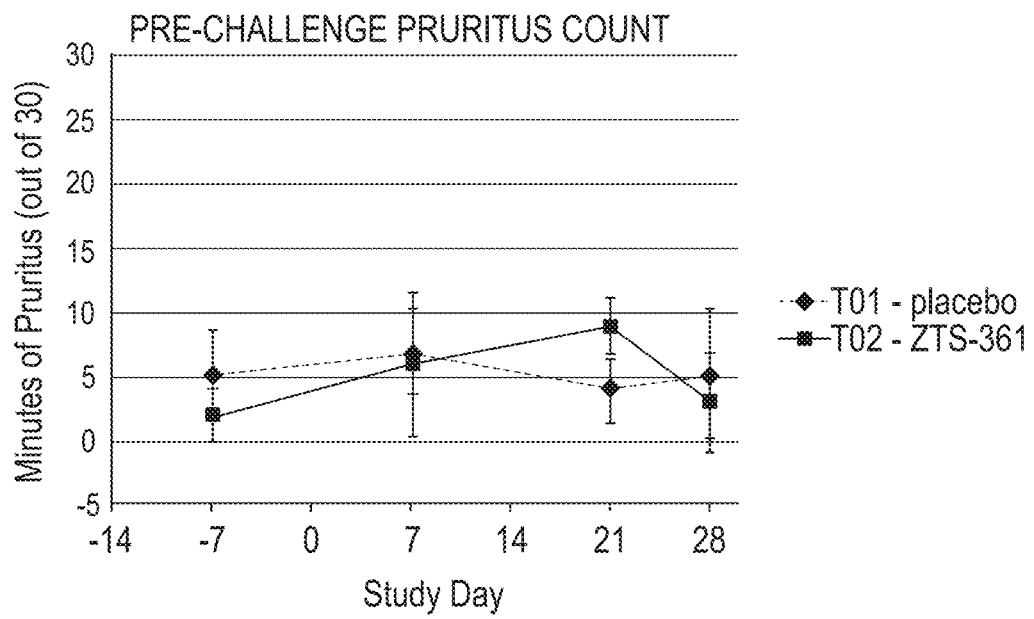
FIGS. 10A and 10B are of graphs showing the In vivo evaluation of the efficacy of a felinized15H05 anti IL-31 antibody termed ZTS-361 in a cat pruritus challenge model.

The efficacy of the fully felinized anti feline IL-31 mAb ZTS-361 was assessed for its ability to neutralize pruritic behavior in an IL-31 induced in vivo cat model. FIG. 10A shows the baseline pre-challenge pruritic behavior for the T01 vehicle placebo and T02 antibody ZTS-361 groups from day −7 through day 28 with day zero being the day of antibody administration to group T02. As shown in this graph, the variance of pruritic behavior scored for both T01 and T02 groups prior to IL-31 challenge varied little with the number of pruritic events observed between 0 and 10 within the 30 minute observation period. This study differed from the preliminary feline challenge model described above in section A.13 in that on day zero cats were dosed with 4 mg/kg ZTS-361 subcutaneously without combination with feline IL-31 to generate a pre-bound complex. This represents a more rigorous assessment of efficacy as antibody ZTS-361 will be in circulation for seven days prior to the first IL-31 challenge requiring the antibody to have sufficient exposure to bind and neutralize circulating IL-31.

Figure 10B:
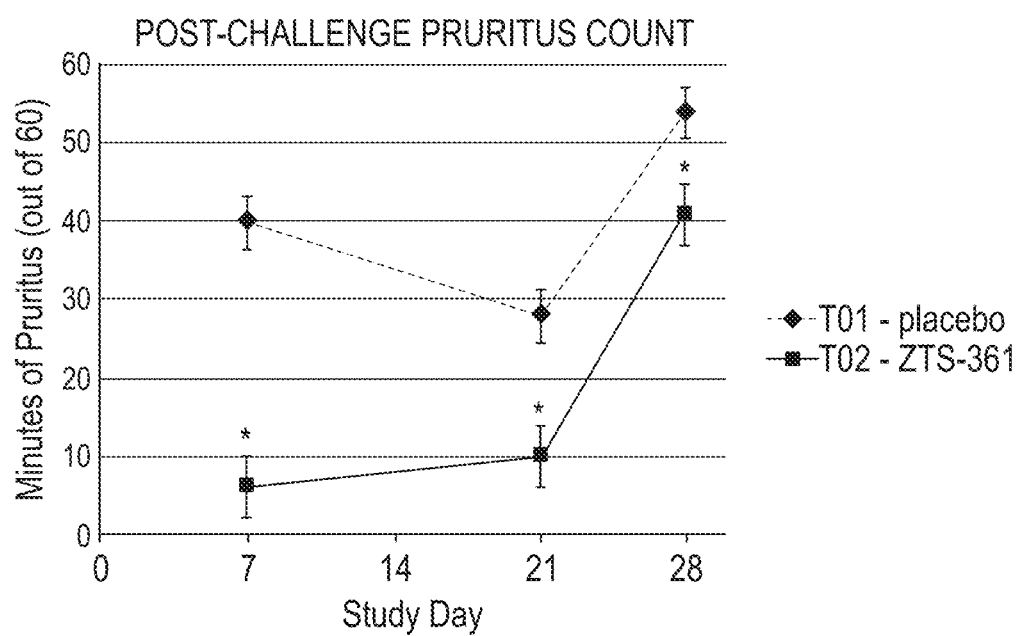

For this study, pruritic behavior was assessed on days 7, 21, and 28 for 1 hour following a 0.5 µg/kg intravenous challenge of the IL-31 protein. FIG. 10B shows the efficacy of antibody ZTS-361 demonstrating a significant reduction in pruritus observed on days 7 (p<0.0001), 21 (p<0.0027), and 28 (p<0.0238) following IL-31 challenge when compared to vehicle placebo control. Data from this challenge model support previous observations demonstrating the efficacy of mouse: feline 15H05 chimera and support the cell-based potency and relevance of the epitope on feline IL-31 recognized by the 15H05 CDRs. These data further support the ability of antibody ZTS-361 to neutralize pruritus induced by feline IL-31 in vivo and suggest this antibody may serve as a therapeutic in the treatment of IL-31 mediated disease in cats including atopic dermatitis.

Recent data examining the plasma levels of IL-31 in client owned animals shows an increased amount of the cytokine in circulation among dogs with atopic and allergic dermatitis compared to normal laboratory beagles (FIG. 11A). A recent study was performed to determine serum IL-31 levels in cats with a presumptive diagnosis of allergic dermatitis (AD) from several different geographic regions in the USA. FIG. 11B shows the results from this assessment indicating that, like dogs with atopic and allergic dermatitis, 73 cats surveyed with this presumptive diagnosis had mean circulating IL-31 levels of 8799 fg/ml compared to 205 fg/ml in the 17 age-matched control cats. To understand the levels of canine IL-31 in a previous model development study, the pharmacokinetic profile of canine IL-31 was analyzed in dogs following administration of a subcutaneous dose of 1.75 µg/kg. FIG. 11C shows peak plasma levels within the first hour reaching a maximum of about 30 ng/ml and a maintained level of about 400 pg/ml at three hours. Based on these findings it is reasonable to believe that an intravenous dose of 0.5 µg/kg feline IL-31 used in this feline model will result in a circulating amount that is far excessive to that observed in the naturally occurring disease state for dogs and cats.

1.15. Analytical Methods Used for Advancement of Lead Felinized Anti IL-31 Antibodies During the process of cell line development, various analytical methods are employed to ensure the antibody therapeutic can be manufactured in a consistent manor. Close attention to analytical methods which ensure (but are not limited to) product identity, purity, and potency are critical for consistent production of lead monoclonal antibodies and strong correlation to potency and safety outcomes in the target animal species. As antibodies are homodimers of two heterodimeric units held together through inter-chain disulphide bonds, any disruption in the pairing process can lead to non-uniformity of the protein drug product. Two analytical methods well suited to monitor the disassociation of antibodies are non-reducing (NR) sodium dodecyl sulphate (SDS) polyacrylamide gel electrophoresis (PAGE) and non-reducing (NR) capillary gel electrophoresis (CGE).

NR SDS-PAGE provides a convenient qualitative method for determining the mass of individual proteins species in a test sample. SDS hydrophobically associates with proteins uniformly conferring a net negative charge to the protein thus allowing separation of individual components based on mass. Following electrophoretic separation on a polyacrylamide gel, proteins are stained with a dye like Coomassie blue to allow for detection. Non-linearity of staining prevents absolute quantitation of individual protein bands but does allow for estimates using software capable of densiometric analysis (VersaDoc, Bio-Rad). Capillary gel electrophoresis, commonly known as CGE, subjects proteins to SDS again resulting in a uniform negative charge and dissociates non-covalent protein complexes. In the presence of an electric field, the SDS-coated proteins migrate toward the anode and are detected using ultraviolet light absorbance at a fixed wavelength of 220 nm. Separation is based on the size of the components in the sample within a capillary filled with replaceable SDS-polymer gel sieving matrix. In non-reducing CGE, an alkylating agent iodoacetamide (IAM) is added to minimize disulfide bond shuffling during sample preparation. The intact IgG is separated from any fragmented species, allowing quantitation of purity. Software for CGE analysis (examples are Empower or 32 Karat) utilizes the time corrected area (TCA) which is defined as the individual peak area by the migration time. Total TCA is defined as the sum of the TCAs for all peaks greater than or equal to 0.3%. Percent monomeric intact IgG and subspecies can thus be calculated based on their individual TCAs as a percent of the total TCA.

Figure 12:
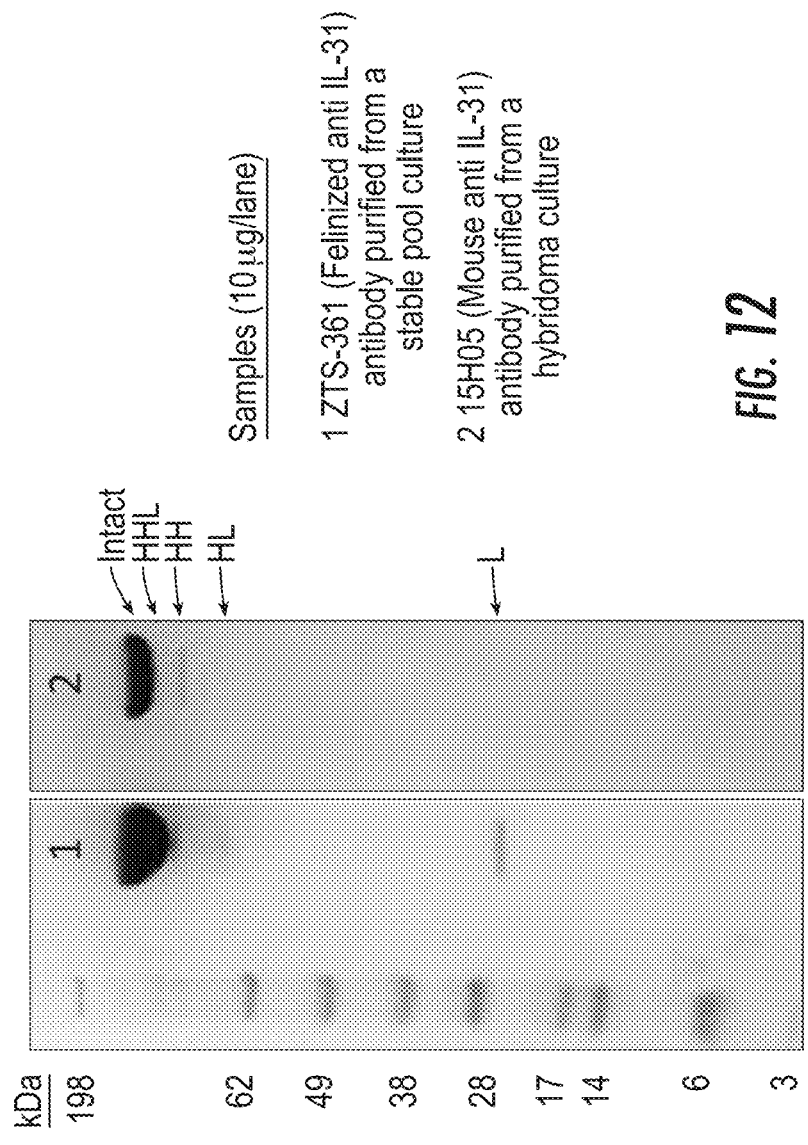
FIG. 12 shows a 4-12% non-reducing SDS PAGE comparing lane 1 which isZTS-361, the heavy chain for which is (SEQ ID NO: 121; FEL_15H05_VH1) combined with feline IgG heavy chain constant (SEQ ID NO: 173; Feline_HC_AlleleA_1). For ZTS-361, the light chain is (SEQ ID NO: 135; FEL-15H05-VL1_FW2) combined with feline IgG light chain constant (SEQ ID NO: 175; Feline_LC_Kappa_G_minus). Lane 2 is mouse 15H05, the heavy chain for which is (SEQ ID NO: 67; MU_15H05_VH) combined with mouse IgG heavy chain constant (SEQ ID NO: 188; Mouse_HC_IgG1). For mouse 15H05, the light chain is (SEQ ID NO: 69; F MU_15H05_VL) combined with mouse IgG light chain constant (SEQ ID NO: 190; Mouse_LC_Kappa). Intact refers to an IgG with two heavy chains and two light chains held together by interchain disulfide bonds with an expected molecular weight of ~150 kDa. HHL refers to "Heavy Heavy Light" and is an IgG with one light chain missing and an expected molecular weight of ~125 kDa. HH refers to "Heavy Heavy" and is an IgG with both light chains missing and an expected molecular weight of ~100 kDa. HL refers to "Heavy Light" and is an IgG with one heavy and one light chain and an expected molecular weight of ~75 kDa. L refers to "Light" and is an IgG with one light chain and an expected molecular weight of ~25 kDa, also referred to herein as free light chain.
Figures 13A, 13B:
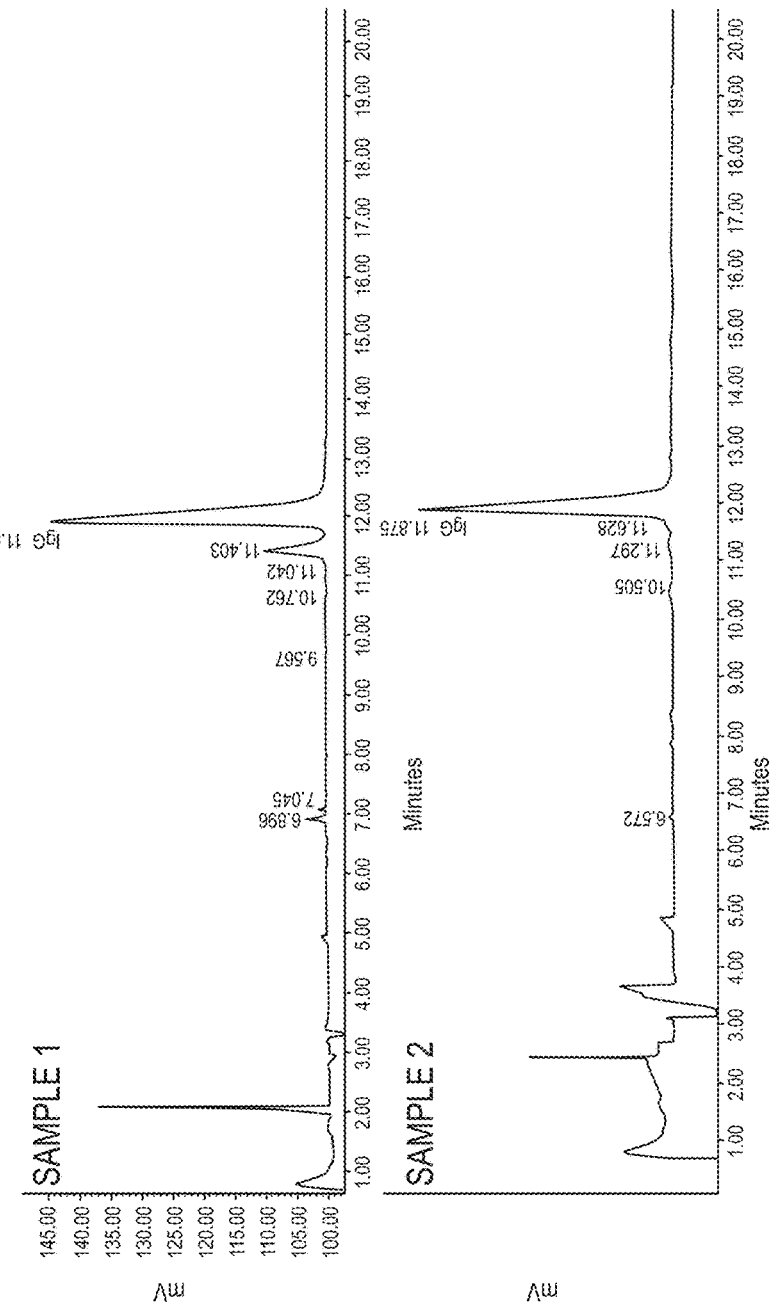
FIG. 13A shows the results for non-reducing capillary gel electrophoresis (NR-CGE) comparing IgG from stable cell lines expressing ZTS-361 or mouse 15H05 (each described above). The percent monomer and subspecies are calculated from the experimental output using NR-CGE shown as the electropherograms in FIG. 13B. The time corrected area (TCA) is defined as the individual peak area from the instrument output divided by the migration time. Total TCA is defined as the sum of the TCAs for all peaks greater than or equal to 0.3%. Percent monomer intact IgG (% Monomer) and individual fragments (% HHL and % L) are calculated based on their individual TCAs as a percent of the total TCA. % Fragments are the sum of all the peak areas migrating with a lower molecular weight than that of intact IgG.

Given the promising in vivo efficacy data for ZTS-361 described for the feline model of pruritus (section 1.14), further characterization of various lots of antibody were determined using these described analytical methods. During this process, it was identified that stable pools expressing felinized anti IL-31 (ZTS-361) antibody had increased levels of lower molecular weight species (including free light chain) visible by Coomassie staining of an SDS-PAGE relative to the mouse progenitor hybridoma 15H05 (FIG. 12). Herein, intact, or intact monomer, refers to an IgG with two heavy chains and two light chains held together by interchain disulfide bonds with an expected molecular weight of ~150 kDa. HHL refers to herein as "Heavy Heavy Light" an IgG with one light chain missing and an expected molecular weight of ~125 kDa. HH refers to herein as "Heavy Heavy" an IgG with both light chains missing and an expected molecular weight of ~100 kDa. HL refers to herein as "Heavy Light" an IgG with one heavy and one light chain and an expected molecular weight of ~75 kDa. L refers to herein as "Light" an IgG with one light chain and an expected molecular weight of ~25 kDa, also refered to herein as free light chain. Quantitative assessment of this same material using NR CGE revealed significantly less intact monomeric IgG (83%) for ZTS-361 when compared to the mouse progenitor 15H05 (94.7%) (FIG. 13A). FIG. 13B shows the electropherograms following resolution of samples by NR CGE. Data from these peaks at differing retention times were used to quantitate the percent TCA of total for sample 1 (ZTS-361) and sample 2 (mouse 15H05). The sum of the minor peaks with a lower molecular weight than the major intact IgG peak are used to calculate the percent fragments indicated in FIG. 13A (% fragments). Stable CHO pools producing ZTS-361 resulted in 17% of the final antibody product found as a fragmented form of the felinized IgG compared to only 5.3% with the mouse hybridoma 15H05.

Figure 14A:
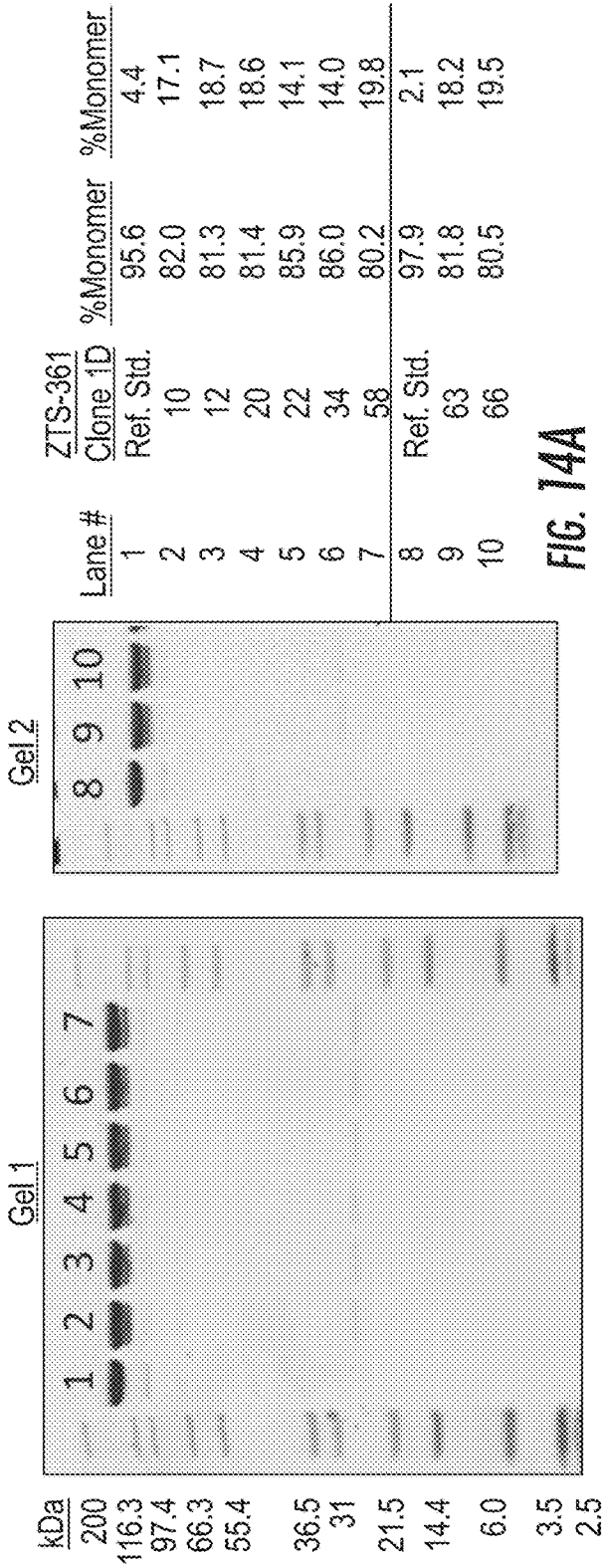
FIG. 14A shows a 4-12% non-reducing SDS PAGE comparing IgG from individual stable CHO clones of ZTS-361 (described above and in section 1.9 of example section) Lanes 1 and 8 are an IgG reference standard for comparison. Percent monomer is calculated from densiometric analysis of each band migrating to an expected molecular weight of ~150 kDa using BioRad VersaDoc software. % Fragments are the sum of the individual bands with lower molecular weights.
Figure 14B:
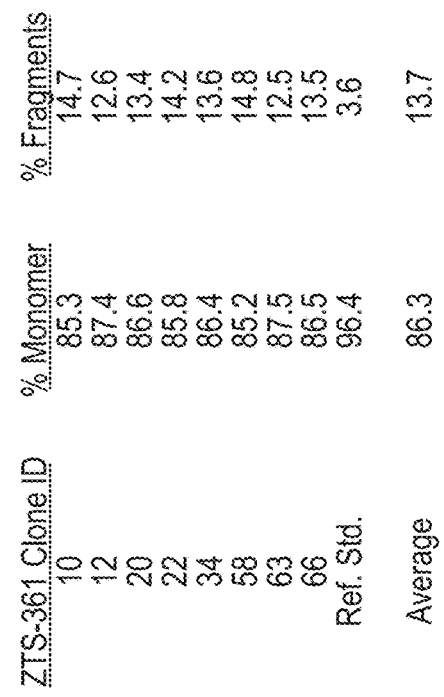
FIG. 14B Shows the results for non-reducing capillary gel electrophoresis (NR-CGE) comparing IgG from individual stable CHO clones of ZTS-361. The time corrected area (TCA) is defined as the individual peak area from the instrument output divided by the migration time. Total TCA is defined as the sum of the TCAs for all peaks greater than or equal to 0.3%. Percent monomer intact IgG (% Monomer) and percent fragments (% Fragments) are calculated based on their individual TCAs as a percent of the total TCA. % Fragments are the sum of all the peak areas migrating with a lower molecular weight than that of intact IgG.

To facilitate the understanding of this phenomenon, single clonal CHO cell isolates were derived from the ZTS-361 clonal pool to see if the percentage of intact IgG monomer varied between the individual clones. FIG. 14A shows a Coomassie-stained NR SDS-PAGE with purified antibody derived from cultures of 8 individual clones stably expressing ZTS-361. For comparison the lanes labeled 1 and 8 show a reference standard antibody known to have a high percentage of intact IgG monomer (~97%). Qualitative densiometric determinations of band intensity are shown on the right of the Figure. Clonal variation of percent intact monomer ranges from 80.2% to 86% with an average of ~82%. Likewise the quantitation of percent fragments ranged from 14.0% to 19.5% for the individual clones with an average of 17.5%. FIG. 14B shows the quantitative assessment of these individual clones using NR-CGE. Less variation is observed using this method with an average percent intact monomer of 86.3% and a percentage of lower molecular weight species of 13.7% observed across the 8 clones tested. While a high level of consistency was observed with the percentage of intact IgG monomer for ZTS-361 among the individual clones, it was of interest to understand why the overall level of intact IgG monomer was lower than that observed for the mouse version of the antibody. It is important to note that antibodies, not limited to but including felinized antibodies, produced from transient expression systems (examples are HEK and CHO cells) resulted in production of IgGs with a high level of the percent monomeric form (~88% to ~92%) (data not shown). Correspondingly the amount antibody produced from these transient cultures is significantly less than that from a stable CHO line. While not wishing to be bound by any one theory, the occurrence of fragmented antibody species seen with felinized and other species may be observed under conditions where the host cell is producing exceptionally high amounts of antibody and inherent limitations in the culture conditions and/or the antibodies molecular composition are observed.

1.16. Consideration of Primary Amino Acid Sequences of the IgG Kappa Light Chain Constant Domain from Multiple Species of Mammals Analysis of potential limitations to the felinized antibody ZTS-361 began with consideration of the primary antibody sequence. ZTS-361 is composed of a heavy chain which includes a variable region (SEQ ID NO: 121; FEL_15H05_VH1), the corresponding nucleotide sequence for which is (SEQ ID NO: 122; FEL_15H05_VH1) combined with a feline IgG heavy chain constant region (SEQ ID NO: 173; Feline_HC_AlleleA_1)n the corresponding nucleotide sequence for which is (SEQ ID NO: 174; Feline_HC_AlleleA_1) and a light chain which includes a variable region (SEQ ID NO: 135; FEL-15H05-VL1_FW2), the corresponding nucleotide sequence for which is (SEQ ID NO: 136; FEL-15H05-VL1_FW2) combined with a feline IgG light chain constant region (SEQ ID NO: 175; Feline_LC_Kappa_G_minus), the corresponding nucleotide sequence for which is (SEQ ID NO: 176; Feline_LC_Kappa_G_minus). The functional properties of naturally-occurring feline antibody heavy chain constant regions has been previously described by Strietzel et al. (2014 Veterinary Immunology and Immunopathology April 15; 158(3-4): 214-223). We describe herein the cloning and expression of felinized antibody ZTS-361 using the heavy chain constant region (SEQ ID NO: 171; Feline_HC_AlleleA_1). SEQ ID NO: 171 Feline HC AlleleA 1 corresponds to feline IgG1a in Strietzel et al. 2014 supra and appears to be functionally equivalent to human IgG1. Comparison of these functional attributes and alignment of this heavy chain constant region with other constant regions from a diverse set of species did not reveal any obvious areas of concern that would lead to inefficiencies in formation of the intact IgG monomer (data not shown).

Similar analysis of the kappa constant chain used in ZTS-361 (SEQ ID NO: 175; Feline_LC_Kappa_G_minus) reveals a unique aspect of the kappa constant light chain diversity observed in at least the feline and canine sequences. Different species utilize the kappa light chain in their immunoglobulin repertoire at different frequencies. FIG. 15 shows representative c-terminal amino acids and corresponding nucleotides for several kappa light chain constants from the species indicated. The percentage of kappa light chain utilization by IgGs from the species depicted are according to; Canine, Feline, and Pig (Arun et al. 1996 Zentralbl Veterinarmed. November; 43(9):573-6), Mink (Bovkun et al. 1993 Eur J Immunol. August; 23(8): 1929-34), Mouse (Woloschak et al. 1987 Mol Immunol. July; 24(7):751-7), Human (Barandun et al. 1976 Blood. January; 47(1):79-89). Routine generation of monoclonal antibodies is done using mice. As depicted in FIG. 15 the mouse utilizes the kappa light chain ~95% of the time when compared to the lambda light chain. In contrast dogs and cats primarily use the lambda light chain in their immunoglobulin repertoire (9% and 8% respectively). By comparison, two non-human (pig and mink) and human mammals show a balanced utilization kappa and lambda light chain usage (50%, 46%, and ~50% respectively). The position of the most c-terminal cysteine is annotated in this Figure and aligned across the different species. This cysteine is critical in the formation of the quaternary complex generated to form the intact IgG structure as it participates in the formation of the inter-chain covalent disulphide bond with the heavy constant chain. While not wishing to be bound to any one theory, it is of great interest to note that at least canine and feline kappa light chains contain multiple amino acids following the terminal cysteine. These additional amino acid residues have both polarity (glutamine) and charge (arginine, aspartic and glutamic acids). These residues are typically found in environments where they participate with hydrogen bond interactions which include, but are not limited to, interactions with the external aqueous environment. The nature and position of these additional residues beyond the terminal cysteine may interfere with the formation of an inter-chain disulphide bond that is necessary to form the IgG heterodimer. Two mammals (pig and mink) having fewer additional residues beyond the c-terminal cysteine and use kappa and lambda light chains at approximately equivalent ratios (50% and 46% respectively). Generation of recombinant forms of ZTS-361 with variations and deletions of amino acids at the c-terminus of the kappa light chain constant immediately following the cysteine at amino acid position 107 of SEQ ID NO: 175 were created using transient expression from HEK cells and tested for percent monomeric IgG by NR-CGE (data not shown). As mentioned previously, the production of unpaired light chain and lower molecular weight IgG complexes are more apparent under conditions whereby the antibody is being overproduced from a stable clonal cell. NR-CGE is however capable of detecting a differential in the amount of intact monomeric IgG versus lower molecular weight contaminants from cultures produced by transient transfection of cells (example HEK and CHO). This allows for a qualitative assessment of the percent monomeric IgG produced from transient cultures. This qualitative use of NR-CGE from transient cultures allowed for assay of multiple modifications and deletions to the c-terminus of the kappa constant chain of ZTS-361 for presence of percent monomeric IgG (data not shown). While not wishing to be bound by any one theory, deletion of the residues QRE from the c-terminus of the feline kappa constant chain appears to be the most optimal for production of monomeric recombinant feline IgG. Other additions to the c-terminus appear to be allowed. In general, one or two additional amino acids added beyond the cysteine at position 107 of Feline LC Kappa G minus (SEQ ID NO: 175) appear to be tolerated using qualitative assessment of percent monomer from transient produced IgG. Using these same qualitative assays it appears that even three additional amino acids added contiguously to the c-terminal end of the cysteine at position 107 in place of the native QRE amino acid residues may be tolerated if the amino acids have a minimal electrostatic charge influence. It is noted herein that the number and chemical properties of additional amino acids following the cysteine at position 107 of Feline LC Kappa G minus (SEQ ID NO: 175) will impact the efficient formation of the inter-chain disulphide bond between a kappa light chain constant and the corresponding Ig heavy chain constant. It is conceivable that modifications and/or deletions to this region may have advantageous effects of producing uniform intact IgG from a stable recombinant cell line.

The human and mouse kappa light chain c-terminal amino acid is the terminal cysteine therefore no additional amino acid residues are available to interact with the external environment during formation of the disulphide bond with the heavy chain constant. Therefore, it is hypothesized herein that these additional c-terminal residues in at least feline and canine kappa light chain constants present limitations to the formation of this disulphide bond that may not be ordinarily observed in nature due to the low abundance of these antibody species but may be highly relevant to the overproduction of these speciated forms in a laboratory setting. Such limitations may include the lack of formation of the disulphide bond between the c-terminus of the kappa light and the heavy chain constant chain leading to the presence of HHL, HH, HL, and L species previously described when recombinant antibody is produced from a stable cell line. These lower molecular weight species are undesirable in the production of a uniform drug product and their presence could be problematic from a quality and safety perspective.

Further to this observation are the codons which encode the amino acid residues in this region that appear below each amino acid letter in FIG. 15. In mammals there are three stop codons that signal termination polypeptide translation in the ribosome (TAA, TGA, and TAG). While not wishing to be bound by any one specific theory, it was observed that the majority of codons which encode for the amino acids following (and including) the c-terminal cysteine are one nucleotide away from a stop codon (FIG. 15, light grey letters in the codons). We hypothesize herein that somatic mutation at these various nucleotide positions may have led to the selection of an optimal immunoglobulin kappa constant chain length and amino acid composition that allows for efficient expression and correct chain pairing of an IgG kappa antibody. Subtle differences cannot be overlooked when assessing the allowance of appropriate amino acid which may exist at the c-terminus contiguous to the terminal cysteine. Noted herein is the observation that addition of residues EA on the pig light chain or Q on the mink light chain may have little to no deleterious impact on the formation of the inter-chain disulphide and expression of the intact IgG molecule. These species show equivalent use of kappa and lambda light chains and are described in the allowed region for acceptability of these additions. Pertaining to, but not limited to, canine and feline c-terminal kappa light chain residues, the distance from the c-terminal cysteine and the charged nature of the arginine and (aspartic and glutamic acid) residues is believed to have significant impact on the ability of a feline and canine antibody to efficiently and correctly form the covalent disulphide bond with its respective heavy chain.

1.17. Quaternary Structural Observations of the Feline Heavy Chain and Kappa Light Chain Interface FIG. 16A is a pictoral representation of the expected structure of a feline IgG with a heavy and light chain equivalent to ZTS-361 (supportive analytical data not shown). The positions of intra and inter-chain disulphide bonds are shown highlighting the heavy chain cysteine (CYS15) and light chain cysteine (CYS107) on only one arm of the structure for simplification. CYS15, the depicted amino acid residue is position 15 of Feline HC AlleleA wt (SEQ ID NO: 171) and Feline HC AlleleA 1 (SEQ ID NO: 173), with the depicted nucleotide residue nos. being residue nos. 43-45 of Feline HC AlleleA wt (SEQ ID NO: 172) and 43-45 of Feline HC AlleleA 1 (SEQ ID NO: 174) respectively. CYS107, the depicted amino acid residue is position 107 of Feline LC Kappa G minus (SEQ ID NO: 175) and Feline LC Kappa G minus QRE minus (SEQ ID NO: 186), with the depicted nucleotide residue nos. being residue nos. 319-321 of Feline LC Kappa G minus (SEQ ID NO: 176) and 319-321 of Feline LC Kappa G minus QRE minus (SEQ ID NO: 187). As mentioned previously, the composition of feline ZTS-361 is functionally equivalent to human IgG1; however, the nature of the disulphide bonding pattern is more similar to that of a human IgG2 (data not shown). FIG. 16B shows a homology model representing the two F(ab')$_2$ arms of ZTS-361 highlighting the approximate position of CYS15 and CYS107 for clarity using MOE software (Chemical Computing Group, Montreal, QC, Canada). FIG. 16C shows the contribution of additional electrostatic charges to the local environment that are contributed by the kappa light chain constant residues QRE that immediately follow CYS107. The charge from these three amino acids is represented as wire surface shells in this Figure. Homology models represent regions comprised of random coil structure with less accuracy than those found in ordered secondary structural elements like alpha helices and ordered beta sheets. This, however, is less of a consideration for CYS15 of the heavy chain as this region of the IgG constant domain is well defined by a wealth of structural data and the ordered nature of this region with the conserved IgG structure. Likewise, the CYS107 of the light chain has been resolved in numerous antibody structures and its proximity to CYS15 of the heavy chain can be appreciated. The addition of residues in the model beyond the terminal light chain cysteine can only be defined based on the geometry of adjacent residues and calculations of local energy minimums. This representation of the feline kappa light chain of ZTS-361 represents a best effort at producing a working model to generate a hypothesis for experimental design. Taken together, these results suggest that additional amino acid residues beyond the terminal cysteine in the kappa light chain of feline (and likely other species) is detrimental to efficient pairing with the heavy chain likely leading to mispairing and poor production of antibody.

1.18. Generation of Felinized Anti IL-31 Antibody ZTS-1505 with a Modified Kappa Constant C-Terminus Given the potential limitations of consistently producing a homogeneous antibody preparation with ZTS-361 it was deemed necessary to find a solution to the lack of percent monomer produced. Towards, but not limited to, this effort was the generation of ZTS-1505, the heavy chain including a variable region (SEQ ID NO: 121; FEL_15H05_VH1), the corresponding nucleotide sequence for which is (SEQ ID NO: 122; FEL_15H05_VH1) combined with a feline IgG heavy chain constant region (SEQ ID NO: 173; Feline_H-C_AlleleA_1), the corresponding nucleotide sequence for which is (SEQ ID NO: 174; Feline_HC_AlleleA_1). For ZTS-1505, the light chain includes a variable region (SEQ ID NO: 135; FEL-15H05-VL1_FW2), the corresponding nucleotide sequence for which is (SEQ ID NO: 136; FEL-15H05-VL1_FW2) combined with a feline IgG light chain constant region (SEQ ID NO: 186; Feline_LC_Kappa_G-_minus_QRE_minus), the corresponding nucleotide sequence for which is (SEQ ID NO: 187; Feline_LC_Kappa_G_minus_QRE_minus). ZTS-1505 is identical to ZTS-361, except with the removal of the three additional residues QRE off the c-terminal most end of the light chain kappa constant in an effort to avoid the undesired effects of producing antibody with lower molecular weight species resulting from inefficient pairing with the kappa light chain. It is envisioned that removal of these residues is beneficial to the process of producing monomeric IgG. However, the present invention is not necessarily limited to this one modification in the kappa light chain since other changes to the kappa light chain have been made and appear to have a neutral or even beneficial effect based on preliminary experimental data in transient expression (data not shown).

FIG. 17A describes the variable and constant sequences used to construct antibodies ZTS-361 and ZTS-1505 highlighting the different light chain used for ZTS-1505. Creation of a stable CHO cell line expressing ZTS-1505 is described in section 1.9 of this application. Assessment of antibody quality was of high interest so individual clones from a stable CHO transfection were surveyed for their ability to produce monomeric antibody. FIG. 17B shows the results for quantitative assessment of these individual clones using NR-CGE. 23 individual stable CHO clones were assessed and a high level of consistency was observed in the percent monomer produced with an average of 90.3%. This represents a 4% increase from the average percent monomer produced with individual clonal isolates of ZTS-361 (FIG. 14B) and a 7.3% increase observed with the stable pool (FIG. 13A). FIG. 17C shows a direct comparison of an individual stable CHO cell line expressing antibody ZTS-361 and ZTS-1505 under different culture conditions. Of note, antibodies described in FIGS. 12, 13A and 13B, and 14A and 14B were grown in culture conditions equivalent to culture condition A in FIG. 17C and these conditions are described in section 1.9 of this application. Both cell lines were grown for 14 days and the percent viability, titer (antibody yield in g/L), and percent monomer by NR-CGE were determined. The percent viability was consistent across all the conditions tested with both cell lines. The percent monomer by NR-CGE showed a consistent 4-5% improvement in percent monomer comparing ZT-1505 to ZTS-361 indicating again that the kappa light chain constant in ZTS-1505 lacking the additional QRE residues had a positive effect on chain association between the feline heavy chain constant and kappa light chain. Even more striking was the improvement in the amount of ZTS-1505 antibody produced compared to ZTS-361. ZTS-1505 produced, on average, a 3.5 fold improvement in the production of antibody from a stable CHO cell when compared to ZTS-361 possessing the wildtype kappa light chain constant.

To insure the kappa light chain constant modification did not affect the affinity and potency of ZTS-1505, comparative analysis was performed using biacore and inhibition of IL-31 mediated pSTAT signaling in canine and feline cells. Table 1 below describes the results for biacore analysis using multiple species of IL-31 protein as a surface capture. These results show nearly identical affinity to canine, feline, and equine IL-31 protein was observed for ZTS-1505 possessing the light chain kappa constant modification when compared to ZTS-361 having the wildtype feline kappa constant c-terminus. Also described here is the expected binding phenotype for ZTS-1505 to the feline 15H05 and feline 11E12 mutants described section 1.2 of this application. Modification of the c-terminus of the kappa constant chain did not alter the selectivity for the epitope as demonstrated by the lack of ZTS-1505 binding to the feline 15H05 mutant protein and the retention of binding to the feline 11E12 mutant, equivalent to ZTS-361.

from those species whose native germline encodes these additional residues is beneficial to both the production of homogeneous recombinant antibody for these species and beneficial to the amount of antibody produced from a stable cell line (e.g., yield improvement). Furthermore such modifications, while enhancing the quality and quantity of the antibody produced, have no negative impact on affinity and potency of the antibody to the IL-31 target protein. It is noted herein that these factors may be beneficial to the production of recombinant antibodies for therapeutic use in multiple species.

1.19. Confirmation of NR CGE Results with Anti IL-31 mAb 1505 and Further Demonstration for the Utility of the Modified Kappa Constant C-Terminus with an Anti NGF Antibody It was of interest to determine if the increased production of percent monomeric IgG was applicable to different antibodies whose protein targets are dissimilar to IL-31. To accomplish this, an additional set of stable CHO cell line pools were generated with felinized antibodies recognizing the feline beta-nerve growth factor (NGF) (ZTS-768 and ZTS-943). The sequence for antibody ZTS-768 heavy chain is (SEQ ID NO: 220; ZTS_768_VH), the corresponding nucleotide sequence for which is (SEQ ID NO: 221; ZTS_768_VH) combined with a feline IgG heavy chain constant region (SEQ ID NO: 171; Feline_HC_AlleleA_wt), the corresponding nucleotide sequence for which is (SEQ ID NO: 172; Feline_HC_AlleleA_wt). The sequence for antibody ZTS-943 heavy chain is (SEQ ID NO: 224; ZTS_943_VH), the corresponding nucleotide sequence for which is (SEQ ID NO: 225; ZTS_943_VH) combined with a feline IgG heavy chain constant region (SEQ ID NO: 171; Feline_HC_AlleleA_wt), the corresponding nucleotide

TABLE 1

| | | | | | | Capture Protein SEQ ID NO Biacore $K_D$ (M) IL-31 Species | | | | |
|---|---|---|---|---|---|---|---|---|---|---|
| | | | | | | 157 | 155 | 165 | 163 Feline 15H05 | 161 Feline 11E12 |
| | | Antibody SEQ ID NO | | | | | | | | |
| mAb ID | Description | VH | VL | HC | LC | Feline | Canine | Equine | mutant | mutant |
| 15H05 | Mouse hybridoma | 67 | 69 | 188 | 190 | 3.06E−10 | 1.91E−12 | 3.06E−10 | 2.39E−08 | 1.15E−08 |
| ZTS-361 | Stable CHO cell line | 121 | 135 | 173 | 175 | 6.25E−10 | 2.41E−12 | 6.25E−10 | no binding | 1.72E−08 |
| ZTS-1505 | Stable CHO cell line | 121 | 135 | 173 | 186 | 5.75E−10 | 1.83E−12 | 5.75E−10 | no binding | 1.95E−08 |

Table 2 below shows the cellular potency data comparing ZTS-1505 with ZTS-361. The light chain kappa constant modification for ZTS-1505 did not impact the ability of this antibody to inhibit cellular pSTAT signaling induced by canine and feline IL-31 on canine DH82 and feline FCWF-4 cells respectively as indicated by the comparable $IC_{50}$ values.

TABLE 2

| | Inhibition of IL-31 induced pSTAT3 $IC_{50}$ (µg/ml) | |
|---|---|---|
| mAb ID | Canine IL-31 on Canine DH82 cells | Feline IL-31 on Feline FCWF-4 cells |
| Mouse 15H05 | 11.17 | 6 |
| ZTS-361 | 22.99 | 8.85 |
| ZTS-1505 | 21.81 | 4.53 |

Taken together these results suggest the removal, or modification, of the c-terminal end of the kappa light chain sequence for which is (SEQ ID NO: 172; Feline_HC_AlleleA_wt). For ZTS-768 the light chain variable is (SEQ ID NO: 222; ZTS_768_VL), the corresponding nucleotide sequence for which is (SEQ ID NO: 223; ZTS_768_VL). For ZTS-768, this light chain variable region is combined with a feline IgG light chain constant region (SEQ ID NO: 175; Feline_LC_Kappa_G_minus), the corresponding nucleotide sequence for which is (SEQ ID NO: 176; Feline_LC_Kappa_G_minus). For ZTS-943, the light chain variable region is (SEQ ID NO: 226; ZTS_943_VL), the corresponding nucleotide sequence for which is (SEQ ID NO: 227; ZTS_943_VL) combined with a feline IgG light chain constant region (SEQ ID NO: 186; Feline_LC_Kappa_G_minus_QRE_minus), the corresponding nucleotide sequence for which is (SEQ ID NO: 187; Feline_LC_Kappa_G_minus_QRE_minus). For a direct comparison to anti IL-31 antibodies, stable pools of ZTS-361 and ZTS-1505 were also generated using identical culture and purification conditions to the anti NGF antibodies.

Figure 18A:
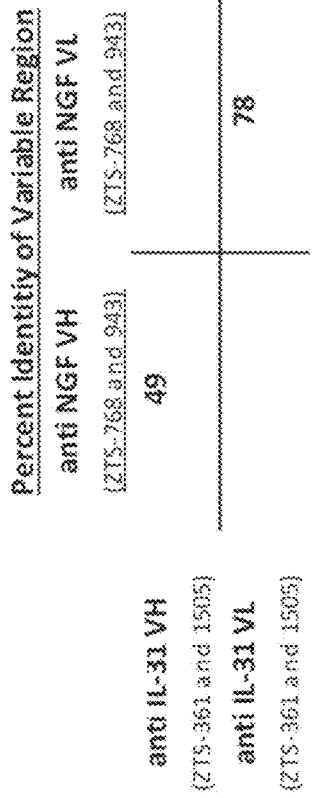
FIG. 18A shows the percent identity comparing the variable regions of these anti feline NGF antibodies to anti IL-31 calculated using the ClustallW software.
Figure 18B:
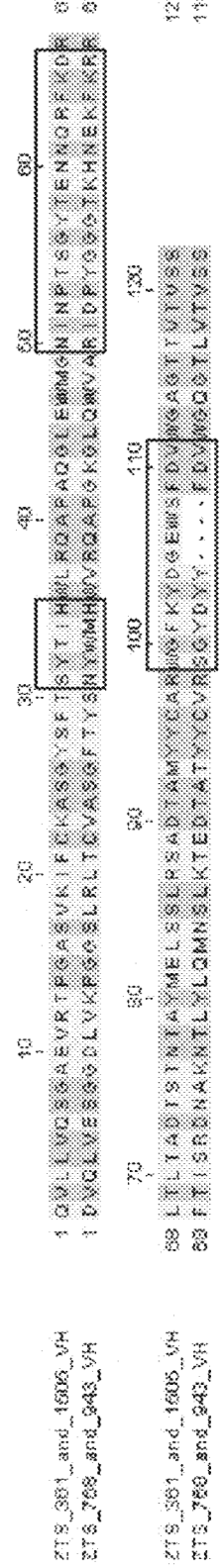
FIGS. 18B and 18C show the alignment of the anti feline IL-31 and NGF antibodies variable heavy and light chains respectively with the CDRs outlined with boxes.
Figure 18C:
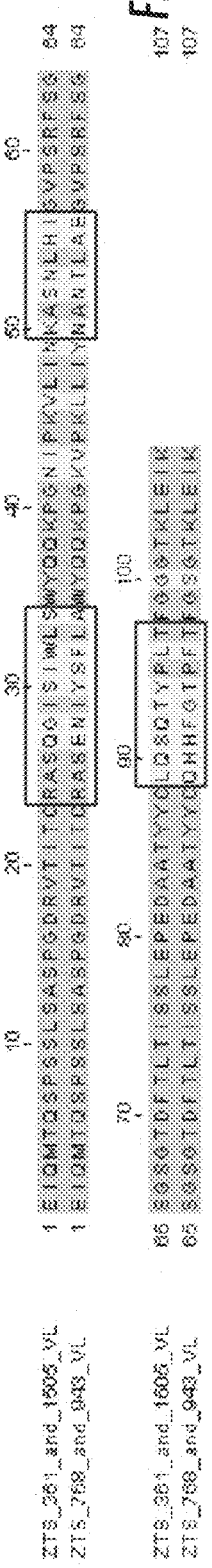

NR CGE was used to determine the percent monomeric intact IgG and subspecies following production and purification of the four antibodies described above. By comparison of these antibodies generated and purified using identical methods it was possible to assess the utility of incorporating the modified kappa constant C-terminus between structurally disparate antibodies recognizing distinct protein targets. FIG. 18A shows the percent identity comparing the variable regions of these anti feline NGF antibodies to anti IL-31 calculated using the ClustallW software. FIGS. 18B and 18C show the alignment of the anti feline IL-31 and NGF antibodies variable heavy and light chains respectively with the CDRs outlined with boxes. Clearly the anti IL-31 and anti NGF antibodies are distinct from one another with a lack of overall identity, especially within the antigen binding regions highlighted as CDRs.

FIG. 19 shows the results from the NR CGE comparing anti feline IL-31 and anti feline NGF antibodies with and without the modified kappa constant C-terminus. Consistent with previous findings, the anti IL-31 antibody containing the wildtype kappa light chain (ZTS-361) was observed to have 80.74% monomeric IgG with a predominant 8.71% of the HHL subspecies. A clear improvement in the percent monomer was again observed following the removal of the three C-terminal residues to generate ZTS-1505 (89.17% monomer with 5.9% HHL). NR CGE analysis of purified IgG from the anti feline NGF mAb containing the wildtype kappa light chain (ZTS-768) resulted in a similar amount of monomer and subspecies being isolated (80.81% monomer with 12.33% HHL) as compared to anti IL-31 ZTS-361. Notably, the same pattern was observed following removal of the C-terminal residues from the anti feline NGF antibody yielding 88.59% monomer with the predominant subspecies being 5.98% HHL.

These results suggest a structural distinction exists between a feline IgG protein which contains the wildtype amino acid residues (QRE) on the C-terminus of the kappa light chain versus an IgG with these residues removed. The experimental results described herein support that the use of this kappa light chain modification results in the production of monomeric feline IgGs with a reduced amount of subspecies contaminants. Further to this, the results herein clearly demonstrate that this method applies to structurally disparate antibodies which recognize completely distinct targets and therefore this modification will likely be applicable to the broad genus of feline antibodies as well as other mammalian antibodies possessing additional C-terminal amino acids on the kappa light chain constant region. While not wishing to be bound by any one theory, this light chain modification appears to result in a higher fidelity of immunoglobulin chain pairing during the induced production from stable CHO cell lines resulting in a higher amount of monomeric IgG and potentially a higher overall antibody yield. Both of these attributes are highly desirable from the standpoint of manufacturing commercial grade antibody therapeutics.

1.20 Identification of Anti Equine IL-31 Antibodies Which Bind to an Equivalent Region on the Equine IL-31 Protein Compared to mAb 15H05 Binding to Feline IL-31

Given the promising in vivo efficacy in the feline model of pruritus using antibodies from the mouse 15H05 lineage described herein, it was desirable to identify novel antibody substrates which bind to a similar region on the equine ortholog of the IL-31 protein. Towards this end, mice were immunized with recombinant equine IL-31 (SEQ ID No. 165) for the purpose of identifying antibodies that bind to equine IL-31.

Figure 6B:
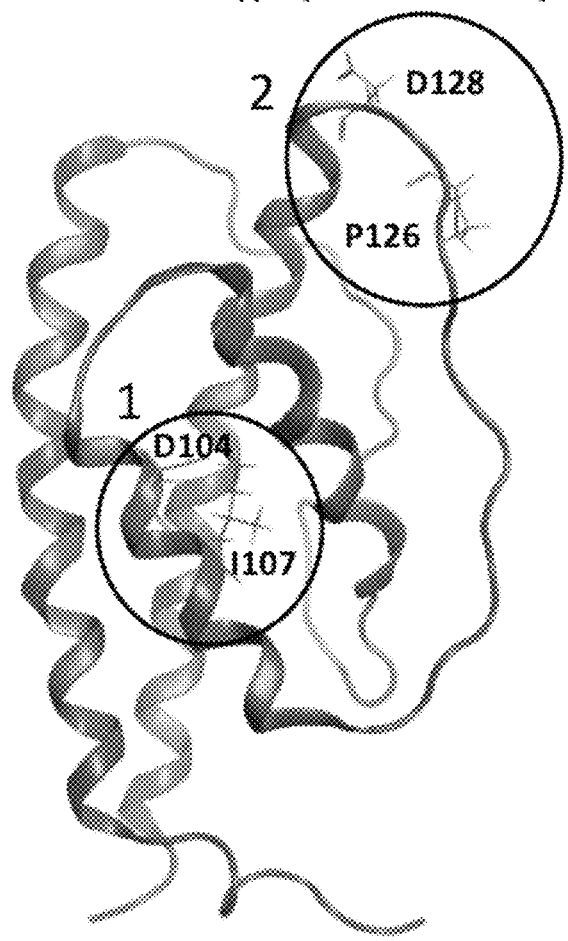
FIG. 6B shows the feline IL-31 homology model highlighting the positions of two amino acids involved with binding of antibodies 11E12 (site 1) and 15H05 (site 2).
Figure 6C:
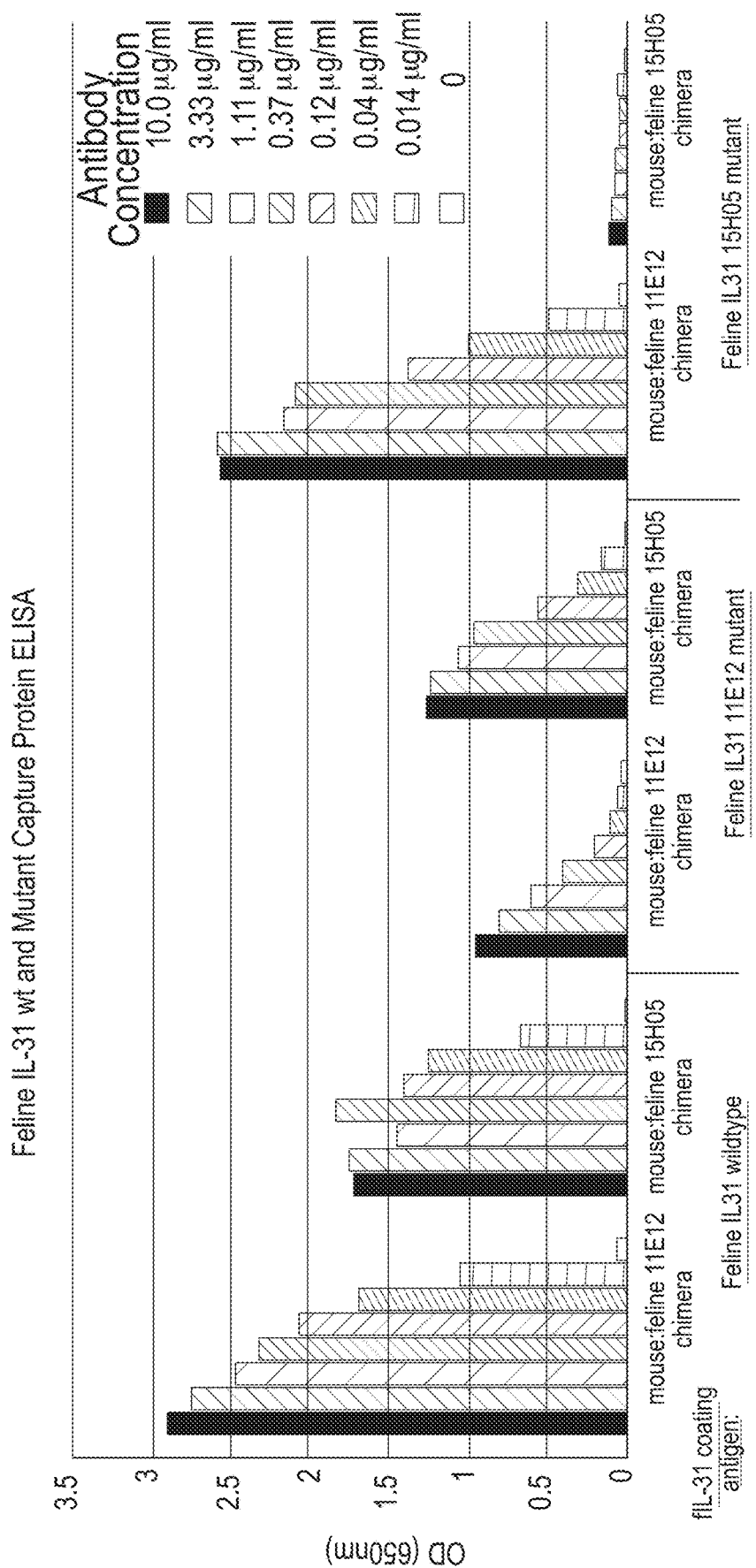
FIG. 6C is a graph showing the results obtained for binding of monoclonal antibodies 11E12 and 15H05 to wild-type feline IL-31 and to mutant IL-31 proteins 15H05 (SEQ ID NO: 163) and 11E12 (SEQ ID NO: 161) when the wild-type and these mutants are used as the coating antigens.
Figure 7A:
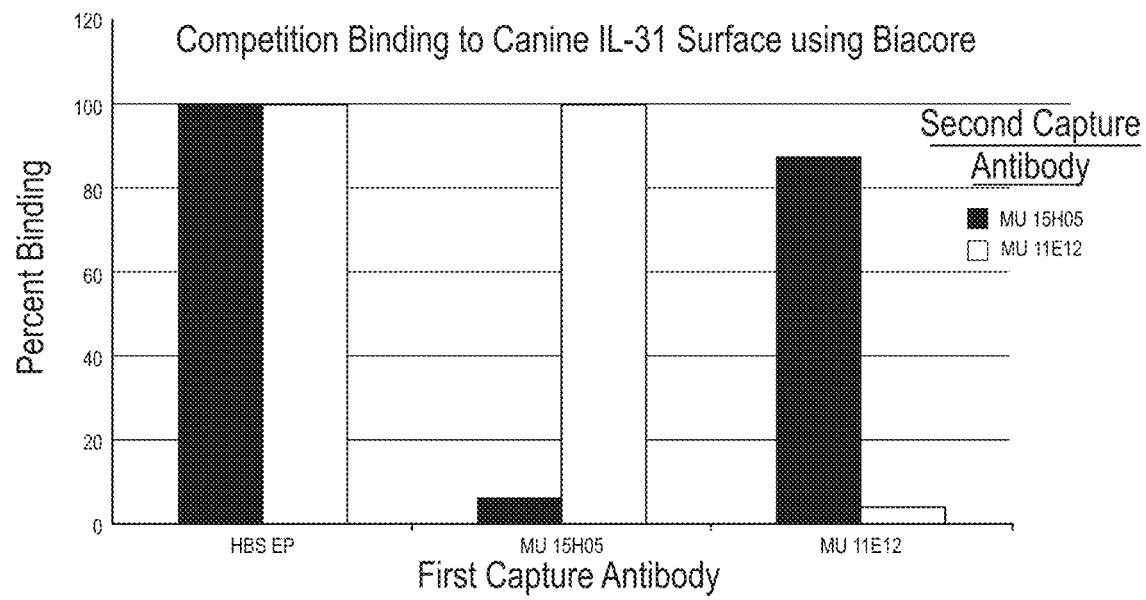
FIGS. 7A and 7B are of graphs showing competition binding assessments of mAbs 15H05 and 11E12 using Biacore.
Figure 7B:
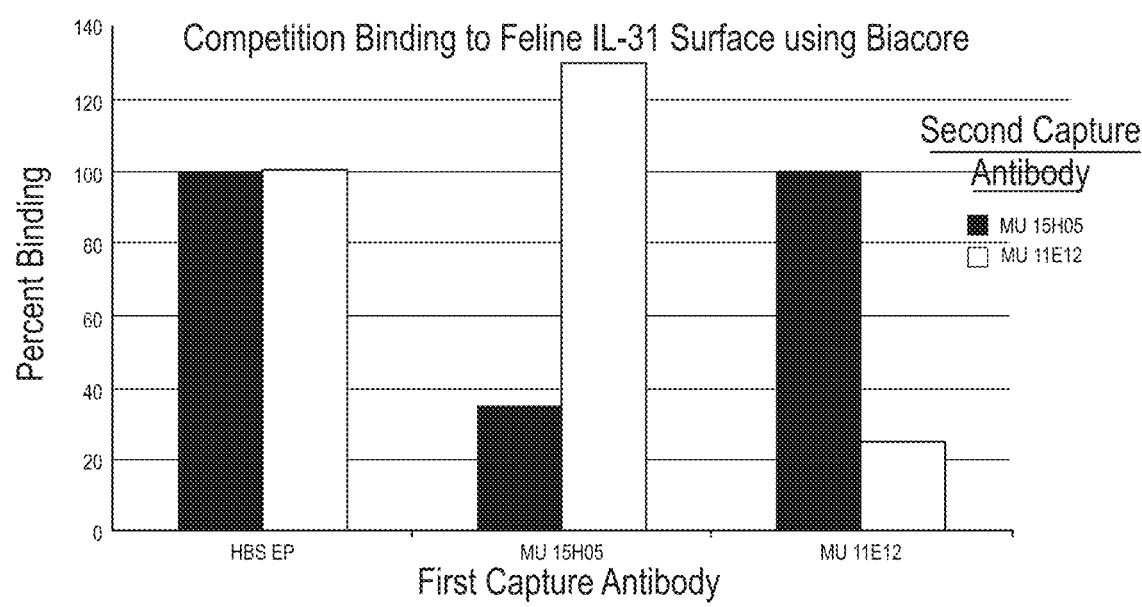
Figure 20:
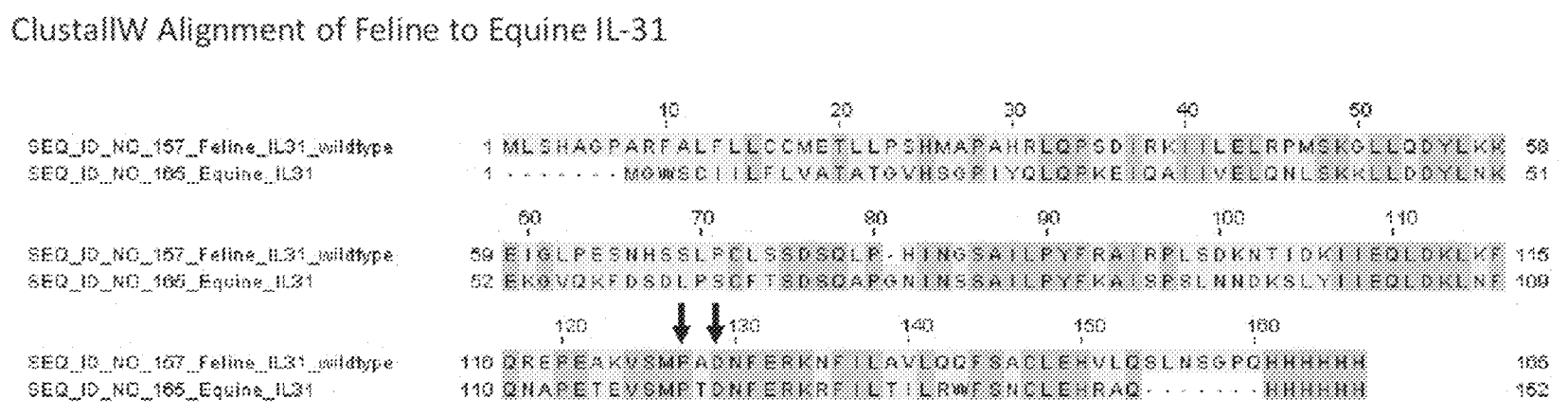

Serum antibody titers from immunized animals were determined using an ELISA as described previously. Donor splenocytes from a single responsive mouse were used for fusion and hybridoma supernatants were screened for antibodies that bind to the equine IL-31 protein by ELISA. This resulted in the identification of two mouse antibodies that bind to a region on the equine IL-31 protein comparable to the binding site of antibody 15H05 on feline IL-31. Section 1.10 of this application describes the characterization of the binding site of antibody 15H05 with illustration of the approximate binding site on a homology model of feline IL-31 in FIG. 6B. FIG. 20 shows an alignment of feline IL-31 wildtype (SEQ ID No. 157) with equine IL-31 (SEQ ID No. 165) using the ClustallW software. The arrows above the alignment indicate residues P126 and D128 which are described in section 1.10 as being contained within the binding region of antibody 15H05 to feline IL-31 at site 2 (FIG. 6B). These two anti equine IL-31 antibodies that share this binding site in the equine IL-31 protein are 04H07 and 06A09.

Figures 21A, 21B:
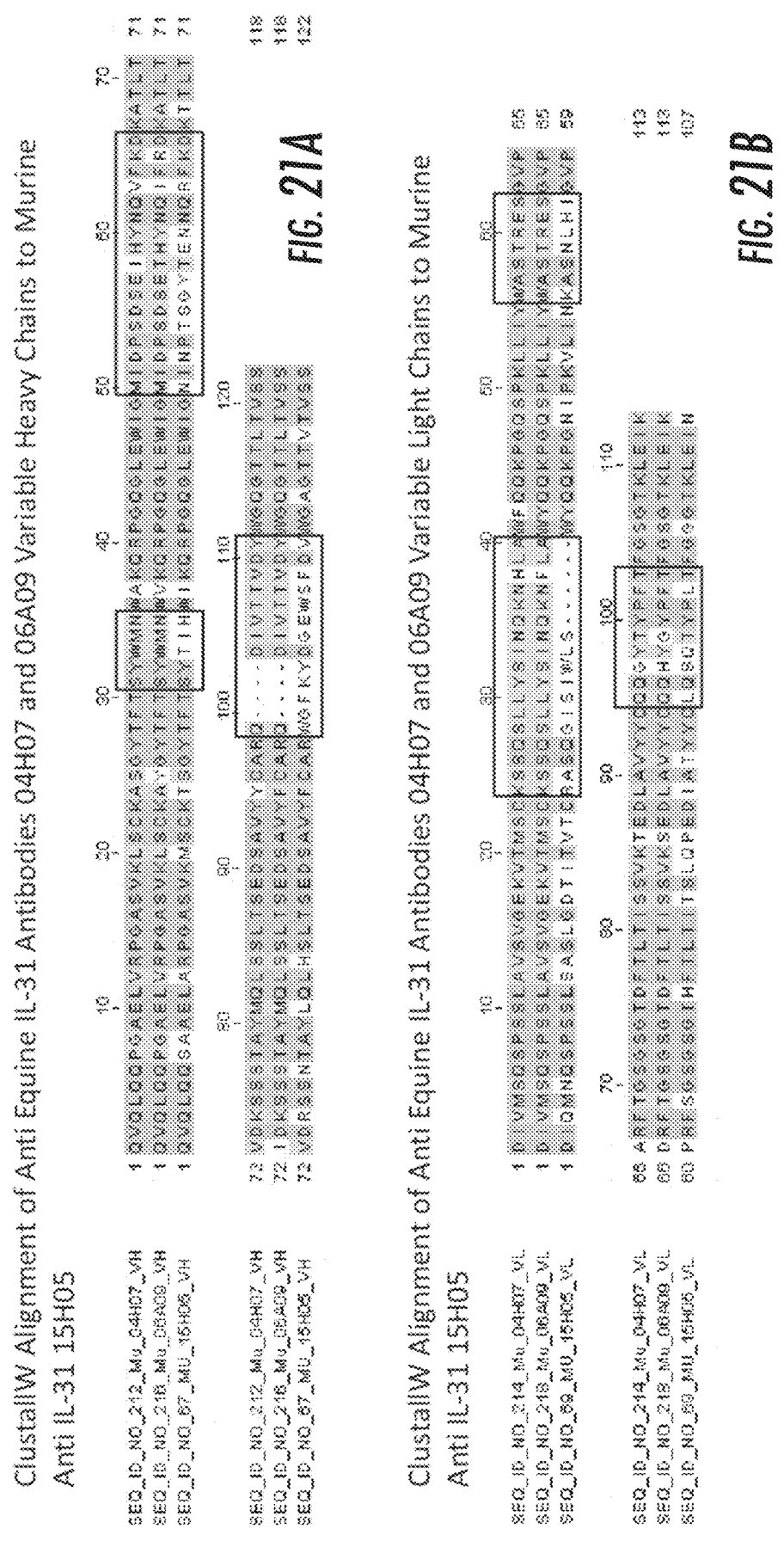

Anti equine IL-31 04H07 and 06A09 were further subcloned to generate a hybridoma producing homogeneous antibody and for sequencing of the variable heavy and light chains. The mouse anti IL-31 variable sequences determined for antibody 04H07 are as follows, 04H07 variable heavy chain (SEQ ID NO: 212; Mu_04H07_VH), the corresponding nucleotide sequence for which is (SEQ ID NO: 213; Mu_04H07_VH), 04H07 variable light chain (SEQ ID NO: 214; Mu_04H07_VL), the corresponding nucleotide sequence for which is (SEQ ID NO: 215; Mu_04H07_VL). 06A09 variable heavy chain (SEQ ID NO: 216; Mu_06A09_VH), the corresponding nucleotide sequence for which is (SEQ ID NO: 217; Mu_06A09_VH), 06A09 variable light chain (SEQ ID NO: 218; Mu_06A09_VL), the corresponding nucleotide sequence for which is (SEQ ID NO: 219; Mu_06A09_VL). FIGS. 21A and 21B show an alignment of the variable heavy (FIG. 21A) and light (FIG. 21B) chains of 04H07 and 06A09 compared to mouse antibody 15H05 using ClustallW. For comparison, the location of each of the six CDRs are outlined with boxes. Anti equine IL-31 antibodies 04H07 and 06A09 are highly similar to one another likely emerging from a common clonal lineage. The anti feline IL-31 antibody 15H05 is clearly distinct in the amino acid sequences of the CDRs and the lengths of CDRH3 and CDRL1 compared to anti equine IL-31 04H07 and 06A09. It is of interest that the binding site of antibody 15H05 to feline IL-31 is conserved when compared to the equine protein (FIG. 20 arrows). These results further exemplify that structurally distinct CDRs are capable of recognizing a common epitope region on two IL-31 orthologs.

1.21. Alanine Scanning of the CDRs on Anti IL-31 Antibody ZTS-1505

The region of an antibody responsible for antigen recognition represents the paratope. A paratope is created by a combination of amino acids in the complementarity determining regions (CDRs) of both the heavy and light chain variable regions. The binding between antibody and antigen is often mediated by side chains of CDR residues with side chains or carbohydrate moieties of the antigen. To help define critical side chains involved in antibody recognition alanine scanning mutagenesis was performed on each CDR residue in both the heavy and light chain. These mutants were then individually tested for the ability to bind feline IL-31 using the biacore and evaluated for inhibition of IL-31-mediated signaling in the FCWF-4 cell based assay.

Figure 22:
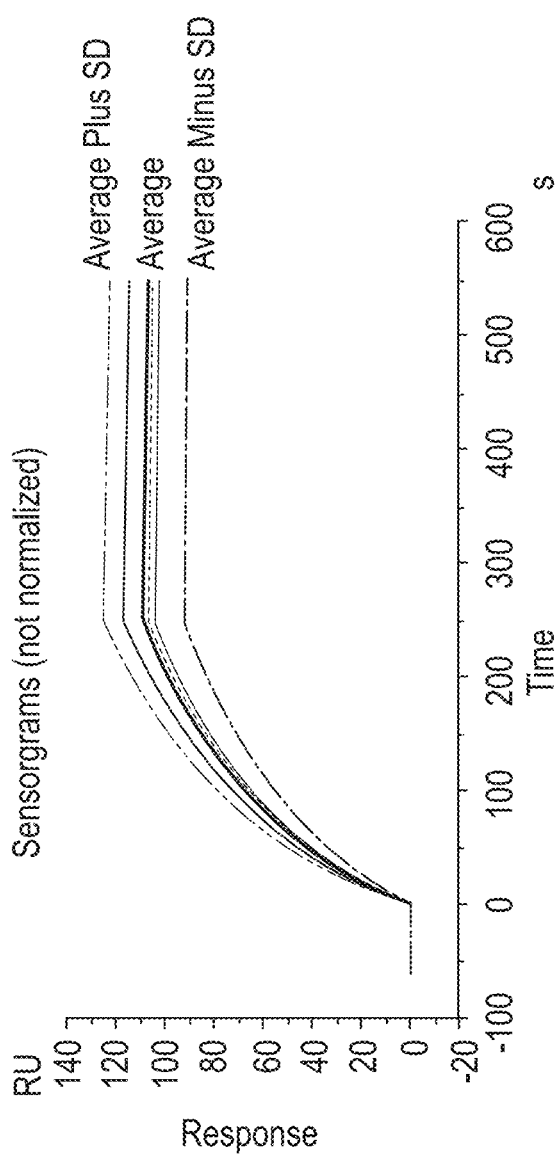
FIG. 22 is of a Biacore Sensorgram showing the average profile of anti-IL31 antibody ZTS-1505+/−3 standard deviations used to define a threshold of response for screening of Alanine substituted CDR mutants.

To determine the relative affinity of the alanine scanning mutant mAbs to the parent mAb binding profiles to feline IL-31 coated chips was determined at 100 nM using a Biacore T200. The mean response unit of four replicates of the parent mAb+/−3 standard deviations was used to generate parameters to define a threshold of response units comprising both the on- and off-rates antibody binding (FIG. 22). The percentage of data points for each mutant fell within this threshold was then used to define a "% similarity score" (FIG. 23). The similarity score resulting from the substitution of alanine at each heavy and light chain CDR position in antibody ZTS-1505 is shown in FIGS. 23 and 24 respectively.

To determine the relative activity of the ZTS-1505 mutant antibodies in the cell based assay each antibody was assessed for its ability to inhibit feline-IL-31-mediated STAT phosphorylation in Fcwf-4 cells at 15 ug/mL. Relative inhibition of STAT phosphyrlation was determine by evaluating the % inhibition of stat phosphorylation of each mutant relative to parent. Results from substitiution of alanine at each CDR position of ZTS-1505 for the heavy and light chain are shown as "percent inhibition relative to parent" in FIGS. 23 and 24 respectively. By evaluating the effect that individual alanine substitutions have on binding affinity and cell based activity the side chains of each CDR amino acid residue can be individually assessed for its role in antigen recognition. CDR residues that can be changed to alanine and retain activity are likely to be amenable to a variety of amino acid substitutions and represent residues that are not critical in antigen recognition. Based on these data, at least residue 4 (I) from SEQ ID NO 1; residues 1-3 (NIN), 5-7 (TSG), 9-11 (TEN) and 13 (Q) from SEQ ID NO 2; residues 4 (K), 6 (D) and 13 (V) from SEQ ID NO 3 are non-critical residues for antigen binding in heavy chain CDR 1, 2 and 3, respectively. Light chain residues CDR residues that are not critical for binding include residues 3-7 (SQGIS) from SEQ ID NO 4, residue 3 (S) and 5 (L) from SEQ ID NO 5, and residue 4 (Q), 5 (T) and 9 (T) in SEQ ID NO 6 from CDRL1, 2, and 3, respectively.

1.22. Binding Affinity and Cellular Potency of two Felinized Versions of the ZIL8 Antibody Section 1.6 above of this example section describes the identification of a canine antibody that recognizes feline IL-31 termed ZIL8. Initial screening revealed that this antibody is capable of binding the feline IL-31 protein, however its binding is affected by the 15H05 mutation. It was therefore of interest to pursue a felinized form of this antibody for use as a therapeutic in cats. Towards this end, a felinization strategy was followed as previously described in section 1.8 of this application. Grafting of the ZIL8 CDRS onto the appropriate feline frameworks yielded antibodies ZTS-5864 and ZTS-5865. The sequence for antibody ZTS-5864 heavy chain is (SEQ ID NO: 228; ZTS_5864_VH), the corresponding nucleotide sequence for which is (SEQ ID NO: 229; ZTS_5864_VH) combined with a feline IgG heavy chain constant region (SEQ ID NO: 173; Feline_H-C_AlleleA_1), the corresponding nucleotide sequence for which is (SEQ ID NO: 174; Feline_HC_AlleleA_1). For ZTS-5864 the light chain variable is (SEQ ID NO: 230; ZTS_5864_VL), the corresponding nucleotide sequence for which is (SEQ ID NO: 231; ZTS_5864_VL). For ZTS-5864, this light chain variable region is combined with a feline IgG light chain constant region (SEQ ID NO: 236; Feline_LC_Lambda), the corresponding nucleotide sequence for which is (SEQ ID NO: 237; Feline_LC_Lambda). The sequence for antibody ZTS-5865 heavy chain is (SEQ ID NO: 232; ZTS_5865_VH), the corresponding nucleotide sequence for which is (SEQ ID NO: 233; ZTS_5865_VH) combined with a feline IgG heavy chain constant region (SEQ ID NO: 173; Feline_H-C_AlleleA_1), the corresponding nucleotide sequence for which is (SEQ ID NO: 174; Feline_HC_AlleleA_1). For ZTS-5865 the light chain variable is (SEQ ID NO: 234; ZTS_5865_VL), the corresponding nucleotide sequence for which is (SEQ ID NO: 235; ZTS_5865_VL). For ZTS-5865, this light chain variable region is combined with a feline IgG light chain constant region (SEQ ID NO: 236; Feline_LC_Lambda), the corresponding nucleotide sequence for which is (SEQ ID NO: 237; Feline_LC_Lambda).

Figures 25A, 25B:
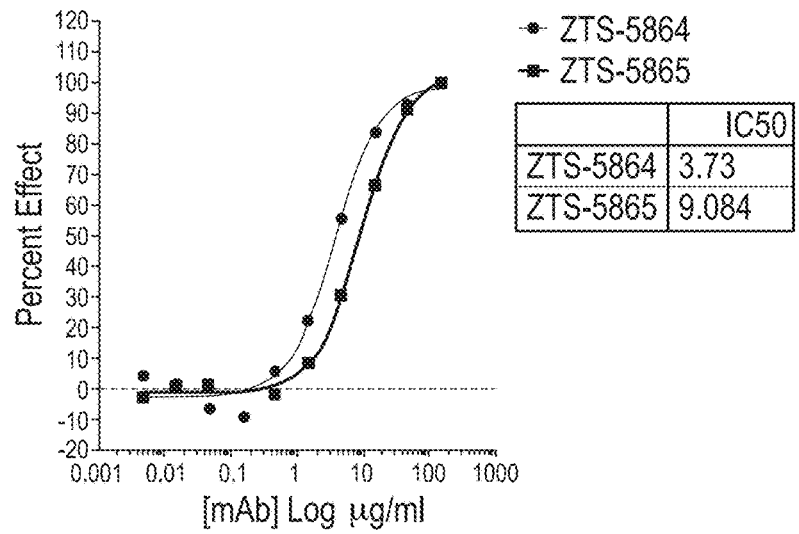
FIGS. 25A and 25B show the binding affinity and cellular potency, respectively, of the two felinized antibodies designated herein as ZTS-5864 and ZTS-5865.

FIGS. 25A and 25B show this affinity and cellular potency of the two felinized antibodies ZTS-5864 and ZTS-5865. Both antibodies have high affinity to feline IL-31 with ZTS-5864 having an approimantely 4 fold increase in affinity (KD (M)) when compared to ZTS-5864. Cellular potency was assessed using feline IL-31 to stimulate pSTAT3 signalling in FCFW4 cells. $IC_{50}$ values were calculated for each antibody as described previously in this application. ZTS-5864 is approximately 3 fold more potent when comparing its $IC_{50}$ value to that of ZTS-5865. It is worth noting that both antibodies are considered potent with $IC_{50}$s in the range of those antibodies previously described herein from the 15H05 lineage (FIG. 3). The relevance of these potencies using pSTAT3 signalling from feline FCFW4 cells were previously qualified with positive in vivo efficacy results using chimeric and felinized antibodies in a feline model of pruritus (FIG. 9 and FIGS. 10A and 10B).

Figure 26:
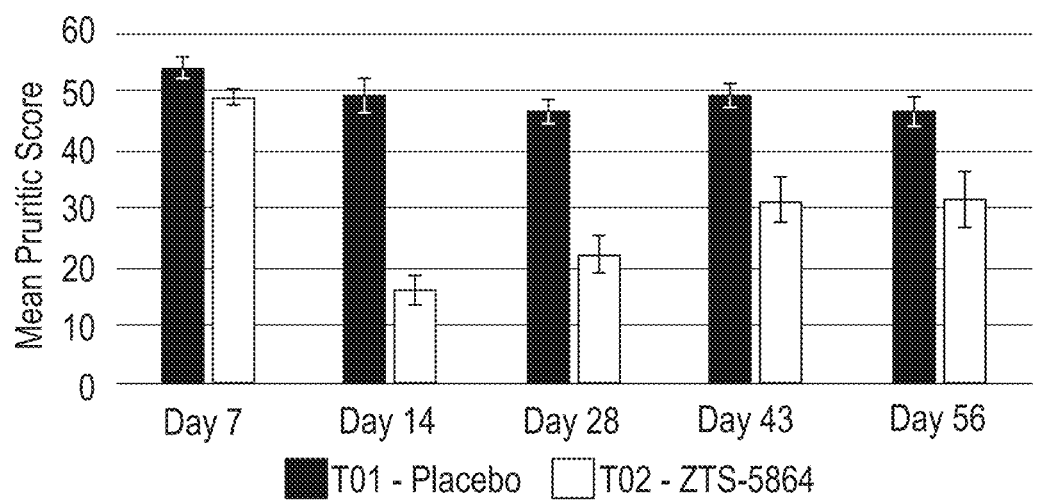
FIG. 26 is a graph depicted the results of an in vivo evaluation of the efficacy of the felinized ZTS-5864 anti-IL-31 antibody in a cat pruritus challenge model.

1.23 In Vivo Evaluation of the Efficacy of Felinized ZTS-5864 Anti IL-31 Antibody in a Cat Pruritus Challenge Model In vivo efficacy of ZTS-5864 was assessed in a feline IL-31 model of induced pruritus as described previously in section 1.14 of this example section. FIG. 26 shows the results from this study. Predose (day −7) indicates that the animals in T01 and T02 groups have an equivalent pruritic response to IL-31 challenge prior to dosing. Very little change was observed in the T01 pruritic response over the course of the study out to 56 days. In contrast ZTS-5864 (3.0 mg/mg) given subcutaneously on day zero attenuated the pruritic effect of the IL-31 challenge throughout the entire course of study to day 56 (FIG. 26, T02). The continued decrease in mean pruritic score for T02 at day 56 indicates the antibody will likely maintain efficacy beyond this timepoint. These results accentuate the robust criteria used for the selection of anti feline IL-31 antibodies in this application. These results further support the positioning of these speculated antibodies as therapeutics for the treatment of IL-31 mediated disorders in cats.

What is claimed is:

1. An anti-IL31 antibody, which is a variant of a parent antibody, the parent antibody comprising:
   a VH-CDR1 comprising the amino acid sequence set forth in SEQ ID NO: 19, a VH-CDR2 comprising the amino acid sequence set forth in SEQ ID NO: 20, a VH-CDR3 comprising the amino acid sequence set forth in SEQ ID NO: 21, a VL-CDR1 comprising the amino acid sequence set forth in SEQ ID NO: 22, a VL-CDR2 comprising the amino acid sequence set forth in SEQ ID NO: 23, and a VL-CDR3 comprising the amino acid sequence set forth in SEQ ID NO: 24, wherein the variant antibody is selected from a) a variant wherein the Alanine (A) at position 14 of SEQ ID NO: 20 of the parent antibody is substituted with a Serine (S); or b) a variant wherein the Serine (S) at position 5 of SEQ ID NO: 19 of the parent antibody is substituted with an Asparagine (N) and the Alanine (A) at position 14 of SEQ ID NO: 20 of the parent antibody is substituted with a Serine (S).

2. The variant antibody of claim 1, wherein the variant antibody comprises:
   a VL chain comprising the amino acid sequence set forth in SEQ ID NO: 230 and a VH chain comprising the amino acid sequence set forth in SEQ ID NO: 228; or
   a VL chain comprising the amino acid sequence set forth in SEQ ID NO: 234 and a VH chain comprising the amino acid sequence set forth in SEQ ID NO: 232.

3. The variant antibody of claim 1, wherein the variant antibody is a chimeric antibody.

4. The variant antibody of claim 1, wherein the variant antibody is felinized.

5. A method for treating a pruritic or allergic condition selected from the group consisting of atopic dermatitis, allergic dermatitis, and pruritus in a cat, the method comprising: administering to said cat an effective amount of the variant antibody of claim 1.

6. A pharmaceutical composition comprising the variant antibody of claim 1 and a pharmaceutically acceptable carrier.

* * * * *